US007838728B2

(12) United States Patent
Schmidt

(10) Patent No.: US 7,838,728 B2
(45) Date of Patent: Nov. 23, 2010

(54) MODULATING DEVELOPMENTAL PATHWAYS IN PLANTS

(75) Inventor: Eduard Daniel Leendert Schmidt, Oosterbeek (NL)

(73) Assignee: Expressive Research B.V., Wageningen (NL)

(*) Notice: Subject to any disclaimer, the term of this patent is extended or adjusted under 35 U.S.C. 154(b) by 624 days.

(21) Appl. No.: 10/521,518

(22) PCT Filed: Jul. 17, 2003

(86) PCT No.: PCT/NL03/00524

§ 371 (c)(1), (2), (4) Date: Feb. 28, 2006

(87) PCT Pub. No.: WO2004/007712

PCT Pub. Date: Jan. 22, 2004

(65) Prior Publication Data

US 2006/0265783 A1 Nov. 23, 2006

(30) Foreign Application Priority Data

Jul. 17, 2002 (EP) .................................. 02077908

(51) Int. Cl.
*C12N 15/82* (2006.01)

(52) U.S. Cl. ...................... 800/278; 800/290; 800/279; 800/286

(58) Field of Classification Search ...................... None
See application file for complete search history.

(56) References Cited

U.S. PATENT DOCUMENTS

| | | | | |
|---|---|---|---|---|
| 5,859,338 | A * | 1/1999 | Meyerowitz et al. | ........ 800/298 |
| 2002/0069433 | A1 | 6/2002 | Schmidt et al. | |

FOREIGN PATENT DOCUMENTS

| | | |
|---|---|---|
| WO | WO97/43427 | 11/1997 |
| WO | WO98/22594 | 5/1998 |
| WO | WO01/29240 A2 | 4/2001 |
| WO | WO01/29240 A3 | 4/2001 |
| WO | WO02/46439 A2 | 6/2002 |

OTHER PUBLICATIONS

Century et al (1997, Science 278:1963-1965).*
Clark et al (1993, Development 119:397-418).*
Christensen et al (2000, Cell 100:469-478).*
Schmidt, E.D.L., et al., "A Leucine-Rich Repeat Containing Receptor-Like Kinase Marks Somatic Plant Cells Competent to Form Embryos", Development, Company of Biologists 1997, 124: (10)2049-2062.
Zhang, X., "Leucine-Rich Repeat Receptor-Kinases in Plants", Plant Molecular Biology Reporter 1998, 16:301-311.

* cited by examiner

*Primary Examiner*—Stuart F. Baum
(74) *Attorney, Agent, or Firm*—Hoffmann & Baron, LLP

(57) ABSTRACT

The invention relates to a method to modulate plant growth or development by modifying genes in plants. The invention among others relates to modifying RKS genes or gene products as found in *Arabidopsis thaliana* or other plants. The invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein.

9 Claims, 36 Drawing Sheets

Different domains of RKS proteins

Figure 1:
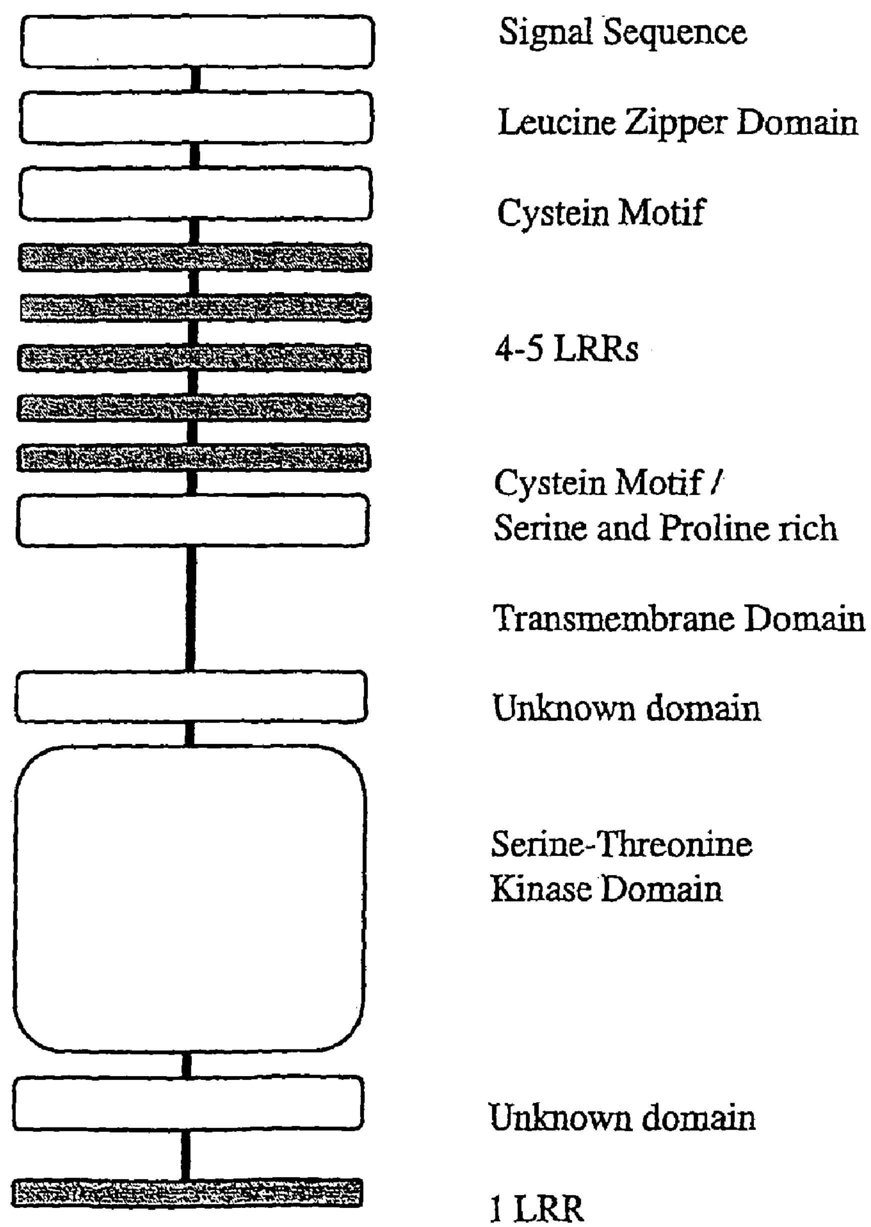
Figure 2:
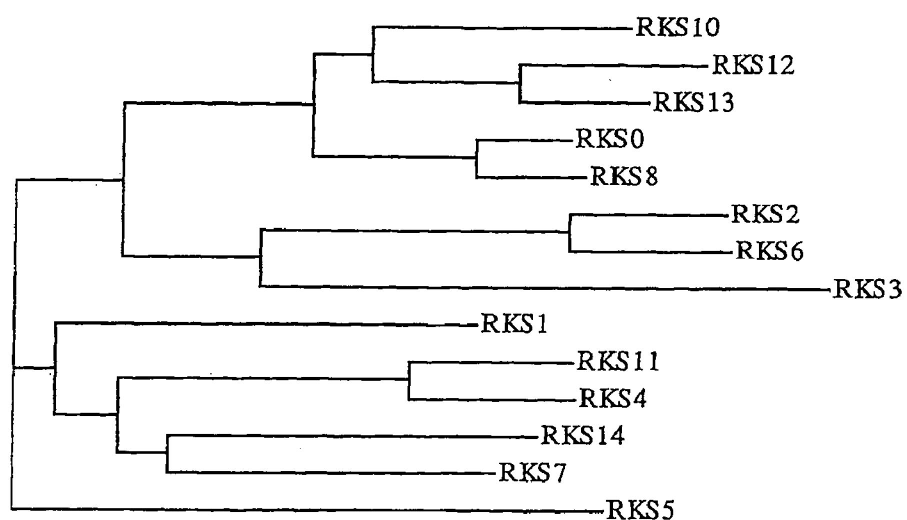
Figure 3:
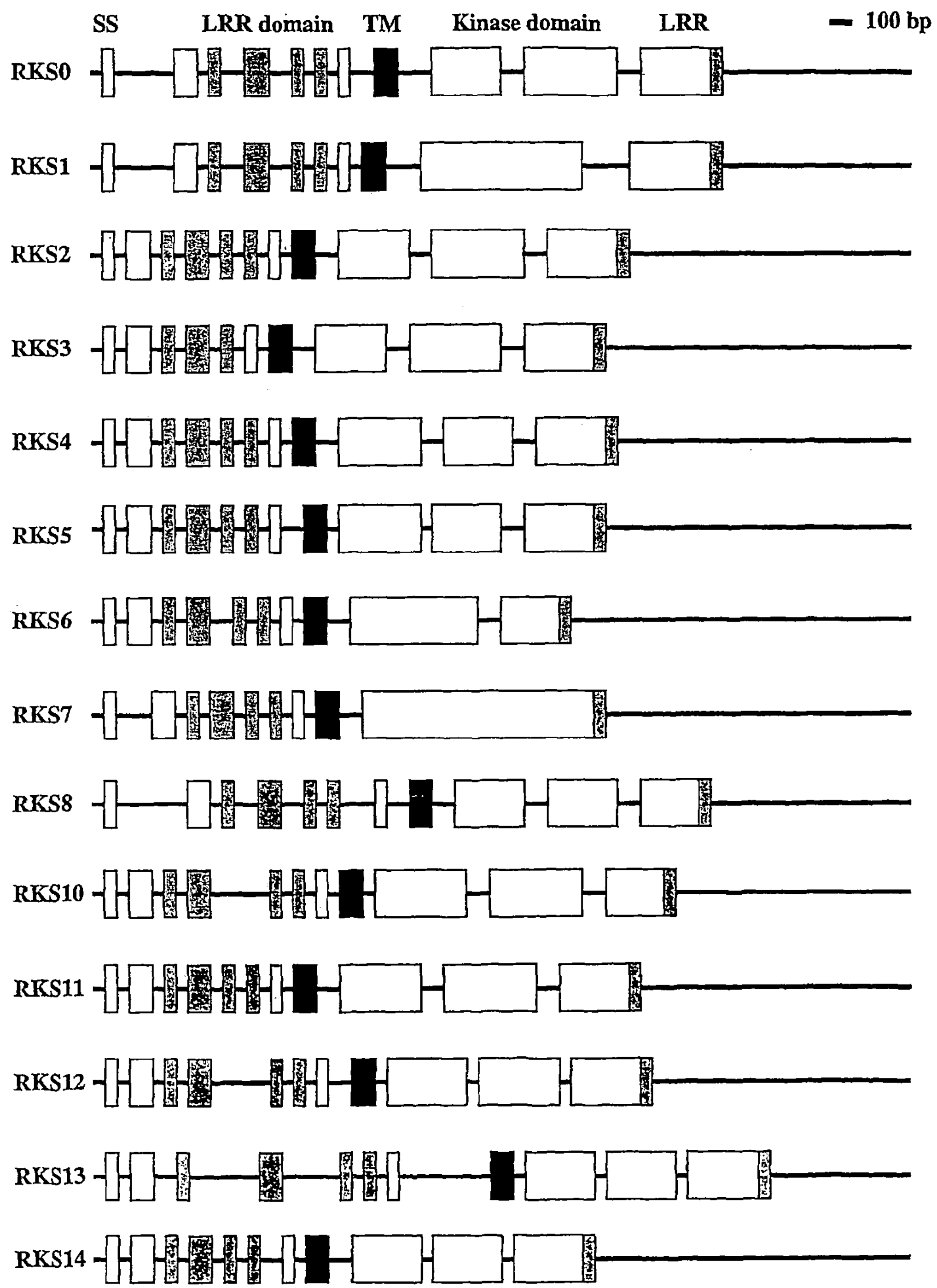

Developmental tree of the different Receptor Kinases like SERK (RKS) genes.

Intron-Exon structure of the RKS genes in *Arabidopsis thaliana* var. Columbia.
SS signal sequence; LRR leucine rich repeat domain; TM transmembrane domain.

Chromosomal location of RKS genes in *Arabidopsis thaliana*

GT-RKS4 determines seeling size in *Nicotiana tabacum*.

Modifications in the expression proficle of GT-RKS4 modulates organ size within seedlings of *Nicotiana tabacum*.

GT-RKS4-7S-T2

GT-RKS4-6S-T2

GT-RKS4-3S-T2

GT-RKS4 determines organ size in *Nicotiana tabacum*.

GT-RKS4 determines plant size in *Nicotiana tabacum*

Empty vector control

GT-RKS4-15S-6T2

GT-RKS4-15S-3T2

GT-RKS4-15S-7T2

GT-RKS4-15S-9T2

Stable transformed GT-RKS4-antisense in *Arabidopsis thaliana*

Wildtype WS

GT-RKS4-16a

Overexpression of antisense GT-RKS4-1a reduces plant and organ size.

Ectopic expression of RKS4 and GASA3 gene products both result in increases flower size in *Arabidopsis thaliana* WS RKS10S T1-10
results in a decrease in size
of cotyl-like apical epidermal cells

RKS10S T1-10 pGreen 4K

RKS10antisense T1-4
results in an increase in size
of the cotyl epidermal cells

Flower development from the same influorescense in transgenic *Arabidopsis thaliana*

Fasciation in transgenic *Arabidopsis thaliana*

Root growth of transgenic *Arabidopsis thaliana*

Root growth of transgenic *Arabidopsis thaliana*

Root growth of transgenic *Arabidopsis thaliana*

Effects of RKS10 transgenic constructs on plant development of 45 days old *Arabidopsis* WS Root cells of transgenic *Arabidopsis thaliana*

Influorescences of T1 transgenic *Arabidopsis* WS plants

Influorescences of T1 transgenic *Arabidopsis* WS plants

RKS10a T1 expression constructs in *Arabidopsis thalinana*

Flower stem

Sepal

Petal

Stamen

Carpel

RKS13 regulates
flower meristem identity in
*Arabidopsis thaliana*

Male sterile transgenes in *Arabidopsis thaliana*

RKS10S T1-10
no pollen formed

RKS10a T1-11
almost no pollen pGreen4K
normal pollen

ELS 2 157.21S T1-11 T2-2
pollen development aborted

MODULATING DEVELOPMENTAL PATHWAYS IN PLANTS

This application is the U.S. National Phase of International Application No. PCT/NL2003/000524 filed on Jul. 17, 2003, which is hereby incorporated by reference in its entirety, and which claims the benefit of European Patent Application No. 02077908.9 filed on Jul. 17, 2002.

INCORPORATION OF SEQUENCE LISTING

Incorporated herein by reference in its entirety is the Sequence Listing for the application. The Sequence Listing is disclosed on a computer-readable ASCII text file titled, “sequence.txt”, created on Jan. 22, 2009. The sequence.txt file is 387 kb in size.

The invention relates to a method to modulate plant growth or development by modifying genes in plants. The invention among others relates to modifying RKS genes or gene products as found in *Arabidopsis thaliana* or other plants. The different domains of RKS gene products essentially have the following functions: The first domain of the predicted protein structure at the N-terminal end consists of a signal sequence, involved in targeting the protein towards the plasma membrane. Protein cleavage removes this sequence from the final mature protein product (Jain et al. 1994, J. Biol. Chemistry 269: 16306-16310). The second domain consists of different numbers of leucine zipper motifs, and is likely to be involved in protein dimerization. The next domain contains a conserved pair of cystein residues, involved in disulphate bridge formation. The next domain consists of 5 (or in the case of RKS3 only 4) leucine rich repeats (LRRs) shown in a gray colour, likely to be involved in ligand binding (Kobe and Deisenhofer 1994, TIBS 19: 415-420). This domain is again bordered by a domain containing a conserved pair of cystein residues involved in disulphate bridge formation often followed by a serine/proline rich region. The next domain displays all the characteristics of a single transmembrane domain. At the predicted cytoplasmic site of protein a domain is situated with unknown function, followed by a domain with serine/threonine kinase activity (Schmidt et al. 1997, Development 124: 2049-2062, WO 01/29240). The kinase domain is followed by a domain with unknown function whereas at the C-terminal end of the protein part of a leucine rich repeat is positioned, probably involved in protein-protein interactions. Plant homologs of the Arabidopsis RKS genes can be found by comparison of various plant database (see also Table 2) and comprise amongst others:

Y14600|SBRLK1|*Sorghum bicolor*

BF004020|BF004020|EST432518 KV1 *Medicago truncatata*

AW934655|AW934655|EST353547 tomato

AW617954|AW617954|EST314028 *L. pennellii*

AA738544|AA738544|SbRLK2 *Sorghum bicolor*

AA738545|AA738545|SbRLK3 *Sorghum bicolor*

BG595415|BG595415|EST494093 cSTS *Solanum tuberosa*

AI896277|AI896277|EST265720 tomato

BF643238|BF643238|NF002H05EC1F1045

AA738546|AA738546|SbRLK4 *Sorghum bicolor*

BE658174|BE658174|GM700005A20D5 Gm-r1070 *Glycine max*

BF520845|BF520845|EST458318 DSIL *Medicago truncata*

AC069324|AC069324|*Oryza sativa*

AW761055|AW761055|s170d06.y1 Gm-c1027 *Glycine max*

BE352622|BE352622|WHE0425_G11_M21ZS Wheat

BG647340|BG647340|EST508959 HOGA *Medicago truncata*

AY028699|AY028699|*Brassica napus*

AW666082|AW666082|sk31h04.y1 Gm-c1028 *Glycine max*

AA738547|AA738547|SbRLK5 *Sorghum bicolor*

BG127658|BG127658|EST473220 tomato

L27821|RICPRKI|*Oryza sativa*

BG238468|BG238468|sab51a09.y1 Gm-c1043 *Glycine max*

BG441204|BG441204|GA_Ea0012C15f *Gossypium arbo.*

AW667985|AW667985|GA_Ea0012C15 *Gossypium arbore.*

AW233982|AW233982|sf32g05.y1 Gm-c1028 *Glycine max*

AP003235|AP003235|*Oryza sativa*

BF460294|BF460294|074A05 Mature tuber

AY007545|AY007545|*Brassica napus*

AC087544|AC087544|*Oryza sativa*

AB041503|AB041503|*Populus nigra*

The invention furthermore relates to modifying ELS genes or gene products or functional equivalents thereof which are for example derived from at least two different genes in the Arabidopsis genome. They show high homology on protein level with the corresponding transmembrane RKS gene products. However, they lack a transmembrane domain while they do contain a signaling sequence at the N-terminal end. Therefore these proteins are thought to be positioned within vesicles within the plant cell or at the outside of the plasma membrane, within the cell wall of the plant cell. A number of homologs have been detected in other plant species, such as:

AF370543|AF370543|*Arabidopsis thaliana*

AF324989|AF324989|*Arabidopsis thaliana*

AV520367|AV520367|*Arabidopsis thaliana*

AV553051|AV553051|*Arabidopsis thaliana*

BF642233|BF642233|NF050C09IN1F1069

AW559436|AW559436|EST314484 DSIR *Medicago truncata*

BG456991|BG456991|NF099F02PL1F1025

AW622146|AW622146|EST312944 tomato

BF260895|BF260895|HVSMEf0023D15f *Hordeum vulgare*

BE322325|BE322325|NF022E121N1F1088

BG414774|BG414774|HVSMEk0003K21f *Hordeum vulgare*

BE460627|BE460627|EST412046 tomato

BI204894|BI204894|EST522934 cTOS *Lycopersicon esculentum*

BI205306|BI205306|EST523346 cTOS *Lycopersicon esculentum*

BI204366|BI204366|EST522406 cTOS *Lycopersicon esculentum*

AW443205|AW443205|EST308135 tomato

AW031110|AW031110|EST274417 tomato

BI180080|BI180080|EST521025 cSTE *Solanum tuberosa*

BF644761|BF644761|NF015A11EC1F1084

AV526127|AV526127|*Arabidopsis thaliana*

AV556193|AV556193|*Arabidopsis thaliana*

BE203316|BE203316|EST403338 KV1 *Medicago truncatata.*

AW649615|AW649615|EST328069 tomato

BE512465|BE512465|946071E06

BI204917|BI204917|EST522957 cTOS *Lycopersicon esculentum*

BG590749|BG590749|EST498591

BG648725|BG648725|EST510344 HOGA *Medicago truncata*

BG648619|BG648619|EST510238 HOGA *Medicago truncata*

BG597757|BG597757|EST496435 cSTS *Solanum tuberosa*

AW221939|AW221939|EST298750 tomato

BE704836|BE704836|Sc01__

BG124409|BG124409|EST470055 tomato

BF051954|BF051954|EST437120 tomato

BG320355|BG320355|Zm03__05h01__*Zea mays*

AV526624|AV526624|*Arabidopsis thaliana*

AW933960|AW933960|EST359803 tomato

AW221278|AW221278|EST297747 tomato

BE405514|BE405514|WHE1212_C01_F02ZS Wheat

BG314461|BG314461|WHE2495_A12A23ZS *Triticum*

BF258673|BF258673|HVSMEf0016G01f *Hordeum vulgare*

BG262637|BG262637|WHE0938_E03_I06ZS Wheat

AW030188|AW030188|EST273443 tomato

BG653580|BG653580|sad76b11.y1 Gm-c1051 *Glycine max*

BG319729|BG319729|Zm03__05h01_A Zm03__*Zea mays*

BF053590|BF053590|EST438820 potato

BE454808|BE454808|HVSMEh0095C03f *Hordeum vulgare*

BI075801|BI075801|IP1__21_D05.b1_A002

BE367593|BE367593|PI1__9_F02.b1_A002 *Sorghum bicolor*

2e-074 BF260080|BF260080|HVSMEf0021A22f *Hordeum vulgare*

BF627921|BF627921|HVSMEb0006I23f *Hordeum vulgare*

BG598491|BG598491|EST503391 cSTS *Solanum tuberosa*

AW038168|AW038168|EST279825 tomato

BG343258|BG343258|HVSMEg0005D23f *Hordeum vulgare*

AW925684|AW925684|HVSMEg0005D23 *Hordeum vulgare*

BG416093|BG416093|HVSMEk0009L18f *Hordeum vulgare*

AW683370|AW683370|NF011C09LF1F1069

BE420108|BE420108|WWS020.ClR000l01 ITEC WWS Wheat

AW350720|AW350720|GM210009A10F4 Gm-r1021 *Glycine max*

AW616564|AW616564|EST322975 L. *Hirsutum trichome*

AW011134|AW011134|ST17B03 Pine

BF630746|BF630746|HVSMEb0013N06f *Hordeum vulgare*

AW926045|AW926045|HVSMEg0006Cl0 *Hordeum vulgare*

BE519800|BE519800|HV_CEb0021El2f *Hordeum vulgare*

BG343657|BG343657|HVSMEg0006Cl0f *Hordeum vulgare*

BG933682|BG933682|OVl__16_C09.b1_A002

BE433368|BE433368|EST399897 tomato

AW219797|AW219797|EST302279 tomato

BF629324|BF629324|HVSMEb0010N06f *Hordeum vulgare*

BE597128|BE597128|PI1__71_A07.g1_A002

AW220075|AW220075|EST302558 tomato

AW616639|AW616639|EST323050 L. *Hirsutum trichome*

BF645214|BF645214|NF032FllEC1Fl094

AW924540|AW924540|WS1__70_Hl2.b1_A002

AI775448|AI775448|EST256548 tomato

AW983360|AW983360|HVSMEg0010F15f *Hordeum vulgare*

BF270171|BF270171|GA_Eb0007B13f *Gossypium arbor.*

BE919631|BE919631|EST423400 potato

AW037836|AW037836|EST279465 tomato

BF008781|BF008781|ss79h09.y1 Gm-c1064 *Glycine max*

BF254651|BF254651|HVSMEf0004K05f *Hordeum vulgare*

BE599797|BE599797|PI1__79_H01.g1_A002

BE599026|BE599026|PI1__86_E03.g1_A002

R89998|R89998|16353 Lambda-PRL2 *Arabidopsis*

BG841108|BG841108|MEST15-G02.T3 ISUM4-TN *Zea mays*

AW307218|AW307218|sf54c07.y1 Gm-c1009 *Glycine max*

AI496325|AI496325|sb05c09.y1 Gm-c1004 *Glycine max*

AJ277703|ZMA277703|*Zea mays*

AL375586|CNS0616P|*Medicago truncatula* EST

AW350549|AW350549|GM210009A10A12 Gm-r1021 *Glycine max*

BE125918|BE125918|DG1__59_F02.b1_A002

BF053901|BF053901|EST439131 potato

BE921389|BE921389|EST425266 potato

BE597551|BE597551|PI1__71_A07.b1__

BE360092|BE360092|DG1__61_C09.b1_A002

BE660084|BE660084|49| GmaxSC *Glycine max*

AJ277702|ZMA277702|*Zea mays*

The invention also relates to modifying SBP/SPL gene or products which represent a family of transcription factors with a bipartite nuclear localization signal (The SQUAMOSA PROMOTER-BINDING PROTEIN-LIKE (SBP/SPL) gene family of *Arabidopsis thaliana*, Columbia ecotype). Upon activation (probably by RKS mediated phosphorylation, the bipartite nuclear localization signal becomes linear and available for the nuclear translocation of the protein. Within the plant nucleus, the transcription factor regulates transcription by interaction with specific promoter elements. In *Arabidopsis thaliana*, this family is represented by at least 16 different members (see following list). In many other plant species, we also identified members of this transcription factor family (See list on page 7).

Functional interaction between RKS and SBP proteins was shown by studies in transgenic tobacco plants in which SBP5 and RKS0 were both overexpressed under the control of an enhanced 35S promoter (data not shown). At the tip of double overexpressing plants, embryo structures appeared whereas in the SBP5 overexpressing plants alone or the RKS0 overexpressing plants alone no phenotype was detectable at the root tips of transgenic tobacco plants. These results show that both RKS and SBP proteins are involved together in a signalling cascade, resulting in the reprogramming of developmental fate of a determined meristem. (ref dissertation: Plant Journal 1997: 12, 2 367-377; Mol. Gen. Genet. 1996: 250, 7-16; Gene 1999, 237, 91-104, Genes and Development 1997: 11, 616-628), Proc. Natl. Acad. Sci. USA 1998: 95, 10306-10311; The Plant Journal 2000: 22, 523-529; Science 1997: 278, 1963-1965; Plant Physiol. Biochem. 2000: 38, 789-796; Cell 1996: 84, 61-71; Annu. Rev. Plant Physiol. Plant Mol. Biol. 1999: 50, 505-537

| name | genetic code |
|---|---|
| ATSPL1 | At2g47070* |
| ATSPL2 | At5g43270 |
| ATSPL3 | At2g33810* |
| ATSPL4 | At1g53160* |
| ATSPL5 | At3g15270 |
| ATSPL6 | At1g69170 |
| ATSPL7 | At5g18830 |
| ATSPL8 | At1g02065 |
| ATSPL9 | At2g42200* |
| ATSPL10 | At1g27370* |
| ATSPL11 | At1g27360* |
| ATSPL12 | At3g60030 |
| ATSPL13 | At5g50570 |
| ATSPL14 | At1g20980 |
| ATSPL15 | At3g57920 |
| ATSPL16 | At1g76580 |

*annotation in database not complete and/or correct

In many other plant species, we identified members of this transcription factor family, plant homologs of the *Arabidopsis* SBP/SPL proteins are for example:

AB023037|AB023037|*Arabidopsis thaliana*

BG789832|BG789832|sae56b07.y1 Gm-c1051 *Glycine max*

BG123992|BG123992|EST469638 tomato

BG595750|BG595750|EST494428 cSTS *Solanum tuberosum*

AF370612|AF370612|*Arabidopsis thaliana*

BF728335|BF728335|1000060H02.x1 1000—*Zea mays*

X92079|AMSBP2|*A. majus*

AW331087|AW331087|707047A12.x1 707—Mixed adult . . . 128 *zea mays*

AJ011643|ATH011643|*Arabidopsis thaliana*

L34039|RICRMSOA|*Oryza sativa*

AJ011638|ATH011638|*Arabidopsis thaliana*

AJ011639|ATH011639|*Arabidopsis thaliana*

AJ132096|ATH132096|*Arabidopsis thaliana*

BF482644|BF482644|WHE2301-2304_A21A21ZS Wheat

BF202242|BF202242|WHE0984_D01_G02ZS Wheat

BE057470|BE057470|sm58e10.y1 Gm-c1028 *Glycine max*

AJ011628|ATH011628|*Arabidopsis thaliana*

AJ011629|ATH011629|*Arabidopsis thaliana*

AJ011617|ZMA011617|*Zea mays*

AJ011637|ATH011637|*Arabidopsis thaliana*

AJ011622|AMA011622|*Antirrhinum majus*

AJ011621|AMA011621|*Antirrhinum majus*

AJ011635|ATH011635|*Arabidopsis thaliana*

AJ011623|AMA011623|*Antirrhinum majus*

BF650908|BF650908|NF098D09EC1F1076

AJ242959|ATH242959|*Arabidopsis thaliana*

Y09427|ATSPL3|*A. thaliana* mRNA

AJ011633|ATH011633|*Arabidopsis thaliana*

AW691786|AW691786|NF044B06ST1F1000

BE058432|BE058432|sn16a06.y1 Gm-c1016 *Glycine max*

AW728623|AW728623|GA_Ea0017G06 *Gossypium arbore.*

BG442540|BG442540|GA_Ea0017G06f *Gossypium arbo.*

AJ011626|ATH011626|*Arabidopsis thaliana*

AJ011625|ATH011625|*Arabidopsis thaliana*

AI993858|AI993858|701515182 *A. thaliana*

BG593787|BG593787|EST492465 cSTS *Solanum tuberosum*

BF634536|BF634536|NF060C08DT1F1065 Drought *Medicago*

BE806499|BE806499|ss59f10.y1 Gm-c1062 *Glycine max*

AW933950|AW933950|EST359793 tomato

AC008262|AC008262|*Arabidopsis*
B28493|B28493|T10A24TF TAMU *Arabidopsis thaliana*

AJ011644|ATH011644|*Arabidopsis thaliana*

AC018364|AC018364|*Arabidopsis thaliana*

AL092429|CNS00VLB|*Arabidopsis thaliana*

BE435668|BE435668|EST406746 tomato

BG097153|BG097153|EST461672 potato

BE440574|BE440574|sp47b09.y1 Gm-c1043 *Glycine max*

AI443033|AI443033|sa31a08.y1 Gm-c1004 *Glycine max* U89496|ZMU89496|*Zea mays* liguleless1

AW433271|AW433271|sh54g07.y1 Gm-c1015 *Glycine max*

AW932595|AW932595|EST358438 tomato

AW096676|AW096676|EST289856 tomato

AJ011616|ZMA011616|*Zea mays*

AW036750|AW036750|EST252139 tomato

BF626329|BF626329|HVSMEa0018F24f *Hordeum vulgare*

AJ011614|ZMA011614|*Zea mays*

AJ011642|ATH011642|*Arabidopsis thaliana*

BE022435|BE022435|sm85h04.y1 Gm-c1015 *Glycine max* X92369|AMSPB1|*A. majus*

AC015450|AC015450|*Arabidopsis thaliana*

AC079692|AC079692|*Arabidopsis thaliana*

AJ011632|ATH011632|*Arabidopsis thaliana*

AJ011631|ATH011631|*Arabidopsis thaliana*

BE455349|BE455349|HVSMEh0097E20f *Hordeum vulgare*

AJ242960|ATH242960|*Arabidopsis thaliana*

AJ011610|ATH011610|*Arabidopsis thaliana*

AJ132097|ATH132097|*Arabidopsis thaliana*

AL138658|ATT2O9|*Arabidopsis thaliana*

AJ011615|ZMA011615|*Zea mays*

BE499739|BE499739|WHE0975_ Wheat

AW398794|AW398794|EST309294 *L. pennellii*

AJ011618|ZMA011618|*Zea mays*

AW747167|AW747167|WS1__66_F11.b1__

AJ011577|ATH011577|*Arabidopsis thaliana*

AI992727|AI992727|701493410 *A. thaliana*

BE060783|BE060783|HVSMEg0013F15f *Hordeum vulgare*

BE804992|BE804992|ss34h10.y1 Gm-c1061 *Glycine max*

BE325341|BE325341|NF120H09ST1F1009

AC007369|AC007369|*Arabidopsis thaliana*

AJ011619|ZMA011619|*Zea mays*

BI099345|BI099345|IP1__37_H10.b1_A002

BI071295|BI071295|C054P79U *Populus*

AZ920400|AZ920400|1006019G01.y2 1006—

AZ919034|AZ919034|1006013G02.x3 1006—

BE805023|BE805023|ss35d09.y1 Gm-c1061 *Glycine max*

BG582086|BG582086|EST483824 GVN *Medicago truncata*

AJ011609|ATH011609|*Arabidopsis thaliana*

BE023083|BE023083|sm90e08.y1 Gm-c1015 *Glycine max*

Furthermore, the invention relates to modifying NDR-NHL-genes or gene products. All proteins belonging to this family contain one (and sometimes even more than one) transmembrane domain. *Arabidopsis* contains a large number of NDR-NHL genes, such as:

aad21459, aaf18257, aac36175, k10d20 (position 40852-41619), aad21460, cab78082, aad21461, aad42003, aaf02134, aaf187656, aaf02133, cab43430, cab88990, cab80950, aad25632, aaf23842, a1163812, f20d21-35, t13 m11-12, f1e22-7, t23g18, f5d14-4266, t32f12-16, f11f19-11, f11f19-12, f11f19-13, t20p8-13, 112k2, f23h14, k10d20-44043, k10d20-12, t19f11-6, t19f11-5, t10d17-10, f22o6-150, f3d13-5, m3e9-80, t25p22-30, mhf15-4, mhf15-5, mrn17-4, mlf18-9, mgn6-11994, mjj3-9667, f14f18-60, At1g17620 F11A6, At5g11890, At2g27080, At5g36970, mlf18, At1g65690 F1E22, At4g01110 F2N1, At2g35980 f11f19, At4g01410 F3D13, At1g54540 F20D21, At2g46300 t3f17, At5g21130, At3g11650 T19F11, At5g06320 MHF15, At5g06330 MHF15, At2g01080 f15b18, At2g35460 t32f12, At2g27260 f12k2, At2g35970 f11f19, At5g53730 MGN6, At5g22870 MRN17, At4g09590, At3g54200, At1g08160 T6D22, At5g22200, At3g52470, At2g35960 f11f19, At3g52460, At5g56050 MDA7, At3g20590 K10D20, At1g61760 T13M11, At3g20600 K10D20, At1g13050 F3F19, At3g11660 T19F11, At3g44220, At1g64450 F1N19, At3g26350 F20C19 C, At4g05220, At5g45320 K9E15, At4g23930, At4g13270, At4g39740, At1g45688 F2G19 W, At5g42860 MBD2, At1g32270 F27G20, At4g30660, At2g45430 f4123, At4g30650, At1g69500 F10D13 and ndr1, At2g27080; T20P8.13, At5g21130, At1g65690, At5g36970, At1g54540, At5g06320, At5g11890, At1g17620, At3g11650, At2g22180, At5g22870, At2g35980, At2g46300, At4g05220, At2g35460, At2g27260, At4g01410, At5g22200, At1g61760, At3g52470, At5g53730, At4g01110, At2g35960, At3g52460, At4g09590, At2g35970, At3g26350, At3g11660, At3g44220, At1g08160, At2g01080, At5g06330, At5g56050, At3g20600, NDR1, At3g54200, At3g20590, At4g39740, At1g32270 syntaxin, putative, At1g13050, At5g45320, At3g20610, At4g26490, At5g42860, At1g45688, At4g26820

NDR-NHL genes belong to a large family of which one of the first identified is the defence-associated gene HIN1 (Harpin-induced gene). HIN1 is transcriptionally induced by harpins and bacteria, that elicit hypersensitive responses in tobacco. It is thus believed that the genes of the invention also play A role in the hypersensitive reaction. Especially (see also chapter 8) since the genes of the invention bear relation to brassinoid-like responses and since brassinoid pathway compounds have been found to interact in this same defence system in plants. Other plant species also contain members of this large gene family, such as:

Plant homologs of the *Arabidopsis* NDR/NHL genes:

BG582276|BG582276|EST484016 GVN *Medicago truncata*

AV553539|AV553539|*Arabidopsis thaliana*

AC069325|AC069325|*Arabidopsis thaliana*

AV526693|AV526693|*Arabidopsis thaliana*

BG583456|BG583456|EST485208 GVN *Medicago truncata*

AW267833|AW267833|EST305961 DSIR *Medicago truncata*

BE997791|BE997791|EST429514 GVSN *Medicago truncata*

BG580928|BG580928|EST482657 GVN *Medicago truncata*

BF520916|BF520916|EST458389 DSIL *Medicago truncata*

AV544651|AV544651|*Arabidopsis thaliana*

AV543762|AV543762|*Arabidopsis thaliana*

AW559665|AW559665|EST314777 DSIR *Medicago truncata*

BG581012|BG581012|EST482741 GVN *Medicago truncata*

AV552164|AV552164|*Arabidopsis thaliana*

BE999881|BE999881|EST431604 GVSN *Medicago truncata*

AW031098|AW031098|EST274405 tomato

AI998763|AI998763|701546833 *A. thaliana*

AW219286|AW219286|EST301768 tomato

BE124562|BE124562|EST393597 GVN *Medicago truncata*

AV540371|AV540371|*Arabidopsis thaliana*

AV539549|AV539549|*Arabidopsis thaliana*

BG647432|BG647432|EST509051 HOGA *Medicago truncata*

BE434210|BE434210|EST405288 tomato

BG725849|BG725849|sae42g02.y1 Gm-c1051 *Glycine max*

AP003247|AP003247|*Oryza sativa*

BE348073|BE348073|sp11a11.y1 Gm-c1042 *Glycine max*

AW508383|AW508383|si40c06.y1 Gm-r1030 *Glycine max*

AI856504|AI856504|sb40b07.y1 Gm-c1014 *Glycine max*

BE556317|BE556317|sq01b07.y1 Gm-c1045 *Glycine max*

AA713120|AA713120|32681 *Arabidopsis*

AV541531|AV541531|*Arabidopsis thaliana*

AI894456|AI894456|EST263911 tomato

AW704493|AW704493|sk53g11.y1 Gm-c1019 *Glycine max*

AW219298|AW219298|EST301780 tomato

BF425685|BF425685|ss03c11.y1 Gm-c1047 *Glycine max*

AV422557|AV422557|*Lotus japonicus*

BE190816|BE190816|sn79a08.y1 Gm-c1038 *Glycine max*

BG580331|BG580331|EST482056 GVN *Medicago truncata*

AV423251|AV423251|*Lotus japonicus*

AI896088|AI896088|EST265531 tomato

AV413427|AV413427|*Lotus japonicus*

AV426656|AV426656|*Lotus japonicus*

AV416256|AV416256|*Lotus japonicus*

AL385732|CNS0690I|*Medicago truncatula*

AB016877|AB016877|*Arabidopsis thaliana*

AV419449|AV419449|*Lotus japonicus*

AI486269|AI486269|EST244590 tomato

AV411690|AV411690|*Lotus japonicus*

AV419925|AV419925|*Lotus japonicus*

AV418222|AV418222|*Lotus japonicus*

AV409427|AV409427|*Lotus japonicus*

AC005287|AC005287|*Arabidopsis thaliana*

AV426716|AV426716|*Lotus japonicus*

AV411791|AV411791|*Lotus japonicus*

BG351730|BG351730|131E12 Mature tuber

BG046452|BG046452|saa54b12.y1 Gm-c1060 *Glycine max*

AI781777|AI781777|EST262656 tomato

BE451428|BE451428|EST402316 tomato

AI772944|AI772944|EST254044 tomato

AI895510|AI895510|EST264953 tomato

AW030762|AW030762|EST274017 tomato

AW218859|AW218859|EST301341 tomato

BE203936|BE203936|EST396612 KV0 *Medicago truncata*

AV410289|AV410289|*Lotus japonicus*

AW032019|AW032019|EST275473 tomato

AW030868|AW030868|EST274158 tomato

AV421824|AV421824|*Lotus japonicus*

BG646408|BG646408|EST508027 HOGA *Medicago truncata*

AF325013|AF325013|*Arabidopsis thaliana*

AC007234|AC007234|*Arabidopsis thaliana*

AW217237|AW217237|EST295951 tomato

AC034257|AC034257|*Arabidopsis thaliana*

AW625608|AW625608|EST319515 tomato

AW031064|AW031064|EST274371 tomato

AF370332|AF370332|*Arabidopsis thaliana*

AB006700|AB006700|*Arabidopsis thaliana*

AW035467|AW035467|EST281205 tomato

AL163812|ATF14F18|*Arabidopsis thaliana*

AI896652|AI896652|EST266095 tomato

AI730803|AI730803|BNLGHi7970 Cotton

AW034775|AW034775|EST278811 tomato

Figure 5:
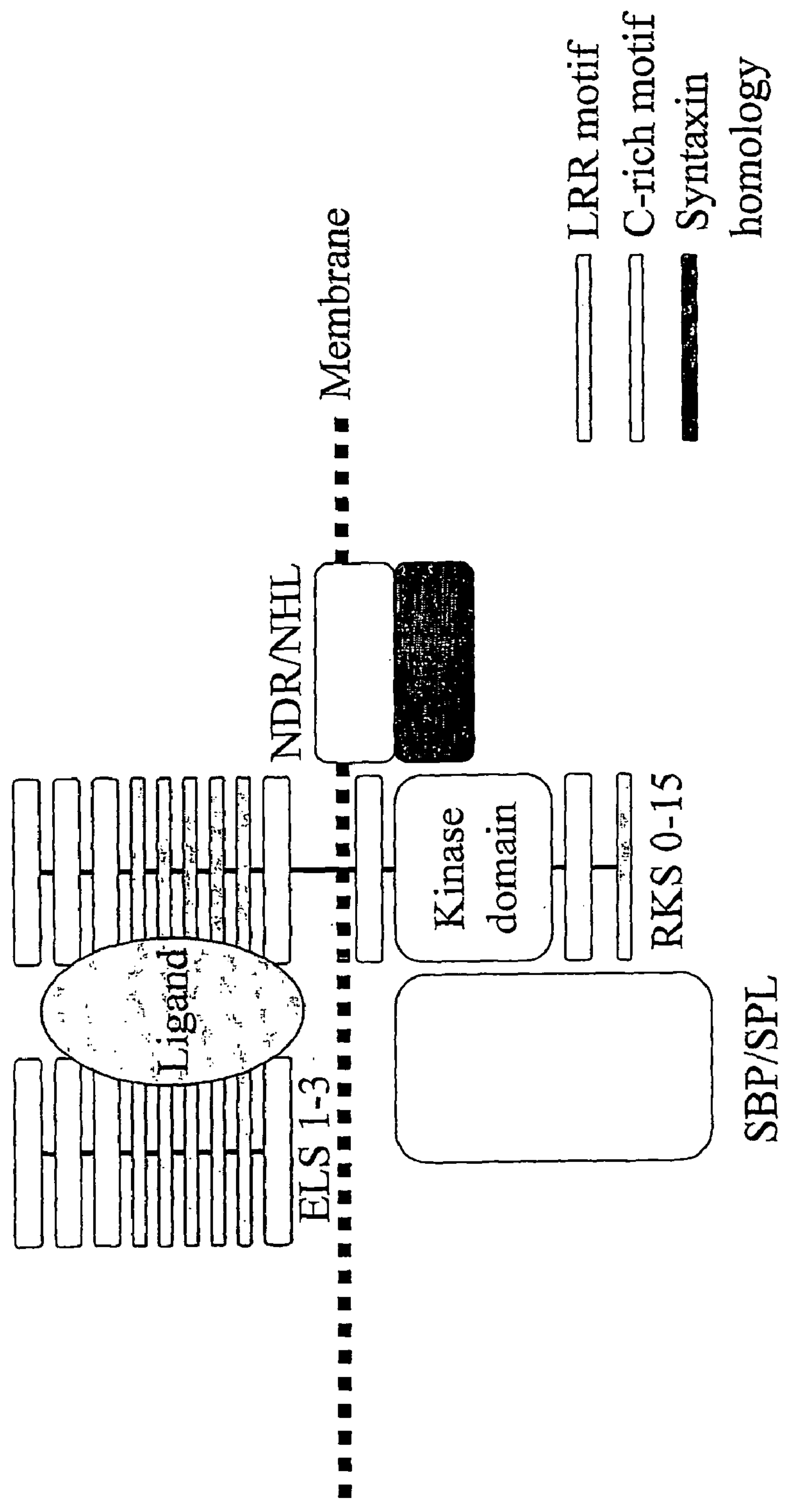

The invention provides the insight that RKS proteins or functional equivalents thereof play part in a signaling complex (herein also called the RKS signaling complex) comprising molecules of RKS proteins, ELS (Extracellular Like SERK) proteins, NDR/NHL proteins and SBP/SPL (Squamosa Binding Protein) proteins, and the corresponding protein ligands (see for example table 3) whereby each of these proteins interplay or act in such a way that modifying genes, or modifying expression of genes, encoding ELS, RKS, NDR/NHL or SBP/SPL, proteins or said ligands may lead to functionally equivalent results (FIG. 5. Two-hybrid interaction experiments have for example shown in vitro interaction between RKS 0 and NDR0/NHL28 and members of the SBP/SPL family. Here we show that in vivo the individual components of this signaling complex are regulating identical processes, as based on functional genomics on transgenic plants, overexpressing or co-suppressing single components or combinations of components in this transmembrane signalling complex. ELS gene products are derived from at least two different genes in the *Arabidopsis* genome. They show high homology on protein level with the corresponding transmembrane RKS gene products.

However, they lack a transmembrane domain while they do contain a signalling sequence at the N-terminal end. Therefore these proteins are thought to be positioned within vesicles within the plant cell or at the outside of the plasma membrane, within the cell wall of the plant cell. A number of homologues have been detected in other plant species (see list on page 3). ELS proteins are involved in the heterodimerizing complex with the RKS transmembrane receptor at the outer membrane site. ELS molecules are either in competition or collaboration with RKS molecules involved in the high affinity binding of the ligand. The signal transmitted from the ligand onto the RKS proteins is then transporter over the membrane towards the N-terminal site of RKS protein, located on the other site of the membrane. The activation stage of the RKS molecule is changed, as a result of transphosphorylation by dimerizing receptor kinase dimerizing partners. Subsequently the signal is transmitted to other proteins, one family of such proteins is defined as the SBP/SPL family of transcription factors, the other family of proteins is represented by the NDR/NHL members.

The different obvious phenotypes created by modifying the RKS gene products could be effected by one process regulating all different effects in transgenic plants.

All the phenotypes observed can be effected by the process of brassinosteroid perception. In chapter 1, RKS genes are clearly involved in plant size and organ size. Loss of RKS expression results in a dwarf phenotype, similar as observed with brassinosteroid synthesis mutants. It was already known in literature that the phenotypes observed from modifying the RKS genes are also observed when modifying the brassinosteroid pathway genes and/or their regulation, thereby altering the amount and nature of the brassinosteroids in plants. Literature which describes the phenotypic effects of modifying the brassinosteroid pathway can, amongst others, be found in: Plant Journal 26: 573-582 2001; Plant Journal 1996 9(5) 701-713, genetic evidence for an essential role of brassinosteroids in plant development; J. Cell Biochem Suppl. 21a 479 (1995); Mandava 1988 Plant growth-promoting brassinosteroids, Ann. Rev. Plant. Physiol. Plant Mol. Biol. 39 23-52; Plant Physiol 1994 104: 505-513; Cell 85 (1996) 171-182; Clouse et al. 1993 J. Plant Growth Regul. 12 61-66; Clouse and Sasse (1998) Annu. Rev. Plant Physiol. Plant Mol. Biol 49 427-451; Sasse, Steroidal Plant Hormones. Springer-Verlag Tokyo pp 137-161 (1999).

It is thus believed, without being bound to any theory, that modification of the RKS genes will result in a modification of the brassinosteroid pathway, thereby giving the various phenotypes that are shown below.

"Functionally equivalent" as used herein is not only used to identify the functional equivalence of otherwise not so homologous genes encoding ELS, RKS, NDR/NHL or SBP/SPL proteins, but also means an equivalent gene or gene product of genes encoding ELS, RKS, NDR/NHL or SBP/SPL proteins in *Arabidopsis Thaliana*, e.g. identifying a homologue found in nature in other plants or a homologue comprising a deliberate nucleic acid modification, such as a deletion, truncation, insertion, or deliberate codon substitution which may be made on the basis of similarity in polarity, charge, solubility, hydrophobicity, and/or the amphipathic nature of the residues as long as the biological activity of the polypeptide is retained. Homology is generally over at least 50% of the full-length of the relevant sequence shown herein. As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Deliberate amino acid substitution may be made on the basis of similarity in polarity, charge, solubility, hydrophobicity, and/or the amphipathic nature of the residues as long as the biological activity of the polypeptide is retained. In a preferred embodiment, all percentage homologies referred to herein refer to percentage sequence identity, e.g. percent (%) amino acid sequence identity with respect to a particular reference sequence can be the percentage of amino acid residues in a candidate sequence that are identical with the amino acid residues in the reference sequence, after aligning the sequences and introducing gaps, if necessary, to achieve the maximum percent sequence identity, without considering any conservative substitutions as part of the sequence identity. Amino acid similarity or identity can be determined by genetic programs known in the art.

'Plant cell', as used herein, amongst others comprises seeds, suspension cultures, embryos, meristematic regions, callous tissues, protoplasts, leaves, roots, shoots, bulbs, gametophytes, sporophytes, pollen and microspores. A target plant to be modified according to the invention may be selected from any monocotyledonous or dicotyledonous plant species, such as for example ornamental plants, vegetables, arable crops etc. 'Dicotyledoneae' form one of the two divisions of the flowering plants or angiospermae in which the embryo has two or more free or fused cotyledons. 'Monocotyledoneae' form one of the two divisions of the flowering plants or angiospermae in which the embryo has one cotyledon. 'Angiospermae' or flowering plants are seed plants characterized by flowers as specialized organs of plant reproduction and by carpels covering the ovaries. Also included are gymnospermae. Gymnospermae are seed plants characterized by strobili as specialized organs for plant reproduction and by naked sporophylls bearing the male or female reproductive organs, for example woody plants. 'Ornamental' plants are plants that are primarily in cultivation for their habitus, special shape, (flower, foliage or otherwise) colour or other characteristics which contribute to human well being indoor as cut flowers or pot plants or outdoors in the man made landscape, for example bulbous plant species like *Tulipa, Freesia, Narcissus, Hyacinthus* etc. 'Vegetables' are plants that are purposely selected or bred for human consumption of foliage, tubers, stems, fruits, flowers or parts of them and that may need an intensive cultivation regime. 'Arable crops' are generally purposely bred or selected for human objectivity's (ranging from direct or indirect consumption, feed or industrial applications such as fibers) for example soybean, sunflower, corn, peanut, maize, wheat, cotton, safflower and rapeseed.

The invention provides a method for modulating a developmental pathway of a plant comprising modifying a gene encoding for a gene product or protein belonging to a developmental cascade or signaling complex comprising modifying at least one gene encoding a gene product belonging to the complex of RKS proteins, ELS proteins, NDR/NHL proteins, SBP/SPL proteins and ligand proteins. In one embodiment, the invention provides a method for modulating or modifying organ size. Plant or plant organ size is determined by both cell elongation and cell division rate. Modifying either one or both processes results in a change in final organ size. Increasing the level of specific members of the family of RKS genes results in an increase in organ size, growth rate and yield. Modulating plant growth, organ size and yield of plant organs is the most important process to be optimized in plant performance. Here we show that modulating the level of members of the family of the RKS signaling complex with a method according to the invention is sufficient to modulate these processes. The invention provides herewith a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating cellular division during plant growth or organ formation, in particular wherein said gene comprises an RKS4 or RKS10 gene or functional equivalent thereof. Inactivation of endogenous RKS gene product results in a decrease in plant growth, proving that the normal function of these endogenous RKS gene products is the regulation of growth and organ size. Use of a method according to invention for elevation of the levels of the regulating of the RKS signaling complex in plant cells is provided in order to increase for example the size of plant organs, the growth rate, the yield of harvested crop, the yield of total plant material or the total plant size. Decreasing the levels of endogenous RKS gene product is provided in order to decrease the size of plant organs, the growth rate, or the total plant size.

In another embodiment, the invention relates to cell division.

The mitotic cell cycle in eukaryotes determines the total number of cells within the organism and the number of cells within individual organs. The links between cell proliferation, cell differentiation and cell-cycle machinery are of primary importance for eukaryotes, and regulation of these processes allows modifications during every single stage of development. Here we show that modulating the level of members of the family of the RKS signaling complex is sufficient to modulate these processes. The invention provides herewith a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating cellular division during plant growth or organ formation, in particular wherein said gene comprises an RKS4 or RKS10 gene or functional equivalent Herewith the invention provides a method for modulating the number of cells to be formed within an eukaryotic organism as a whole or for modulating the cell number within individual organs is, which of primary importance in modulating plant developmental processes, especially of arable plants. Here we show that members of the RKS signaling complex are able to regulate the number of cellular divisions, thereby regulating the total number of cells within the organism or different organs.

In a further embodiment, the invention relates to the regeneration of apical meristem. Modification the levels of different RKS and ELS genes within plants allows the initiation and/or outgrowth of apical meristems, resulting in the formation of large numbers of plantlets from a single source. A number of gene products that is able to increase the regeneration potential of plants is known already. Examples of these are KNAT1, cycD3, CUC2 and IPT. Here we show that modulation of the endogenous levels of RKS genes results in the formation of new shoots and plantlets in different plant species like *Nicotiana tabacum* and *Arabidopsis thaliana*. Herewith the invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein, allowing modulating apical meristem formation, in particular wherein said gene comprises an ELS1, RKS0, RKS3, RKS4, RKS8 or RKS10 gene or functional equivalent thereof. A direct application of such a method according to the invention is the stable or transient expression of RKS and ELS genes or gene products in order to initiate vegetative reproduction. Regeneration can be induced after overexpression of for example RKS0 and ELS1; or by co-suppression of for example the endogenous RKS3, RKS4, RKS8 or RKS10 genes. Overexpression or co-suppression of these RKS and ELS gene products can be either transient, or stable by integration of the corresponding expression cassettes in the plant genome. A further example of essentially identical functions for example ELS1 and RKS0 overexpressing plants is for example shown in the detailed description, example 3, where both transgenic constructs are able to induce the regeneration capacity of in vitro cultured *Arabidopsis* callus. Another example comprises functional interaction between RKS and SBP proteins which was shown by studies in transgenic tobacco plants in which SBP5 and RKS0 were both overexpressed under the control of an enhanced 35S promoter. At the tip of double overexpressing plants, embryostructures appeared whereas in the SBP5 overexpressing plants alone or the RKS0 overexpressing plants alone no phenotype was detectable at the root tips of transgenic tobacco plants. These results show that both RKS and SBP proteins are involved together in a signaling cascade, resulting in the reprogramming of developmental fate of a determined meristem.

Furthermore, it is herein also shown that several RKS genes are able to regulate proper identity and development of meristems and primordia. The invention for example also relates to fasciation, Fasciation is normally a result from an increased size of the apical meristem in apical plant organs. Modulation of the number of cells within the proliferating zone of the shoot apical meristem results in an excess number of cellular divisions, giving rise to excess numbers of primordia formed or to stems in which the number of cells is increased. The invention herewith provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating fasciation, in particular wherein said gene comprises an RKS0, RKS3, RKS8 or RKS10 gene or functional equivalent thereof. Here we for example show that modulation of the levels of RKS gene products in plants like *Arabidopsis thaliana* can result in fasciated stems. A direct application as provided herein is the regulated formation of fasciation in plant species in which such a trait is desired like ornamental plants. Regulation of the initiation and extent of fasciation, either by placing the responsible RKS encoding DNA sequences under the control of stage or tissue specific promoters, constitutive promoters or inducible promoters results in plants with localized or consitutive fasciation of stem tissue. Another application is modulating the number of primordia by regulation of the process of fasciation. An example is provided by for example sprouts, in which an increased number of primordia will result in an increased numbers of sprouts to be harvested. Fasciation can also result in a strong modification in the structural architecture of the inflorescence, resulting in a terminal group of flowers resembling the Umbelliferae type.

Identical phenotypes can be observed when transgenic plants are produced that contain the NHL10 cDNA under control of an enhanced 35S promoter. The resulting phenotype of the resulting flowers show that flower organ primordia are switched in identity, similar as observed for RKS10 and RKS13. These meristematic identity switches are normally never observed in *Arabidopsis* and the fact that two different classes of genes are able to display the same phenotypes in transgenic plants is a clear indication for a process in which both members of the RKS and the NDR/NHL families are involved. The invention also relates to root development. Fasciation is normally a result from an increased size of the apical meristem in apical plant organs. Modulation of the number of cells within the proliferating zone of the root apical meristem results in an excess number of cellular divisions, giving rise to excess numbers of primordia formed or to roots in which the number of cells is increased. Adaptation to soil conditions is possible by regulation of root development of plants. Here we describe several processes in root development that can be manipulated by modification of the levels of RKS signaling complex within the root. The invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating root development, in particular wherein said gene comprises an ELS1, ELS2, RKS1, RKS3, RKS4, RKS6, RKS8 or RKS10 gene or functional equivalent thereof. Root length, a result by either root cells proliferation or elongation, can for example be increased by overexpression of for example RKS3, RKS4, RKS6 and ELS2, or inactivation of the endogenous RKS10 gene product. Root length can also be decreased by decreasing of endogenous RKS1 levels or by strong overexpression of RKS10. The initiation of lateral roots is also regulated by RKS gene products. Overexpression of for example RKS10 can result in a strong increase in the initiation and outgrowth of lateral roots. Co-suppression of RKS1 also resulted in the initiation and outgrowth of large numbers of lateral roots. Root hair formation and elongation is important in determining the total contact surface between plant and soil. A strong increase of root hair length (elongation) can be obtained by overexpression of ELS1 and RKS3 gene products. As the roots of terrestrial plants are involved in the acquisition of water and nutrients, anchorage of the plant, synthesis of plant hormones, interaction with the rhizosphere and storage functions, increasing or decreasing root length, for example for flexible adaptations to different water levels, can be manipulated by overexpressing or cosuppressing RKS and/or ELS gene products. Modulation of the total contact surface between plant cells and the outside environment can be manipulated by regulation lateral root formation (increased by RKS10 overexpression and co-suppression of RKS1). Finally the contact surface between plant cells and the soil can be influenced by modulation of the number of root hairs formed or the elongation of the root hairs, as mediated by ELS1 and RKS3.

In a further embodiment, the invention relates to apical meristem identity. All parts of the plant above the ground are generally the result on one apical shoot meristem that has been initiated early at embryogenesis and that gives rise to all apical organs. This development of a single meristem into complex tissue and repeated patterns is the result of tissue and stage-dependent differentiation processes within the meristems and its resulting offspring cells. The control of meristem formation, meristem identity and meristem differentiation is therefore an important tool in regulating plant architecture and development. Here we present evidence the function of RKS and ELS gene products in regulation of the meristem identity and the formation and outgrowth of new apical meristems. The invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating meristem identity, in particular wherein said gene comprises an ELS1, RKS8, RKS10 or RKS13 gene or functional equivalent thereof. Introduction of for example the RKS10 gene product or an other member of the RKS signaling complex under the control of a tissue and/or stage specific promoter as provided herein allows localized and time regulated increases in the levels of gene product. For example the meristematic identity in a determined meristem might thereby be switched back into an undetermined meristem, thereby changing for example a terminal flower into an undetermined generative meristem.

Figure 29:
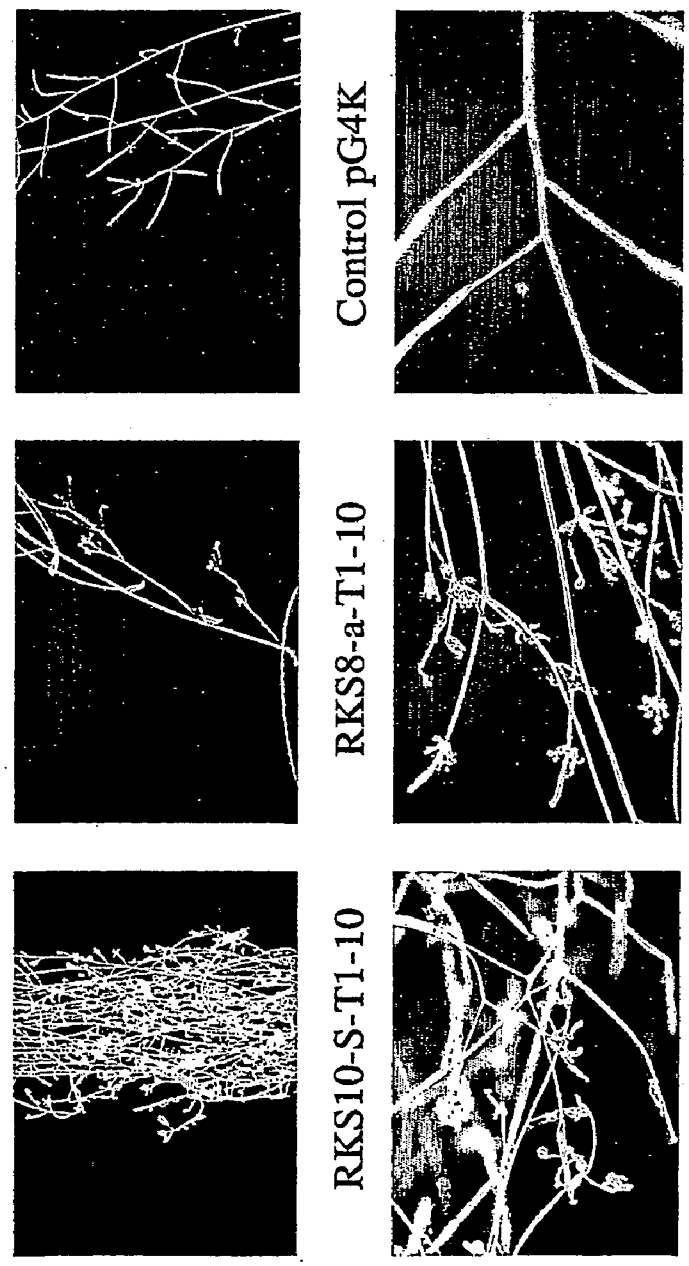
Figure 30:
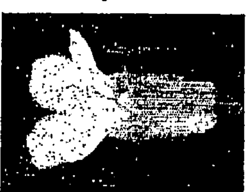
Figure 30:
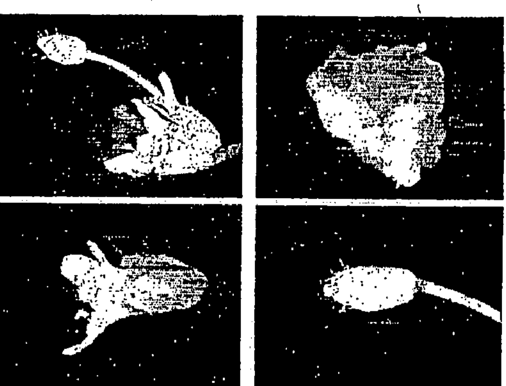

Another application might be found in changing the meristematic identity at an early time point, during early vegetative growth, thereby switching the vegetative meristem into a generative meristem, allowing early flowering. Modulation of meristem identity in terminal primordia, like for example as shown in FIG. 30, where flower organ primordia are converted into terminal flower primordia, allows the formation of completely new types of flowers and fused fruitstructures. Constitutive overexpression of RKS gene products results in plants with many apical meristems, as can clearly been seen in FIG. 29, where RKS10 overexpression results in an extremely bushy phenotype.

In another embodiment, the invention relates to male sterility. Male sterility is a highly desired trait in many plant species. For example, manipulation of pollen development is crucial for F1 hybrid seed production, to reduce labour costs and for the production of low-environmental impact genetically engineered crops. In order to produce hybrid seed from inbred plant lines, the male organs are removed from each flower, and pollen from another parent is applied manually to produce the hybrid seed. This labour-intensive method is used with a number of vegetables (e.g. hybrid tomatoes) and with many ornamental plants. Transgenic approaches, in which one or more introduced gene products interfere with normal pollen initiation and development is therefore highly desired. Especially when the number of revertants (growing normal pollen) is extremely low.

Male sterility in plants is a desired trait that has been shown already in many plant species as a result of the inactivation of expression of a number of genes essential for proper stamen development, mitotic divisions in the pollen stem cells, or male gametogenesis. A method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein, allowing modulating pollen development, in particular wherein said gene comprises an ELS2 or RKS10 gene or functional equivalent thereof.

Here we present data that show that overexpression of gene products, like transmembrane receptor kinases (RKS) and extracellular proteins (ELS) can also result in the formation of male sterility. The ability to induce male sterility by overexpressing specific genes as provided herein allows the opportunity to produce transgenic overexpressing plants in which the pollen development is inhibited. Stable single copy homozygous integration of such overexpressing traits into the plant genome will render such plants completely sterile, making them excellent material for the production of F1 hybrid seed. Furthermore, the combined integration of a male sterility inducing overexpressing gene coupled directly with another desired transgene result in transgenic plants which are unable to produce transgenic seed, making these transgenic plants excellent material for outside growth without problems affecting transgenic pollen spreading throughout the environment, thereby eliminating possible crosses with wild plant species or other non-transgenic crops. The combination of a desired transgene flanked on both sites by different male-sterility inducing overexpressing genes would decrease the frequency of pollen formation to an extremely low level.

An example is an overexpressing construct of RKS10 at the 5'end of integrated DNA fragment, the desired transgene expression cassette in the middle and at the 3'end of the integrated DNA the ELS2 overexpressing construct. This complete DNA fragment is integrated into the genome by conventional techniques, like particle bombardment, *Agrobacterium* transformation etc. Another possible application concerns the modification of pollen in ornamental plant species like lily, where the release of pollen from cut flowers can be avoided by making transgenic plants in which pollen development is initiated by release from the stamen is prevented (a desired trait that can be obtained by overexpressing for example ELS2, resulting in partial pollen development). Hereby the ornamental value of the stamen with pollen is not lost, but release of pollen is inhibited.

Furthermore, surprisingly we observe that NDR NHL gene products share homology with the family of syntaxins, involved in vesicle transport, positioning of cell wall formation and cytokinesis.

TABLE 1

| Homology between members of the syntaxin family and the NDR NHL family | | | |
|---|---|---|---|
| NHL10 = At2g35980 | | | |
| (SEQ ID NO: 1) | | | |
| maaeqplnga | fygpsvpppa | pkgyyrrghg | rgcgccllsl |
| fvkviisliv | ilgvaalifw | livrpraikf | hvtdasltrf |
| dhtspdnilr | ynlaltvpvr | npnkriglyy | drieahayye |
| gkrfstitlt | pfyqghkntt | vltptfqgqn | lvifnagqsr |
| tlnaerisgv | ynieikfrlr | vrfklgdlkf | rrikpkvdcd |
| dlrlplstsn | gttttstvfp | ikcdfdf | |

TABLE 1-continued

| Homology between members of the syntaxin family and the NDR NHL family | | | |
|---|---|---|---|
| At1g32270 syntaxin, | | | |
| (SEQ ID NO: 2) | | | |
| MVRSNDVKFQ | VYDAELTHFD | LESNNNLQYS | LSLNLSIRNS |
| KSSIGIHYDR | FEATVYYMNQ | RLGAVPMPLF | YLGSKNTMLL |
| RALFEGQTLV | LLKGNERKKF | EDDQKTGVYR | IDVKLSINFR |
| VMVLHLVTWP | MKPVVRCHLK | IPLALGSSNS | TGGHKKMLLI |
| GQLVKDTSAN | LREASETDHR | RDVAQSKKIA | DAKLAKDFEA |
| ALKEFQKAQH | ITVERETSYI | PFDPKGSFSS | SEVDIGYDRS |
| QEQRVLMESR | RQEIVLLDNE | ISLNEARIEA | REQGIQEVKH |
| QISEVMEMFK | DLAVMVDHQG | TIDDIDEKID | NLRSAAAQGK |
| SHLVKASNTQ | GSNSSLLFSC | SLLLFFFLSG | DLCRCVCVGS |
| ENPRLNPTRR | KAWCEEEDEE | QRKKQQKKKT | MSEKRRREEK |
| KVNKPNGFVF | CVLGHK* | | |

Below the homology is shown between NHL10 (Upper line) and a syntaxin protein. (bottom line). The identical amino acids are shown in the middle line.

```
IVRPRAIKFHVTDASLTRFDHTSPDNILRYNLALTVPVRNPNKRIGLYYDRIEAHAYYEG
 VR    KF V DA LT FD  S  N L Y L L    RN    IG  YDR EA  YY
MVRSNDVKFQVYDAELTHFDLESNNN-LQYSLSLNLSIRNSKSSIGIHYDRFEATVYYMN

KRFSTITLTPFYQGHKNTTVLTPTFQGQNLVIFNAGQSRTLNAERISGVYNIEIKFRLRV
 R        FY G KNT  L   F GQ LV                GVY I  K
QRLGAVPMPLFYLGSKNTMLLRALFEGQTLVLLKGNERKKFEDDQKTGVYRIDVKLSINF

RFKLGDLKFRRIKPKVDCDDLRLPLSTSNGTTT
R     L     KP V C  L  PL       T
RVMVLHLVTWPMKPVVRCH-LKIPLALGSSNST
```

That syntaxins and NDR/NHL genes share large homology becomes even more clear when performing a database search searching for homologous sequences with the sequence At1g32270

| gene code: | predicted function: |
|---|---|
| At1g32270 syntaxin, putative | Syntaxin |
| At5g46860 syntaxin related protein | Syntaxin |
| AtVam3p (gb\|AAC49823.1) | |
| At4g17730 syntaxin | Syntaxin |
| At5g16830 syntaxin homologue | Syntaxin |
| At3g11650 unknown protein | Putative syntaxin |
| At2g35460 similar to harpin-induced protein | Putative syntaxin |
| At5g06320 harpin-induced protein-like | Putative syntaxin |
| At2g35980 similar to harpin-induced protein | Putative syntaxin |
| At1g65690 hypothetical protein | NDR HNL |
| At4g05220 putative protein | Putative syntaxin |
| At3g05710 putative syntaxin protein | Syntaxin |
| AtSNAP33 | |
| At2g27080 unknown protein | NDR HNL |
| At3g52470 putative protein | Putative syntaxin |
| At1g61760 hypothetical protein | Putative syntaxin |
| At5g21130 putative protein | NDR HNL |
| At3g52400 syntaxin-like protein synt4 | Syntaxin |
| At2g35960 putative harpin-induced protein | Putative syntaxin |
| At5g06330 harpin-induced protein-like | Putative syntaxin |
| At5g26980 tSNARE | Syntaxin |
| At5g36970 putative protein | Putative syntaxin |
| At3g44220 putative protein | Putative syntaxin |
| At3g03800 s-syntaxin-like protein | Syntaxin |
| At2g35970 putative harpin-induced protein | Putative syntaxin |
| At4g09590 putative protein | Putative syntaxin |

-continued

| gene code: | predicted function: |
|---|---|
| At4g23930 putative protein | |
| At1g61290 similar to syntaxin-related protein | Syntaxin |
| At3g11660 unknown protein | Putative syntaxin |
| At1g54540 hypothetical protein | Putative syntaxin |
| At3g24350 syntaxin-like protein | Syntaxin |
| At5g22200 NDR1/HIN1-like | NDR HNL |
| At1g11250 syntaxin-related protein At-SYR1 | Syntaxin |
| At5g53880 | |
| At3g11820 putative syntaxin | Syntaxin |
| At3g54200 | Putative syntaxin |
| At5g05760 t-SNARE SED5 | Syntaxin |
| At5g53730 | Putative syntaxin |
| At4g03330 SYR1-like syntaxin 1 | Syntaxin |
| At3g47910 | |
| At5g08080 syntaxin-like protein | Syntaxin |
| At5g11890 | Putative syntaxin |
| At1g17620 | Putative syntaxin |
| At2g22180 | Putative syntaxin |
| At5g22870 | Putative syntaxin |
| At2g46300 | Putative syntaxin |
| At2g27260 | Putative syntaxin |
| At4g01410 | Putative syntaxin |
| At5g22200 | Putative syntaxin |
| At4g01110 | Putative syntaxin |
| At3g52460 | Putative syntaxin |
| At3g26350 | Putative syntaxin |
| At1g08160 | Putative syntaxin |
| At2g01080 | Putative syntaxin |
| At5g56050 | Putative syntaxin |
| At3g20600 | Putative syntaxin |
| At3g20590 | Putative syntaxin |
| At4g39740 | Putative syntaxin |
| At1g32270 | Putative syntaxin |
| At1g13050 | Putative syntaxin |
| At5g45320 | Putative syntaxin |
| At3g20610 | Putative syntaxin |
| At4g26490 | Putative syntaxin |
| At5942860 | Putative syntaxin |
| At1g45688 | Putative syntaxin |
| At4g26820 | Putative syntaxin |

This observation provides the explanation for understanding the mechanism by which the RKS/NDR-NHL complex functions. Cell wall immobilized RKS gene products (containing the extensin-like extracellular domain) respond to a local ligand signal, in combination with the heterodimerizing ELS protein (s) either as homodimers, as RKS heterodimers or in combination with the heterodimerizing ELS protein(s).

Predicted ligands for the RKS/ELS receptor binding consist of peptide ligands (based on the LRR ligand binding domain of this class of receptors). These ligands are normally produced as a pre pro protein. The N-terminal signal sequence is removed by the transport through the Golgi system and allows modification of the ligand at this stage (e.g. glycosylation). The ligands can then be secreted after which further processing is possible (e.c. proteolytic cleavage, removal of sugar groups etc.) The resulting peptide, possible as a monomer or a (hetero)dimerizing molecule binds the transmembrane receptor complex with high affinity, resulting in transmission of the signal from the ligand through the transmembrane receptor component towards the other site of the membrane.

One class of ligands interacting with the RKS and/or ELS receptors consists of the family of pre(pro)proteins shown hereunder in table 3.

TABLE 3

Ligands within the RKS signaling complex (herein also called RKS/ELS ligand proteins)

For each ligand (A to N) the genomic structure before splicing and processing 5'-towards 3' is given. Exons are indicated in large letters; introns and surrounding sequences (including leader 5'-and trailer sequences 3'-) are indicated in small letters. Beneath each DNA sequence the amino acid sequence of the pre-pro-peptide is given. The first line represents the signal sequence The second (set of) lines represents the pro-peptide. The last line represents the conserved Cysteine motif.

A. At1g22690
(SEQ ID NO: 3)

```
   1 attaaacgcc aaacactaca tctgtgtttt cgaacaatat
     tgcgtctgcg tttccttcat

  61 ctatctctct cagtgtcaca atgtctgaac taagagacag
     ctgtaaacta tcattaagac

 121 ataaactacc aaagtatcaa gctaatgtaa aaattactct
     catttccacg taacaaattg

 181 agttagctta agatattagt gaaactaggt ttgaattttc
     ttcttcttct tccatgcatc

 241 ctccgaaaaa agggaaccaa tcaaaactgt ttgcatatca
     aactccaaca ctttacagca

 301 aatgcaatct ataatctgtg atttatccaa taaaaacctg
     tgatttatgt ttggctccag

 361 cgatgaaagt ctatgcatgt gatctctatc caacatgagt
     aattgttcag aaaataaaaa

 421 gtagctgaaa tgtatctata taaagaatca tccacaagta
     ctattttcac acactacttc

 481 aaaatcacta ctcaagaaat ATGAAGAAGA TGAATGTGGT
     GGCTTTTGTT ACGCTGATCA

 541 TCTCTTTTCT TCTGCTTTCT CAGgtaaact gttaaaacca
     ttttcaagac tacctttcct

 601 ctatttcaga caaaccaaag taaaacaatg aaaaatctct
     ctggtctttc atagGTACTT

 661 GCAGAGTTGT CATCATCCAG CAACAATGAA ACTTCCTCTG
     TTTCTCAGgt aagagtgata

 721 caaaaacata ctaaacaaac tttcaagaga gtaatatata
     aggaaatgtt ggcttctttt

 781 ttttgttgct aatcagACGA ATGACGAGAA CCAAACTGCG
     GCGTTTAAGA GAACATACCA

 841 CCATCGTCCA AGAATCAgtt agtctactct ttcaacactc
     taattccttt gttctaagta

 901 tttttttgc cccccacaac ctttttttta ttaaatgagc
     caatttttat agATTGTGGG

 961 CATGCATGCG CAAGGAGATG CAGTAAGACA TCGAGGAAGA
     AAGTTTGTCA CAGAGCCTGT

1021 GGAAGTTGTT GTGCCAAGTG TCAGTGTGTG CCGCCGGGAA
     CCTCCGGCAA CACAGCATCA

1081 TGTCCTTGCT ACGCCAGTAT CCGTACACAT GGCAATAAAC
     TCAAATGTCC TTAAaagact

1141 tctcatttct caactatagt ctcatcttct gattatgttt
     cttcttttgt tatgttgcat

1201 gtgtgatgtg tgagcttatt attatgttga ttgttgacat
     aattcaacta tataatttgt
```

TABLE 3-continued

Ligands within the RKS signaling complex (herein also called RKS/ELS ligand proteins)

```
1261 atcgattccg aataataaga tgagtgattt tattggctat
     taagtttttt tttttttttt

1321 ttgggcacaa tggctattaa gttttaaaca tctgatttta
     ttggttacaa aaaacaacaa

1381 agtttcattt tcatattaac acaaaatctc catacatatt
     accaacccaa aaaaatacac

1441 aagggggaga gagaccaacg gttcttggtt cagagtttgc
     atcttgtttg agccgtcacc

1501 gtttcttaga cttaacagcc acaacacctt tataaagctt
     cacgcgatcc ttcaacgcat

1561 ctcgccgagg ccgagccacc ttattgtttg gatcaaacaa
     caaaacttct tcaaacgcat

1621 tcaatgccaa aggc
```

(SEQ ID NO: 4)
MKKMNVVAFVTLIISFLLLSQVLA
ELSSSSNNETSSVSQTNDENQTAAFKRTYHHRPRIN
CGHACARRCSKTSEKKVCHRACGSCCAKCQCVPPGTSGNTASCPCYASIR
THGNKLKCP*

B. At1g74670
(SEQ ID NO: 5)

```
   1 gaaaaaaaga agaaaagata atggtccgta ttaatatagt
     tgaaaacttg aaactacttt

  61 ttagtttgta tataatacag tagactaggg atccagttga
     gtttctttct ttattttgag

 121 tttgtgttta tgtttgattt tacgttttta tatgtaaata
     agatatttta cgaattatgg

 181 ttttatttgg gtagaagttg tagaatgact taaacaatca
     agtggcagaa tgagatatat

 241 aaagtaatat aatatatgta ccgttattaa cttattgtac
     atgtgaatga ggaagcttac

 301 acacacacac cttctataaa tagctgacaa aactggttgt
     tacacacaac acattcataa

 361 atctctcaaa gtaagaacta agagctttac tacagtccta
     ctctctacac atcttctctc

 421 tctctcaaga gctagtcATG GCCAAACTCA TAACTTCTTT
     TCTCTTACTC ACAATTTTAT

 481 TCACTTTCGT TTGTCTCACT ATGTCAAAAG AAGCTGAGTA
     CCATCCAGAA AGTgtaagtt

 541 tttatttttt ggtaaaatag aaagtgtaag ttttataatt
     cattcaatty tttttgcctt

 601 tccctttcta tttattgcta taaatctaat acccgcgtta
     aaatttgttt tgaaattaaa

 661 cagTATGGAC CAGGAAGTCT GAAATCATAC Cgtaagtaaa
     aacttcttct tcttttatga

 721 atcttgtttc ttattatata tcaaataaaa actcgattat
     catgattgca gAATGTGGAG

 781 GACAATGCAC AAGGAGATGT AGCAACACAA AGTATCATAA
     GCCATGCATG TTCTTCTGCC

 841 AAAAGTGTTG TGCTAAATGC CTTTGTGTCC CTCCAGGCAC
     GTACGGCAAC AAACAAGTGT

 901 GTCCTTGTTA CAACAACTGG AAGACTCAAC AAGGTGGACC
     AAAATGTCCA TAAacaaaaa

 961 cattgagaga gaaaccccaa tctgtttcct attttattta
     attatttcca gtatgctttt

1021 gttgtcgtga tggttaaatt atagtgtttt tgcaggtatc
     atttatcatc gataaacaat

1081 atcatataaa atcttctatg tttctttcac gttttgtttc
     ttttgttgta gtcaatacac

1141 gaaatgtgta tggaccttct aattaggaat atataaaatt
     ttatttatta attagataat

1201 ctttcgtata gttaaaattc caaggattac ttttgattcg
     tttgggacaa tctattttat

1261 atttacttt ctaagtttgt ataactatat cttaaaagtg
     ttagacagag tcctaatgat

1321 tttagtataa ttgttactat ttagttacgc ttcgaaaatt
     tggaactttt ccaaagtggt

1381 ctatatcaat ttgattcact aatctgcgct tccttctagt
     tttttacaat tatggagatt

1441 tttcgacgat gat
```

(SEQ ID NO: 6)
MAKLITSFLLTILFTFVCLTMS
KEAEYHPESYGPGSLKSYQ
CGGQCTRRCSNTKYHKPCMFFCQKCCAKCLCVPPGTYGNKQVCPCYNNWK
TQQGGPKCP*

C. At1g75750
(SEQ ID NO: 7)

```
   1 cacaactttt atacgcacca ccaaccgacc cattttgaaa
     aagagaaaat aaaccacaaa

  61 aacacacata aataatatgc tgataacaat gtcttaaaaa
     tctatttacc atttctagta

 121 atcaatatct attgcaaaaa atatttataa gaatacaaat
     gaaaaatgat aaaatacaaa

 181 tgatttctca attacctaaa aaatataaaa atgtcttact
     ttattttcag ccactgttgg

 241 aaagtacttg caatcatatc gtattttgaa ttataaaact
     cagaaacaat tattttccct

 301 gaaaagttaa aactttttaat aagatattta taaaataaaa
     agaatagtct agaccgaaaa

 361 tggggtcggt tgtccatcca aaggagtgct ataaatagaa
     ccctccaagt tctcattagg

 421 acacaacaac taaaaccaca tttatcatta cagtctgatt
     tgagctaagt tctctcatca

 481 taaactctcc ttggagaatc ATGGCTATTT CAAAAGCTCT
     TATCGCTTCT CTTCTCATAT

 541 CTCTTCTTGT TCTCCAACTC GTCCAGGCTG ATGTCgtacg
     tctttttcat cacaaactaa

 601 ttatactcaa tataatactt atgttttcaa aaacatattt
     ctcacatgtt acaacaatat

 661 tcttgcagGA AAACTCACAG AAGAAAAATG GTTACGCAAA
     GAAGATCGGt aattatatga

 721 tttttattaa acctaacgtt aaatttagag tgagattaat
     aatctgtgtt tttctttttt

 781 gtatatatag ATTGTGGGAG TGCGTGTGTA GCACGGTGCA
     GGCTTTCGAG GAGGCCGAGG
```

TABLE 3-continued

Ligands within the RKS signaling complex (herein also called RKS/ELS ligand proteins)

```
 841 CTGTGTCACA GAGCGTGCGG GACTTGCTGC TACAGGTGCA
     ACTGTGTGCC TCCGGGTACG

 901 TACGGAAACT ACGACAAGTG CCAGTCCTAC GCTAGCCTCA
     CCACCCACGG TGGACGCCGC

 961 AAGTGCCCAT AAgaagaaac aaagctctta attgctgcgg
     ataatgggac gatgtcgttt

1021 tgttagtatt tactttggcg tatatatgtg gatcgaataa
     taaacgagaa cgtacgttgt

1081 cgttgtgagt gtgagtactg tattattaat ggttctattt
     gtttttactt gcaagttttc

1141 ttgttttgaa tttgtttttt tcatatttgt atatcgattc
     gtgcattatt gtattatttc

1201 aatttgtaat aagattatgt tacctttgag tggttgttta
     tcatactttt tttctatggt

1261 aagaggtttt ggaaaagtat cgagaatgat atataaagta
     atttgatat  cgacgcaaga

1321 tgataactac tagactagct gagtataaga atattgatgt
     atatatttgc ggacaatttt

1381 gaatttatta taccattatt taatcacgac catataaaaa
     taattcttgt ttgcgttata

1441 atttgtgtta atacgataga gtagacaaat ga
```

(SEQ ID NO: 8)
MAISKALIASLLISLLVLQLVQA
DVENSQKKNGYAKKID
CGSACVARCRLSRRPRLCHRACGTCCYRCNCVPPGTYGNYDKCQCYASLT
THGGRRKCP*

D. At2g14900
(SEQ ID NO: 9)

```
   1 ataactaaca atggttgagt ggagatgtgc ttttagtcaa
     gtggttaaat atatttgact

  61 tcgttttttt cattggagtt tgactctact aagttgtgtt
     tcctcgcgta gtaagaattg

 121 gttatggatt agaccgtatc gatctaaaga tgtcaaagaa
     aaaaaaatgt ggttgtgtaa

 181 agtaaatatg tagattgtgg cggattaaag tatgttttga
     ttcacatcat tattgttatt

 241 ttttcatgaa ttctaaatgt aaagttctta taatcttatg
     ttacttttta caaattgtaa

 301 ggattactct gaaatttggt atcgaattct aagacaaata
     caaaataaca atgactgaac

 361 aagttgataa aacataatgg aaggaataat actgcagttc
     tattaaatac taaagaagtt

 421 ggtagattgg cctataaaag gagaataaag agaccacaag
     aaggtctatt attcggggac

 481 taaagaaagc caaagaaaac ATGAAAATAA TAGTCTCCAT
     CTTAGTGTTA GCCTCTCTTC

 541 TTCTAATCAG TTCATCTCTT GCTTCGGCTA CTATATCAGg
     ttggttctaa tctcttcaag

 601 aatcttcttc tctctatttt tttttcttc ataaagttag
     ttatgttatg attggtttag

 661 gtcacaattg tttctttatg ctttcgtttc cataagaaaa
     atattacaaa tattaactag

 721 aacaacataa catgcaaacg agtaatacaa aattcattat
     tatgatcaaa acaatcatga

 781 attagttgga cttatttgtt aaattccgaa aatctcacta
     aaataaagtg aacttcatct

 841 acatggcttt agacgcaaaa tctttaaggg tatctacaca
     aatttggaat gaataatttc

 901 ttgcgatggt agtgtagaag gatctagaag atccacaaga
     tcattagtgt atcttctaga

 961 tcctttttaca ttgagaagtg aggagatatt tgttgtatta
     gaaagaatta tagtgaagta

1021 aattttttaa ctatgtacga tcatttatat acgatacttt
     tattaaggat cttgtggatc

1081 ttctagATGC TTTTGGTAGT GGCGCGGTAG CTCCGGCACC
     GCAGAGCAAA GATGGACCGG

1141 CGTTAGAGAA ATGGTGTGGA CAGAAATGTG AAGGGAGATG
     CAAAGAAGCG GGGATGAAAG

1201 ATCGGTGTTT GAAGTATTGT GGGATATGTT GCAAAGACTG
     TCAGTGTGTT CCTTCAGGCA

1261 CTTATGGGAA TAAGCATGAA TGTGCTTGCT ATCGTGACAA
     GCTCAGTAGC AAAGGCACTC

1321 CTAAATGTCC TTGAttctat ttctttccaa ccaaaaattt
     aaataaatga ataagagaga

1381 tccagtaaac taatataaaa ctataaatgg atcttttgtt
     tatgatttt  tttttttcat

1441 ttctattttt acgaatttgt cttggtcttt ttgaagtaag
     tttttaaata ttgaaaagtg

1501 ctaaaattat gtggaaatcg ataatgttaa tgaatgatat
     aatatataag tcctcagttt

1561 ttgtaagaaa cttgaatata aataatattt catcaaacat
     aataaataaa tatattgtat

1621 aattagattg gctcaaccga tataaacaat tgaatcgaat
     tttttcttct aaatatttaa

1681 tcatccaaat ttgtattgta ccaatgaatg agatggttat
     gaggactaga agatagagag

1741 gagaagaacg tgtttggtaa aataattatg atggagttga
     gacaactttt aagagatttt

1801 aaaaagactg actaacgtgt taggttcatc acgt
```

(SEQ ID NO: 10)
MKIIVSILVLASLLLISSSLASATIS
DAFGSGAVAPAPQSKDGPALEKW
CGQKCEGRCKEAGMKDRCLKYCGICCKDCQCVPSGTYGNKHECACYRDKL
SSKGTPKCP*

E. At2g18420
(SEQ ID NO: 11)

```
   1 gccaatgggt aactgaggaa gaaggataag accaaaaaaa
     aaactaaaat ggacagattg

  61 aattagtaaa aagataaatt ctaaaaaccg aaacaaatct
     taagttggtg tatatacatc

 121 tgcattgacc aacaaaagaa agtagactga aatttatttg
     aaaatgatct tgtaaaggca

 181 tattatatat ttaatttagg aaatgaatgt taaatccttt
     aaattgtttt gatttcacaa
```

TABLE 3-continued

Ligands within the RKS signaling complex (herein also called RKS/ELS ligand proteins)

```
 241 aaggataaag aaatattggt tacatacatc ttaatgtgtt
     gaccaaaaca aataaaatgt

 301 gataagaaac aataaaacca ttttgaccaa agttcttata
     gttttaatat tctttaattg

 361 tcatttgtta gtgactaata atattacatt aaacctaatg
     tataaataga agccccatct

 421 tctacgcctt tataattagc aacaaccaaa aacattcatt
     tgtcattttg tctcctcttt

 481 tgtttctctt gatcactagt ATGGCTGTAT TCAGAGTCTT
     GCTTGCTTCT CTTCTCATAT

 541 CTCTTCTTGT CCTCGACTTC GTCCATGCCG ATATGGTGgt
     acaattttaa caaccaaata

 601 tattttctta tttgatttta tttttcaca acttttgtct
     acgttctaat ggaatttttt

 661 tcaaaatatt catgcagACG TCGAATGACG CCCCTAAAAT
     CGgtaatatc tctatcatat

 721 aaacacgtac gttgaatttc tatatacgtg tgtttaattg
     aagttttggt tggaaattgt

 781 atgtatttgt agattgcaac agcaggtgcc aagagCGGTG
     CAGTCTTTCG AGTAGGCCAA

 841 ATCTTTGTCA CAGAGCGTGC GGGACTTGCT GCGCTAGGTG
     CAACTGCGTG GCACCGGGCA

 901 CATCCGGAAA CTACGACAAA TGTCCGTGCT ATGGTAGCCT
     AACCACCCAC GGAGGACGCA

 961 GAAAGTGTCC Ttaaaaactc tgtcgctgtt tgatttgatt
     tcgtttataa tactttactt

1021 ttatgagagt aattgtggtt attttcttgg gaattattaa
     aaagcaaaag aaagagaatg

1081 ttatacgtca tgtgcaactc ttcgatcttt gttttagtgt
     ttatccaatt tgtacttgtt

1141 ggtttggttc ctggttaaca ttaggtctga aaaggtattg
     tttttcatta tacaattcac

1201 taaataggca tcgtacttgc atataaaata aagaatgaag
     agagaagtaa aagagttttc

1261 ttttttact catggaagtt aggcaatggg tttaaatatg
     gtaacaacag aattggaggg

1321 gacttaatga actatgacgt aaaactgaga gcgattgaat
     atgtaacgtt accaacaata

1381 ccaataaaat tatgaaagat agtatatgaa attacgttta
     attaatgttt ccgggttgaa

1441 tgtattatat atagaagtaa cagtacgatt tttattacat
     ttttgtacaa gattcctaga

1501 aaggtataac ctctataaag ttaataatag tcttgagtct
     tgactcttcg aggcaaataa

1561 attcaccgca taattaatcg ttcaactatt attctatatt
     ctatataaca tgagcttcaa

1621 caaaagaaac atcaatcata tcttcaacag tatactgcag
     tgtaatgtaa catattcaag

1681 atcaaaccgg acaaaaaagc aagataccgt cgaaacaatc
     aaaccccatg tatcataaac

1741 tcccatcttc tctttcctaa attccccgtc gcttgcacaa
     tc
```

(SEQ ID NO: 12)
MAVFRVLLASLLISLLVLDFVHA DMVTSNDAPKID CNSRCQERCSLSSRPNLCHRACGTCCARCNCVAPGTSGNYDKCPCYGSLT THGGRRKCP*

F. At2g30810
(SEQ ID NO: 13)

```
   1 cttttatttg tttgtgaaaa aaaacaatag cttttatttg
     tcctaggaat tatttaatag

  61 attaaataac agctattttt ctcttatttc ttagtgatta
     aaatatttaa aatacagacc

 121 aaaattaatt gtttatgtta atatatttac tccttaatcc
     tttatattaa aattgtataa

 181 tgcatgtagt taataaattg ttttccaaaa ttcattcata
     attttattcc taaattattt

 241 tggtcaagaa aacacatctt tgaataatta aatgcttcct
     tgtatttgat aatttcttga

 301 tattttaaaa taccttctat actatgccaa tgttattggt
     tataaatagg tttaacatta

 361 atcctgaaat atatcataag aaaatcaaaa gtgaaataag
     agatcaaaAT GATGAAGCTC

 421 ATAGTTGTCT TTGTTATATC CAGTTTGTTG TTTGCTACTC
     AATTTTCTTA Tgtaaaaatt

 481 attattattt tcttcatatt atgatttatg aattcagaga
     aataaagttt tttttttat

 541 gtgtgtatgt acagGGTGAT GAATTAGAGA GTCAAGCTCA
     AGCACCTGCA ATCCATAAGg

 601 tatatttaaa ttataaaata tcaaatactg aataataaat
     aataaatata ttacaacaag

 661 aatatcaata ttatttttca aactacataa ttttaaaata
     ttttattgat aacacaaatg

 721 tatattatta tcgtctccat tgatttgcat tctaaatttg
     tttttgttat ccaaccaatt

 781 tcagAATGGA GGAGAAGGCT CACTTAAACC AGAAGgtaaa
     ttgtttaaaa gatattattt

 841 ttatttatat agtaaatgat tgatcaaatc acaacttaaa
     taatttaatt gttgatttat

 901 atttttctga agAATGTCCA AAGGCATGTG AATATCGATG
     TTCGGCGACA TCTCACAGGA

 961 AACCATGTTT GTTTTTTTGC AACAAATGTT GTAACAAATG
     TTTGTGTGTA CCATCGGGAA

1021 CATATGGACA CAAAGAAGAA TGTCCTTGCT ACAATAATTG
     GACGACCAAA GAAGGTGGAC

1081 CAAAATGTCC ATGAaaacaa aaaattgtaa aagcaaaata
     aaatctatcg ttgttatctc

1141 tcaataaaat ctatgtttgt aatccttgtt tttcaatata
     gaatataata tggagttttc

1201 ataatttctt ctattacaaa attaaagtta atgcacaaat
     aaattgaagg gacttggacc

1261 ttttcgtgta agttctttct ttatatcacg aacaatttag
     atttatattt tcactcttac
```

TABLE 3-continued

Ligands within the RKS signaling complex (herein also called RKS/ELS ligand proteins)

```
1321 aaacacaaaa catggatgct ctttaactct catccaaaca
     aaatgcattt ctctctttct

1381 ttttctaaac atttcacaac aatatcccat attatatcta
     agatatatga tctttttaaa

1441 ttgaatttat ttaggccatg ttttaaaatc gtgtttggtt
     agattgaccc atgaaatgtt

1501 gacatatttt aacattccta aatatgacta aaaatgatta
     aagatattta ataatatatt

1561 tgctctatta aaaatgatta aataaataat aata
```

(SEQ ID NO: 14)
MMKLIVVFVISSLLFATQFSNG
DELESQAQAPAIHKNGGEGSLKPEE
CPKACEYRCSATSHRKPCLFFCNKCCNKCLCVPSGTYGHKEECPCYNNWT
TKEGGPKCP*

G. At2g39540
(SEQ ID NO: 15)

```
   1 taatgctata cttttaatct ataatatata ttagatgtga
     cttaaggaat ttcaatagtt

  61 atacataata ataaaaatga atatttgtta gtgttacaaa
     ctgtgtgtca taatcatcat

 121 tcatcaggat ttcaaaaata tctcaaaatt gttgtaagtt
     catgtaattc gaaatgaatg

 181 tgcactataa gaaataaatt tacaatttaa aaaatgcttc
     aatactggtt acaaaaaaaa

 241 ctttcaatac tagtattata ctacttactt agtcaaaaaa
     gtttatgaat atggtttttt

 301 ctgtatgtta atatttttaa ctgaaaatag taccgacata
     acaagtaaag atatctttat

 361 ttaaagtaac aaacattaat ttcacttcaa attctcacta
     ttaaggattc ctctctttgt

 421 agccacattt caccatcact actttgtttt cgcatatctt
     taaattttgt atacgtagca

 481 aactctttcg agaaaacaag ATGAAGCTCG TCGTTGTACA
     ATTCTTCATA ATCTCTCTTC

 541 TCCTCACATC TTCATTTTCT GTACTTTCAA GTGCTGATTC
     GTgtaagtgt ttacttaatc

 601 tagttaataa ttgtaggtca tgcatggatc attttgaaac
     aagttttctg aaattctaag

 661 attttacata tatatgtgat aaatgaatta gcagCATGCG
     GTGGAAAGTG CAATGTGAGA

 721 TGCTCAAAGG CAGGACAACA TGAAGAATGC CTCAAGTACT
     GCAATATATG TTGCCAGAAG

 781 TGTAATTGTG TTCCTTCGGG AACTTTTGGA CACAAAGATG
     AATGTCCTTG CTACCGTGAT

 841 ATGAAAAACT CCAAAGGTGG ATCCAAGTGT CCTTGAacgt
     tctttgaaga tcctcatcac

 901 atacatataa cttctacgta ctatatgtgt ggaaatatta
     atcacattct atgtttgaaa

 961 tatataaaat aaaatcaatg cccccaatgt tggaaatctt
     caatgtgata tcttaatata

1021 tatcacgaat aaaaaagttt aaatttctca atctcatttt
     taatctttaa tctaatttct
```

TABLE 3-continued

Ligands within the RKS signaling complex (herein also called RKS/ELS ligand proteins)

```
1081 taacacatca acgaatcttt aatctttaat catgtagata
     attatcagag cacctaaaca

1141 ttgcgccgtt ttgtgattat acaaagtaac atcgtgctgt
     ttttgacttt tgaaaaccac

1201 agatccaaaa actgtttact ttcctctaag agaaagcaaa
     gccgagtgag tccaagcgag

1261 ttttgagaga ttcgttgact cactaccgga gaacgacgct
     atgtcagaga ccgccgtgtc

1321 aatcgattcg gaccgatcta agtcggagga agaagacgaa
     gaagagtatt ctccac
```

(SEQ ID NO: 16)
MKLVVVQFFIISLLLTSSFSVLSSA
DSS
CGGKCNVRCSKAGQHEECLKYCNICCQKCNCVPSGTFGHKDECPCYRDMK
NSKGGSKCP*

H. At3g02885 (GASA5)
(SEQ ID NO: 17)

```
   1 cgctttctat tacacttttt tttcttttta gtcgcacttc
     acaattagct taattaattt

  61 cctaaactcg cttattttcc cctttctata tacagatatt
     atcattagtg acattttcat

 121 tttccaaaca gagcgtttag acactagtca actacacaat
     ataattttcc aattttcact

 181 gagagaaatg tttttttttt ttttttccaa ggcaagattt
     tagtcttttg gttctctata

 241 cgtgggtaat tagtgattag taatttacac tgttgagtct
     ttgacattgt ctaagagaca

 301 aaaacgacaa gtgtggtacg taattagaaa ttaaaatgac
     ctacttcccc agaatcacgg

 361 catgaacatt ggcaatacca aatttcttga ataccattga
     aggaaatcca cactaatcat

 421 tttctctata aatatcttta atccgtttta ttgtttctta
     agaatcattc attggcaatc

 481 aagatttttt aaccaaaaaa ATGGCGAATT GTATCAGAAG
     AAATGCTCTT TTCTTCTTGA

 541 CTCTTCTCTT TTTATTGTCA GTCTCCAACC TCGTTCAGgt
     aaaccactca aaacagattc

 601 agtttattaa agtctgatat tgaagtttta tatattacag
     gctgctcgtg gaggtaaaaa

 661 tgaccaaagg ctatacattc cttaaaaatt taatggctat
     tagttttctg atattgaagt

 721 tttatatata tatgacagGC TGCTCGTGGT GGTGGCAAAC
     TCAAACCCCA ACgtacggac

 781 tcaaaacttt tgttgtttca tatgatcata ttaatttatt
     aatcactaat tattgataat

 841 gttgataaat aaactttaaa gtaacaataa tggtgtttat
     tttgtgaaat gtcagttttc

 901 tagtatactg tatgctgtga attataagca tgaacataaa
     gatctcaatg atttgttttt

 961 tgtttgtttg ttgtgatatg cttttttgat ggaaacttca
     attgtagAGT GCAACTCAAA
```

TABLE 3-continued

Ligands within the RKS signaling complex (herein also called RKS/ELS ligand proteins)

1021 GTGTAGCTTC CGTTGTTCAG CAACATCACA CAAGAAGCCA TGCATGTTCT TTTGCCTCAA

1081 GTGTTGCAAA AAATGTCTTT GTGTTCCTCC TGGCACTTTC GGCAACAAAC AAACTTGTCC

1141 ATGTTACAAC AACTGGAAGA CTAAAGAAGG CCGTCCAAAA TGTCCTTAAa acttcttttt 1201 agatatattt gataatattc atctagtttt ggattatcaa acacttacta ctctgtttta 1261 atctgtttct acaagttggc gatttgtctc tacacttttt ttgtgtcttt tgctcttaac 1321 tgttgtgttt gttatacgtg taagcccgcc caatgtgtca tggccgaact tattatggtt 1381 acatatttat gaaatgggct tcattatcaa ttgatttgag cctacaaaaa tgtagccata 1441 aagcccatta agttgtaatt gttaatattt cagtcataaa tatgatttc tatatctatg 1501 atttatctct agtgttgatg atgtttgtat gtggaagtca tgttctattt gcttccacgg 1561 tttaaaaacc atcaacttgc taaggtcaaa ttctaatatt actgtgaaaa acattattta 1621 cgtgcgtaat tatatgaatt tatgaatagg ttttaattcc atttttcct aatagtgttt 1681 tatgtcaaa (SEQ ID NO: 18)
MANCIRRNALFELTLLFLLSVSNLVQAA
RGGGKLKPQQ
CNSKCSFRCSATSHKKPCMFFCLKCCKKCLCVPPGTFGNKQTCPCYNNWK
TKEGRPKCP*

I. At4g09600 (GASA3)
(SEQ ID NO: 19)

1 taggctggca atttaactct gagacgtctt tcttgtatag agaataaaac atacgcgtgt 61 aaaagaaaac gcgtgaatcg aatgatgagt gttaacgttc gatcgagatg ccaccaaatc 121 ttttcattaa aatgaattgt ggaggacata ccacttttaa cgaggtcatt tccactgggt 181 gacatgtgga ctctactttg ggtggcatgt tcatatcttt ccacatcacc atgtaaacgt 241 gaaaacaccc accacactca cttacatctc aaacacatgt cttcattatc gtacgtagct 301 ccaaaaaaaa aaatgaaaac taggtttagt gattctattt cgcaatgtat aatatacaac 361 ttgtaaaaat aaaatatttg aataagcatt ataaataaac ccaaagaggt gttagattta 421 tatacttaat tgtagctact aaatagagaa tcagagagaa tagttttata tcttgcacga 481 aactgcatgc tttttgagac ATGGCAATCT TCCGAAGTAC ACTAGTTTTA CTGCTGATCC 541 TCTTCTGCCT CACCACTTTT GAGgttcata acttttgtct ttacttctcc atgaatcatt 601 tgcttcgtct tatccttaat tcatatgtgt ttgatcaatg ataataattc atcattctct 661 tcagCTTCAT GTTCATGCTG CTGAAGATTC ACAAGTCGGT GAAGGCGTAG TGAAAATTGg 721 tatgtaacgc taacatatat gtaaagtgtt atatctctgt ttatatatga tttttaaacg 781 gttaaaaact agtcatatgt gtataaatat atcatgtgaa gATTGCGGTG GGAGATGCAA

841 AGGTAGATGC AGCAAATCGT CGAGGCCAAA TCTGTGTTTG AGAGCATGCA ACAGCTGTTG

901 TTACCGCTGC AACTGTGTGC CACCAGGCAC CGCCGGGAAC CACCACCTTT GTCCTTGCTA

961 CGCCTCCATT ACCACTCGTC CTGGCCGTCT CAAGTGCCCT TAAacatata cacatacaga 1021 tgtgtgtata tgtcttccgc gagcacacac gtacgtttat gttttaagga caatagtatg 1081 tatgagcagc tataaacaaa ccagaagtta atggttcatg ttgaactagt ataagttgta 1141 tgaactgtgc ttcttttgaa caaccacttt tgctgtaagt ttagcaaccc tatttaataa 1201 attagagatt acaaaaaaaa aaatgaaaaa tgtttaaaaa acgtggattt ttaaatttgg 1261 gattaaaaat taattttcat tttggttgat ttgtcaataa attagctaag ttttgtatac 1321 taggccgttt aagatatgct gttaaatttt tgataataga gttgccttag aagttcataa 1381 ctgtaaatat ctaacttcac ttcaatctca caaacacacg aatcaacttc agcactaaga 1441 atcgaattga ccagaactga aagaaagtaa aagaaaagct gaatacagag aatttaacga (SEQ ID NO: 20)
MAIFRSTLVLLLILFCLTTF
ELHVHAAEDSQVGEGVVKID
CGGRCKGRCSKSSRPNLCLRACNSCCYRCNCVPPGTAGNHHLCPCYASIT
TRGGRLKCP*

J. At4g09610 (GASA2)
(SEQ ID NO: 21)

1 ttaacagttt aacaccataa tgttaaactc ggtttagcat tttggtgtaa ttctacctct 61 ttaaccatac atactaaaga cgcagagaag ttcatatggt agttaatcgt aaatagctaa 121 acttttaatt ggggttaaca tattatttaa cacttaacat ttaactattg atctctcatt 181 ttttttttat taaccaaaat aaattcattt tagaaccaaa cgtttcaaaa actcgtaatg 241 ttttctcatt aaatcttatc tatagctcac acaaagaaaa actacggaca tgcatgcacc 301 caattatata catggattat tatttttagt gttataatat gatacaaaat aaaaaacatt 361 tggatagccg ataggcgata gccactataa atataccaaa gaggttggat tatacatata 421 gccgtaatac caaagagagt atcagataga aalagttcta atattttgta caactcacag 481 aaattgcatg agtttcgaac ATGGCAGTCT TCCGAAGTAC ACTGGTTCTG TTACTAATCA TABLE 3-continued Ligands within the RKS signaling complex (herein also called RKS/ELS ligand proteins)

```
 541 TCGTCTGTCT CACCACTTAT GAGgtttata atatttttgg
     tctttatagt tccccaagaa

 601 cacctagcaa tattatactc aattcatgtt tatatgataa
     tgactgatca ttctcttcag

 661 CTTCACGTCC ACGCTGCTGA TGGTGCAAAG GTCGGTGAAG
     GCGTAGTGAA AATCGgtatg

 721 taaccctaac ttatatataa cacgttggta tataacttaa
     tatttctgat gggtgcactc

 781 tcttcccaac ttatatatat ctttgttatg gagaatgtct
     caagctttta atgagatgtt

 841 atatctcgga gaaggaaact atgaactaaa agctttggat
     tcctttgcaa caaatataaa

 901 cttttgatgg gtttaaacgg attaaattag ttacatgtgt
     ttgatgaatg tatgtatgat

 961 tgtagATTGT GGTGGGAGAT GCAAAGATAG ATGCAGCAAA
     TCTTCGAGAA CGAAGCTATG

1021 CTTGAGAGCG TGCAACAGCT GTTGTTCCCG CTGCAACTGT
     GTGCCACCTG GTACTTCTGG

1081 AAACACCCAC CTTTGTCCTT GCTACGCCTC CATTACCACT
     CACGGTGGCC GCCTCAAGTG

1141 CCCTTAAaat ttcttctgtg tctgtttctg tttctacttc
     tatttcgaat atatgtacat

1201 gtgtgtgtac gtgtgtatgt atacaagtac tgctatgttt
     tggaggacaa aagtatatgt

1261 atgagaagct ataaactaat tagaagttga tggttatgcg
     tattatcaaa ccgtgttact

1321 tctgaacaac caatttcggt ttgttccaag tttggcaacc
     ctaaaataaa aattcaaaat

1381 gattggagac tactcgttaa tagacattga aaacgatgaa
     atctcgttac gtttttatat

1441 tttttgaact gtaatattat tatgcagaag cggttttgta
     atgggccgac aaaaaaaaag

1501 tggttttgta atggatatga ttcggatcta ttctggaaat
     ggtctcaaaa agtagagttg

1561 agatctcaat acgaaaatga accctttcgt ttgatttatc
     aaagcctttt attttgaaaa

1621 cgttaaatcc tcactaggat ctctctt
```

(SEQ ID NO: 22)
MAVFRSTLVLLIIVCLTTY
ELHVHAADGAKVGEGVVKID
CGGRCKDRCSKSSRTKLCLRACNSCCSRCNCVPPGTSGNTHLCPCYASIT
THGGRLKCP**

K. At5g15230 (GASA4)
(SEQ ID NO: 23)

```
   1 aaatattcac cctaaaatga atctaaaaat gtacaaaatc
     acaggaaaat aaaactaagc

  61 agaaatgtcc taagaaaact aaagttttta aaaaataatc
     ttcaaagaga tactccaact

 121 ggtgttataa gcaaaacttg atttatcaaa aacaggttca
     tagtatttta tatttagtac

 181 tataagcttt ccttaaacca tgtgcaaaac catctaccgc
     agtctaatta ccaatagcaa

 241 gtaataaaat gggactaaca ttggaggcat acgtggaata
     atataattgg aggaatacag

 301 taataatgat atgtgttgcc acagggaata attgatacga
     gcaaatgtgt gtatatatag

 361 cttatatgca acatcattgg gtcctcaacc aaaaactcct
     ctctcagtac acttcttttc

 421 atacctcaag agactaaaac tagtttgagg agatttagag
     gagtgtttgg ttctttggat

 481 aacaatatcc caaactgaaa ATGGCTAAGT CATATGGAGC
     TATCTTCCTC TTGACCCTCA

 541 TTGTCCTCTT CATGCTTCAA ACCATGGtaa cacctctatt
     atttttttct tctttcaatg

 601 tttgaaaata ttgaagataa tatatttgat tgttttcctt
     attgacgaac gatatgagac

 661 aaatgtgggt tctattattg tacttttagt tggaatatat
     ttaatttagc ctttttaatg

 721 aaattaattt tacttgtttt tcctctctct ttttttcgtt
     ttttagGTTA TGGCCTCAAG

 781 TGGATCTAAT GTGAAGTGGA GCCAGgtcag ttttattatt
     gaatcgacta gtaattacct

 841 tttaaactat attttatacc tattgttatc tcgtaactta
     acgaaaagtg attaattagt

 901 tacctttttt ggttaatttt cagAAACGTT ATGGACCAGG
     AAGCCTGAAA CGTACCCgta

 961 agtttttttct tcacagctat tcttaaacaa ttttttttta
     atctcataat cgacgaaaaa

1021 taaacaattc aagaaatctt ttattgtgtt ataataaaaa
     aaaataagca tttcagttgc

1081 agaaaataag ttgaaagtga agtgttaagt ggactgtttg
     gtcagatccg tagactcaaa

1141 atatattaga tattgacgaa attgcccctt aatatggtca
     tacagtcaaa gcaacccact

1201 atcttgagac ccacaaaaca gtaaaaaaaa aagctaatga
     atttccacta gattctgttg

1261 tttttattag taataaaaaa tttttgagtg ttaacatttt
     gatattgttt gtatttgaaa

1321 caaccagAAT GCCCATCGGA ATGTGATAGG AGGTGTAAAA
     AGACACAGTA CCACAAGGCT

1381 TGCATTACGT TCTGCAACAA ATGCTGCAGG AAGTGTCTCT
     GTGTGCCTCC GGGTTACTAT

1441 GGGAACAAAC AAGTTTGCTC CTGCTACAAC AACTGGAAAA
     CTCAAGAGGG TGGACCAAAA

1501 TGCCCTTGAa aaaatctccc ttcgttccct ttttataata
     aaaattttca actataacta

1561 aatttccttt gatcaatgtt ttatctactt tattcctaat
     gttgtaatgt tatgtcactc

1621 cttttcggat tttgttctaa atcctaaaaa aaatgagagt
     ggccctatga atgatatttt

1681 tcatgaatac ttgtgtttct aaagatattt tcccattcat
     ccaccaaaaa aaaagatatt
```

TABLE 3-continued

Ligands within the RKS signaling complex (herein also called RKS/ELS ligand proteins)

```
1741 ttccatttcg aaaatagtaa tactataaag ggtaaggcaa
     accaaataat acaatttaaa

1801 aaattcctgc gaaagaagta tgcatatgta gaaaagagtg
     acattgggtc tctcggccca

1861 gtactaaaaa gcccattatt gatttttcca agctttttac
     aaaatcacgt gttctaacgc

1921 gattgctttt tgccgcaatc ttcttttata caagacttgg
     gctttgggca gttggaaata

1981 aataacgaca acgatatttt acaatcggt
```

(SEQ ID NO: 24)

```
MAKSYGAIFLLTLIVLFMLQTMV
MASSGSNVKWSQKRYGPGSLKRTQ
CPSECDRRCKKTQYHKACITFCNKCCRKCLCVPPGYYGNKQVCSCYNNWK
TQEGGPKCP**
```

L. At5g14920
(SEQ ID NO: 25)

```
   1 ttgctcactg gtgcaataat cgaagtgaag agcctcttta
     tatgaaatat ataagcgaca

  61 cagccttatg ggcaaatcga atgctattta tttatttgat
     aagaagatta ataatttcaa

 121 tttgtcatcc actagtctct tggggtactc aaaacatatc
     accaaaaagt ccatagagtt

 181 atttgttctt atttattgat aaagtattcc aagttgatgt
     acgaataaag tggcaatttc

 241 atgtattatc aatataatcc atttttggga atctgatatt
     ttgtttatcc tcgagctctg

 301 agagatatat tttggtgcag tgaaggttca aagctggcat
     gcatgatgca tataataact

 361 gctctggacc taatacttac tacgcattta aattaatatt
     tatggataat atggttaata

 421 aataaggaac ttctatttat atcacaaaag gtcactggtc
     ttcttcgtgt gacttcacca

 481 ctttctcatc tcccacaaaa ATGGCTCTCT CACTTCTTTC
     AGTCTTTATC TTTTTCCATG

 541 TCTTTACCAA Tgtaagttat tcttactttt cataacaaaa
     ggtgttatta tgttaaagac

 601 tacataatag tatacaatta tgtgcattac gttttcgcgt
     attgtaacta actatgtatt

 661 ttgattaatc accgagcagG TTGTTTTTGC TGCTTCAAAT
     GAGGAATCCA ACGCCTTAgt

 721 acgttttcta atttccagtt taattatttc tatgcgtctt
     taactatata ctcaggcatt

 781 tttattgatt attgtgtatg aagttaaatt ttggtatatg
     tttgtattaa atttatagGT

 841 TTCTTTACCA ACGCCAACAC TTCCATCGCC ATCTCCGGCT
     ACCAAACCGC CGTCGCCAGC

 901 TCTCAAACCG CCGACGCCGT CGTACAAGCC ACCCACGCTG
     CCAACTACTC CTATTAAACC

 961 ACCCACCACA AAACCTCCGG TCAAACCTCC AACTATTCCG
     GTTACACCAG TAAAACCTCC

1021 GGTTTCAACT CCTCCGATCA AACTACCGCC GGTACAACCA
     CCTACGTACA AACCCCCAAC

1081 GCCAACAGTT AAACCACCGT CCGTCCAACC ACCTACGTAC
     AAACCCCCAA CTCCAACGGT

1141 TAAACCACCC ACTACATCAC CGGTTAAACC ACCCACTACG
     CCACCAGTTC AATCACCGCC

1201 GGTCCAACCA CCTACGTACA AACCCCCAAC GTCACCGGTT
     AAACCACCCA CCACAACTCC

1261 ACCGGTTAAA CCCCCCACCA CGACGCCACC GGTCCAACCA
     CCTACGTACA ATCCCCCAAC

1321 TACACCGGTT AAACCACCTA CAGCGCCGCC TGTCAAACCT
     CCAACACCAC CTCCCGTAAG

1381 AACTCGGATA Ggtaataata attttctttc aaaagtgtga
     tgattatcgg tcgttgatta

1441 gatcggatgt ataattggac taaattttgg acggtttagA
     TTGCGTGCCT TTATGTGGGA

1501 CGAGGTGTGG GCAACACTCG AGGAAGAACG TATGTATGAG
     AGCGTGCGTC ACGTGCTGCT

1561 ACCGCTGCAA GTGTGTTCCC CCAGGCACCT ACGGTAATAA
     GGAGAAGTGT GGATCTTGTT

1621 ACGCCAACAT GAAGACACGT GGTGGAAAAT CCAAATGTCC
     TTGAAccttt atatgacgat

1681 ggttgttaaa cgaaataatt taaatcaatg gagtttttat
     aagtttgtaa tgcgtttgtt

1741 tttgttatag taatattgag ttggatcttt gtttacggga
     cgtagaatac taaataatga

1801 aaaaaacctt ctcgatgaat taagggtttt atgaatttgt
     tttgtattga ataaatatagg

1861 gatggataaa gttttattat tctaacaggt tactttatta
     ggcatttctt cggctcatgt

1921 aactcttgta tcgctgaaac tatgtaatag atagaagaac
     ctaaaaaaag aaagaaaaca

1981 agaaatgcac atagcgaagc tcaaaagatg agtgttctgc
     tagcggtaat gttgttattc

2041 agttgggtca aatgctctaa ttgcaaatct tatttaggcc
     ttatatagac tcttatgtgc

2101 atatggtcca gcctatttgg gccgatgtgt ttgaagatca
     tttgggaaag tcttgcgcaa

2161 ggag
```

(SEQ ID NO: 26)

```
MALSLLSVFIFFHVFTNVVFAAS
NEESNALVSLPTPTLPSPSPA
TKPPSPALKPPTPSYKPPTLP
TTPIKPPTTKPPVKPPTIPVT
PVKPPVSTPPIKLPPVQPPTY
KPPTPTVKPPSVQPPTYKPPT
PTVKPPTTSPVKPPTTPPVQS
PPVQPPTYKPPTSPVKPPTTT
PPVKPPTTTPVQPPTYNPPT
TPVKPPTAPPVKPPTPPPVRT
RID
CVPLCGTRCGQHSRKNVCMRACVTCCYRCKCVPPGTYGNKEKCGSCYANM
KTRGGKSKCP*
```

M. At5g59845
(SEQ ID NO: 27)

```
   1 gacttgagta tgaatccaat aacccaaaat ttatgcagat
     tttagaatac ttcttataaa
```

TABLE 3-continued

Ligands within the RKS signaling complex
(herein also called RKS/ELS ligand proteins)

```
  61 tcttaaatga ataacacaaa actttaacat acttttaaca
     aatcttgatt gaataacaac

 121 agattctaca tgacatttta aatcactaaa actcttttga
     aatcataaac caataacaac

 181 cccttagttt tttactattt gaattctgac gtactttttt
     attagttgaa tttctataa

 241 tgagaaaaca ttaattattt cttaatcttt gaacttaagc
     cccacaaaaa tcttataaat

 301 tgggacagat ggactagata acaagcgttt cacctactcc
     aaaatttccc tataagtaac

 361 tctttttgta acctcctttt cttcccaaac catcactcct
     tttgcattgt gtgaaacctt

 421 cgagttttct cttcatcttc tcaaagtaac aaactttctc
     caaacagatt attattaaaa

 481 caatctcatc aagaactacg ATGAAATTCC CGGCTGTAAA
     AGTTCTTATT ATCTCTCTTC

 541 TCATCACATC TTCTTTGTTC ATACTCTCAA CCGCGGATTC
     GTgtaagtat acacaatgca

 601 ttttcttatt ttagatactt ttctcattag aaatttagct
     ttcttaataa aattgtattg

 661 tgatgatgga ttaattagCA CCATGCGGAG GAAAATGCAA
     CGTGAGATGT TCAAAGGCAG

 721 GAAGACAAGA TAGGTGTCTC AAGTATTGTA ATATATGTTG
     CGAGAAGTGT AACTATTGTG

 781 TTCCTTCAGG CACTTATGGA AACAAAGATG AATGCCCTTG
     TTACCGCGAT ATGAAGAACT

 841 CCAAAGGCAC GTCCAAATGT CCTTGAtcat gttcttaaga
     ttatccttat agacacaata

 901 tcttgaaatg ttaagattgt gcttgatgcc taaaataatg
     agcttgagat acttctatga

 961 atgaatatgt gaaagatttt gacaataaaa tgatttgatg
     tattaaaata ttcttagtga

1021 agttatatat gtataaatga agtatgaaat atacattgta
     tgttgcttta catgagaaag

1081 ataaatctac aacaatccaa tgtatgaaaa ttttactaag
     ttaactgatc agaaacgtta

1141 attatggttt agaatcttgt ggagagatga ttacttttgt
     aagagaaatt gattgtttgt

1201 tgtcaatgag gataaagtaa gaagccattt ctcaacacat
     ggacttgata gcaaactaaa

1261 caaggctcaa gcattgaaat tgaaacgtct cgatagataa
     gattggctca agaaaagcaa

1321 gtgtttttttg ttgtagaaaa cagaaattga aattactgtc
     tacttt
```

(SEQ ID NO: 28)
MKFPAVKVLIISLLITSSLFILSTA
DSSP
CGGKCNVRCSKAGRQDRCLKYCNICCEKCNYCVPSGTYGNDKECPCYRDM
KNSKGTSKCP*

N. At3g10170
genomic structure before splicing and processing
5'-towards 3' predicted orf sequences are
underlined TABLE 3-continued Ligands within the RKS signaling complex
(herein also called RKS/ELS ligand proteins)

(SEQ ID NO: 29)
CTGTTTTCAGAAAATGGCAACAAAACTTAGCATCATTGTTTTCTCCATTG
TTGTGTTACATCTTCTTCTGTCTGCCCATATGCATGTAAGTGTTTCAACA
CTCTATTCCTCTATGTTCACATTTATCAACTTTATCTTATACGTCCCTGA
ATAAAACACAGCCTATATACTTGGAATCTCCTGCTCGACAACCACAACCA
CCACAGTCGCAACCACAACTGCCGCATCACAATAACTCTCAAGTGAGTTT
CTCGGTTCATCACTACTCAAAAAAAGAGTTTCATCGAATCTACAAAACCT
TTTTAACATCCTTTGCATCTTCTTGTTGATTTTGGCAGTACGGTACTACT
CAAGGCAGTCTTCAACCCCAAGGTAAACCCACTGACTAGCCTAGTTTTTA
ATTAATGTTTGTGCTGAATGCGAAACTAAATCCGCTATTCCACCTTTATT
AGAGTGCGGGCCAAGGTGTGGAGATAGATGCTCGAATACACAATACAAGA
AGCCGTGTTTGTTCTTCTGCAACAAATGTTGTAACAAGTGCTTGTGTGTG
CCCCCAGGTACTTATGGCAATAAGCAAGTATGTCCTTGCTATAACAACTG
GAAGACCAAGAGCGGTGGACCAAAATGCCCTTAGTTTCTCCTCTTAATTA
CTTTAGCATAAACTCCATGTAATTTGTTAATCTACCTATCATAATTTATA
TATGTATTGGACTCTTCCATAATCACATCAGTTCTCTGTGATTATGACGT

Amino acid sequence of the predicted pre-pro-peptide the first line represents the signal sequence the second (set of) lines represents the the pro-peptide the last line represents the conserved Cysteine motif.
(SEQ ID NO: 30)
MATKLSIIVFSIVVLHLLLSAHMH
FLINVCAECETKSAIPPLLE
CGPRCGDRCSNTQYKKPCLFFCNKCCNKCLCVPPGTYGNKQVCPCYNNWK
TKSGGPKCP*

They consist of an N-terminal signal peptide, followed by a variable domain (involved in mobility or cell wall attachment) and a C-terminal domain with 12 conserved cystein residues.

The consensus of this last domain is:

C—C—RC--------C---C--CC—(R/K)C—CVP(P/S)
GT—G(N/H)---C—CY--------G--KCP* (SEQ ID NO: 31)

(-)=any amino acid;

(C)=conserved C-residue (/)=either one or the other amino acid at this position;

*=stopcodon

Figure 4:
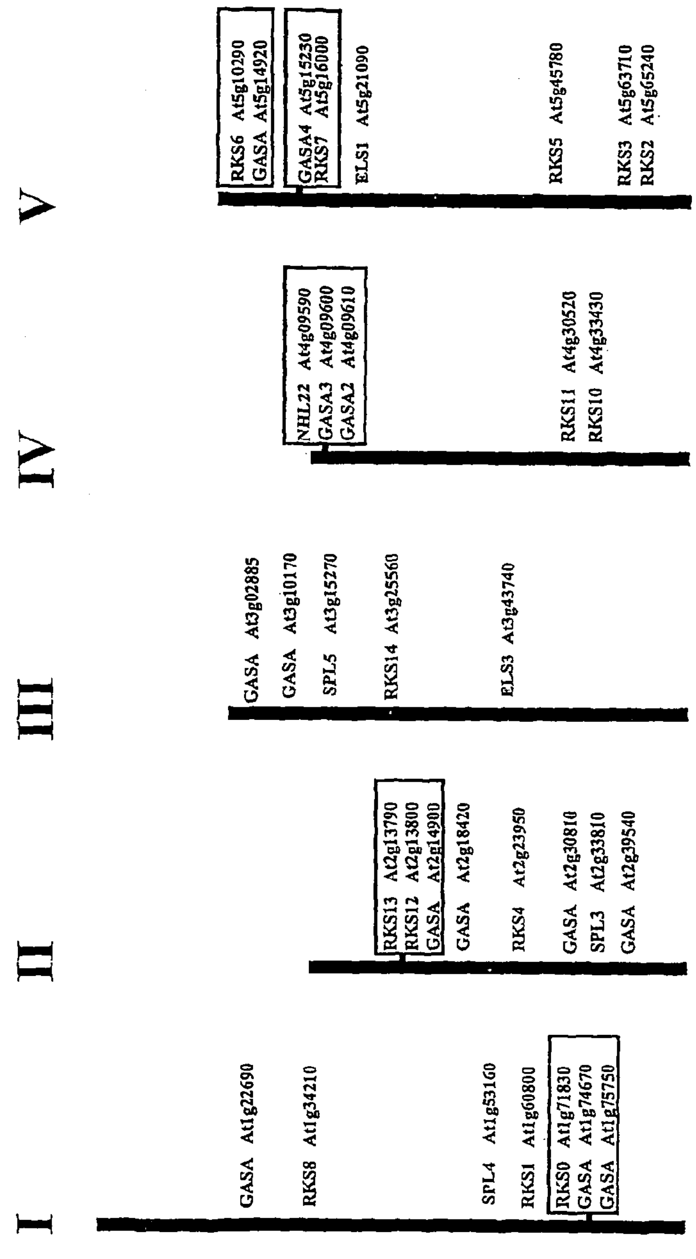
Figure 6:
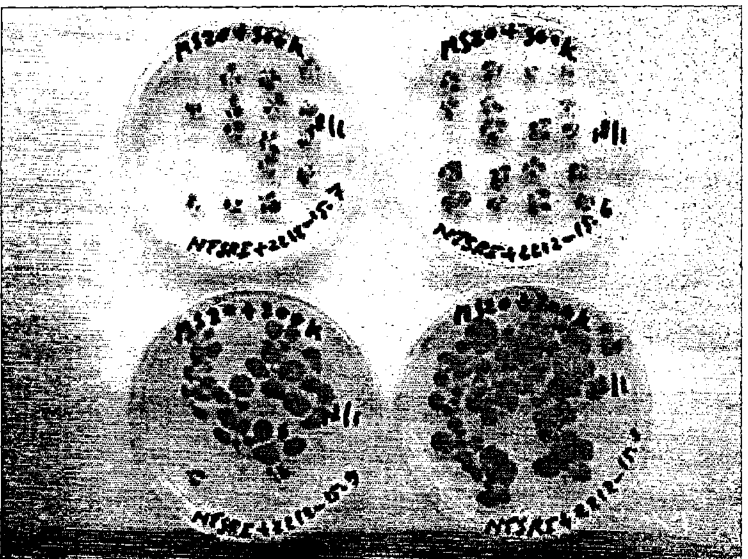

Some members of this gene family have been described previously, and represent the GASA family in *Arabidopsis thaliana* (Plant Mol. Biol. 36 (1998). Similar family members containing the same structural motifs are present in rice (like GASR1) and tomato (Plant Journal 2 (1992) 153-159; Mol. Gen. Genet. 243 (1994) Taylor and Scheuring). In *Arabidopsis*, the GASA gene family represents 14 different members, similar as the number for the RKS gene family. Our data on the similar phenotypes for RKS4 and GASA3 (FIG. 6) and the fact that there are similar numbers of ligands and receptors suggest that there is a single GASA ligand molecule interaction with a single RKS molecule. T-DNA knock out phenotypes observed with several of the other GASA peptide ligand genes also show modifications of organ and plant size like the appearance of extreme dwarf plants resembling brassinosteroid insensitive mutants. Co-localization of RKS genes and GASA ligands on the genome (see FIG. 4) could provide clues of molecular interactions between GASA molecules and RKS molecules (similar as for S locus proteins and S locus receptor kinases).

Furthermore, in the chapter discussing the effects of roots in RKS transgenic plants, it was shown that overexpression of RKS genes can result in the formation of lateral roots (FIG.

26). One of the GASA ligands is involved in the formation and/or outgrowth of lateral roots as discussed in Mol. Gen. Genet. 243, 1994, 148-157.

Intracellularly, this signal is transmitted onto membrane (but not necessarily plasma membrane) associated NDR-NHL proteins. At least some of the functions of the syntaxin-like NDR-NHL proteins would thereby result in the regulation of vesicle transport and/or the positioning of new cell wall formation. Neighboring cells are known to influence and determine the developmental state and the differentiation of cells. In transgenic plants with RKS and/or NDR-NHL expression cassettes the positioning of new cell walls is modified, resulting in abnormal neighboring cells, resulting in abnormal development of groups of cells like flower meristem primordia as observed and shown with RKS0, RKS13 and NHL10.

Predicted Amino Acid Sequence of the *Arabidopsis thaliana* ELS1 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The last domain might be involved in attachment to other proteins or structures within the cell wall.

TABLE 2 overview of accessions numbers of RKS signal complex genes in *arabidopsis* and in rice:

| Gene | code | contig | gene prediction in At database | *Oryza sativa japonica* contig | approximate position in bp around: |
|---|---|---|---|---|---|
| RKS0 | At1g71830 | f14o23 | ok | OSJNBa0036B21 | 52.000 |
| RKS1 | At1g60800 | f8a5 | ok | P0038C05 | 60.000 |
| RKS2 | At5g65240 | mqn23 | ok | OJ1212_C08 | 8000 |
| RKS3 | At5g63710 | mbk5 | ok | see rks2 | |
| RKS4 | At2g23950 | t29e15 | wrong, exon missing | P0708B04 | 35.000 |
| RKS5 | At5g45780 | mra19 | wrong, exon missing | OJ1077_A12 | 102.000 |
| RKS6 | At5g10290 | wt e 23 | ok | see rks2 | |
| RKS7 | At5g16000 | ku e 24 | ok | P0038C05 | 60.000 |
| RKS8 | At1g34210 | f23m19 | ok | OJ1134_B10 | 90.000 & 1000 2 different genes ! |
| RKS10 | At4g33430 | en d 25 | wrong, exon missing | see rks0 | |
| RKS11 | At4g30520 | wu d 20 | wrong, exon missing | see rks4 | |
| RKS12 | At2g13800 | f13j11 | wrong, exon missing | see rks10 | |
| RKS13 | At2g13790 | f13j11 | ok | P0633E08 | 36.000 |
| RKS14 | At3g25560 | mwl2 | wrong, exon missing | OSJNBb0015G09 | 36.000 |
| ELS1 | At5g21090 | ch e 52 | ok | P0003H10 | 53.000 |
| ELS2 | possibly allelic variant of ELS1 no genomic sequence identified yet | | | | see els1 |
| ELS3 | At3g43740 | by c 21 | ok | P0468B07 | 52.000 |

Homology between aa sequences from *arabidopsis* proteins are compared with the rice databases using protein sequences based on *Oryza sativa japonica* contig sequences.

*Arabidopsis thaliana* ELS1 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 32)
ttactctcaaattccttttcgatttccctctcttaaacctccgaaagctc
acATGGCGTCTCGAAACTATCGGTGGGAGCTCTTCGCAGCTTCGTTAACC
CTAACCTTAGCTTTGATTCACCTGGTCGAAGCAAACTCCGAAGGAGATGC
TCTCTACGCTCTTCGCCGGAGTTTGACAGATCCAGACCATGTCCTCCAGA
GCTGGGATCCAACTCTTGTTAATCCTTGTACCTGGTTCCATGTCACCTGT
AACCAAGACAACCGCGTCACTCGTGTGGATTTGGGAAATTCAAACCTCTC
TGGACATCTTGCGCCTGAGCTTGGGAAGCTTGAACATTTACAGTATCTAG
AGCTCTACAAAAACAACATCCAAGGAACTATACCTTCCGAACTTGGAAAT
CTGAAGAATCTCATCAGCTTGGATCTGTACAACAACAATCTTACAGGGAT
AGTTCCCACTTCTTTGGGAAAATTGAAGTCTCTGGTCTTTTTACGGCTTA
ATGACAACCGATTGACGGTCCAATCCCTAGAGCACTCACGGCAATCCCAA
GCCTTTAAAGTTGTGACGTCTCAAGCAATGATTTGTGTGGACAATCCCAC
AAACGGACCCTTTGCTCACATTCCTTTACAGAACTTTGAGAACAACCCGA
GATTGGAGGGACCGGAATTACTCGGTCTTGCAAGCTACGACACTAACTGC
ACCTGAacaactggcaaaacctgaaaatgaagaattggggggtgaccttg
taagaacacttcaccactttatcaaatatcacatctactatgtaataagt
atatatatgtagtccaaaaaaaaaaaaaaaaa
```

```
(SEQ ID NO: 33)
MASRNYRWELFAASL
TLTLALIHLVEANSEG

DALYALRRSLTDP
DHVLQSWDPTLVN

PCTWFHVTCNQDNRVTRV

                  DLGNSNLSGHLA
P ELGKLEHLQYLELYKNNIQGTI
PSELGNLKNLISLDLYNNNLTGIV
PTSLGKLKSLVFLRLNDNRLTGPI
PRALTAIPSLKVVDVSSNDLCGTI
PTNGPFAHIPLQNFENNPRLEGPE

LLGLASYDTNCT
```

*Arabidopsis thaliana* ELS2 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 34)
aaaattactcaaattcctattagattactctcttcgacctccgatagctc
acATGGCGTCTCGAAACTATCGGTGGGAGCTCTTCGCAGCTTCGTTAATC
CTAACCTTAGCTTTGATTCACCTGGTCGAAGCAAACTCCGAAGGAGATGC
TCTTTACGCTCTTCGCCGGAGTTTAACAGATCCGGACCATGTCCTCCAGA
GCTGGGATCCAACTCTTGTTAATCCTTGTACCTGGTTCCATGTCACCTGT
AACCAAGACAACCGCGTCACTCGTGTGGATTTGGGGAATTCAAACCTCTC
TGGACATCTTGCGCCTGAGCTTGGGAAGCTTGAACATTTACAGTATCTAG
AGCTCTACAAAAACAACATCCAAGGAACTATACCTTCCGAACTTGGAAAT
CTGAAGAATCTCATCAGCTTGGATCTGTACAACAACAATCTTACAGGGAT
AGTTCCCACTTCTTTGGGAAAATTGAAGTCTCTGGTCTTTTTACGGCTTA
ATGACAACCGATTGACGGGGCAATCCCTAGAGCACTCACTGCCAATCCCA
AGCCTTAAAAGTTGTGGATGTCTAAGCAATGATTTGTGTGGAACAATCCC
AACAAACGGACCTTTTGCTCACATTCCTTTACAGAACTTTGAGAACAACC
CGAGGTTGGAGGGACCGGAATTACTCGGTCTTGCAAGCTACGACACTAAC
TGCACCTGAagaaattggcaaaacctgaaaatgaagaattgggggggacc
ttgtaagaacacttcaccactttatcaaatatcacatctactatgtaata
agtatatatatgtagtccaaaaaaaaaatgaagaatcgaatagtaatatc
atctggtctcaattgagaactttgaggtctgtgtatgaaaattaaagatt
gtactgtaatgttcggttgtgggattctgagaagtaacatttgtattggt
atggtatcaagttgttctgccttgtctgcaaaaaaaaa
```

Predicted Amino Acid Sequence of the *Arabidopsis thaliana* ELS2 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The last domain might be involved in attachment to other proteins or structures within the cell wall.

```
(SEQ ID NO: 35)
MASRNYRWELFAASL
ILTLALIHLVEANSEG

DALYALRRSLTDP
DHVLQSWDPTLVN

PCTWFHVTCNQDNRVTRV

             DLGNSNLSGHLA
P ELGKLEHLQYLQLYKNNIQGTI
PSELGNLKNLISLDLYNNNLTGIV
PTSLGKLKSLVFLRLNDNRLTGPI
PRALTAIPSLKVVDVSSNDLCGTI
PTNGPFAHIPLQNFENNPRLEGPE

LLGLASYDTNCT
```

*Arabidopsis thaliana* ELS3 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 36)
ttctctctccggcgaaaaccATGGTGGCGCAAAACAGTCGGCGGGAGCTT
CTAGCAGCTTCCCTGATCCTAACTTTAGCTCTAATTCGTCTAACGGAAGC
AAACTCCGAAGGGGACGCTCTTCACGCGCTTCGCCGGAGCTTATCAGATC
CAGACAATGTTGTTCAGAGTTGGGATCCAACTCTTGTTAATCCTTGTACT
TGGTTTCATGTCACTTGTAATCAACACCATCAAGTCACTCGTCTGGATTT
```

-continued

```
GGGGAATTCAAACTTATCTGGACATCTAGTACCTGAACTTGGGAAGCTTG
AACATTTACAATATCTTGAACTCTACAAAAACGAGATTCAAGGAACTATA
CCTTCTGAGCTTGGAAATCTGAAGAGTCTAATCAGTTTGGATCTGTACAA
CAACAATCTCACCGGGAAAATCCCATCTTCTTTGGGAAAATTGAAGCGGC
TTAACGAAAACCGATTGACCGGTCCTATTCCTAGAGAACTCACAGTTATT
TCAAGCCTTAAAGTTGTTGATGTCTCAGGGAATGATTTGTGTGGAACAAT
TCCAGTAGAAGGACCTTTTGAACACATTCCTATGCAAAACTTTGAGAACA
ACCTGAGATTGGAGGGACCAGAACTACTAGGTCTTGCGAGCTATGACACC
AATTGCACTTAAaaagaagttgaagaa
```

Predicted Amino Acid Sequence of the *Arabidopsis thaliana* ELS3 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The last domain might be involved in attachment to other proteins or structures within the cell wall.

```
(SEQ ID NO: 37)
MVAQNSRRELLAASL
ILTLALIRLTEANSEG

DALHALRRSLSDP
DNVVQSWDPTLVN

PCTWFHVTCNQHHQVTRL

             DLGNSNLSGHLV
P ELGKLEHLQYLELYKNEIQGTI
PSELGNLKSLISLDLYNNNLTGKI
P     SSLGKLKRLNENRLTGPI
PRELTVISSLKVVDVSGNDLCGTI
PVEGPFEHIPMQNFENNLRLEGPE

LLGLASYDTNCT
```

*Arabidopsis thaliana* RKS0 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 38)
atttttattttatttttactctttgtttgttttaatgctaatgggtttt
taaaagggttatcgaaaaaatgagtgagtttgtgttgaggttgtctctgt
aaagtgttaatggtggtgattttcggaagttagggttttctcggatctga
agagatcaaatcaagattcgaaatttaccattgttgtttgaaATGGAGTC
GAGTTATGTGGTGTTTATCTTACTTTCACTGATCTTACTTCCGAATCATT
CACTGTGGCTTGCTTCTGCTAATTTGGAAGGTGATGCTTTGCATACTTTG
AGGGTTACTCTAGTTGATCCAAACAATGTCTTGCAGAGCTGGGATCCTAC
GCTAGTGAATCCTTGCACATGGTTCCATGTCACTTGCAACAACGAGAACA
GTGTCATAAGAGTTGATTTGGGGAATGCAGAGTTATCTGGCCATTTAGTT
CCAGAGCTTGGTGTGCTCAAGAATTTGCAGTATTTGGAGCTTTACAGTAA
CAACATAACTGGCCCGATTCCTAGTAATCTTGGAAATCTGACAAACTTAG
TGAGTTTGGATCTTTACTTAAACAGCTTCTCCGGTCCTATTCCGGAATCA
TTGGGAAAGCTTTCAAAGCTGAGATTTCTCCGGCTTAACAACAACAGTCT
CACTGGGTCAATTCCTATGTCACTGACCAATATTACTACCCTTCAAGTGT
TAGATCTATCAAATAACAGACTCTCTGGTTCAGTTCCTGACAATGGCTCC
TTCTCACTCTTCACACCCATCAGTTTTGCTAATAACTTAGACCTATGTGG
ACCTGTTACAAGTCACCCATGTCCTGGATCTCCCCCGTTTTCTCCTCCAC
```

-continued

```
CACCTTTTATTCAACCTCCCCCAGTTTCCACCCCGAGTGGGTATGGTATA
ACTGGAGCAATAGCTGGTGGAGTTGCTGCAGGTGCTGCTTTGCCCTTTGC
TGCTCCTGCAATAGCCTTTGCTTGGTGGCGACGAAGAAGCCCACTAGATA
TTTTCTTCGATGTCCCTGCCGAAGAAGATCCAGAAGTTCATCTGGGACAG
CTCAAGAGGTTTTCTTTGCGGGAGCTACAAGTGGCGAGTGATGGGTTTAG
TAACAAGAACATTTTGGGCAGAGGTGGGTTTGGGAAAGTCTACAAGGGAC
GCTTGGCAGACGGAACTCTTGTTGCTGTCAAGAGACTGAAGGAAGAGCGA
ACTCCAGGTGGAGAGCTCCAGTTTCAAACAGAAGTAGAGATGATAAGTAT
GGCAGTTCATCGAAACCTGTTGAGATTACGAGGTTTCTGTATGACACCGA
CCGAGAGATTGCTTGTGTATCCTTACATGGCCAATGGAAGTGTTGCTTCG
TGTCTCAGAGAGAGGCCACCGTCACAACCTCCGCTTGATTGGCCAACGCG
GAAGAGAATCGCGCTAGGCTCAGCTCGAGGTTTGTCTTACCTACATGATC
ACTGCGATCCGAAGATCATTCACCGTGACGTAAAAGCAGCAAACATCCTC
TTAGACGAAGAATTCGAAGCGGTTGTTGGAGATTTCGGGTTGGCAAAGCT
TATGGACTATAAAGACACTCACGTGACAACAGCAGTCCGTGGCACCATCG
GTCACATCGCTCCAGAATATCTCTCAACCGGAAAATCTTCAGAGAAAACC
GACGTTTTCGGATACGGAATCATGCTTCTAGAACTAATCACAGGACAAAG
AGCTTTCGATCTCGCTCGGCTAGCTAACGACGACGACGTCATGTTACTTG
ACTGGGTGAAAGGATTGTTGAAGGAGAAGAAGCTAGAGATGTTAGTGGAT
CCAGATCTTCAAACAAACTACGAGGAGAGAGAACTGGAACAAGTGATACA
AGTGGCGTTGCTATGCACGCAAGGATCACCAATGGAAAGACCAAAGATGT
CTGAAGTTGTAAGGATGCTGGAAGGAGATGGGCTTGCGGAGAAATGGGAC
GAATGGCAAAAAGTTGAGATTTTGAGGGAAGAGATTGATTTGAGTCCTAA
TCCTAACTCTGATTGGATTCTTGATTCTACTTACAATTTGCACGCCGTTG
AGTTATCTGGTCCAAGGTAAaaaaaaaaaaaaaaaaa
```

Predicted Amino Acid Sequence of the *Arabidopsis thaliana* RKS0 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 39)
MESSYVVFILLSLILLPNHSL
WLASANLEG

DALHTLRVTLVDP
NNVLQSWDPTLVN

PCTWFHVTCNNENSVIRV

                     DLGNAELSGHLV
P ELGVLKNLQYLELYSNNITGPI
PSNLGNLTNLVSLDLYLNSFSGPI
PESLGKLSKLRFLRLNNNSLTGSI
PMSLTNITTLQVLDLSNNRLSGSV
PDNGSFSLFTPISFANNLDLCGPV

TSHPCPGSPPFSPPPP
FIQPPPVSTPSGYGITG

AIAGGVAAGAAL
PFAAPAIAFAWW
```

-continued

```
RRRKPLDIFFDVPAEEDPE
VHLGQLKRFSLRELQVAS

DGFSNKNILGRGGFGKVYKGRLAD
GTLVAVKRLKEERTPGGELQFQ
TEVEMISMAVHRNLLRLRGFCM
TPTERLLVYPYMANGSVASCLR
ERPPSQPPLDWPTRKRIALGSA
RGLSYLHDHCDPKIIHRDVKAA
NILLDEEFEAVVGDFGLAKLMD
YKDTHVTTAVRGTIGHIAPEYL
STGKSSEKTDVFGYGIMLLELI
TGQRAFDLARLANDDDVMLLDW
VKGLLKEKKLEMLVDPDLQTNY
EERELEQVIQVALLCTQGSPME
RPKMSEVVRMLE

GDGLAEKWDEWQKVEILREEIDLS

PNPNSDWILDSTYNLHAVELSGPR
```

*Arabidopsis thaliana* RKS1 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 40)
ccaaagttgattgctttaagaagggatATGGAAGGTGTGAGATTTGTGGT
GTGGAGATTAGGATTTCTGGTTTTTGTATGGTTCTTTGATATCTCTTCTG
CTACACTTTCTCCTACTGGTGTAAACTATGAAGTGACAGCTTTGGTTGCT
GTGAAGAATGAATTGAATGATCCGTACAAAGTTCTTGAGAATTGGGATGT
GAATTCAGTTGATCCTTGTAGCTGGAGAATGGTTTCTTGCACTGATGGCT
ATGTCTCTTCACTGGATCTTCCTAGCCAAAGCTTGTCTGGTACATTGTCT
CCTAGAATCGGAAACCTCACCTATTTACAATCAGTGGTGTTGCAAAACAA
TGCAATCACTGGTCCAATTCCGGAAACGATTGGGAGGTTGGAGAAGCTTC
AGTCACTTGATCTTTCGAACAATTCATTCACCGGGGAGATACCGGCCTCA
CTTGGAGAACTCAAGAACTTGAATTACTTGCGGTTAAACAATAACAGTCT
TATAGGAACTTGCCCTGAGTCTCTATCCAAGATTGAGGGACTCACTCTAG
TCGACATTTCGTATAACAATCTTAGTGGTTCGCTGCCAAAAGTTTCTGCC
AGAACTTTCAAGGTAATTGGTAATGCGTTAATCTGTGGCCCAAAAGCTGT
TTCAAACTGTTCTGCTGTTCCCGAGCCTCTCACGCTTCCACAAGATGGTC
CAGATGAATCAGGAACTCGTACCAATGGCCATCACGTTGCTCTTGCATTT
GCCGCAAGCTTCAGTGCAGCATTTTTTGTTTTCTTTACAAGCGGAATGTT
TCTTTGGTGGAGATATCGCCGTAACAAGCAAATATTTTTTGACGTTAATG
AACAATATGATCCAGAAGTGAGTTTAGGGCACTTGAAGAGGTATACATTC
AAAGAGCTTAGATCTGCCACCAATCATTTCAACTCGAAGAACATTCTCGG
AAGAGGCGGATACGGGATTGTGTACAAAGGACACTTAAACGATGGAACTT
TGGTGGCTGTCAAACGTCTCAAGGACTGTAACATTGCGGGTGGAGAAGTC
CAGTTTCAGACAGAAGTAGAGACTATAAGTTTGGCTCTTCATCGCAATCT
CCTCCGGCTCCGCGGTTTCTGTAGTAGCAACCAGGAGAGAATTTTAGTCT
ACCCTTACATGCCAAATGGGAGTGTCGCATCACGCTTAAAAGATAATATC
CGTGGAGAGCCAGCATTAGACTGGTCGAGAAGGAAGAAGATAGCGGTTGG
GACAGCGAGAGGACTAGTTTACCTACACGAGCAATGTGACCCGAAGATTA
TACACCGCGATGTGAAAGCAGCTAACATTCTGTTAGATGAGGACTTCGAA
GCAGTTGTTGGTGATTTTGGGTTAGCTAAGCTTCTAGACCATAGAGACTC
TCATGTCACAACTGCAGTCCGTGGAACTGTTGGCCACATTGCACCTGAGT
ACTTATCCACGGGTCAGTCCTCAGAGAAGACTGATGTCTTTGGCTTTGGC
ATACTTCTCCTTGAGCTCATTACTGGTCAGAAAGCTCTTGATTTTGGCAG
ATCCGCACACCAGAAAGGTGTAATGCTTGACTGGGTGAAGAAGCTGCACC
AAGAAGGGAAACTAAAGCAGTTAATAGACAAAGATCTAAATGACAAGTTC
GATAGAGTAGAACTCGAAGAAATCGTTCAAGTTGCGCTACTCTGCACTCA
ATTCAATCCATCTCATCGACCGAAAATGTCAGAAGTTATGAAGATGCTTG
AAGGTGACGGTTTGGCTGAGAGATGGGAAGCGACGCAGAACGGTACTGGT
GAGCATCAGCCACCGCCATTGCCACCGGGGATGGTGAGTTCTTCGCCGCG
TGTGAGGTATTACTCGGATTATATTCAGGAATCGTCTCTTGTAGTAGAAG
CCATTGAGCTCTCGGGTCCTCGATGAttatgactcactgtttttaaaaaa
```

Predicted Amino Acid Sequence of the *Arabidopsis thaliana* RKS1 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 41)
MEGVRFVVWRLGFL
VFVWFFDISSATLSPTGVNYEV

TALVAVKNELNDP
YKVLENWDVNSVD

PCSWRMVSCTDGYVSSL
              DLPSQSLSGT
LSPRIGNLTYLQSVLQNNAITGPI
PETIGRLEKLQSLDLSNNSFTGEI
PASLGELKNLNYLRLNNNSLIGTC
PESLSKIEGLTLVDISYNNLSGSL
PKVSARTFK    VIGNALICGPK

AVSNCSAVPEPLTL
PQDGPDESGTRTNG

HHVALAFAASFS
AAFFVFFTSGMFLWW

RYRRNKQIFFDVNEQYDPE
VSLGHLKRYTFKELRSAT

NHFNSKNILGRGGYGIVYKGHLND
GTLVAVKRLKDCNIAGGEVQFQ
TEVETISLALHRNLLRLRGFCS
SNQERILVYPYPMPNGSVASRLK
DNIRGEPALDWSRRKKIAVGTA
RGLVYLHEQCDPKIIHRDVKAA
NILLDEDFEAVVGDFGLAKLLD
HRDSHVTTAVRGTVGHIAPEYL
STGQSSEKTDVFGFGILLLELI
TGQKALDFGRSAHQKGVMLDW
VKKLHQEGKLKQLIDKDLNDKF
DRVELEEIVQVALLCTQFNPSH
RPKMSEVMKMLE

GDGLAERWEATQNGTGEHQPPPLPPGMVSSS

PRVRYYSDYIQESSLVVEAIELSGPR
```

*Arabidopsis thaliana* RKS2 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

Italics indicate the presence of an alternatively spliced gene product.

(SEQ ID NO: 42)
tcaattttggtagctcttagaaaaATGGCTCTGCTTATTATCACTGCCTT
AGTTTTAGTAGTTTATGGTCATCTGTGTCACCAGATGCTCAAGGGGATG
CATTATTTGCGTTGAGGAGCTCGTTACGTGCATCTCCTGAACAGCTTAGT
GATTGGAACCAGAATCAAGTCGATCCTTGTACTTGGTCTCAAGTTATTTG
TGATGACAAGAAACATGTTACTTCTGTAACCTTGTCTTACATGAACTTCT
CCTCGGGAACACTGTCTTCAGGAATAGGAATCTTGACAACTCTCAAGACT
CTTACATTGAAGGGAAATGGAATAATGGGTGGAATACCAGAATCCATTGG
AAATCTGTCTAGCTTGACCAGCTTAGATTTGGAGGATAATCACTTAACTG
ATCGCATTCCATCCACTCTCGGTAATCTCAAGAATCTACAGTTCTTCAGG
ACCTTGAGTAGGAATAACCTTAATGGTTCTATCCCGGATTCACTTACAGG
TCTATCAAAACTGATAAATATTCTGCTCGACTCAAATAATCTCAGTGGTG
AGATTCCTCAGAGTTTATTCAAAATCCCAAAATACAATTTCACAGCAAAC
AACTTGAGCTGTGGTGGCACTTTCCCGCAACCTTGTGTAACCGAGTCCAG
TCCTTCAGGTGATTCAAGCAGTAGAAAAACTGGAATCATCGCTGGAGTTG
TTAGCGGAATAGCGGTTATTCTACTAGGATTCTTCTTCTTTTTCTTCTGC
AAGGATAAACATAAAGGATATAAACGAGACGTATTTGTGGATGTTGCAGG
AACGAACTTTAAAAAAGGTTTGATTTCAGGTGAAGTGGACAGAAGGATTG
CTTTTGGACAGTTGAGAAGATTTGCATGGAGAGAGCTTCAGTTGGCTACA
GATGAGTTCAGTGAAAAGAATGTTCTCGGACAAGGAGGCTTTGGGAAAGT
TTACAAAGGATTGCTTTCGGATGGCACCAAAGTCGCTGTAAAAAGATTGA
CTGATTTTGAACGTCCAGGAGGAGATGAAGCTTTCCAGAGAGAAGTTGAG
ATGATAAGTGTAGCTGTTCATAGGAATCTGCTTCGCCTTATCGGCTTTTG
TACAACACAAACTGAACGACTTTTGGTGTATCCTTTCATGCAGAATCTAA
GTGTTGCATATTGCTTAAGAGAGATTAAACCCGGGGATCCAGTTCTGGAT
TGGTTCAGGAGGAAACAGATTGCGTTAGGTGCAGCACGAGGACTCGAATA
TCTTCATGAACATTGCAACCCGAAGATCATACACAGAGATGTGAAAGCTG
CAAATGTGTTACTAGATGAAGACTTTGAAGCAGTGGTTGGTGATTTTGGT
TTAGCCAAGTTGGTAGATGTTAGAAGGACTAATGTAACCACTCAGGTCCG
AGGAACAATGGGTCATATTGCACCAGAATGTATATCCACAGGGAAATCGT
CAGAGAAAACCGATGTTTTCGGGTACGGAATTATGCTTCTGGAGCTTGTA
ACTGGACAAAGAGCAATTGATTTCTCGCGGTTAGAGGAAGAAGATGATGT
CTTATTGCTAGACCATGTGAAGAAACTGGAAAGAGAGAAGAGATTAGAAG
ACATAGTAGATAAGAAGCTTGATGAGGATTATATAAAGGAAGAAGTTGAA
ATGATGATACAAGTAGCTCTGCTATGCACACAAGCAGCACCGGAAGAACG
ACCAGCGATGTCGGAAGTAGTAAGAATGCTAGAAGGAGAAGGGCTTGCAG
AGAGATGGGAAGAGTGGCAGAATCTTGAAGTGACGAGACAAGAAGAGTTT
CAGAGGTTGCAGAGGAGATTTGATTGGGGTGAAGATTCCATTAATAATCA
AGATGCTATTGAATTATCTGGTGGAAGATAGaaacaaaaaa Predicted Amino Acid Sequence of the *Arabidopsis thaliana* RKS2 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 3 complete and 2 incomplete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions. Italics indicate an alternatively spliced gene product.

```
(SEQ ID NO: 43)
MALLIITALVFSSL
WSSVSPDAQG

DALFALRSSLR
ASPEQLSDWNQNQVD

PCTWSQVICDDKKHVTSV
      TLSYMNFSS  GTLSSGI
G    ILTTLKTLTLKGNGIMGGI
PESIGNLSSLTSLDLEDNHLTDRI
PSTLGNLKNLQFLTLSRNNLNGSI
PDSLTGLSKLINILLDSNNLSGEI
PQSLFKIPKYN   FTANNLSCGG

TFPQPCVTESSPSGDSSSRKTG

IIAGVVSGIAVIL
LGFFFFFC

KDKHKGYKRDVFVDVAGTNFKKGLISGE
VDRRIAFGQLRRFAWRELQLAT

DEFSEKNVLGQGGFGKVYKGLLSD
GTKVAVKRLTDFERPGGDEAFQ
REVEMISVAVHRNLLRLIGFCT
TQTERLLVYPFMQNLSVAYCLR
EIKPGDPVLDWFRRKQIALGAA
RGLEYLHEHCNPKIIHRDVKAA
NVLLDEDFEAVVGDFGLAKLVD
VRRTNVTTQVRGTMGHIAPECI
STGKSSEKTDVFGYGIMLLELV
TGQRAIDFSRLEEEDDVLLLDH
VKKLEREKRLEDIVDKKLDEDY
IKEEVEMMIQVALLCTQAAPEE
RPAMSEVVRMLE

GEGLAERWEEWQNLEVTRQEEFQ

RLQRRFDWGEDSINNQDAIELSGGR
```

*Arabidopsis thaliana* RKS3 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 44)
aacggtgaaagtttccatgatcctcttcgaggattcattcaaagaaattg
ctttagatggaacaatcagaaattgatcttacaatgtttcATGGCCTTAG
CTTTTGTGGGAATCACTTCGTCAACAACTCAACCAGATATCGAAGGAGGA
GCTCTGTTGCAGCTCAGAGATTCGCTTAATGATTCGAGCAATCGTCTAAA
ATGGACACGCGATTTTGTGAGCCCTTGCTATAGTTGGTCTTATGTTACCT
GCAGAGGCCAGAGTGTTGTGGCTCTAAATCTTGCCTCGAGTGGATTCACA
GGAACACTCTCTCCAGCTATTACAAAACTGAAGTTCTTGGTTACCTTAGA
GTTACAGAACAATAGTTTATCTGGTGCCTTACCAGATTCTCTTGGGAACA
TGGTTAATCTACAGACTTTAAACCTATCAGTGAATAGTTTCAGCGGATCG
ATACCAGCGAGCTGGAGTCAGCTCTCGAATCTAAAGCACTTGGATCTCTC
ATCCAATAATTTAACAGGAAGCATCCCAACACAATTCTTCTCAATCCCAA
CATTCGATTTTTCAGGAACTCAGCTTATATGCGGTAAAAGTTTGAATCAG
CCTTGTTCTTCAAGTTCTCGTCTTCCAGTCACATCCTCCAAGAAAAAGCT
GAGAGACATTACTTTGACTGCAAGTTGTGTTGCTTCTATAATCTTATTCC
TTGGAGCAATGGTTATGTATCATCACCATCGCGTCCGCAGAACCAAATAC
GACATCTTTTTTGATGTAGCTGGGGAAGATGACAGGAAGATTTCCTTTGG
ACAACTAAAACGATTCTCTTTACGTGAAATCCAGCTCGCAACAGATAGTT
TCAACGAGAGCAATTTGATAGGACAAGGAGGATTTGGTAAAGTATACAGA
GGTTTGCTTCCAGACAAAACAAAAGTTGCAGTGAAACGCCTTGCGGATTA
CTTCAGTCCTGGAGGAGAAGCTGCTTTCCAAAGAGAGATTCAGCTCATAA
GCGTTGCGGTTCATAAAAATCTCTTACGCCTTATTGGCTTCTGCACAACT
TCCTCTGAGAGAATCCTTGTTTATCCATACATGGAAAATCTTAGTGTTGC
ATATCGACTAAGAGATTTGAAAGCGGGAGAGGAAGGATTAGACTGGCCAA
CAAGGAAGCGTGTAGCTTTTGGTTCAGCTCACGGTTTAGAGTATCTACAC
GAACATTGTAACCCGAAGATCATACACCGCGATCTCAAGGCTGCAAACAT
ACTTTTAGACAACAATTTTGAGCCAGTTCTTGGAGATTTCGGTTTAGCTA
```

-continued

```
AGCTTGTGGACACATCTCTGACTCATGTCACAACTCAAGTCCGAGGCACA
ATGGGTCACATTGCGCCAGAGTATCTCTGCACAGGAAAATCATCTGAAAA
AACCGATGTTTTTGGTTACGGTATAACGCTTCTTGAGCTTGTTACTGGTC
AGCGCGCAATCGATTTTTCACGCTTGGAAGAAGAGGAAAATATTCTCTTG
CTTGATCATATAAAGAAGTTGCTTAGAGAACAGAGACTTAGAGACATTGT
TGATAGCAATTTGACTACATATGACTCCAAAGAAGTTGAAACAATCGTTC
AAGTGGCTCTTCTCTGCACACAAGGCTCACCAGAAGATAGACCAGCGATG
TCTGAAGTGGTCAAAATGCTTCAAGGGACTGGTGGTTTGGCTGAGAAATG
GACTGAATGGGAACAACTTGAAGAAGTTAGGAACAAAGAAGCATTGTTGC
TTCCGACTTTACCGGCTACTTGGGATGAAGAAGAAACCACCGTTGATCAA
GAATCTATCCGATTATCGACAGCAAGATGAagaagaaacagagagagaaa
gatatctatgaaaa
```

Predicted Amino Acid Sequence of the *Arabidopsis thaliana* RKS3 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 4 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 45)
MALAFVGITSSTTQPDIEG

GALLQLRDSLNDSSNRL
KWTRDFVS

PCYSWSYVTCRGQSVVAL

                   NLASSGFTGTLS
P AITKLKFLVTLELQNNSLSGAL
PDSLGNMVNLQTLNLSVNSFSGSI
PASWSQLSNLKHLDLSSNNLTGSI
PTQFFSIPTFEFSGTQLICGKS

LNQPCSSSRLPVTSSKKKLRD

ITLTASCVASIIL
FLGAMVMYHHH

RVRRTKYDIFFDVAGEDDR
KISFGQLKRFSLREIQLAT

DSFNESNLIGQGGFGKVYRGLLPD
KTKVAVKRLADYFSPGGEAAFQ
REIQLISVAVHKNLLRLIGFCT
TSSERILVYPYMENLSVAYRLR
DLKAGEEGLDWPTRKRVAFGSA
HGLEYLHEHCNPKIIHRDLKAA
NILLDNNFEPVLGDFGLAKLVD
TSLTHVTTQVRGTMGHIAPEYL
CTGKSSEKTDVFGYGITLLELV
TGQRAIDFSRLEEEENILLLD
HIKKLLREQRLRDIVDSNLTTY
DSKEVETIVQVALLCTQGSPED
```

-continued

RPAMSEVVKMLQ

GTGGLAEKWTEWEQLEEVRNKEALLL

PTLPATWDEEETTVDQESIRLSTAR

*Arabidopsis thaliana* RKS4 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 46)
tcttccttctccttctggtaatctaatctaaagcttttcATGGTGGTGAT
GAAGATATTCTCTGTTCTGTTACTACTATGTTTCTTCGTTACTTGTTCTC
TCTCTTCTGAACCCAGAAACCCTGAAGTGGAGGCGTTGATAAACATAAAG
AACGAGTTACATGATCCACATGGTGTTTTCAAAAACTGGGATGAGTTTTC
TGTTGATCCTTGTAGCTGGACTATGATCTCTTGTTCTTCAGACAACCTCG
TAATTGGCTTAGGAGCTCCAAGTCAGTCTCTTTCAGGAACTTTATCTGGG
TCTATTGGAAATCTCACTAATCTTCGACAAGTGTCATTACAGAACAATAA
CATCTCCGGTAAAATCCCACCGGAGATTTGTTCTCTTCCCAAATTACAGA
CTCTGGATTTATCCAATAACCGGTTCTCCGGTGAAATCCCCGGTTCTGTT
AACCAGCTGAGTAATCTCCAATATCTGTTGAACAACAACTCATTATCTGG
GCCCTTTCCTGCTTCTCTGTCTCAAATCCCTCACCTCTCTTTCTTAGACT
TGTCTTATAACAATCTCAGAGGTCCTGTTCCTAAATTTCCTGCAAGGACA
TTCAATGTTGCTGGGAACCCTTTGATTTGTAAAAACAGCCTACCGGAGAT
TTGTTCAGGATCAATCAGTGCAAGCCCTCTTTCTGTCTCTTTACGTTCTT
CATCAGGACGTAGAACCAACATATTAGCAGTTGCACTTGGTGTAAGCCTT
GGCTTTGCTGTTAGTGTAATCCTCTCTCTCGGGTTCATTTGGTATCGAAA
GAAACAAAGACGGTTAACGATGCTTCGCATTAACAAGCAAGAGGAAGGGT
TACTTGGGTTGGGAAATCTAAGAAGCTTCACATTCAGGGAACTTCATGTA
GCTACGGATGGTTTTAGTTCCAAGAGTATTCTTGGTGCTGGTGGGTTTGG
TAATGTCTACAGAGGAAAATTCGGGGATGGGACAGTGGTTGCAGTGAAAC
GATTGAAAGATGTGAATGGAACCTCCGGGAACTCACAGTTTCGTACTGAG
CTTGAGATGATCAGCTTAGCTGTTCATAGGAATTTGCTTCGGTTAATCGG
TTATTGTGCGAGTTCTAGCGAAAGACTTCTTGTTTACCCTTACATGTCCA
ATGGCAGCGTCGCCTCTAGGCTCAAAGCTAAGCCAGCGTTGGACTGGAAC
ACAAGGAAGAAGATAGCGATTGGAGCTGCAAGAGGGTTGTTTTATCTACA
CGAGCAATGCGATCCCAAGATTATTCACCGAGATGTCAAGGCAGCAAACA
TTCTCCTAGATGAGTATTTTGAAGCAGTTGTTGGGGATTTTGGACTAGCA
AAGCTACTCAACCACGAGGATTCACATGTCACAACCGCGGTTAGAGGAAC
TGTTGGTCACATTGCACCTGAGTATCTCTCCACCGGTCAGTCATCTGAGA
AAACCGATGTCTTTGGGTTCGGTATACTTTTGCTAGAGCTCATCACAGGA
ATGAGAGCTCTCGAGTTTGGCAAGTCTGTTAGCCAGAAAGGAGCTATGCT
AGAATGGGTGAGGAAGCTACACAAGGAAATGAAAGTAGAGGAGCTAGTAG
ACCGAGAACTGGGGACAACCTACGATAGAATAGAAGTTGGAGAGATGCTA
CAAGTGGCACTGCTCTGCACTCAGTTTCTTCCAGCTCACAGACCCAAAAT
GTCTGAAGTAGTTCAGATGCTTGAAGGAGATGGATTAGCTGAGAGATGGG
CTGCTTCACATGACCATTCACATTTCTACCATGCCAACATGTCTTACAGG
ACTATTACCTCTACTGATGGCAACAACCAAACCAAACATCTGTTTGGCTC
CTCAGGATTTGAAGATGAAGATGATAATCAAGCGTTAGATTCATTCGCCA
TGGAACTATCTGGTCCAAGGTAGtaaatcttggacacagaaagaaacaga
tataatatccccatgacttcaattttgtt Predicted Amino Acid Sequence of the *Arabidopsis thaliana* RKS4 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 47)
MVVMKLITMKIFSVLLLL
CFFVTCSLSSEPRNPEV

EALINIKNELHDP
HGVFKNWDEFSVD

PCSWTMISCSSDNLVIGL
GAPSQSLSGTLS
G SIGNLTNLRQVSLQNNNISGKI
PPEICSLPKLQTLDLSNNRFSGEI
PGSVNQLSNLQYLRLNNNSLSGPPF
PASLSQIPHLSFLDLSYNNLRGPV
PKFPARTFNVAGNPLICKNS

LPEICSGSISASPL
SVSLRSSSGRRTN

ILAVALGVSLGFAVSVIL
SLGFIWY

RKKQRRLTMLRINKQEE
GLLGLGNLRSFTFRELHVAT

DGFSSKSILGAGGFGNVYRGKFGD
GTVVAVKRLKDVNGTSGNSQFR
TELEMISLAVHRNLLRLIGYCA
SSSERLLVYPYMSNGSVASRLK
AKPALDWNTRKKIAIGAA
RGLFYLHEQCDPKIIHRDVKAA
NILLDEYFEAVVGDFGLAKLLN
HEDSHVTTAVRGTVGHIAPEYL
STGQSSEKTDVFGFGILLLELI
TGMRALEFGKSVSQKGAMLEW
VRKLHKEMKVEELVDRELGTTY
DRIEVGEMLQVALLCTQFLPAH
RPKMSEVVQMLE

GDGLAERWAASHDHSHFYHANM
SYRTITSTDGNNQTKHLFG

SSGFEDEDDNQALDSFAMELSGPR

*Arabidopsis thaliana* RKS5 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 48)
ctagagaattcttatactttttctacgATGGAGATTTCTTTGATGAAGTT
TCTGTTTTTAGGAATCTGGGTTTATTATTACTCTGTTCTTGACTCTGTTT
CTGCCATGGATAGTCTTTTATCTCCCAAGGTGGCTGCGTTAATGTCAGTG
AAGAACAAGATGAAAGATGAGAAAGAGGTTTTGTCTGGTTGGGATATTAA
CTCTGTTGATCCTTGTACTTGGAACATGGTTGGTTGTTCTTCTGAAGGTT
TTGTGGTTTCTCTAGAGATGGCTAGTAAAGGATTATCAGGGATACTATCT
ACTAGTATTGGGGAATTAACTCATCTTCATACTTTGTTACTTCAGAATAA
TCAGTTAACTGGTCCGATTCCTTCTGAGTTAGGCCAACTCTCTGAGCTTG
AAACGCTTGATTTATCGGGGAATCGGTTTAGTGGTGAAATCCCAGCTTCT
TTAGGGTTCTTAACTCACTTAAACTACTTGCGGCTTAGCAGGAATCTTTT
ATCTGGGCAAGTCCCTCACCTCGTCGCTGGCCTCTCAGGTCTTTCTTTCT
TGGATCTATCTTTCAACAATCTAAGCGGACCAACTCCGAATATATCAGCA
AAAGATTACAGGAAATGCATTTCTTTGTGGTCCAGCTTCCCAAGAGCTTT
GCTCAGATGCTACACCTGTGAGAAATGCTGCAATCGATCTGCAGCGACGG
GTTTGTCTGAAAAGGACAATAGCAAACATCACAGCTTAGTGCTCTCTTTT -continued

```
GCATTTGGCATTGTTGTTGCCTTTATCATCTCCCTAATGTTTCTCTTCTT
CTGGGTGCTTTGGCATCGATCACGTCTCTCAAGATCACACGTGCAGCAAG
ACTACGAATTTGAAATCGGCCATCTGAAAAGGTTCAGTTTTCGCGAAATA
CAAACCGCAACAAGCAATTTTAGTCCAAAGAACATTTTGGGACAAGGAGG
GTTTGGGATGGTTTATAAAGGGTATCTCCCAAATGGAACTGTGGTGGCAG
TTAAAAGATTGAAAGATCCGATTTATACAGGAGAAGTTCAGTTTCAAACC
GAAGTAGAGATGATTGGCTTAGCTGTTCACCGTAACCTTTTACGCCTCTT
TGGATTCTGTATGACCCCGGAAGAGAGAATGCTTGTGTATCCGTACATGC
CAAATGGAAGCGTAGCTGATCGTCTGAGAGATTGGAATCGGAGGATAAGC
ATTGCACTCGGCGCAGCTCGAGGACTTGTTTACTTGCACGAGCAATGCAA
TCCAAAGATTATTCACAGAGACGTCAAAGCTGCAAATATTCTACTTGATG
AGAGCTTTGAAGCAATAGTTGGCGATTTTGGTCTAGCAAAGCTTTTAGAC
CAGAGAGATTCACATGTCACTACCGCAGTCCGAGGAACCATTGGACACAT
CGCTCCCGAGTACCTTTCCACTGGACAGTCCTCAGAGAAAACCGATGTTT
TCGGATTCGGAGTACTAATCCTTGAACTCATAACAGGTCATAAGATGATT
GATCAAGGCAATGGTCAAGTTCGAAAAGGAATGATATTGAGCTGGGTAAG
GACATTGAAAGCAGAGAAGAGATTTGCAGAGATGGTGGACAGAGATTTGA
AGGGAGAGTTTGATGATTTGGTGTTGGAGGAAGTAGTGGAATTGGCTTTG
CTTTGTACACAGCCACATCCGAATCTAAGACCGAGGATGTCTCAAGTGTT
GAAGGTACTAGAAGGTTTAGTGGAACAGTGTGAAGGAGGGTATGAAGCTA
GAGCTCCAAGTGTCTCTAGGAACTACAGTAATGGTCATGAAGAGCAGTCC
TTTATTATTGAAGCCATTGAGCTCTCTGGACCACGATGAtagacttcata
gtgtcttaactagtcttcttgattttgttgtcattgtcatggc
```

Predicted Amino Acid Sequence of the *Arabidopsis thaliana* RKS5 Protein.

Different domains are spaced and shown from the N-terminus towards the C-terminus. Overall domain structure is similar as described in Schmidt et al (1997).

At the predicted extracellular domain the first domain represents a signal sequence. The second domain contains no leucine zipper motif, in contrast to the other RKS proteins. The third domain contains conserved cysteine residues, involved in disulphate bridge formation. The fourth domain contains a leucine rich repeat domain, consisting of 5 complete repeats of each approximately 24 amino acid residues. The fifth domain contains many serine residues, and is likely to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 49)
MEISLMKFLFLGIWVYYYS
VLDSVSAMDSLLSPKV

AALMSVKNKMKDE
KEVLSGWDINSVD

PCTWNMVGCSSEGFVVS

                LEMASKGLSGILS
T SIGELTHLHTLLLQNNQLTGPI
PSELGQLSELETLDLSGNRFSGEI
PASLGFLTHLNYLRLSRNLLSGQV
PHLVAGLSGLSFLDLSFNNLSGPT
PNISAK     DYRKCISLWSSFPR

ALLRCYTCEKCCNR
SAATGLSEKDNSK

HHSLVLSFAFGIVV
AFIISLMFLFFWVLWH

RSRLSRSHVQQDYEF
EIGHLKRFSFREIQTAT
```

-continued

```
SNFSPKNILGQGGFGMVYKGYLPN
GTVVAVKRLKDPIYTGEVQFQ
TEVEMIGLAVHRNLLRLFGFCM
TPEERMLVYPYMPNGSVADRLR
DWNRRISIALGAA
RGLVYLHEQCNPKIIHRDVKAA
NILLDESFEAIVGDFGLAKLLD
QRDSHVTTAVRGTIGHIAPEYL
STGQSSEKTDVFGFGVLILELI
TGHKMIDQGNGQVRKGMILSW
VRTLKAEKRFAEMVDRDLKGEF
DDLVLEEVVELALLCTQPHPNL
RPRMSQVLKV

LEGLVEQCEGGYEARA

PASVSRNYSNGHEEQSFIIEAIELSGPR
```

*Arabidopsis thaliana* RKS6 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 50)
attgtttccttcttttgggattttctccttggatggaaccagctcaatta
atgagatgagATGAGAATGTTCAGCTTGCAGAAGATGGCTATGGCTTTTA
CTCTCTTGTTTTTTGCCTGTTTATGCTCATTTGTGTCTCCAGATGCTCAA
GGGGATGCACTGTTTGCGTTGAGGATCTCCTTACGTGCATTACCGAATCA
GCTAAGTGACTGGAATCAGAACCAAGTTAATCCTTGCACTTGGTCCCAAG
TTATTTGTGATGACAAAAACTTTGTCACTTCTCTTACATTGTCAGATATG
AACTTCTCGGGAACCTTGTCTTCAAGAGTAGGAATCCTAGAAAATCTCAA
GACTCTTACTTTAAAGGGAAATGGAATTACGGGTGAAATACCAGAAGACT
TTGGAAATCTGACTAGCTTGACTAGTTTGGATTTGGAGGACAATCAGCTA
ACTGGTCGTATACCATCCACTATCGGTAATCTCAAGAAACTTCAGTTCTT
GACCTTGAGTAGGAACAAACTTAATGGGACTATTCCGGAGTCACTCACTG
GTCTTCCAAACCTGTTAAACCTGCTGCTTGATTCCAATAGTCTCAGTGGT
CAGATTCCTCAAAGTCTGTTTGAGATCCCAAAATATAATTTCACGTCAAA
CAACTTGAATTGTGGCGGTCGTCAACCTCACCCTTGTGTATCCGCGGTTG
CCCATTCAGGTGATTCAAGCAAGCCTAAAACTGGCATTATTGCTGGAGTT
GTTGCTGGAGTTACAGTTGTTCTCTTTGGAATCTTGTTGTTTCTGTTCTG
CAAGGATAGGCATAAAGGATATAGACGTGATGTGTTTGTGGATGTTGCAG
GTGAAGTGGACAGGAGAATTGCATTTGGACAGTTGAAAAGGTTTGCATGG
AGAGAGCTCCAGTTAGCGACAGATAACTTCAGCGAAAAGAATGTACTTGG
TCAAGGAGGCTTTGGGAAAGTTTACAAAGGAGTGCTTCCGGATACACCCA
AAGTTGCTGTGAAGAGATTGACGGATTTCGAAAGTCCTGGTGGAGATGCT
GCTTTCCAAAGGGAAGTAGAGATGATAAGTGTAGCTGTTCATAGGAATCT
ACTCCGTCTTATCGGGTTCTGCACCACACAAACAGAACGCCTTTTGGTTT
ATCCCTTCATGCAGAATCTAAGTCTTGCACATCGTCTGAGAGAGATCAAA
GCAGGCGACCCGGTTCTAGATTGGGAGACGAGGAAACGGATTGCCTTAGG
AGCAGCGCGTGGTTTTGAGTATCTTCATGAACATTGCAATCCGAAGATCA
TACATCGTGATGTGAAAGCAGCTAATGTGTTACTAGATGAAGATTTTGAA
GCAGTGGTTGGTGATTTTGGTTTAGCCAAGCTAGTAGATGTTAGAAGGAC
TAATGTGACTACTCAAGTTCGAGGAACAATGGGTCACATTGCACCAGAAT
ATTTATCAACAGGGAAATCATCAGAGAGAACCGATGTTTTCGGGTATGGA
ATTATGCTTCTTGAGCTTGTTACAGGACAACGCGCAATAGACTTTTCACG
TTTGGAGGAAGAAGATGATGTCTTGTTACTTGACCACGTGAAGAAACTGG
AAAGAGAGAAGAGATTAGGAGCAATCGTAGATAAGAATTTGGATGGAGAG
TATATAAAAGAAGAAGTAGAGATGATGATACAAGTGGCTTTGCTTTGTAC
ACAAGGTTCACCAGAAGACCGACCAGTGATGTCTGAAGTTGTGAGGATGT
TAGAAGGAGAAGGGCTTGCGGAGAGATGGGAAGAGTGGCAAAACGTGGAA
GTCACGAGACGTCATGAGTTTGAACGGTTGCAGAGGAGATTTGATTGGGG
TGAAGATTCTATGCATAACCAAGATGCCATTGAATTATCTGGTGGAAGAT
GAccaaaaacatcaaacctt
```

Predicted Amino Acid Sequence of the *Arabidopsis thaliana* RKS6 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 51)
MRMFSL
QKMAMAFTLLFFACLCSFVSPDAQG

DALFALRISLRALP
NQLSDWNQNQVN

PCTWSQVICDDKNFVTSL

TLSDMNFSGTLSSRV
GILENLKTLTLKGNGITGEI
PEDFGNLTSLTSLDLEDNQLTGRI
PSTIGNLKKLQFLTLSRNKLNGTI
PESLTGLPNLLNLLLDSNSLSGQI
PQSLFEIPKYNFTSNNLNCGG

RQPHPCVSAVAHSGDSSKPKTG

IIAGVVAGVTVVL
FGILLFLFC

KDRHKGYRRDVFVDVAGE
VDRRIAFGQLKRFAWRELQLAT

DNFSEKNVLGQGGFGKVYKGVLPD
TPKVAVKRLTDFESPGGDAAFQ
REVEMISVAVHRNLLRLIGFCT
TQTERLLVYPFMQNLSLAHRLR
EIKAGDPVLDWETRKRIALGAA
RGFEYLHEHCNPKIIHRDVKAA
NVLLDEDFEAVVGDFGLAKLVD
VRRTNVTTQVRGTMGHIAPEYL
STGKSSERTDVFGYGIMLLELV
TGQRAIDFSRLEEEDDVLLLDH
VKKLEREKRLGAIVDKNLDGEY
IKEEVEMMIQVALLCTQGSPED
RPVMSEVVRMLE

GEGLAERWEEWQNVEVTRRHEFE

RLQRRFDWGEDSMHNQDAIELSGGR

*Arabidopsis thaliana* RKS7 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 52)
acatcttgttttctgctcattcctctgtttcaacaATGGAGAGTACTATT
GTTATGATGATGATGATAACAAGATCTTTCTTTTGCTTCTTGGGATTTTT
ATGCCTTCTCTGCTCTTCTGTTCACGGATTGCTTTCTCCTAAAGGTGTTA
ACTTTGAAGTGCAAGCTTTGATGGACATAAAAGCTTCATTACATGATCCT -continued CATGGTGTTCTTGATAACTGGGATAGAGATGCTGTTGATCCTTGTAGTTG
GACAATGGTCACTTGTTCTTCTGAAAACTTTGTCATTGGCTTAGGCACAC
CAAGTCAGAATTTATCTGGTACACTATCTCCAAGCATTACCAACTTAACA
AATCTTCGGATTGTGCTGTTGCAGAACAACAACATAAAAGGAAAAATTCC
TGCTGAGATTGGTCGGCTTACGAGGCTTGAGACTCTTGATCTTTCTGATA
ATTTCTTCCACGGTGAAATTCCTTTTTCAGTAGGCTATCTACAAAGCCTG
CAATATCTGAGGCTTAACAACAATTCTCTCTCTGGAGTGTTTCCTCTGTC
ACTATCTAATATGACTCAACTTGCCTTTCTTGATTTATCATACAACAATC
TTAGTGGTCCTGTTCCAAGATTTGCTGCAAAGACGTTTAGCATCGTTGGG
AACCCGCTGATATGTCCAACGGGTACCGAACCAGACTGCAATGGAACAAC
ATTGATACCTATGTCTATGAACTTGAATCAAACTGGAGTTCCTTTATACG
CCGGTGGATCGAGGAATCACAAAATGGCAATCGCTGTTGGATCCAGCGTT
GGGACTGTATCATTAATCTTCATTGCTGTTGGTTTGTTTCTCTGGTGGAG
ACAAAGACATAACCAAAACACATTCTTTGATGTTAAAGATGGGAATCATC
ATGAGGAAGTTTCACTTGGAAACCTGAGGAGATTTGGTTTCAGGGAGCTT
CAGATTGCGACCAATAACTTCAGCAGTAAGAACTTATTGGGGAAAGGTGG
CTATGGAAATGTATACAAAGGAATACTTGGAGATAGTACAGTGGTTGCAG
TGAAAAGGCTTAAAGATGGAGGAGCATTGGGAGGAGAGATTCAGTTTCAG
ACAGAAGTTGAAATGATCAGTTTAGCTGTTCATCGAAATCTCTTAAGACT
CTACGGTTTCTGCATCACACAAACTGAGAAGCTTCTAGTTTATCCTTATA
TGTCTAATGGAAGCGTTGCATCTCGAATGAAAGCAAAACCTGTTCTTGAC
TGGAGCATAAGGAAGAGGATAGCCATAGGAGCTGCAAGAGGGCTTGTGTA
TCTCCATGAGCAATGTGATCCGAAGATTATCCACCGCGATGTCAAAGCAG
CGAATATACTTCTTGATGACTACTGTGAAGCTGTGGTTGGCGATTTTGGT
TTAGCTAAACTCTTGGATCATCAAGATTCTCATGTGACAACCGCGGTTAG
AGGCACGGTGGGTCACATTGCTCCAGAGTATCTCTCAACTGGTCAATCCT
CTGAGAAAACAGATGTTTTTGGCTTCGGGATTCTTCTTCTTGAGCTTGTA
ACCGGACAAAGAGCTTTTGAGTTTGGTAAAGCGGCTAACCAGAAAGGTGT
GATGCTTGATTGGGTTAAAAAGATTCATCAAGAGAAGAAACTTGAGCTAC
TTGTGGATAAAGAGTTGTTGAAGAAGAAGAGCTACGATGAGATTGAGTTA
GACGAAATGGTAAGAGTAGCTTTGTTGTGCACACAGTACCTGCCAGGACA
TAGACCAAAAATGTCTGAAGTTGTTCGAATGCTGGAAGGAGATGGACTTG
CAGAGAAATGGGAAGCTTCTCAAAGATCAGACAGTGTTTCAAAATGTAGC
AACAGGATAAATGAATTGATGTCATCTTCAGACAGATACTCTGATCTTAC
CGATGACTCTAGTTTACTTGTGCAAGCAATGGAGCTCTCTGGTCCTAGAT
GAaatctatacatgaatctgaagaagaagaagaacatgcatctgtttctt
gaatcaagagggattcttgtttttttgtataatagagaggtttttttggag
ggaaatgttgtgtctctgtaactgtataggcttgttgtgtaagaagttat
tactgcacttagggttaattcaaagttctttacataaaaaatgattagtt
gcgttgaatagagggaacactttgggagatttcatgtatgaaatttggaa
aaaaaaaaaaaaaaaaa Predicted Amino Acid Sequence of the *Arabidopsis thaliana* RKS7 Protein.

Different domains are spaced and shown from the N-terminus towards the C-terminus. Overall domain structure is similar as described in Schmidt et al (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 53)
MESTIVMMMMITRSFF
CFLGFLCLLCSSVHGLLSPKGVNFEV

QALMDIKASLHDP

-continued

```
HGVLDNWDRDAVD

PCSWTMVTCSSENFVIG

                   LGTPSQNLSGTL
SPSITNLTNLRIVLLQNNNIKGKI
PAEIGRLTRLETLDLSDNFFHGEI
PFSVGYLQSLQYLRLNNNSLSGVF
PLSLSNMTQLAFLDLSYNNLSGPV
PRFAA    KTFSIVGNPLICPT

GTEPDCNGTTLIPMSMNL
NQTGVPLYAGGSRNHKMA

IAVGSSVGTVSLIFIAVGLFLWW

RQRHNQNTFFDVKDGNHHE
EVSLGNLRRFGFRELQIAT

NNFSSKNLLGKGGYGNVYKGILGD
STVVAVKRLKDGGALGGEIQFQ
TEVEMISLAVHRNLLRLYGFCI
TQTEKLLVYPYMSNGSVA
SRMKAKPVLDWSIRKRIAIGAA
RGLVYLHEQCDPKIIHRDVKAA
NILLDDYCEAVVGDFGLAKLLD
HQDSHVTTAVRGTVGHIAPEYL
STGQSSEKTDVFGFGILLLELV
TGQRAFEFGKAANQKGVMLDW
VKKIHQEKKLELLVDKELLKKKSY
DEIELDEMVRVALLCTQYLPGH
RPKMSEVVRMLE

GDGLAEKWEASQRSDS
VSKCSNRINELMSSS

DRYSDLTDDSSLLVQAMELSGPR
```

*Arabidopsis thaliana* RKS8 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

(SEQ ID NO: 54)

```
gtttttttttttttaccctcttggaggatctgggaggagaaatttgcttt
tttttggtaaATGGGGAGAAAAAAGTTTGAAGCTTTTGGTTTTGTCTGCT
TAATCTCACTGCTTCTTCTGTTTAATTCGTTATGGCTTGCCTCTTCTAAC
ATGGAAGGTGATGCACTGCACAGTTTGAGAGCTAATCTAGTTGATCCAAA
TAATGTCTTGCAAAGCTGGGATCCTACGCTTGTTAATCCGTGTACTTGGT
TTCACGTAACGTGTAACAACGAGAACAGTGTTATAAGAGTCGATCTTGGG
AATGCAGACTTGTCTGGTCAGTTGGTTCCTCAGCTAGGTCAGCTCAAGAA
CTTGCAGTACTTGGAGCTTTATAGTAATAACATAACCGGGCCGGTTCCAA
GCGATCTTGGGAATCTGACAAACTTAGTGAGCTTGGATCTTTACTTGAAC
AGCTTCACTGGTCCAATTCCAGATTCTCTAGGAAAGCTATTCAAGCTTCG
CTTTCTTCGGCTCAACAATAACAGTCTCACCGGACCAATTCCCATGTCAT
TGACTAATATCATGACCCTTCAAGTTTTGGATCTGTCGAACAACCGATTA
TCCGGATCTGTTCCTGATAATGGTTCCTTCTCGCTCTTCACTCCCATCAG
TTTTGCTAACAACTTGGATCTATGCGGCCCAGTTACTAGCCGTCCTTGTC
CTGGATCTCCCCCGTTTTCTCCTCCACCACCTTTTATACCACCTCCCATA
GTTCCTACACCAGGTGGGTATAGTGCTACTGGAGCCATTGCGGGAGGAGT
TGCTGCTGGTGCTGCTTTACTATTTGCTGCCCCTGCTTTAGCTTTTGCTT
GGTGGCGTAGAAGAAAACCTCAAGAATTCTTCTTTGATGTTCCTGCCGAA
GAGGACCCTGAGGTTCACTTGGGGCAGCTTAAGCGGTTCTCTCTACGGGA
ACTTCAAGTAGCAACTGATAGCTTCAGCAACAAGAACATTTTGGGCCGAG
GTGGGTTCGGAAAAGTCTACAAAGGCCGTCTTGCTGATGGAACACTTGTT
GCAGTCAAACGGCTTAAAGAAGAGCGAACCCCAGGTGGCGAGCTCCAGTT
TCAGACAGAAGTGGAGATGATAAGCATGGCCGTTCACAGAAATCTCCTCA
GGCTACGCGGTTTCTGTATGACCCCTACCGAGAGATTGCTTGTTTATCCT
TACATGGCTAATGGAAGTGTCGCTTCCTGTTTGAGAGAACGTCCACCATC
ACAGTTGCCTCTAGCCTGGTCAATAAGACAGCAAATCGCGCTAGGATCAG
CGAGGGGTTTGTCTTATCTTCATGATCATTGCGACCCCAAAATTATTCAC
CGTGATGTGAAAGCTGCTAATATTCTGTTGGACGAGGAATTTGAGGCGGT
GGTAGGTGATTTCGGGTTAGCTAGACTTATGGACTATAAAGATACTCATG
```

-continued

```
TCACAACGGCTGTGCGTGGGACTATTGGACACATTGCTCCTGAGTATCTC
TCAACTGGAAAATCTTCAGAGAAAACTGATGTTTTTGGCTACGGGATCAT
GCTTTTGGAACTGATTACAGGTCAGAGAGCTTTTGATCTTGCAAGACTGG
CGAATGACGATGACGTTATGCTCCTAGATTGGGTGAAAGGGCTTTTGAAG
GAGAAGAAGCTGGAGATGCTTGTGGATCCTGACCTGCAAAGCAATTACAC
AGAAGCAGAAGTAGAACAGCTCATACAAGTGGCTCTTCTCTGCACACAGA
GCTCACCTATGGAACGACCTAAGATGTCTGAGGTTGTTCGAATGCTTGAA
GGTGACGGTTTAGCGGAGAAATGGGACGAGTGGCAGAAAGTGGAAGTTCT
CAGGCAAGAAGTGGAGCTCTCTTCTCACCCCACCTCTGACTGGATCCTTG
ATTCGACTGATAATCTTCATGCTATGGAGTTGTCTGGTCCAAGATAAacg
acattgtaatttgcctaacagaaaagagaaagaacagagaaatattaaga
gaatcacttctctgtattctt
```

Predicted Amino Acid Sequence of the *Arabidopsis thaliana* RKS8 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

(SEQ ID NO: 55)

```
MGRKKFEAFGFVCLISLLLLFNSL
WLASSNMEG

DALHSLRANLVDP
NNVLQSWDPTLVN

PCTWFHVTCNNENSVIRV

                  DLGNADLSGQLV
P QLGQLKNLQYLELYSNNITGPV
PSDLGNLTNLVSLDLYLNSFTGPI
PDSLGKLFKLRFLRLNNNSLTGPI
PMSLTNIMTLQVLDLSNNRLSGSV
PDNGSFSLFTPISFANNLDLCGPV

TSRFCPGSPPFSPPPP
FIPPPIVPTPGGYSATG

AIAGGVAAGAAL
LFAAPALAFAWW

RRRKPQEFFFDVPAEEDPE
VHLGQLKRFSLRELQVAT

DSFSNKNILGRGGFGKVYKGRLAD
GTLVAVKRLKEERTPGGELQFQ
TEVEMISMAVHRNLLRLRGFCM
TPTERLLVYPYMANGSVASCLR
ERPPSQLPLAWSIRQQIALGSA
RGLSYLHDHCDPKIIHRDVKAA
NILLDEEFEAVVGDFGLARLMD
YKDTHVTTAVRGTIGHIAPEYL
STGKSSEKTDVFGYGIMLLELI
```

```
-continued
TGQRAFDLARLANDDDVMLLDW
VKGLLKEKKLEMLVDPDLQSNY
TEAEVEQLIQVALLCTQSSPME
RPKMSEVVRMLE

GDGLAEKWDEWQKVEVLRQEVELS

SHPTSDWILDSTDNLHAMELSGPR
```

*Arabidopsis thaliana* rks10 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 56)
atcaggggttttaacaatgatggattttctctgatgagggatagttctag
ggtttgtttttaatctcttgaggataaaATGGAACGAAGATTAATGATCC
CTTGCTTCTTTTGGTTGATTCTCGTTTTGGATTTGGTTCTCAGAGTCTCG
GGCAACGCCGAAGGTGATGCTCTAAGTGCACTGAAAAACAGTTTAGCCGA
CCCTAATAAGGTGCTTCAAAGTTGGGATGCTACTCTTGTTACTCCATGTA
CATGGTTTCATGTTACTTGCAATAGCGACAATAGTGTTACACGTGTTGAC
CTTGGGAATGCAAATCTATCTGGACAGCTCGTAATGCAACTTGGTCAGCT
TCCAAACTTGCAGTACTTGGAGCTTTATAGCAATAACATTACTGGGACAA
TCCCAGAACAGCTTGGAAATCTGACGGAATTGGTGAGCTTGGATCTTTAC
TTGAACAATTTAAGCGGGCCTATTCCATCAACTCTCGGCCGACTTAAGAA
ACTCCGTTTCTTGCGTCTTAATAACAATAGCTTATCTGGAGAAATTCCAA
GGTCTTTGACTGCTGTCCTGACGCTACAAGTTCTGGATCTCTCAAACAAT
CCTCTCACCGGAGATATTCCTGTTAATGGTTCCTTTTCACTTTTCACTCC
AATCAGTTTTGCCAACACCAAGTTGACTCCCCTTCCTGCATCTCCACCGC
CTCCTATCTCTCCTACACCGCCATCACCTGCAGGGAGTAATAGAATTACT
GGAGCGATTGCGGGAGGAGTTGCTGCAGGTGCTGCACTTCTATTTGCTGT
TCCGGCCATTGCACTAGCTTGGTGGCGAAGGAAAAAGCCGCAGGACCACT
TCTTTGATGTACCAGCTGAAGAGGACCCAGAAGTTCATTTAGGACAACTG
AAGAGGTTTTCATTGCGTGAACTACAAGTTGCTTCGGATAATTTTAGCAA
CAAGAACATATTGGGTAGAGGTGGTTTTGGTAAAGTTTATAAAGGACGGT
TAGCTGATGGTACTTTAGTGGCCGTTAAAAGGCTAAAAGAGGAGCGCACC
CAAGGTGGCGAACTGCAGTTCCAGACAGAGGTTGAGATGATTAGTATGGC
GGTTCACAGAAACTTGCTTCGGCTTCGTGGATTTTGCATGACTCCAACCG
AAAGATTGCTTGTTTATCCCTACATGGCTAATGGAAGTGTTGCCTCCTGT
TTAAGAGAACGTCCCGAGTCCCAGCCACCACTTGATTGGCCAAAGAGACA
GCGTATTGCGTTGGGATCTGCAAGAGGGCTTGCGTATTTACATGATCATT
GCGACCCAAAGATTATTCATCGAGATGTGAAAGCTGCAAATATTTTGTTG
GATGAAGAGTTTGAAGCCGTGGTTGGGGATTTTGGACTTGCAAAACTCAT
GGACTACAAAGACACACATGTGACAACCGCAGTGCGTGGGACAATTGGTC
ATATAGCCCCTGAGTACCTTTCCACTGGAAAATCATCAGAGAAAACCGAT
GTCTTTGGGTATGGAGTCATGCTTCTTGAGCTTATCACTGGACAAAGGGC
TTTTGATCTTGCTCGCCTCGCGAATGATGATGATGTCATGTTACTAGACT
GGGTGAAAGGGTTGTTAAAAGAGAAGAAATTGGAAGCACTAGTAGATGTT
GATCTTCAGGGTAATTACAAAGACGAAGAAGTGGAGCAGCTAATCCAAGT
GGCTTTACTCTGCACTCAGAGTTCACCAATGGAAAGACCCAAAATGTCTG
AAGTTGTAAGAATGCTTGAAGGAGATGGTTTAGCTGAGAGATGGGAAGAG
TGGCAAAAGGAGGAAATGTTCAGACAAGATTTCAACTACCCAACCCACCA
TCCAGCCGTGTCTGGCTGGATCATTGGCGATTCCACTTCCCAGATCGAAA
ACGAATACCCCTCGGGTCCAAGATAAgattcgaaacacgaatgtttttc
tgtattttgtttttctctgtatttattgagggttttagcttc
```

Predicted Amino Acid Sequence of the *Arabidopsis thaliana* RKS10 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 4 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 57)
MERRLMIPCFFWLILVL
DLVLRVSGNAEG

DALSALKNSLADP
NKVLQSWDATLVT

PCTWFHVTCNSDNSVTRV

                DLGNANLSGQLV
M QLGQLPNLQYLELYSNNITGTI
PEQLGNLTELVSLDLYLNNLSGPI
PSTLGRLKKLRFLRLNNNSLSGEI
PRSLTAVLTLQVLDLSNNPLTGDI
PVNGSFSLTPISFANTK  LT PL

PASPPPPISPTPPSPAGSNRITG

AIAGGVAAGAAL
LFAVPAIALAWW

RRKKPQDHFFDVPAEEDPE
VHLGQLKRFSLRELQVAS

DNFSNKNILGRGGFGKVYKGRLAD
GTLVAVKRLKEERTQGGELQFQ
TEVEMISMAVHRNLLRLRGFCM
TPTERLLVYPYMANGSVASCLR
ERPESQPPLDWPKRQRIALGSA
RGLAYLHDHCDPKIIHRDVKAA
NILLDEEFEAVVGDFGLAKLMD
YKDTHVTTAVRGTIGHIAPEYL
STGKSSEKTDVFGYGVMLLELI
TGQRAFDLARLANDDDVMLLDW
VKGLLKEKKLEALVDVDLQGNY
KDEEVEQLIQVALLCTQSSPME
RPKMSEVVRMLE

GDGLAERWEEWQKEEMFRQDFNYPTHH

PAVSGWIIGDSTSQIENEYPSGPR
```

*Arabidopsis thaliana* RKS 11 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 58)
ttgttaacctctcgtaactaaaatcttccATGGTAGTAGTAACAAAGAAG
ACCATGAAGATTCAAATTCATCTCCTTTACTCGTTCTTGTTCCTCTGTTT
CTCTACTCTCACTCTATCTTCTGAGCCCAGAAACCCTGAAGTTGAGGCGT
TGATAAGTATAAGGAACAATTTGCATGATCCTCATGGAGCTTTGAACAAT
TGGGACGAGTTTTCAGTTGATCCTTGTAGCTGGGCTATGATCACTTGCTC
TCCCGACAACCTCGTCATTGGACTAGGAGCGCCGAGCCAGTCTCTCTCGG
GAGGTTTATCTGAGTCTATCGGAAATCTCACAAATCTCCGACAAGTGTCA
TTGCAAAATAACAACATCTCCGGCAAAATTCCACCGGAGCTCGGTTTTCT
ACCCAAATTACAAACCTTGGATCTTTCCAACAACCGATTCTCCGGTGACA
TCCCTGTTTCCATCGACCAGCTAAGCAGCCTTCAATATCTGAGACTCAAC
AACAACTCTTTGTCTGGGCCCTTCCCTGCTTCTTTGTCCCAAATTCCTCA
CCTCTCCTTCTTGGACTTGTCTTACAACAATCTCAGTGGCCCTGTTCCTA
```

-continued

```
AATTCCCAGCAAGGACTTTAAACGTTGCTGGTAATCCTTTGATTTGTAGA
AGCAACCCACCTGAGATTTGTTCTGGATCAATCAATGCAAGTCCACTTTC
TGTTTCTTTGAGCTCTTCATCAGGACGCAGGTCTAATAGATTGGCAATAG
CTCTTAGTGTAAGCCTTGGCTCTGTTGTTATACTAGTCCTTGCTCTCGGG
TCCTTTTGTTGGTACCGAAAGAAACAAAGAAGGCTACTGATCCTTAACTT
AAACGCAGATAAACAAGAGGAAGGGCTTCAAGGACTTGGGAATCTAAGAA
GCTTCACATTCAGAGAACTCCATGTTTATACAGATGGTTTCAGTTCCAAG
AACATTCTCGGCGCTGGTGGATTCGGTAATGTGTACAGAGGCAAGCTTGG
AGATGGGACAATGGTGGCAGTGAAACGGTTGAAGGATATTAATGGAACCT
CAGGGGATTCACAGTTTCGTATGGAGCTAGAGATGATTAGCTTAGCTGTT
CATAAGAATCTGCTTCGGTTAATTGGTTATTGCGCAACTTCTGGTGAAAG
GCTTCTTGTTTACCCTTACATGCCTAATGGAAGCGTCGCCTCTAAGCTTA
AATCTAAACCGGCATTGGACTGGAACATGAGGAAGAGGATAGCAATTGGT
GCAGCGAGAGGTTTGTTGTATCTACATGAGCAATGTGATCCCAAGATCAT
TCATAGAGATGTAAAGGCAGCTAATATTCTCTTAGACGAGTGCTTTGAAG
CTGTTGTTGGTGACTTTGGACTCGCAAAGCTCCTTAACCATGCGGATTCT
CATGTCACAACTGCGGTCCGTGGTACGGTTGGCCACATTGCACCTGAATA
TCTCTCCACTGGTCAGTCTTCTGAGAAAACCGATGTGTTTGGGTTCGGTA
TACTATTGCTCGAGCTCATAACCGGACTGAGAGCTCTTGAGTTTGGTAAA
ACCGTTAGCCAGAAAGGAGCTATGCTTGAATGGGTGAGGAAATTACATGA
AGAGATGAAAGTAGAGGAACTATTGGATCGAGAACTCGGAACTAACTACG
ATAAGATTGAAGTTGGAGAGATGTTGCAAGTGGCTTTGCTATGCACACAA
TATCTGCCAGCTCATCGTCCTAAAATGTCTGAAGTTGTTTTGATGCTTGA
AGGCGATGGATTAGCCGAGAGATGGGCTGCTTCGCATAACCATTCACATT
TCTACCATGCCAATATCTCTTTCAAGACAATCTCTTCTCTGTCTACTACT
TCTGTCTCAAGGCTTGACGCACATTGCAATGATCCAACTTATCAAATGTT
TGGATCTTCGGCTTTCGATGATGACGATGATCATCAGCCTTTAGATTCCT
TTGCCATGGAACTATCCGGTCCAAGATAAcacaatgaaagaaagatatca
tttttacgatggatcaaacaatccaatgaaaaaa
```

Predicted Amino Acid Sequence of the *Arabidopsis thaliana* RKS11 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 59)
MVVVTKKTMKIQIHLLYSFLFL
CFSTLTLSSEPRNPEV

EALISIRNNLHDP
HGALNNWDEFSVD

PCSWAMITCSPDNLVIGL

               GAPSQSLSGGLS
 ESIGNLTNLRQVSLQNNNISGKI
PPELGFLPKLQTLDLSNNRFSGDI
PVSIDQLSSLQYLRLNNNSLSGPF
PASLSQIPHLSFLDLSYNNLSGPV
PKFPARTFNVAGNPLICRSN
```

-continued

```
PPEICSGSINASPL
SVSLSSSSGRRSNR

LAIALSVSLGSVVIL
VLALGSFCWY

RKKQRRLLILNLNGADKQEE
GLQGLGNLRSFTFRELHVYT

DGFSSKNILGAGGFGNVYRGKLGD
GTMVAVKRLKDINGTSGDSQFR
MELEMISLAVHKNLLRLIGYCA
TSGERLLVYPYMPNGSVASKLK
SKPALDWNMRKRIAIGAA
RGLLYLHEQCDPKIIHRDVKAA
NILLDECFEAVVGDFGLAKLLN
HADSHVTTAVRGTVGHIAPEYL
STGQSSEKTDVFGFGILLLELI
TGLRALEFGKTVSQKGAMLEW
VRKLHEEMKVEELLDRELGTNY
DKIEVGEMLQVALLCTQYLPAH
RPKMSEVVLMLE

GDGLAERWAASHNHSHFYHANI
SFKTISSLSTTSVSRLDAHCNDPTYQMFG

SSAFDDDDDHQPLDSFAMELSGPR
```

*Arabidopsis thaliana* RKS12 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 60)
tttaaaaaccttgctagttctcaattctcatgactttgcttttagtctta
gaagtggaaaATGGAACATGGATCATCCCGTGGCTTTATTTGGCTGATTC
TATTTCTCGATTTTGTTTCCAGAGTCACCGGAAAAACACAAGTTGATGCT
CTCATTGCTCTAAGAAGCAGTTTATCATCAGGTGACCATACAAACAATAT
ACTCCAAAGCTGGAATGCCACTCACGTTACTCCATGTTCATGGTTTCATG
TTACTTGCAATACTGAAAACAGTGTTACTCGTCTTGACCTGGGGAGTGCT
AATCTATCTGGAGAACTGGTGCCACAGCTTGCTCAGCTTCCAAATTTGCA
GTACTTGGAACTTTTTAACAATAATATTACTGGGGAGATACCTGAGGAGC
TTGGCGACTTGATGGAACTAGTAAGCTTGGACCTTTTTGCAAACAACATA
AGCGGTCCCATCCCTTCCTCTCTTGGCAAACTAGGAAAACTCCGCTTCTT
GCGTCTTTATAACAACAGCTTATCTGGAGAAATTCCAAGGTCTTTGACTG
CTCTGCCGCTGGATGTTCTTGATATCTCAAACAATCGGCTCAGTGGAGAT
ATTCCTGTTAATGGTTCCTTTTCGCAGTTCACTTCTATGAGTTTTGCCAA
TAATAAATTAAGGCCGCGACCTGCATCTCCTTCACCATCACCTTCAGGAA
CGTCTGCAGCAATAGTAGTGGGAGTTGCTGCGGGTGCAGCACTTCTATTT
GCGCTTGCTTGGTGGCTGAGAAGAAAACTGCAGGGTCACTTTCTTGATGT
ACCTGCTGAAGAAGACCCAGAGGTTTATTTAGGACAATTTAAAAGGTTCT
CCTTGCGTGAACTGCTAGTTGCTACAGAGAAATTTAGCAAAAGAAATGTA
TTGGGCAAAGGACGTTTTGGTATATTGTATAAAGGACGTTTAGCTGATGA
CACTCTAGTGGCTGTGAAACGGCTAAATGAAGAACGTACCAAGGGTGGGG
AACTGCAGTTTCAAACCGAAGTTGAGATGATCAGTATGGCCGTTCATAGG
AACTTGCTTCGGCTTCGTGGCTTTTGCATGACTCCAACTGAAAGATTACT
TGTTTATCCCTACATGGCTAATGGAAGTGTTGCTTCTTGTTTAAGAGAGC
GTCCTGAAGGCAATCCAGCCCTTGACTGGCCAAAAAGAAAGCATATTGCT
CTGGGATCAGCAAGGGGGCTCGCATATTTACACGATCATTGCGACCAAAA
GATCATTCACCTGGATGTGAAAGCTGCAAATATACTGTTAGATGAAGAGT
TTGAAGCTGTTGTTGGAGATTTTGGGCTAGCAAAATTAATGAATTATAAC
GACTCCCATGTGACAACTGCTGTACGGGGTACGATTGGCCATATAGCGCC
CGAGTACCTCTCGACAGGAAAATCTTCTGAGAAGACTGATGTTTTTGGGT
ACGGGGTCATGCTTCTCGAGCTCATCACTGGACAAAAGGCTTTCGATCTT
GCTCGGCTTGCAAATGATGATGATATCATGTTACTCGACTGGGTGAAAGA
GGTTTTGAAAGAGAAGAAGTTGGAAAGCCTTGTGGATGCAGAACTCGAAG
GAAAGTACGTGGAAACAGAAGTGGAGCAGCTGATACAAATGGCTCTGCTC
TGCACTCAAAGTTCTGCAATGGAACGTCCAAAGATGTCAGAAGTAGTGAG
AATGCTGGAAGGAGATGGTTTAGCTGAGAGATGGGAAGAATGGCAAAAGG
AGGAGATGCCAATACATGATTTTAACTATCAAGCCTATCCTCATGCTGGC
ACTGACTGGCTCATCCCCTATTCCAATTCCCTTATCGAAAACGATTACCC
CTCGGGGCCAAGATAAccttttagaaagggtcatttcttgtgggttcttc
aacaagtatatatataggtagtgaagttgtaagaagcaaaaccccacatt
cacctttgaatatcactactctataa
```

Predicted Amino Acid Sequence of the *Arabidopsis thaliana* RKS12 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 61)
MEHGSSRGFI
WLILFLDFVSRVTGKTQV

DALIALRSSLSSGDHTNNILQ
SWNATHVT

PCSWFHVTCNTENSVTRL

                  DLGSANLSGELV
P QLAQLPNLQYLELFNNNITGEI
PEELGDLMELVSLDLFANNISGPI
PSSLGKLGKLRFLRLYNNSLSGEI
PRSLTALP LDVLDISNNRLSGDI
PVNGSFSQFTSMRFA NNKLRPR

PASPSPSPSGGTS

AAIVVGVAAGAALLFALAWWL

RRKLQGHFLDVPAAEEDPE
VYLGQFKRFSLRELLVAT

EKFSKRNVLGKGRFGILYKGRLAD
DTLVAVKRLNEERTKGGELQFQ
TEVEMISMAVHRNLLRLRGFCM
TPTERLLVYPYMANGSVASCLR
ERPEGNPALDWPKRKHIALGSA
RGLAYLHDHCDQKIIHLDVKAA
NILLDEEFEAVVGDFGLAKLMN
YNDSHVTTAVRGTIGHIAPEYL
STGKSSEKTDVFGYGVMLLELI
TGQKAFDLARLANDDDIMLLDW
VKEVLKEKKLESLVDAELEGKY
VETEVEQLIQMALLCTQSSAME
RPKMSEVVRMLE

GDGLAERWEEWQKEEMPIHDFNYQAY

PHAGTDWLIPYSNSLIENDYPSGPR
```

*Arabidopsis thaliana* RKS13 cDNA

The start codons encoding predicted the methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 62)
taataaacctctaataataatggctttgcttttactctgatgacaagttc
aaaaATGGAACAAAGATCACTCCTTTGCTTCCTTTATCTGCTCCTACTAT
TCAATTTCACTCTCAGAGTCGCTGGAAACGCTGAAGGTGATGCTTTGACT
CAGCTGAAAAACAGTTTGTCATCAGGTGACCCTGCAAACAATGTACTCCA
AAGCTGGGATGCTACTCTTGTTACTCCATGTACTTGGTTTCATGTTACTT
GCAATCCTGAGAATAAAGTTACTCGTGTTGACCTTGGGAATGCAAAACTA
TCTGGAAAGTTGGTTCCAGAACTTGGTCAGCTTTTAAACTTGCAGTACTT
GGAGCTTTATAGCAATAACATTACAGGGGAGATACCTGAGGAGCTTGGCG
ACTTGGTGGAACTAGTAAGCTTGGATCTTTACGCAAACAGCATAAGCGGT
CCCATCCCTTCGTCTCTTGGCAAACTAGGAAAACTCCGGTTCTTGCGTCT
TAACAACAATAGCTTATCAGGGGAAATTCCAATGACTTTGACTTCTGTGC
AGCTGCAAGTTCTGGATATCTCAAACAATCGGCTCAGTGGAGATATTCCT
GTTAATGGTTCTTTTTCGCTCTTCACTCCTATCAGTTTTGCGAATAATAG
CTTAACGGATCTTCCCGAACCTCCGCCTACTTCTACCTCTCCTACGCCAC
CACCACCTTCAGGGGGGCAAATGACTGCAGCAATAGCAGGGGGAGTTGCT
GCAGGTGCAGCACTTCTATTTGCTGTTCCAGCCATTGCGTTTGCTTGGTG
GCTCAGAAGAAAACCACAGGACCACTTTTTGATGTACCTGCTGAAGAAG
ACCCAGAGGTTCATTTAGGACAACTCAAAAGGTTTACCTTGCGTGAACTG
TTAGTTGCTACTGATAACTTTAGCAATAAAAATGTATTGGGTAGAGGTGG
TTTTGGTAAAGTGTATAAAGGACGTTTAGCCGATGGCAATCTAGTGGCTG
TCAAAAGGCTAAAAGAAGAACGTACCAAGGGTGGGGAACTGCAGTTTCAA
ACCGAAGTTGAGATGATCAGTATGGCCGTTCATAGGAACTTGCTTCGGCT
TCGTGGCTTTTGCATGACTCCAACTGAAAGATTACTTGTTTATCCCTACA
TGGCTAATGGAAGTGTTGCTTCTTGTTTAAGAGAGCGTCCTGAAGGCAAT
CCAGCACTTGATTGGCCAAAAAGAAAGCATATTGCTCTGGGATCAGCAAG
GGGGCTTGCGTATTTACATGATCATTGCGACCAAAAAATCATTCACCGGG
ATGTTAAAGCTGCTAATATATTGTTAGATGAAGAGTTTGAAGCTGTTGTT
GGAGATTTTGGGCTCGCAAAATTAATGAATTATAATGACTCCCATGTGAC
AACTGCTGTACGCGGTACAATTGGCCATATAGCGCCCGAGTACCTCTCGA
CAGGAAAATCTTCTGAGAAGACTGATGTTTTTGGGTACGGGGTCATGCTT
CTCGAGCTCATCACTGGACAAAAGGCTTTCGATCTTGCTCGGCTTGCAAA
TGATGATGATATCATGTTACTCGACTGGGTGAAAGAGGTTTTGAAAGAGA
AGAAGTTGGAAAGCCTTGTGGATGCAGAACTCGAAGGAAAGTACGTGGAA
ACAGAAGTGGAGCAGCTGATACAAATGGCTCTGCTCTGCACTCAAAGTTC
TGCAATGGAACGTCCAAAGATGTCAGAAGTAGTGAGAATGCTGGAAGGAG
ATGGTTTAGCTGAGAGATGGGAAGAATGGCAAAAGGAGGAGATGCCAATA
CATGATTTTAACTATCAAGCCTATCCTCATGCTGGCACTGACTGGCTCAT
CCCCTATTCCAATTCCCTTATCGAAAACGATTACCCCTCGGGTCCAAGAT
AAccttttagaaagggtcttttcttgtgggttcttcaacaagtatatata
tagattggtgaagttttaagatgcaaaaaaaa
```

Predicted Amino Acid Sequence of the *Arabidopsis thaliana* RKS13 Protein.

Different domains are spaced and shown from the N-terminus towards the C-terminus. Overall domain structure is similar as described in Schmidt et al. (1997).

At the predicted extracellular domain the first domain represents a signal sequence. The second domain contains leucine zipper motifs, containing 2 times 2 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 63)
MEQRSLLCFLYLL
LLFNFTLRVAGNAEG
```

-continued

```
DALTQLKNSLSSGDP
ANNVLQSWDATLVT

PCTWFHVTCNPENKVTRV

                  DLGNAKLSGKLV
P ELGQLLNLQYLELYSNNITGEI
PEELGDLVELVSLDLYANSISGPI
PSSLGKLGKLRFLRLNNNSLSGEI
PMTLTSVQLQV LDISNNRLSGDI
PVNGSFSLFTPISFANNSLTDLPE

PPPTSTSPTPPPPSG

GQMTAAIAGGVAAGAAL
LFAVPAIAFAWWL

RRKPQDHFFDVPGAEEDPE
VHLGQLKRFTLRELLVAT

DNFSNKNVLGRGGFGKVYKGRLAD
GNLVAVKRLKEERTKGGELQFQ
TEVEMISMAVHRNLLRLRGFCM
TPTERLLVYPYMANGSVASCLR
ERPEGNPALDWPKRKHIALGSA
RGLAYLHDHCDQKIIHRDVKAA
NILLDEEFEAVVGDFGLAKLMN
YNDSHVTTAVRGTIGHIAPEYL
STGKSSEKTDVFGYGVMLLELI
TGQKAFDLARLANDDDIMLLDW
VKEVLKEKKLESLVDAELEGKY
VETEVEQLIQMALLCTQSSAME
RPKMSEVVRMLE

GDGLAERWEEWQKEEMPIHDFNYQA

YPHAGTDWLIPYSNSLIENDYPSGPR
```

*Arabidopsis thaliana* RKS14 cDNA

The start codon encoding the first predicted methionine residue of the gene product has been indicated by bold capitals.

The first stopcodon has been underlined.

Nucleotides predicted to encode protein sequences are in capitals. Leader and trailer sequences are in lowercase letters.

```
(SEQ ID NO: 64)
ctgcaccttagagattaatactctcaagaaaaacaagttttgattcggac
aaagATGTTGCAAGGAAGAAGAGAAGCAAAAAAGAGTTATGCTTTGTTCT
CTTCAACTTTCTTCTTCTTCTTTATCTGTTTTCTTTCTTCTTCTTCTGCA
GAACTCACAGACAAAGTTGTTGCCTTAATAGGAATCAAAAGCTCACTGAC
TGATCCTCATGGAGTTCTAATGAATTGGGATGACACAGCAGTTGATCCAT
GTAGCTGGAACATGATCACTTGTTCTGATGGTTTTGTCATAAGGCTAGAA
GCTCCAAGCCAAAACTTATCAGGAACTCTTTCATCAAGTATTGGAAATTT
AACAAATCTTCAAACTGTATACAGGTTATTGCAGAACAATTACATAACAG
GAAACATCCCTCATGAGATTGGGAAATTGATGAAACTCAAAACACTTGAT
CTCTCTACCAATAACTTCACTGGTCAAATCCCATTCACTCTTTCTTACTC
CAAAAATCTTCACAGGAGGGTTAATAATAACAGCCTGACAGGAACAATTC
CTAGCTCATTGGCAAACATGACCCAACTCACTTTTTTGGATTTGTCGTAT
AATAACTTGAGTGGACCAGTTCCAAGATCACTTGCCAAAACATTCAATGT
TATGGGCAATTCTCAGATTTGTCCAACAGGAACTGAGAAAGACTGTAATG
GGACTCAGCCTAAGCCAATGTCAATCACCTTGAACAGTTCTCAAAGAACT
AAAAACCGGAAAATCGCGGTAGTCTTCGGTGTAAGCTTGACATGTGTTTG
CTTGTTGATCATTGGCTTTGGTTTTCTTCTTTGGTGGAGAAGAAGACATA
ACAAACAAGTATTATTCTTTGACATTAATGAGCAAAACAAGGAAGAAATG
TGTCTAGGGAATCTAAGGAGGTTTAATTTCAAAGAACTTCAATCCGCAAC
TAGTAACTTCAGCAGCAAGAATCTGGTCGGAAAAGGAGGGTTTGGAAATG
TGTATAAAGGTTGTCTTCATGATGGAAGTATCATCGCGGTGAAGAGATTA
AAGGATATAAACAATGGTGGTGGAGAGGTTCAGTTTCAGACAGAGCTTGA
AATGATAAGCCTTGCCGTCCACCGGAATCTCCTCCGCTTATACGGTTTCT
GTACTACTTCCTCTGAACGGCTTCTCGTTTATCCTTACATGTCCAATGGC
AGTGTCGCTTCTCGTCTCAAAGCTAAACCGGTATTGGATTGGGGCACAAG
AAAGCGAATAGCATTAGGAGCAGGAAGAGGGTTGCTGTATTTGCATGAGC
AATGTGATCCAAAGATCATTCACCGTGATGTCAAAGCTGCGAACATACTT
CTTGACGATTACTTTGAAGCTGTTGTCGGAGATTTCGGGTTGGCTAAGCT
TTTGGATCATGAGGAGTCGCATGTGACAACCGCCGTGAGAGGAACAGTGG
GTCACATTGCACCTGAGTATCTCTCAACAGGACAATCTTCTGAGAAGACA
GATGTGTTCGGTTTCGGGATTCTTCTTCTCGAATTGATTACTGGATTGAG
AGCTCTTGAATTCGGAAAAGCAGCAAACCAAAGAGGAGCGATACTTGATT
GGGTAAAGAAACTACAACAAGAGAAGAAGCTAGAACAGATAGTAGACAAG
GATTTGAAGAGCAACTACGATAGAATAGAAGTGGAAGAAATGGTTCAAGT
GGCTTTGCTTTGTACACAGTATCTTCCCATTCACCGTCCTAAGATGTCTG
AAGTTGTGAGAATGCTTGAAGGCGATGGTCTTGTTGAGAAATGGGAAGCT
TCTTCTCAGAGAGCAGAAACCAATAGAAGTTACAGTAAACCTAACGAGTT
TTCTTCCTCTGAACGTTATTCGGATCTTACAGATGATTCCTCGGTGCTGG
TTCAAGCCATGGAGTTATCAGGTCCAAGATGAcaagagaaactatatgaa
tggctttgggtttgtaaaaaa
```

Predicted Amino Acid Sequence of the *Arabidopsis thaliana* RKS14 Protein.

Different domains are spaced and shown from the N-terminus towards the C-terminus. Overall domain structure is similar as described in Schmidt et al. (1997).

At the predicted extracellular domain the first domain represents a signal sequence. The second domain contains a leucine zipper motif, containing 3 leucine residues, each separated by seven other amino acids. The third domain contains conserved cysteine residues, involved in disulphate bridge formation. The fourth domain contains a leucine rich repeat domain, consisting of 5 complete repeats of each approximately 24 amino acid residues. The fifth domain contains many serine and proline residues, and is likely to contain hydroxy-proline residues, and to be a site for O-glycosylation. The sixth domain contains a single transmembrane domain after which the predicted intracellular domains are positioned. The seventh domain has an unknown function. The eight domain represents a serine/threonine protein kinase domain (Schmidt et al. 1997) and is probably also containing sequences for protein/protein interactions. The ninth domain has an unknown function. The last and tenth domain at the C-terminal end represents part of a single leucine rich repeat, probably involved in protein/protein interactions.

```
(SEQ ID NO: 65)
MLQGRREAKKSYALFSSTFF
FFFICFLSSSSAELTDKV

VALIGIKSSLTDP
HGVLMNWDDTAVD

PCSWNMITCSDGFVIR

                  LEAPSQNLSGTLSS
SIGNLTNLQTVYRLLQNNYITGNI
PHEIGKLMKLKTLDLSTNNFTGQI
PFTLSYSKNLHRRV NNNSLTGTI
PSSLANMTQLTFLDLSYNNLSGPV
PRSLAKTFNVMGNSQICPT

GTEKDCNGTQPKPMSITLNSSQR
TKNRK

IAVVFGVSLTCVCLLIIGFGFLLWW

RRRHNKQVLFFDINEQNKE
EMCLGNLRRFNFKELQSAT

SNFSSKNLVGKGGFGNVYKGCLHD
GSIIAVKRLKDINNGGGEVQFQ
TELEMISLAVHRNLLRLYGFCT
TSSERLLVYPYMSNGSVA
SRLKAKPVLDWGTRKRIALGAG
RGLLYLHEQCDPKIIHRDVKAA
NILLDDYFEAVVGDFGLAKLLD
HEESHVTTAVRGTVGHIAPEYL
STGQSSEKTDVFGFGILLLELI
TGLRALEFGKAANQRGAILDW
VKKLQQEKKLEQIVDKDLKSNY
```

-continued

```
DRIEVEEMVQVALLCTQYLPIH
RPKMSEVVRMLE

GDGLVEKWEASSQRAET
NRSYSKPNEFSSS

ERYSDLTDDSSVLVQAMELSGPR
```

LEGENDS

FIG. 1

The different domains of the predicted RKS gene product have the following functions:

The first domain of the predicted protein structure at the N-terminal end consists of a signal sequence, involved in targeting the protein towards the plasma membrane. Protein cleavage removes this sequence from the final mature protein product (Jain et al. 1994, J. Biol. Chemistry 269: 16306-16310). The second domain consists of different numbers of leucine zipper motifs, and is likely to be involved in protein dimerization. The next domain contains a conserved pair of cystein residues, involved in disulphate bridge formation. The next domain consists of 5 (or in the case of RKS3 only 4) leucine rich repeats (LRRs) shown in a gray colour, likely to be involved in ligand binding (Kobe and Deisenhofer 1994, TIBS 19: 415-420). This domain is again bordered by a domain containing a conserved pair of cystein residues involved in disulphate bridge formation often followed by a serine/. proline rich region. The next domain displays all the characteristics of a single transmembrane domain At the predicted cytoplasmic site of protein a domain is situated with unknown function, followed by a domain with serine/threonine kinase activity (Schmidt et al. 1997, Development 124: 2049-2062). The kinase domain is followed by a domain with unknown function whereas at the C-terminal end of the protein part of a leucine rich repeat is positioned, probably involved in protein-protein interactions.

FIG. 2

Alignment of the predicted protein sequences of the different RKS gene products from *Arabidopsis thaliana* with alignX, Vector NTI Suite 5.5 resulted in a phylogenetic tree in which the relative homology between the different RKS members is shown.

FIG. 3

Intron-Exon bounderies of the genomic regions on the chromosomes of *Arabidopsis thaliana* encoding the different RKS gene products. Exons are shown as boxes, whereas intron sequences are shown as lines. Sequences encoding LRR domains are displayed in gray colour, transmembrane regions in black.

FIG. 4.

Cromosomal location of RKS genes in *Arabidopsis thaliana*, showing colocalisation with GASA genes.

FIG. 5. A signaling complex comprising molecules of RKS proteins, ELS proteins, NDR/NHL proteins and SBP/SPL proteins.

FIG. 6.

Second generation (T2) tobacco seedlings germinated on MS medium. Transformations were performed with DNA clone 2212-15, representing the overexpression construct GT-RKS4-s. T2 seedlings derived from T1 plant 15.7 shows co-suppression effects while T1 plant 15.6 shows no obvious changes in level of RKS4. T1 plants 15.9 and 15.3 show overexpression effects. Plant 15.7 has the lowest remaining level of RKS4 gene product, whereas plant 15.3 has the highest level of RKS4 gene product.

FIG. 7

Second generation (T2) tobacco plants. In the upper row the offspring from a co-suppressing T1 plant 15.7 is shown. The middle row shows plants derived from a transgenic T1 plant 15.6 with no clear changes in level of RKS4 is shown while the bottom row shows plants derived from a T1 plant 15.3 in which the levels of RKS4 are increased by the introduction of the overexpression construct GT-RKS4-s.

FIG. 8

Second generation (T2) tobacco plants. Plants derived from a co-suppressing T1 plant 15.7 show a reduction in plant size and a delay in the initiation and outgrowth of primordia. The control empty vector transgenic plants show no visible differences in growth compared with the offspring from the transgenic 15.6 plant, in which the endogenous level of RKS4 gene product was not changed. In the overexpressing plants 15.9 and 15.3 organ size was increased, similar as the number of initiated leaf primordia.

FIG. 9

*Arabidopsis thaliana* WS plants in which the endogenous level of RKS4 gene product is decreased (right picture) due to the presence of a transgenic RKS4 antisense construct (GT-RKS4-16a). The left picture shows a wildtype plant of the same age as the transgenic antisense plant, grown under similar growth conditions. Plant size, organ size and number of organ primordia is decreased in the transgenic antisense plant compared with the wildtype control.

FIG. 10.

*Arabidopsis thaliana* WS plants in which the endogenous level of RKS4 gene product is decreased (bottom left picture) due to the presence of a transgenic RKS4 antisense construct (GT-RKS4-16a). The upper right picture shows a wildtype flower of the same age as the transgenic antisense flower, grown under similar growth conditions. Total flower size is only slightly decreased in the transgenic antisense flower compared with the control flower, whereas organ size of petals is strongly decreased.

*Arabidopsis thaliana* WS plants in which the endogenous level of RKS4 gene product is increased (upper left picture) due to the presence of a transgenic RKS4 overexpressing construct (GT-RKS4-6s). Compared with the wildtype control flower, total flower size of the transgenic flower is clearly increased. Both sepal and petal organ size is clearly increased compared with the control.

For comparison an *Arabidopsis thaliana* WS plant is shown which has been transformed with a construct encoding the GASA3 gene in sense direction, i.e. overexpressing GASA3.

FIG. 11.

Formation of meristematic regions in the hypocotyl of *Arabidopsis thaliana* WS plants under influence of overexpression of RKS4.

RKS4 overexpression results in increases in flower and seed organ size that could be due to increase in cell elongation and/or cell division. In order to analyse the cell division patterns in plants with deregulated RKS4 expression the mitotic activity in transgenic plants was analyzed with the a unstable GUS reporter under the control of a cyclin B1;1 promoter (the Plant Journal 1999 (4) 503-508 Spatio-temporal analysis of mitotic activity with a labile cyclin-GUS fusion protein). *Arabidopsis thaliana* WS seedlings with the pCDG construct did not show gus activity (cell division) in hypocotyls (top) whereas the same pCDG line crossed with a constitutive RKS4 construct showed mitotic activity as indicated by GUS-positive cells (bottom); indicating that RKS4 overexpression activated mitotic activity in hypocotyls.

FIG. 12

In *Arabidopsis thaliana* WS, the seed size is influenced by changing levels of RKS4 gene product. Constitutive overexpression of RKS4 results in increases in seed size (left) compared with control wildtype seeds (right). Antisense constitutive expression of RKS4 cDNA (middle) results in a decrease in seed size compared with the control (right). Magnification is identical in all photos as shown by the bar size.

FIG. 13

Organ size can be influenced by either modulating cell division or cell elongation or a combination of both. In order to identify the total number of cells and the cell size within an organ the apical site of petals of mature Arabidopsis flowers was investigated. Petal organ size is clearly influenced by modulation of RKS4 gene product levels (bottom row for the flowers from which the apical petal epidermal cells were identified). Epidermal cell size is not changed in transgenic plants compared with the control.

FIG. 14

*Arabidopsis thaliana* WS plants in which the endogenous level of RKS10 gene product is increased (right picture) due to the presence of a transgenic RKS10 overexpressing construct. The left picture shows the apical epidermus of a full grown cotyl from an empty vector transgenic seedling of the same age as the transgenic overexpressing cotyl, grown under similar growth conditions.

FIG. 15

*Arabidopsis thaliana* WS plants in which the endogenous level of RKS10 gene product is decreased (right picture) due to the presence of a RKS10 antisense construct The left picture shows a wildtype plant of the same age as the transgenic antisense plant, grown under similar growth conditions. Plant size, organ size and number of organ primordia remains similar in both the transgenic antisense plants and the wildtype control.

FIG. 16

In order to determine organ size variations in transgenic RKS10 transgenic plants compared with empty vector control transgenic plants (pGreen4K), flower organ size was determined of the four open flower stages of *Arabidopsis* inflorescences. The four successive flower stages are photographed under similar magnifications. No obvious changes in organ length could be observed in size of sepals, petals, stamen and carpel between empty vector control flowers (pGreen4K), flowers with an antisense RKS10 construct (a) or plants overexpressing the RKS10 cDNA under the control of a 35S promoter (S

FIG. 17

Tissue cultured auxin treated transgenic *Arabidopsis* T2 seedlings were grown on MS agar plates without hormones for a period of 3 weeks. Regeneration potential was scored and the formation and outgrowth of multiple shoot apical meristem from single seedling origin was displayed as (+). The formation and outgrowth of only one shoot apical meristem, leading to the formation of a normal rosette of leaves from individual plants was displayed as (−). Positive regeneration controls consisted of seedlings overexpressing either KNAT1, CUC2, IPT or cycD3. All of these showed an increase of regeneration capacity (+) compared with a negative control GUS overexpressing plant pGreen5K (−).

Representative examples of RKS and ELS cDNA overexpressing (s) or antisense (a) cosuppressing constructs in transgenic plants are shown in the bottom panels.

FIG. 18.

Tobacco leaf discs were stably transformed with the RKS0 overexpressing construct GT-RKS0-23S and from a single transformation event, large numbers of regeneration plantlets were isolated and subcultured. All of the regenerated plants were potted and flowered. The original transformation event could be kept continuously in tissue culture indefinitely.

FIG. 19

Seedlings from transgenic *Arabidopsis thaliana* containing either constructs overexpressing (s) or co-suppressing by antisense (a) the RKS gene products were screened for the appearance of fasciation. Several examples in which fasciation could be routinely observed are shown together with a negative control plant (pGreen5K, overexpressing the GUS gene) in which fasciation could never be observed.

FIGS. 20-23

Figure 23:
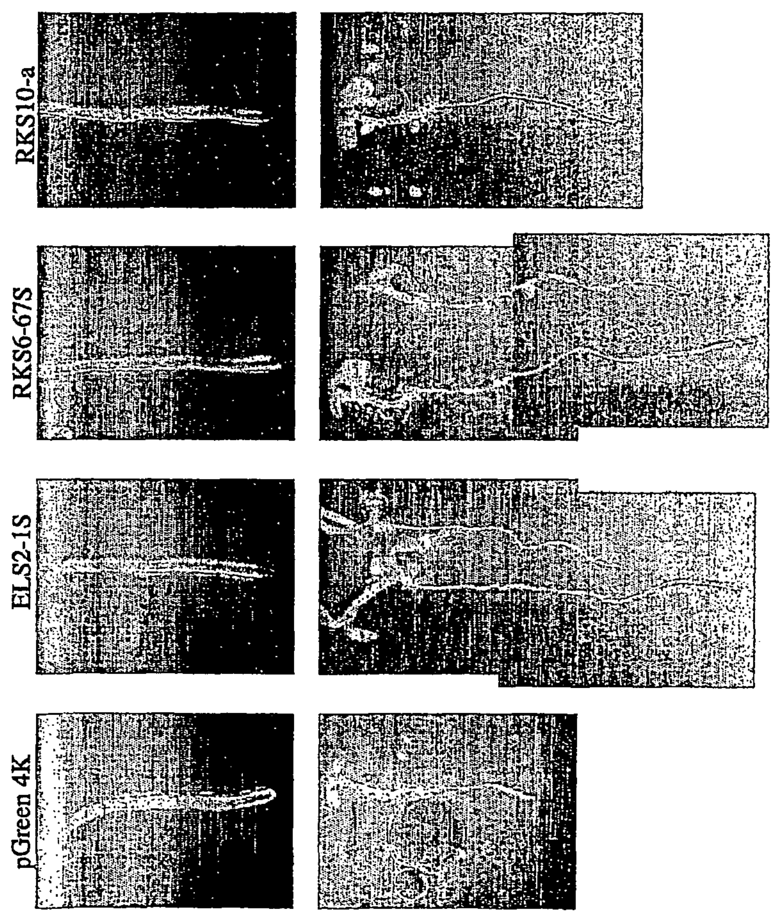
Figure 24:
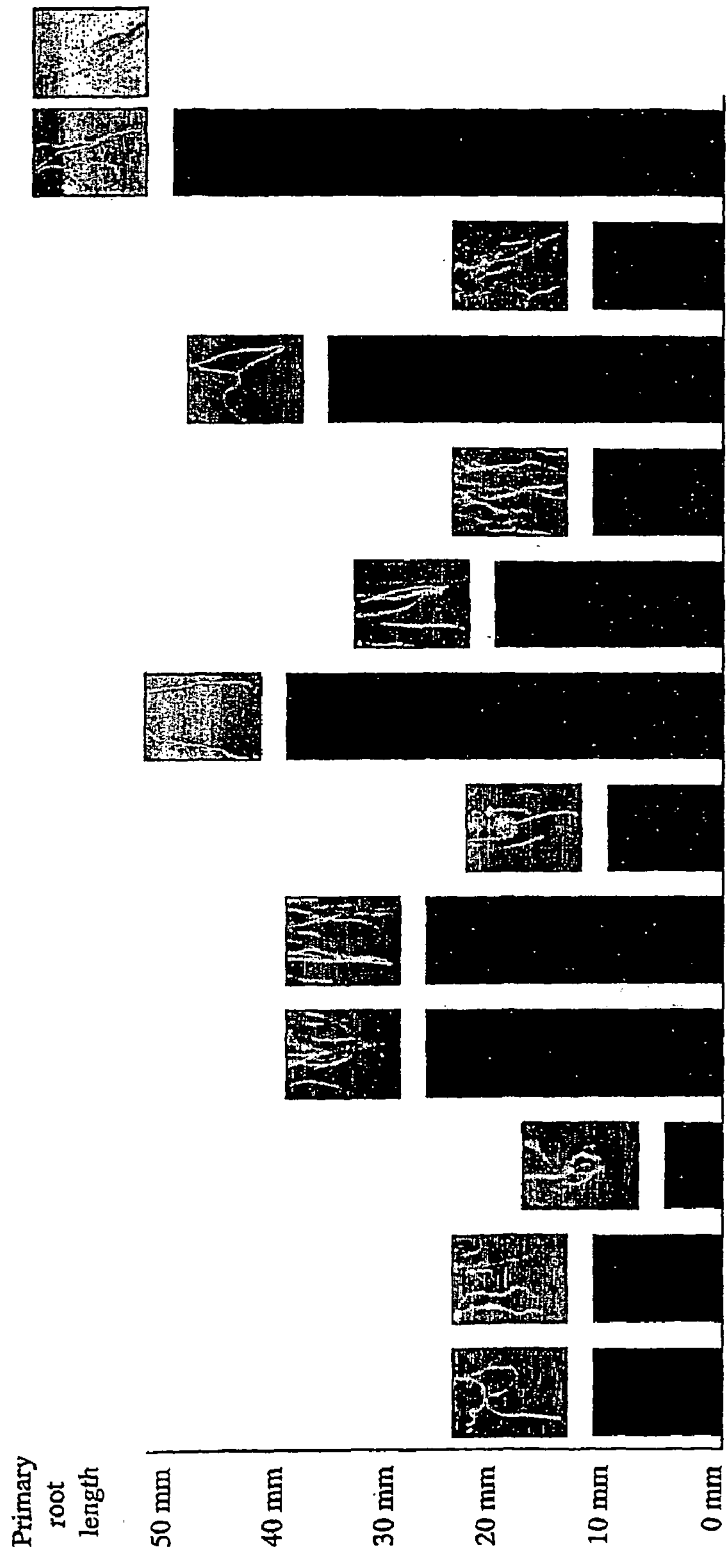
Figure 25:
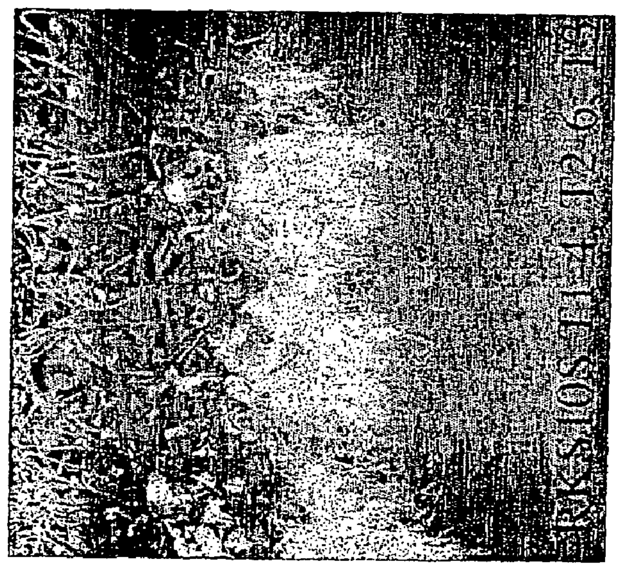
Figure 25:
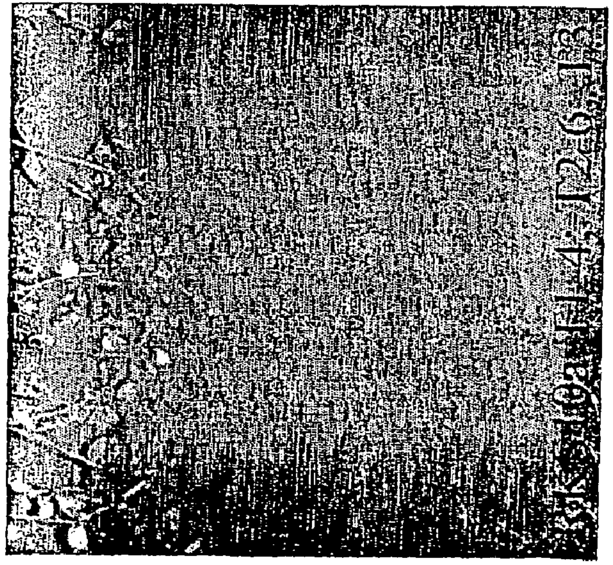
Figure 26:
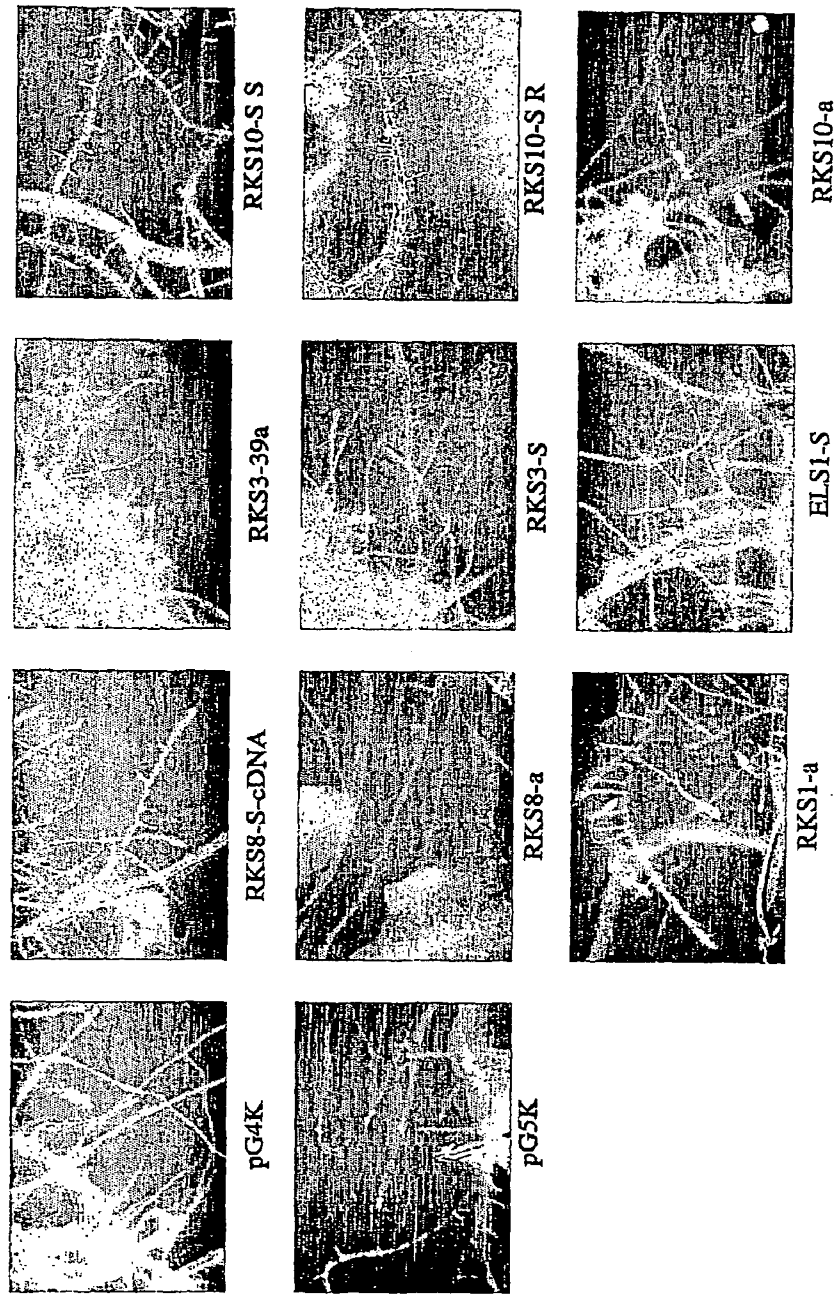
Figure 27:
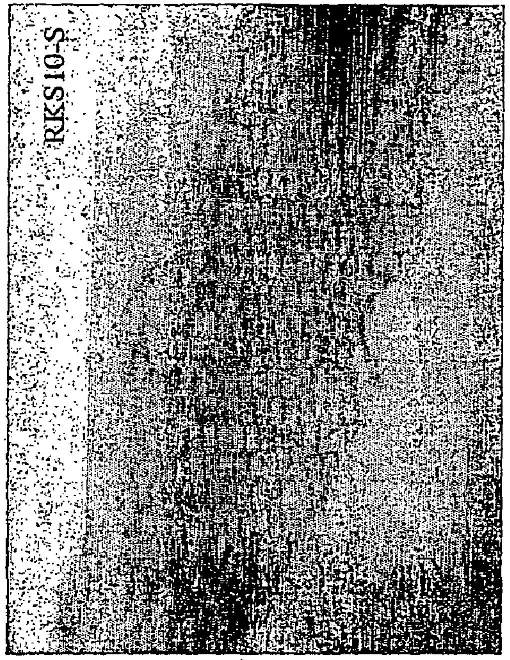

Primary root tips of transgenic *Arabidopsis* plants (top rows) photographed under similar magnification. The bottom rows show the corresponding seedlings (also between each other under the same magnification). FIG. 23 shows the specific *Arabidopsis* transgenes with a strong increase in root outgrowth.

FIG. 24

Average root length of 10-30 transgenic *Arabidopsis* T2 seedlings from one T1 transgenic plant is shown.

FIG. 25

T3 seedlings are shown from a strong co-suppressing RKS10 antisense construct line (T1-4; T2-6; T3 generation) and a strong overexpressing line (T1-4; T2-6; T3 generation). The overexpressing line is different and stronger from the one shown in FIG. 4.1-4.5. Pictures are taken under similar magnifications.

FIG. 26

T2 seed was germinated on horizontal MS agar plates and pictures were taken under similar magnification of representative examples of the lateral root development from transgenic RKS and ELS transgenic roots.

FIG. 27

Pictures taken from transgenic RKS8 or RKS10 overexpressing roots taken directly behind the tip zone. Pictures are taken under same magnification.

FIG. 28

*Arabidopsis thaliana* WS plants in which the endogenous level of RKS or ELS gene product is modified result in the formation of new meristem formation and/or outgrowth, resulting in a complex, bushy inflorescence in transgenic *Arabidopsis* plants compared with control empty vector control plants (pGreen4K). Overexpression of RKS10 and ELS1 (S) and cosuppression with antisense constructs of RKS8 and also RKS10, result in increased numbers of developing generative meristems. The generative shoots are photographed with similar magnification.

FIG. 29

*Arabidopsis thaliana* WS plants in which the endogenous level of RKS gene product is modified result in the formation of new meristem formation and/or outgrowth, resulting in a complex, bushy inflorescence in transgenic *Arabidopsis* plants compared with control empty vector control plants (pGreen4K). The top panel shows adult plants under similar magnification. Compared with the control, RKS10 overexpression results in an extreme bushy phenotypic plant. The results of co-suppressing the RKS8 gene product are less dramatic with respect to the bushiness. However, also in these transgenic plants the number of generative meristems is strongly increased compared with the control. The bottom panel shows the generative shoot in detail under similar magnification.

FIG. 30

Schematic drawing of the different flower organs in an empty vector control pGreen4K flower (left) compared with a complex transgenic flower structure seen in transgenic *Arabidopsis* plants containing an antisense (a) RKS10 construct. The terminal flower meristem produces 2 sepals, 1 petal, 2 stamen, a carpel which is not a closed structure but open with groups of ovules on the inside and outside of this structure, and stigmatic cells protruding from the top part. Two new flowers are protruding from this structure, containing all flower organs in normal numbers.

FIG. 31

Figure 7:
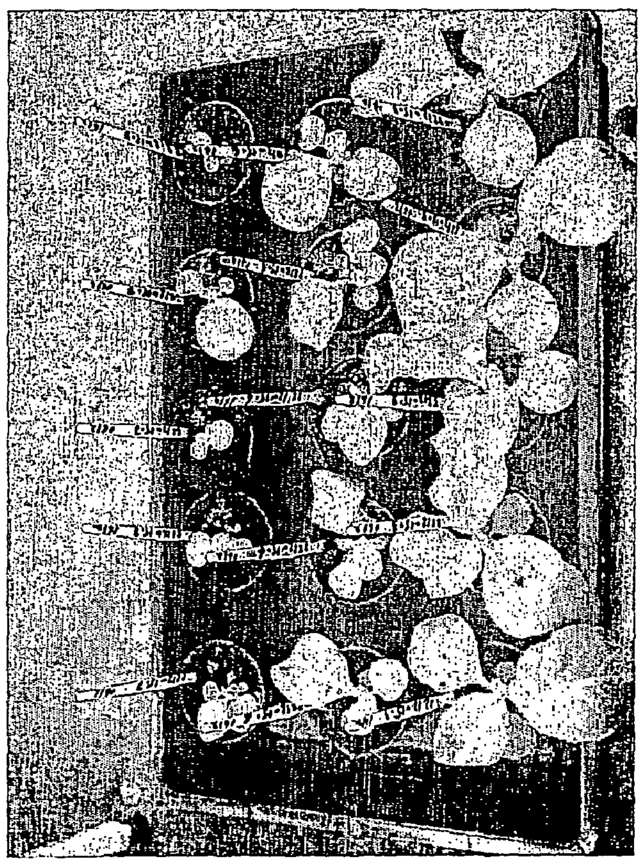
Figure 8:
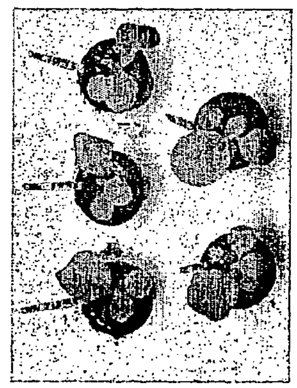
Figure 8:
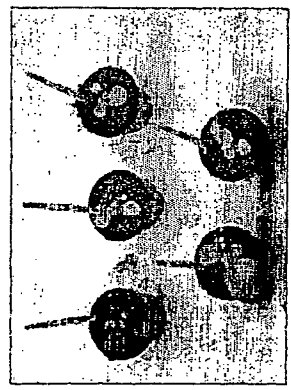
Figure 9:
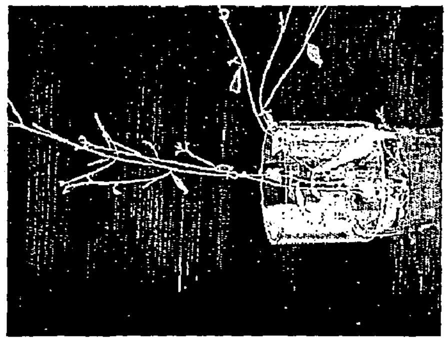
Figure 9:
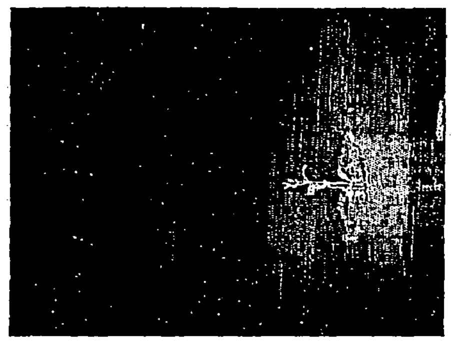
Figure 10:
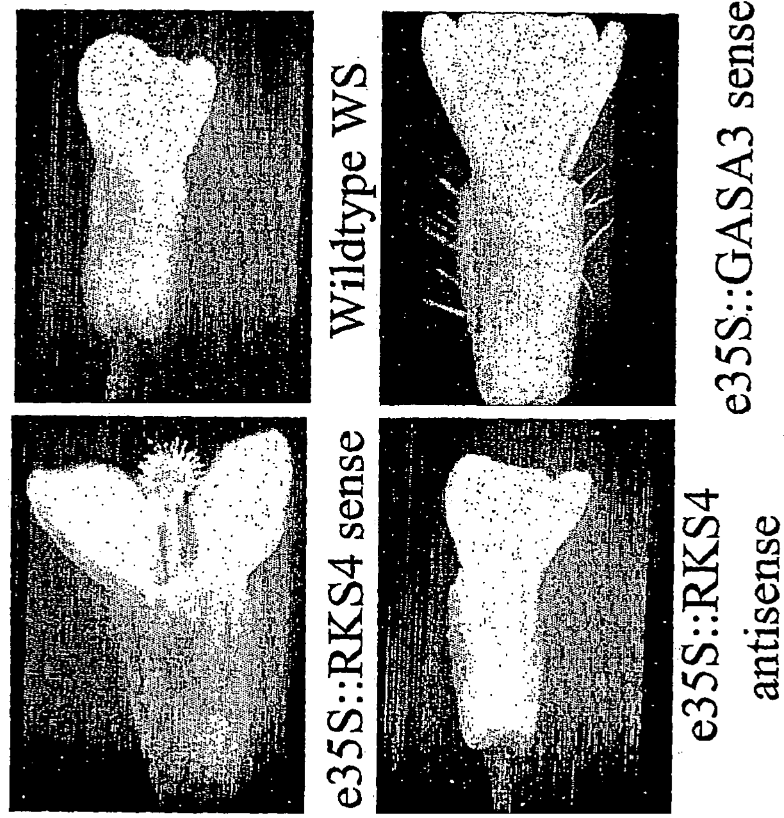
Figure 11:
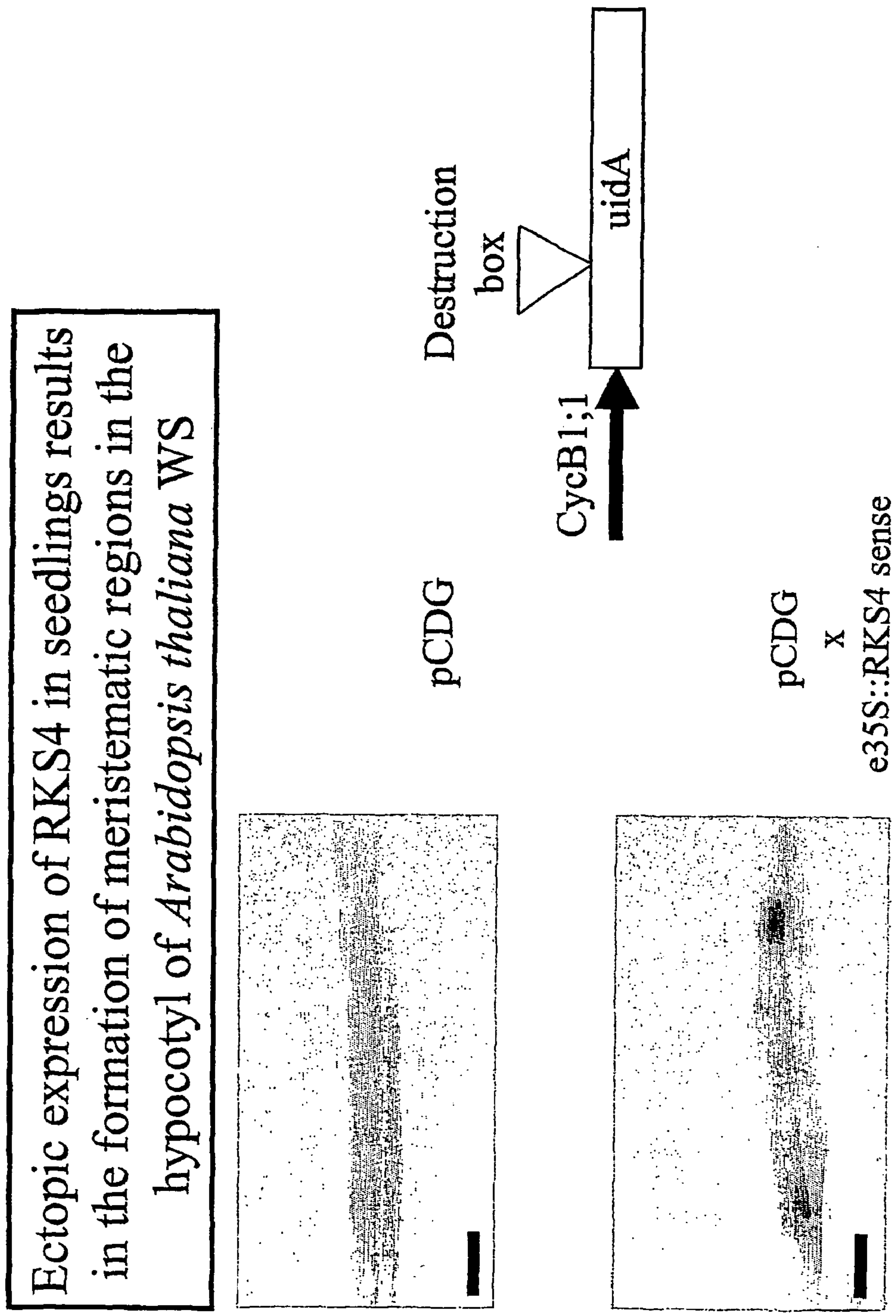
Figure 12:
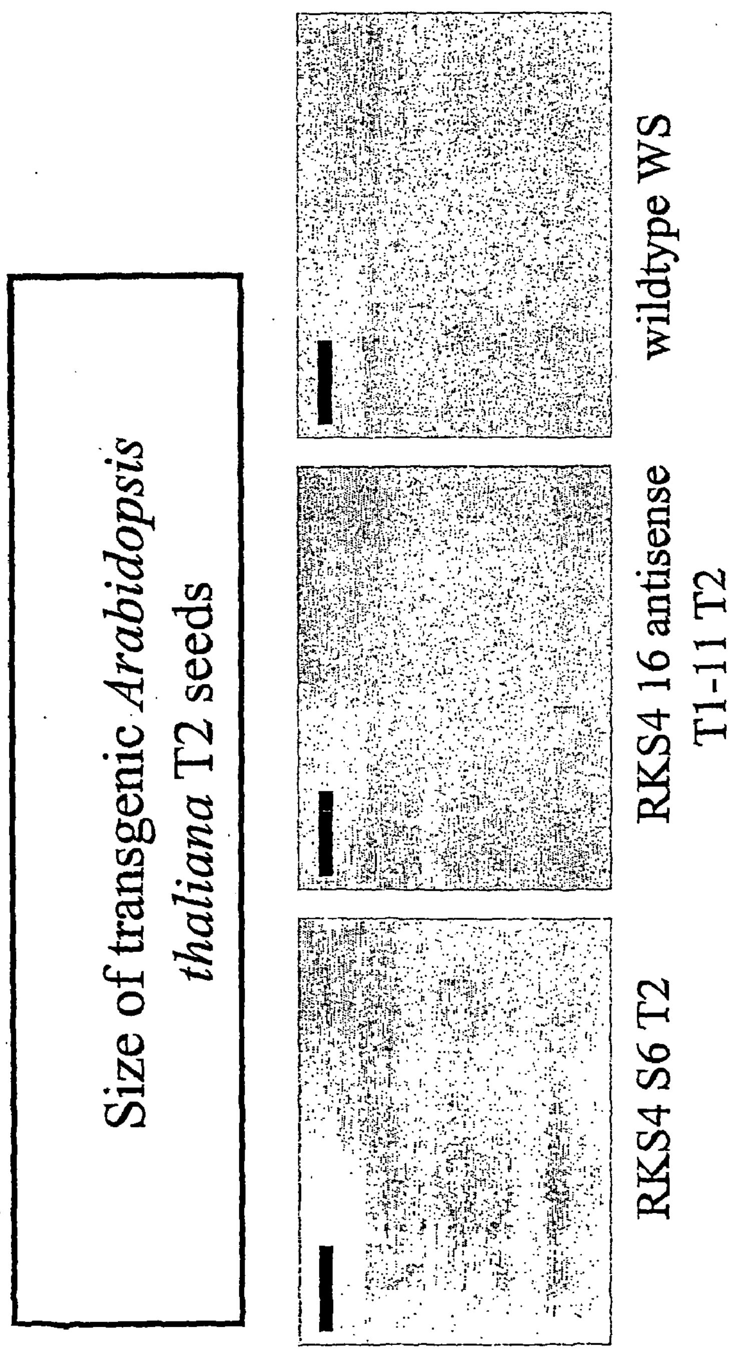
Figure 13:
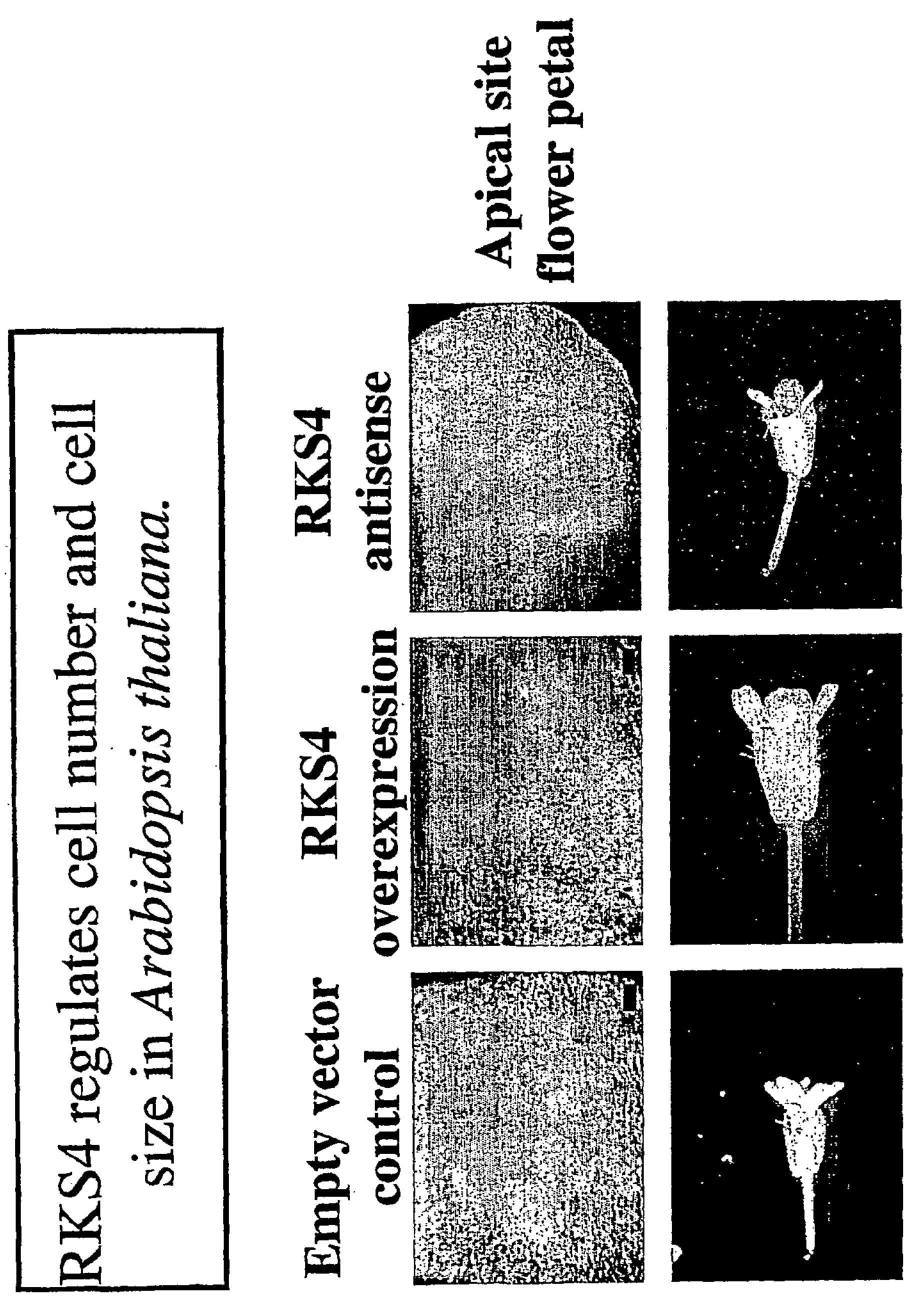

Schematic drawing of the different flower organs in a complex transgenic flower structure seen in transgenic *Arabidopsis* plants T1-11 containing an antisense (a) RKS10 construct. The terminal flower meristem produces 1 sepal, 2 petals, 2 stamen, a carpel which is not a closed structure but open with groups of ovules on the inside and outside of this structure, and stigmatic cells protruding from the top part. An undetermined flower meristem is protruding from the open carpel structure and forms a number of new flowers, including normal flowers (right) and another abnormal flower (left) which consists of a flower with half of the sepal, petal and stamen organs formed and a new terminal flower meristem protruding from this structure, developing in structures as seen in FIG. 7.5. The stamen contain only small numbers of (viable) pollen compared with wildtype stamen (see also chapter 5).

FIG. 32

Schematic drawing of the different flower organs in an empty vector control pGreen4K flower (left) compared with a complex transgenic flower structure seen in a transgenic *Arabidopsis* plant T1-11 containing an antisense (a) RKS10 construct (overview shown in FIG. 7.4). The terminal flower meristem produces half the normal number of sepals, petals and stamen. The remaining part of the flower structure has converted into a new structure containing a new stem containing a single organ structure resembling a fusion between a petal and a sepal. On this structure several (viable) pollen grains can be observed.

FIG. 33

Schematic drawing of the different flower organs in a complex transgenic flower structure seen in a transgenic *Arabidopsis* plant T1-12 containing an antisense (a) RKS10 construct. The terminal flower meristem originating from an undetermined generative meristem is here producing an axillary secondary undetermined meristem (left picture), a single organ resembling a stamen (bottom left), a normal flower and a terminal flower. This terminal flower structure contains 2 normal sepals, 2 normal petals, 2 normal stamen (with only a few viable pollen) and two organs resembling a fusion of sepals/petals/stamen (see also FIG. 7.7). From this terminal flower structure two new flowers emerge (in a similar fashion as observed in FIG. 7.3) containing normal numbers of flower organs (right photos). At the top of this figure a control inflorescense is shown schematically with terminal flower meristems as normally originate from the generative *Arabidopsis thaliana* generative meristem.

FIG. 34

Schematic drawing and detailed pictures of several of the structures as shown in FIG. 7.6. At the right the organs resembling a fusion between sepals/petals/stamen are shown with viable pollen sticking out from these structures. At the top left the single stamen-like organ directly protruding from the main stem is shown.

FIG. 35

Transgenic *Arabidopsis* plants overexpressing the RKS13 gene product show a modification of the normal flower inflorescence architecture, somewhat resembling the structures observed in RKS10 antisense plants. A terminal flower containing a normal seed developing silique and a small number of sepals, petals and stamen, develops at least 4 additional terminal flower meristems that develop abnormally themselves, resulting in open carpel structures and modifications of organ structures.

FIG. 36

Transgenic plants in which the RKS and/or ELS genes are introduced behind a constitutive 35S promoter in an overexpressing (S) or antisense (a) configuration are analyzed for sterility and characterized further for defects in proper pollen development. As a negative control the normal pollen development of a transgene containing the empty expression vector (pG4K) was included. First generation transgenic flowers of RKS10 expressing constructs and second generation control vector and ELS2 are shown under similar magnification. In detail the stigmatic surface and surrounding stamen, are shown under similar magnification, showing the presence or absence of pollen on the stamen or the stigmatic surface.

DETAILED DESCRIPTION

1. Modifying Organ Size

Plant size is determined by both cell elongation and cell division rate. Modifying either one or both processes results in a change in final organ size. Increasing the level of specific members of the family of RKS genes results in an increase in organ size, growth rate and yield. Modulating plant growth, organ size and yield of plant organs is the most important process to be optimized in plant performance. Here we show that modulating the level of members of the family of the RKS signaling complex is sufficient to modulate these processes. The invention provides herewith a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating cellular division during plant growth or organ formation, in particular wherein said gene comprises an RKS4 or RKJS 10 gene or functional equivalent thereof. Inactivation of endogenous RKS gene product results in a decrease in plant growth, proving that the normal function of these endogenous RKS gene products is the regulation of growth and organ size. Elevation of the levels of the regulating of the RKS signaling complex in plant cells is provided in order to increase:

the size of plant organs the growth rate the yield of harvested crop the yield of total plant material the total plant size Decreasing the levels of endogenous RKS gene product is provided in order to decrease:

the size of plant organs the growth rate the total plant size

Results Obtained (See Also FIGS. 6 to 13)

Overexpression and antisense constructs of full length RKS cDNA clones have been made under the control of 35S promoters. Transgenic plants have been produced in *Arabi-*

*dopsis thaliana* and in *Nicotiana tabacum*. Subsequent generations of stably transformed plants were investigated for phenotypes and analyzed in detail. The phenotype observed in transgenic plants with antisense constructs of RKS4 (GT-RKS4-a) could be described as dwarf plants in which all plant organs showed a decrease in organs size and growth rate. Overexpression of RKS4 (GT-RKS4-s) resulted in plants with increased size of organs and an increase in growth rate Since cell size alone was not responsible for the modifications in organ size of petals it can be concluded that RKS4 is involved in the regulation of the cellular divisions during plant growth and organ formation. Overexpression of RKS 4 results in an increase of cellular divisions whereas a decrease in endogenous RKS 4 gene product levels within the plant results in a decrease of cellular division rates.

LITERATURE

Not being the wrong size. R. H. Gomer 2001; Nature reviews 2: 48-54

Cell cycling and cell enlargement in developing leaves of *Arabidopsis*. P. M Donnelly et al. 1999; Developmental biology 215: 407-419

Ectopic expression of *A. integumenta* in Arabidopsis plants results in increased growth of floral organs. B. A. Krizek 1999 Developmental genetics 25: 224-236

Plant organ size control: *A. integumenta* regulates growth and cell numbers during organogenesis. Y. Mizukami and R. L. Fischer PNAS 97: 942-947

Measuring dimensions: the regulation of size and shape. S. J. Day and P. A. Lawrence 2000; Development 127: 2977-2987

A matter of size: developmental control of organ size in plants. Y. Mizukami 2001; Current opinions in plant biology 4: 533-539

2. Cell Division

The mitotic cell cycle in eukaryotes determines the total number of cells within the organism and the number of cells within individual organs. The links between cell proliferation, cell differentiation and cell-cycle machinery are of primary importance for eukaryotes, and regulation of these processes allows modifications during every single stage of development. Here we show that modulating the level of members of the family of the RKS signaling complex is sufficient to modulate these processes. The invention provides herewith a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating cellular division during plant growth or organ formation, in particular wherein said gene comprises an RKS4 or RKJS 10 gene or functional equivalent Herewith the invention provides a method for modulating the number of cells to be formed within an eukaryotic organism as a whole or for modulating the cell number within individual organs is, which of primary importance in modulating plant developmental processes, especially of arable plants. Here we show that members of the RKS signaling complex are able to regulate the number of cellular divisions, thereby regulating the total number of cells within the organism or different organs.

Possible Applications

Elevation of the levels of the regulating RKS signaling complex members in plant cells in order to increase:

the size of plant organs the growth rate the yield of harvested crop the yield of total plant material the total plant size Decreasing the levels of endogenous RKS signaling complex members in order to decrease:

the size of plant organs the growth rate the total plant size

Results Obtained

Overexpression and antisense constructs of full length RKS cDNA clones have been made under the control of 35S promoters. Transgenic plants have been produced in *Arabidopsis thaliana* and in *Nicotiana tabacum*. Subsequent generations of stably transformed plants were investigated for phenotypes and analyzed in detail.

Figure 14:
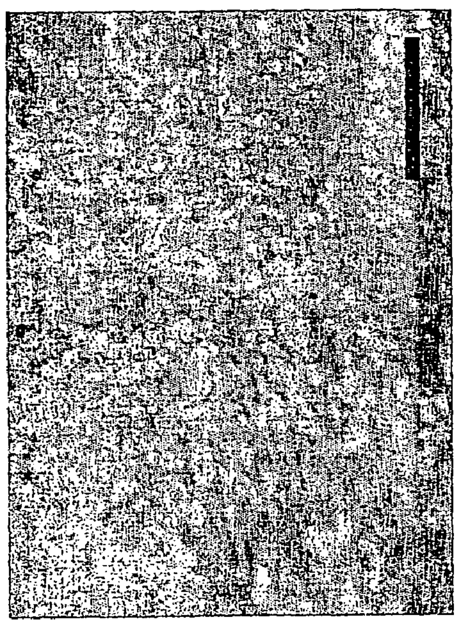
Figure 14:
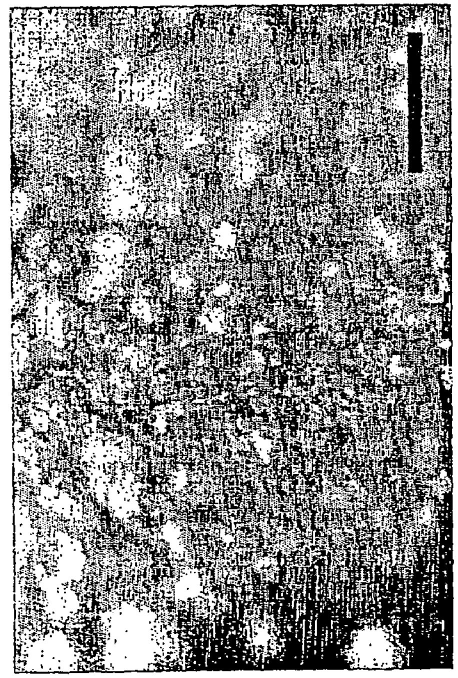
Figure 15:
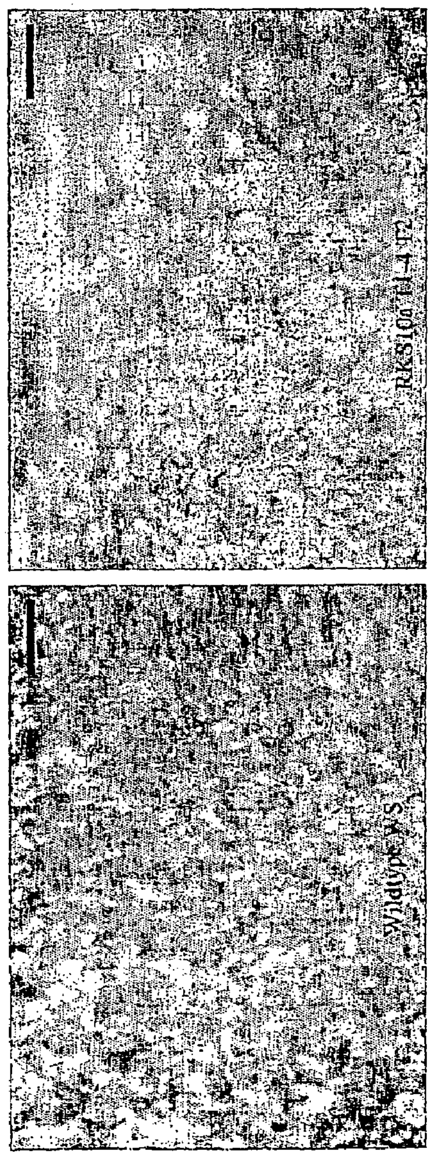

Overexpression of RKS 4 results in an increase of cellular divisions whereas a decrease in endogenous RKS 4 gene product levels within the plant results in a decrease of cellular division. Another example of RKS genes involved in cellular proliferation is provided by RKS10. Overexpression of RKS10 (S) results in a decrease in apical epidermal cells (FIG. 14) compared with control plants containing an empty expression cassette (pGreen4K). Co-suppressing the endogenous RKS 10 gene in plants containing an antisense construct (a) showed clearly larger epidermal cells as the corresponding cells in wildtype control plants (FIG. 15). In contrast to the plant phenotypes shown in RKS4 transgenic plants, no differences in plant or organ size could be observed in the RKS10 transgenic plants or organs. This shows that although the organ size remains constant, the number of cells within these organs is variable due to the differences in size of individual cells. These results indicate that normal RKS4 function within the plant can be described as an activator of cellular division.

Normal RKS10 function also involves an activation process on cellular division rate. This effect is also detectable in the root in the region directly behind the tip zone, where in the RKS10 overexpressing transgenes cellular divisions were detectable in a region where normally cell proliferation has ceased. The plane of divisions of root cells in these transgenes is also clearly different from the normal plane of root cell division, resulting in clumps of cells with all types of division planes possible.

Figure 16:
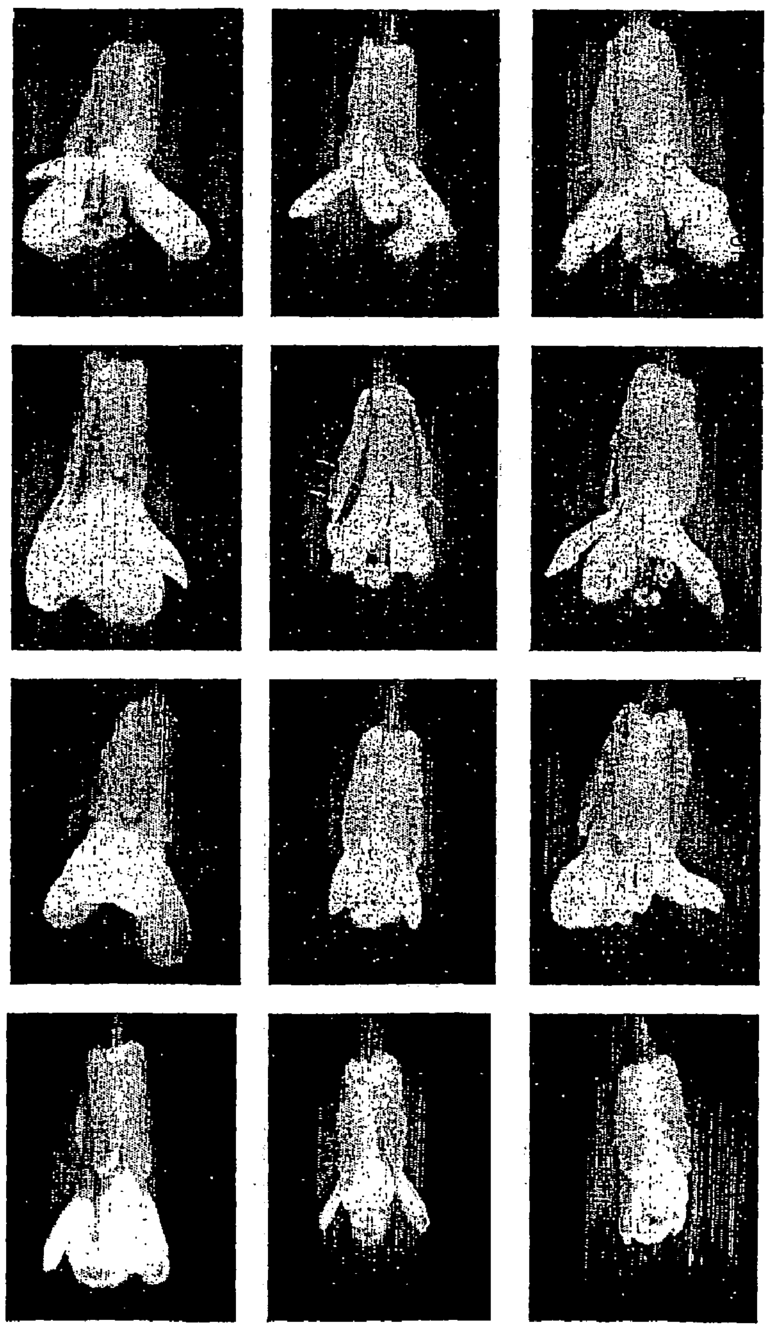

In contrast to RKS4, the final organ size in RKS10 transgenic plants is under the control of other organ size restriction processes, in such a way that the final organ volume remains constant (FIG. 16). RKS4 and RKS10 are essentially involved in the same cell cycle activation process, but either addition organ size controlling functions of these RKS genes or the hierarchical order in which they regulate the cell cycle is different.

LITERATURE

Not being the wrong size. R. H. Gomer 2001; Nature reviews 2: 48-54

Cell cycling and cell enlargement in developing leaves of *Arabidopsis*. P. M Donnelly et al. 1999; Developmental biology 215: 407-419

When plant cells decide to divide. H. Stals and D. Inze 2001. Trends in Plant Science 6: 359-363

Cell cycling and cell enlargement in developing leaves of *Arabidopsis*. P. M. Donnelly et al. 1999. Developmental Biology 215: 407-419

Triggering the cell cycle in plants. B. G. W. den Boer and J. A. H. Murray 2000. Trends in Cell Biology 10: 245-250

3. Regeneration

Modification the levels of different RKS and ELS genes within plants allows the initiation and/or outgrowth of apical meristems, resulting in the formation of large numbers of plantlets from a single source. A number of gene products that is able to increase the regeneration potential of plants is known already. Examples of these are KNAT1, cycD3, CUC2 and IPT. Here we show that modulation of the endogenous levels of RKS genes results in the formation of new shoots and plantlets in different plant species like *Nicotiana tabacum* and *Arabidopsis thaliana*. herewith the invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein, allowing modulating apical meristem formation, in particular wherein said gene comprises an ELS1, RKS0, RKS3, RKS4, RKS8 or RKS10 gene or functional equivalent thereof. A direct application of a method according to the invention is the stable or transient expression of RKS and ELS genes or gene products in order to initiate vegetative reproduction. Regeneration can be induced after overexpression of for example RKS0 and ELS1; or by co-suppression of for example the endogenous RKS3, RKS4, RKS8 or RKS10 genes. Overexpression or co-suppression of these RKS and ELS gene products can be either transient, or stable by integration of the corresponding expression cassettes in the plant genome.

Results Obtained

Overexpression and antisense constructs of full length RKS and ELS cDNA clones have been made under the control of 35S promoters. Transgenic plants have been produced in *Arabidopsis thaliana* and in *Nicotiana tabacum*. Subsequent generations of stably transformed plants were investigated for phenotypes and analyzed in detail.

Figure 17:
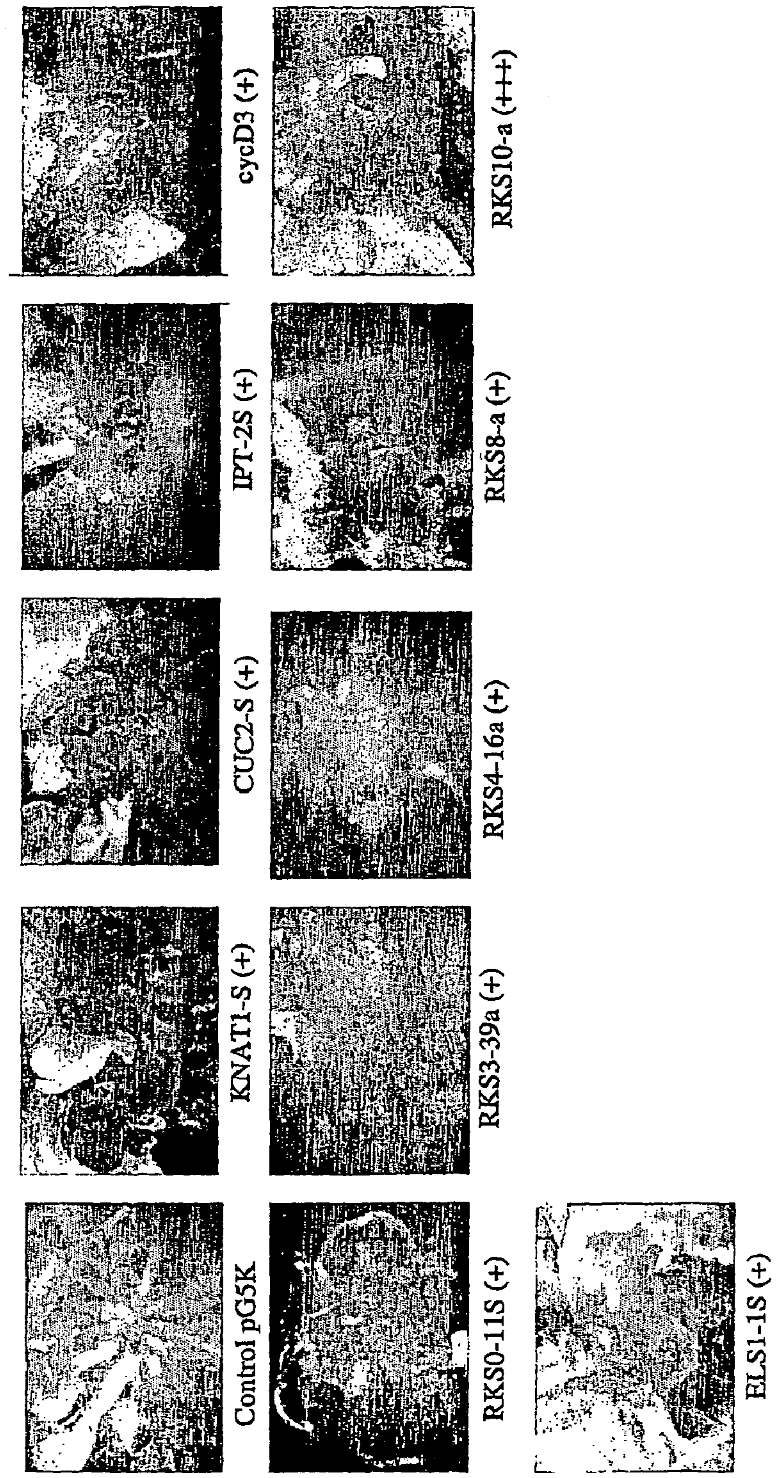

T2 transgenic seedlings of *Arabidopsis* were germinated in liquid MS medium supplemented with 1 mg/L 2,4-D for 1 week, followed by extensive washing and plating of the seedlings onto MS agar plates without hormones. Control transgenic seedstocks containing either a negative control vector (pGreen5K); or positive control overexpression constructs of gene products known to increase the regeneration potential (IPT, KNAT1, CUC2 and cycD3) were characterized for regeneration potential together with seedstocks from plants either overexpressing (s) or co-suppressing (a) all RKS and ELS gene products (FIG. 17). Overexpression of the ELS1 and RKS0 cDNA clones resulted in an increase of shoot apical meristem formation and outgrowth, whereas antisense constructs (a) of these cDNA clones did not increase the regeneration potential (only increased regeneration results are shown). Antisense constructs of RKS3, RKS4, RKS8 and RKS10 also resulted in an increased formation and outgrowth of apical meristems (FIG. 17).

Figure 18:
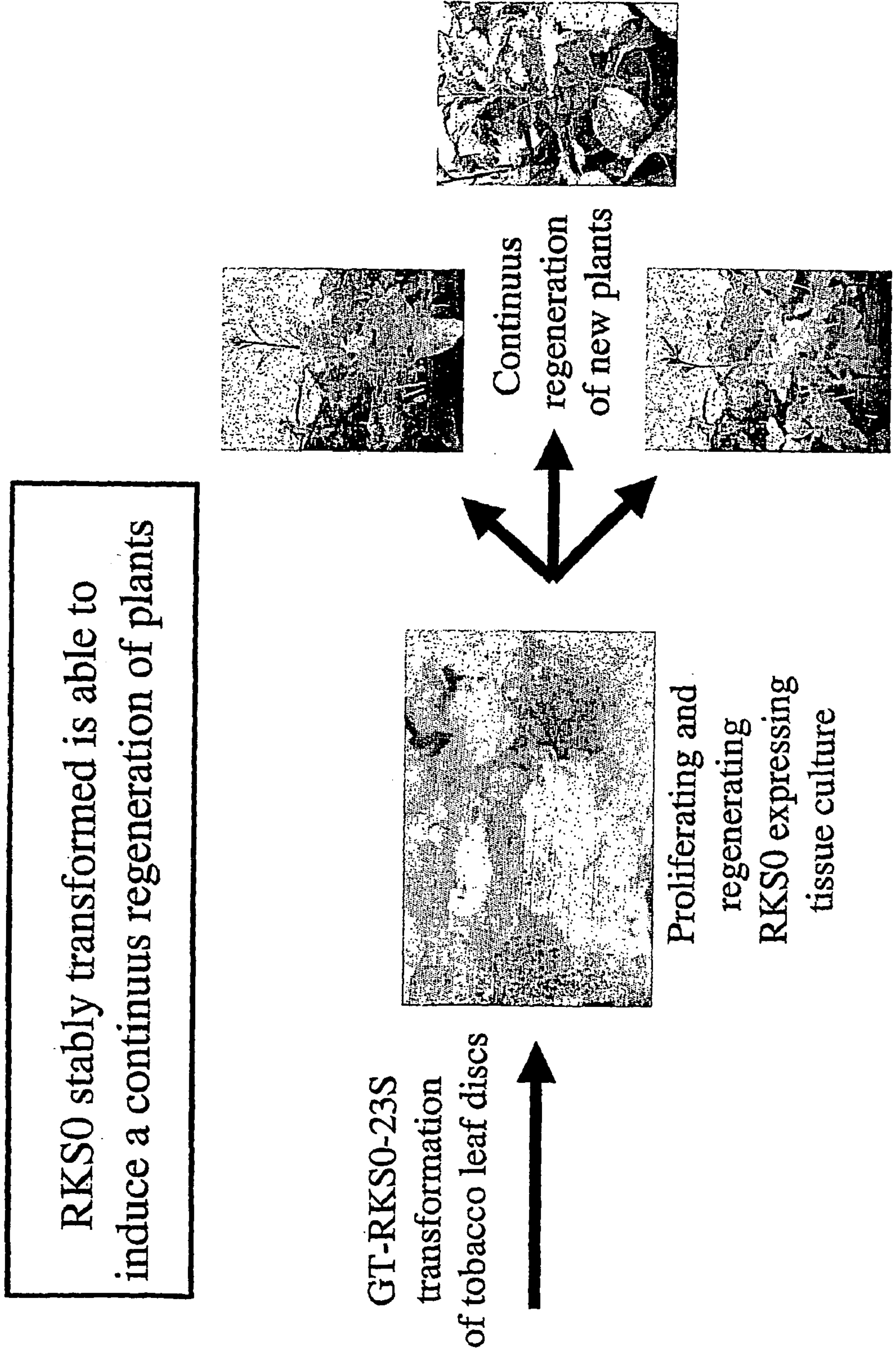

T1 generation *Nicotiana tabacum* tissue cultures transformed with ELS and RKS gene products in either overexpression (s) cassettes or antisense co-suppression (a) cassettes allowed the regeneration of indefinite number of offspring plants from a single transformed cell origin (FIG. 18). An example is shown for the overexpression of the GT-RKS0-23S construct. The resulting plants obtained from one transformation event in general showed no phenotypes. Only a subset of plants displayed RKS0 overexpression phenotypes (like loss of apical dominance and early flowering).

LITERATURE

Mechanisms that control knox gene expression in the *Arabidopsis* shoot. N. On et al. 2000, Development 127: 5523-5532

Overexpression of KNAT1 in lettuce shifts leaf determinate growth to a shoot-like indeterminate growth associated with an accumulation of isopentenyltype cytokinins. G. Frugis et al. 2001. Plant Physiology 126: 1370-1380

KNAT1 induces lobed leaves with ectopic meristems when overexpressed in *Arabidopsis*. Chuck et al. 1996. the Plant Cell 8: 1277-1289

Cytokinin activation of *Arabidopsis* cell division through a D-type cyclin. C. Riou-Khamlichi et al. 1999. Science 283: 1541-1544

4. Fasciation

Fasciation is normally a result from an increased size of the apical meristem in apical plant organs.

Figure 19:
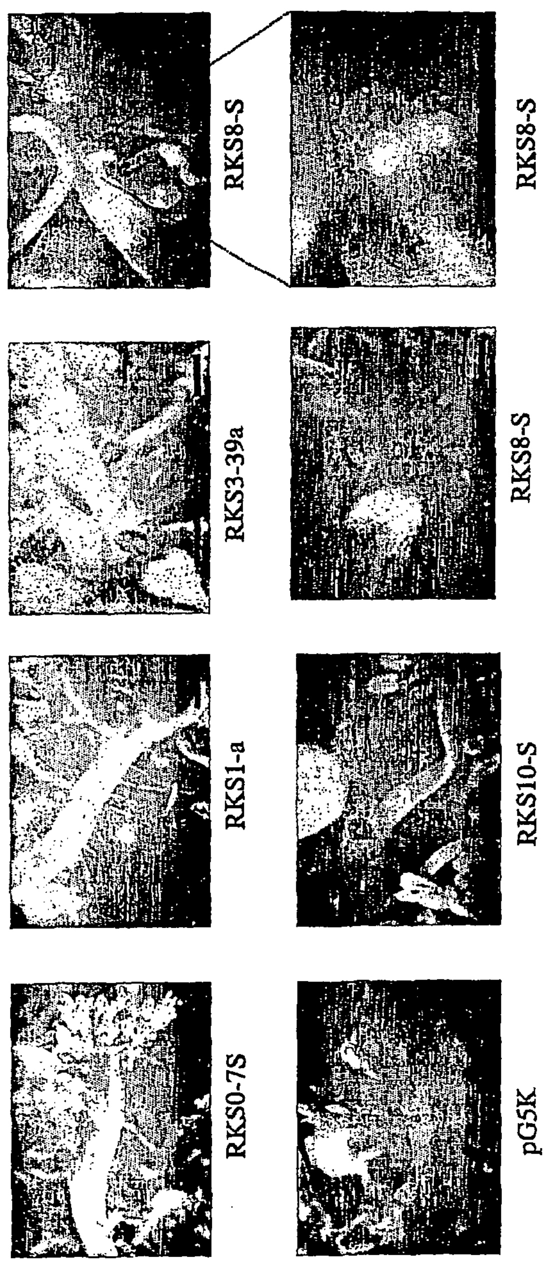
Figure 20:
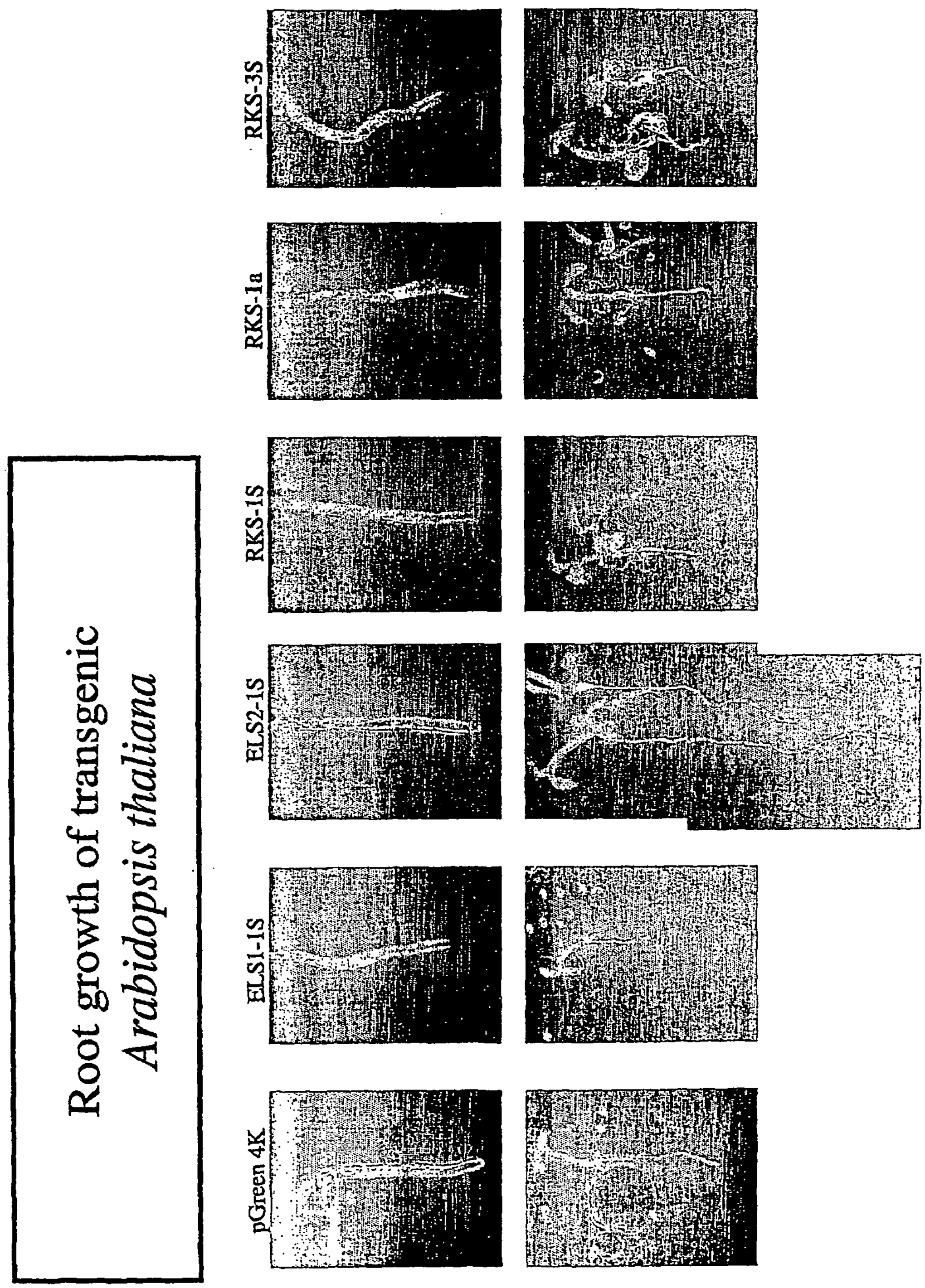
Figure 21:
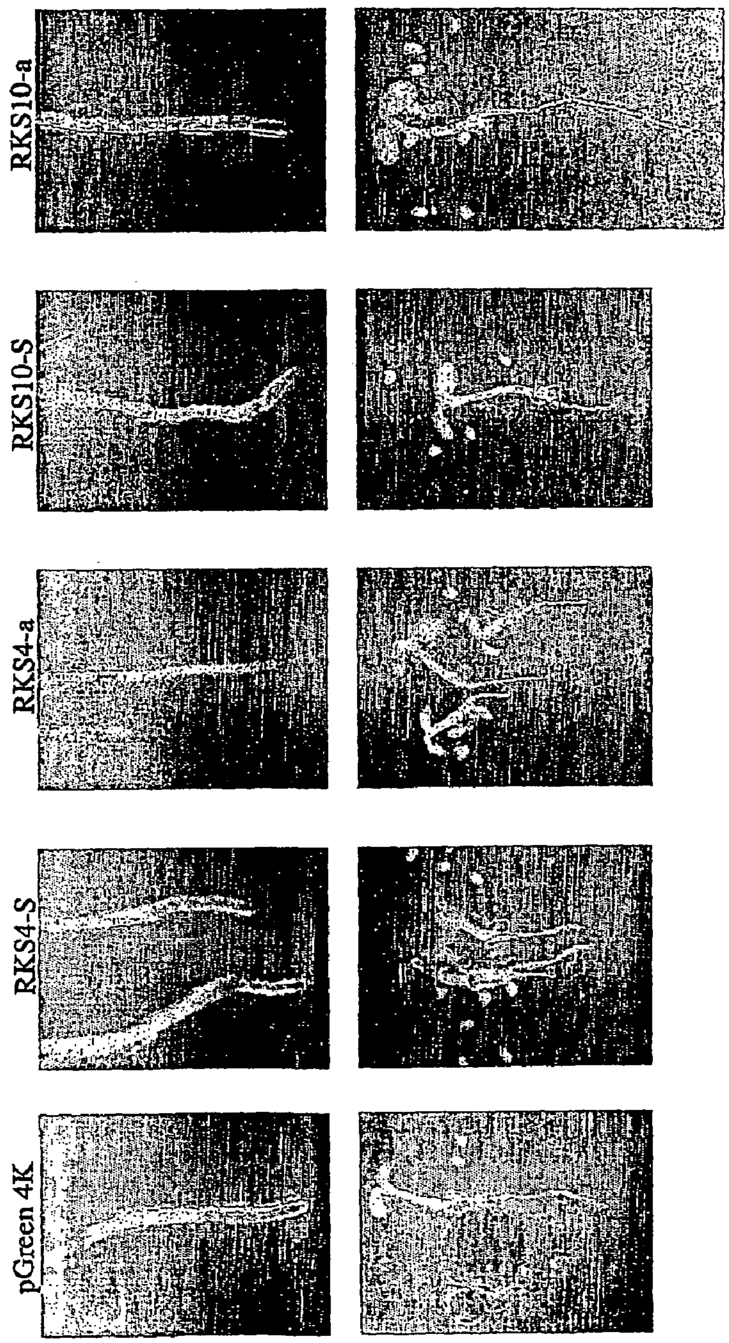
Figure 22:
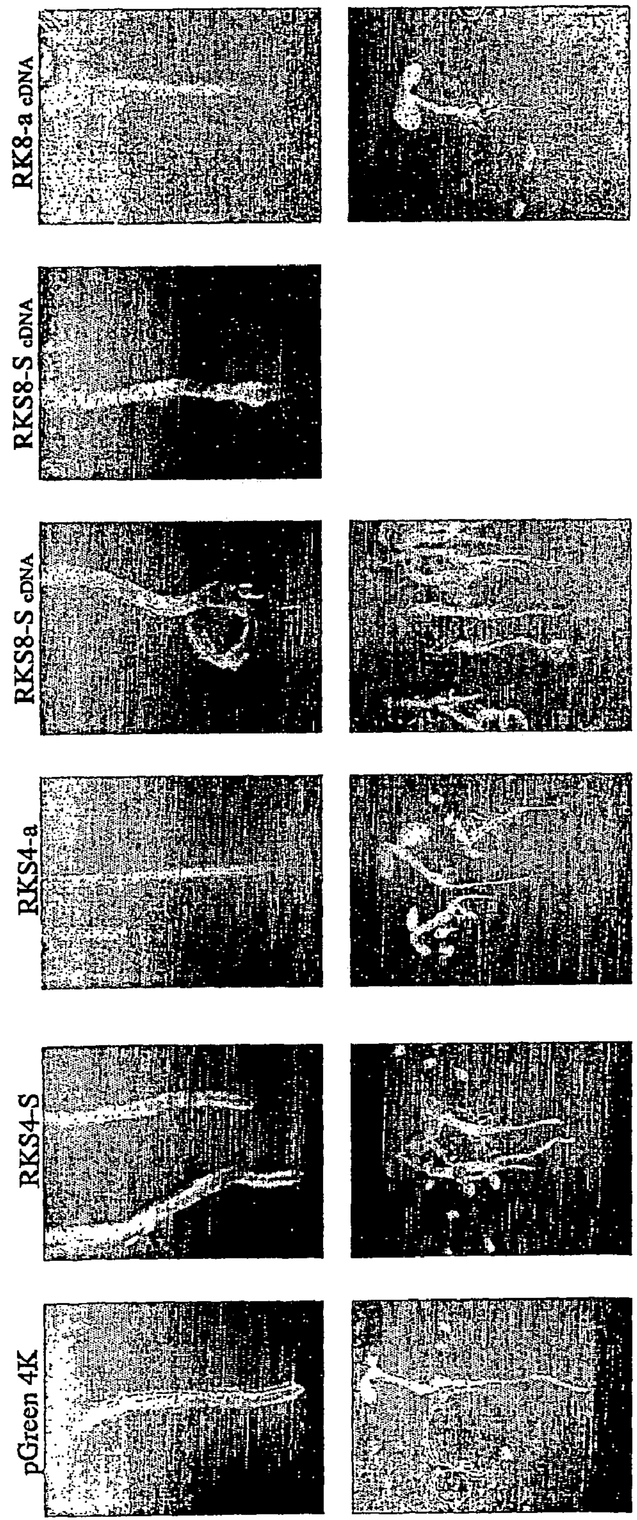

Modulation of the number of cells within the proliferating zone of the shoot apical meristem results in an excess number of cellular divisions, giving rise to excess numbers of primordia formed or to stems in which the number of cells is increased. The invention herewith provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating fasciation, in particular wherein said gene comprises an RKS0, RKS3, RKS8 or RKS10 gene or functional equivalent thereof. Here we for example show that modulation of the levels of RKS gene products in plants like *Arabidopsis thaliana* can result in fasciated stems as shown in FIG. 19. A direct application as provided herein is the regulated formation of fasciation in plant species in which such a trait is desired like ornamental plants. Regulation of the initiation and extent of fasciation, either by placing the responsible RKS encoding DNA sequences under the control of stage or tissue specific promoters, constitutive promoters or inducible promoters results in plants with localized or constitutive fasciation of stem tissue. Another application is modulating the number of primordiae by regulation of the process of fasciation. An example is provided by for example sprouts, in which an increased number of primordia will result in an increased numbers of sprouts to be harvested. Fasciation can also result in a strong modification in the structural architecture of the inflorescence, resulting in a terminal group of flowers resembling the Umbelliferae type (an example is shown in FIG. 19 where the fasciated meristem of a RKS0-7S *Arabidopsis* plant in which endogenous RKS0 gene product levels have been deregulated clearly terminates in an Umbelliferae type inflorescence.

Results Obtained

Overexpression and antisense constructs of full length RKS cDNA clones have been made under the control of 35S promoters. Transgenic plants have been produced in *Arabidopsis thaliana*. Subsequent generations of stably transformed plants were investigated for phenotypes and analyzed in detail. T2 transgenic seedlings of *Arabidopsis* were germinated on MS agar plates without hormones. Control transgenic seedstocks containing a negative control vector (pGreen5K) were tested for their ability to induce fasciation (Overexpression constructs (s) of RKS0, RKS8 and RKS10 cDNA clones resulted in fasciated plants, whereas antisense constructs (a) of these cDNA clones did not increase the regeneration potential (only positive results are shown). Antisense constructs of RKS3 gave also rise to fasciation (FIG. 19).

LITERATURE

Functional domains in plant shoot meristems. U. Brand et al. 2001. Bioassays 23: 134-141.

Dependence of stem cell fate in *Arabidopsis* on a feedback loop regulated by CLV3 activity.

U. Brand et al. 2000. Science 289: 617-619

5. Root Development

Fasciation is normally a result from an increased size of the apical meristem in apical plant organs. Modulation of the number of cells within the proliferating zone of the root apical meristem results in an excess number of cellular divisions, giving rise to excess numbers of primordia formed or to roots in which the number of cells is increased. Adaptation to soil conditions is possible by regulation of root development of plants. Here we describe several processes in root development that can be manipulated by modification of the levels of the RKS signaling complex within the root. The invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating root development, in particular wherein said gene comprises an ELS1, ELS2, RKS1, RKS3, RKS4, RKS6 RKS8 or RKS10 gene or functional equivalent thereof. Root length, a result by either root cells proliferation or elongation, can for example be increased by overexpression of for example RKS3, RKS4, RKS6 and ELS2, or inactivation of the endogenous RKS10 gene product. Root length can also be decreased by decreasing of endogenous RKS1 levels or by strong overexpression of RKS10. The initiation of lateral roots is also regulated by RKS gene products. Overexpression of for example RKS10 can result in a strong increase in the initiation and outgrowth of lateral roots. Co-suppression of RKS1 also resulted in the initiation and outgrowth of large numbers of lateral roots. Root hair formation and elongation is important in determining the total contact surface between plant and soil. A strong increase of root hair length (elongation) can be obtained by overexpression of ELS1 and RKS3 gene products. As the roots of terrestrial plants are involved in the acquisition of water and nutrients, anchorage of the plant, synthesis of plant hormones, interaction with the rhizosphere and storage functions, increasing or decreasing root length, for example for flexible adaptations to different water levels, can be manipulated by overexpressing or cosuppressing RKS and/or ELS gene products. Modulation of the total contact surface between plant cells and the outside environment can be manipulated by regulation lateral root formation (increased by RKS10 overexpression and co-suppression of RKS1). Finally the contact surface between plant cells and the soil can be influenced by modulation of the number of root hairs formed or the elongation of the root hairs, as mediated by ELS1 and RKS3.

Results Obtained

Overexpression and antisense constructs of full length RKS cDNA clones have been made under the control of 35S promoters. Transgenic plants have been produced in *Arabidopsis thaliana*. Subsequent generations of stably transformed plants were investigated for phenotypes and analyzed in detail. T2 transgenic seedlings of *Arabidopsis* were germinated on MS agar plates without hormones. Control transgenic seedstocks containing a negative control vector pGreen4K (empty expression vector) and/or pGreen5K (a GUS overproducing vector) were included as references for normal root development. Seedlings from transgenic *Arabidopsis thaliana* containing either constructs overexpressing (s) or co-suppressing by antisense (a) the RKS gene products were screened for the appearance of fasciation. Several examples in which fasciation could be routinely observed are shown together with a negative control plant (pGreen4K, containing an expressing cassette without an insert cDNA). Seedlings are germinated and grown on vertically placed MS agar plates.

LITERATURE

Cellular organisation of the *Arabidopsis thaliana* root. L. Dolan et al. 1993. Development 119: 71-84

Root development in *Arabidopsis*: four mutants with dramatically altered root morphogenesis. P. N. Benfey et al. 1993. Development 119: 57-70

The development of plant roots: new approaches to underground problems. J. W. Schiefelbeim and P. N. Benfey 1991. the Plant Cell 3: 1147-1154

6. Apical Meristems

All parts of the plant above the ground are generally the result on one apical shoot meristem that has been initiated early at embryogenesis and that gives rise to all apical organs. This development of a single meristem into complex tissue and repeated patterns is the result of tissue and stage-dependent differentiation processes within the meristems and its resulting offspring cells. The control of meristem formation, meristem identity and meristem differentiation is therefore an important tool in regulating plant architecture and development. Here we present evidence the function of RKS and ELS gene products in regulation of the meristem identity and the formation and outgrowth of new apical meristems. The invention provides a method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein allowing modulating meristem identity, in particular wherein said gene comprises an ELS1, RKS8, RKS10 or RKS13 gene or functional equivalent thereof. Introduction of for example the RKS10 gene product or an other member of the RKS signaling complex under the control of a tissue and/or stage specific promoter as provided herein allows localized and time regulated increases in the levels of gene product. For example the meristematic identity in a determined meristem might thereby be switched back into an undetermined meristem, thereby changing for example a terminal flower into an undetermined generative meristem.

Another application might be found in changing the meristematic identity at an early time point, during early vegetative growth, thereby switching the vegetative meristem into a generative meristem, allowing early flowering. Modulation of meristem identity in terminal primordia, like for example as shown in FIG. 30, where flower organ primordia are converted into terminal flower primordia, allows the formation of completely new types of flowers and fused fruit structures. Constitutive overexpression of RKS gene products results in plants with many apical meristems, as can clearly been seen in FIG. 29, where RKS10 overexpression results in an extremely bushy phenotype.

Results Obtained

Figure 28:
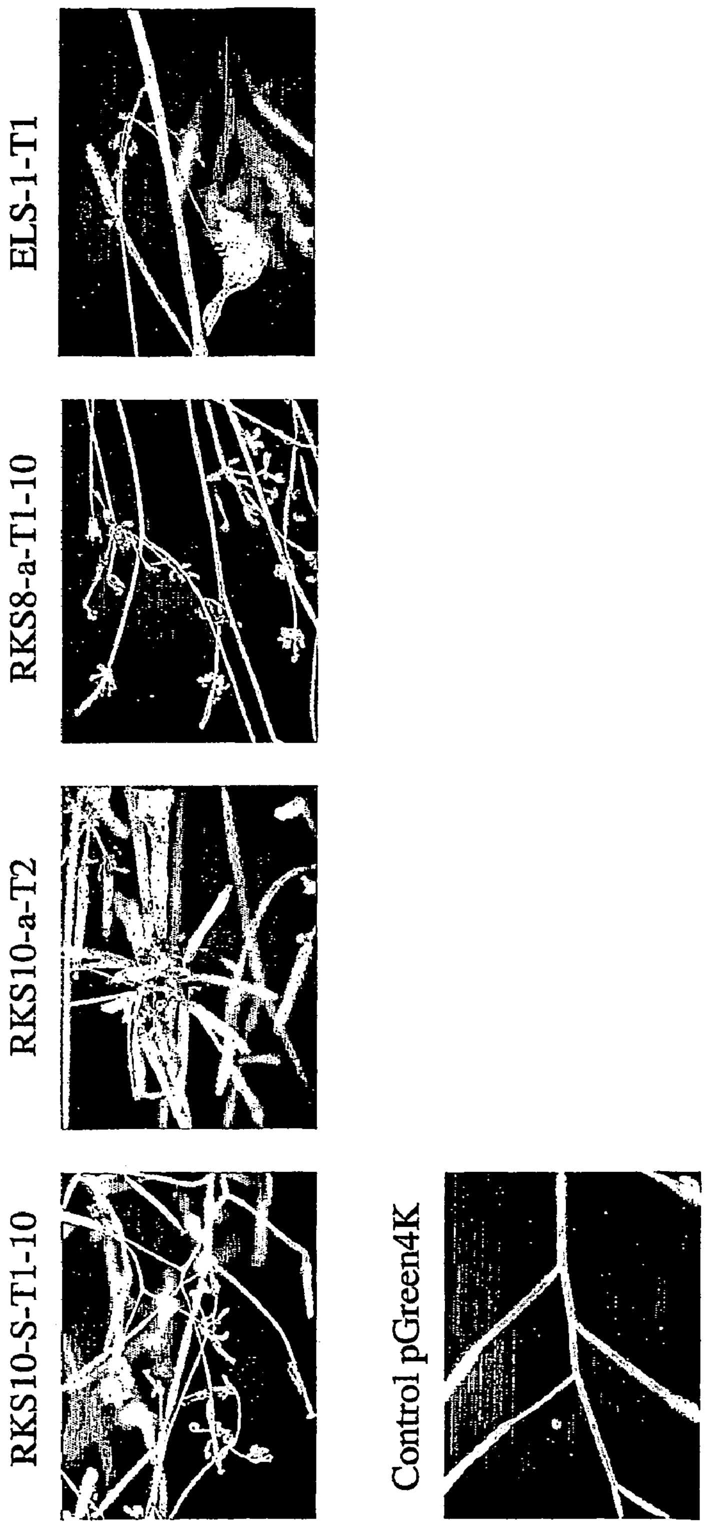

Changing the normal levels of endogenous RKS10 within the plant, either by overexpressing or co-suppressing the RKS10 cDNA, results in an increase in generative meristem development (FIG. 28).

Figure 31:
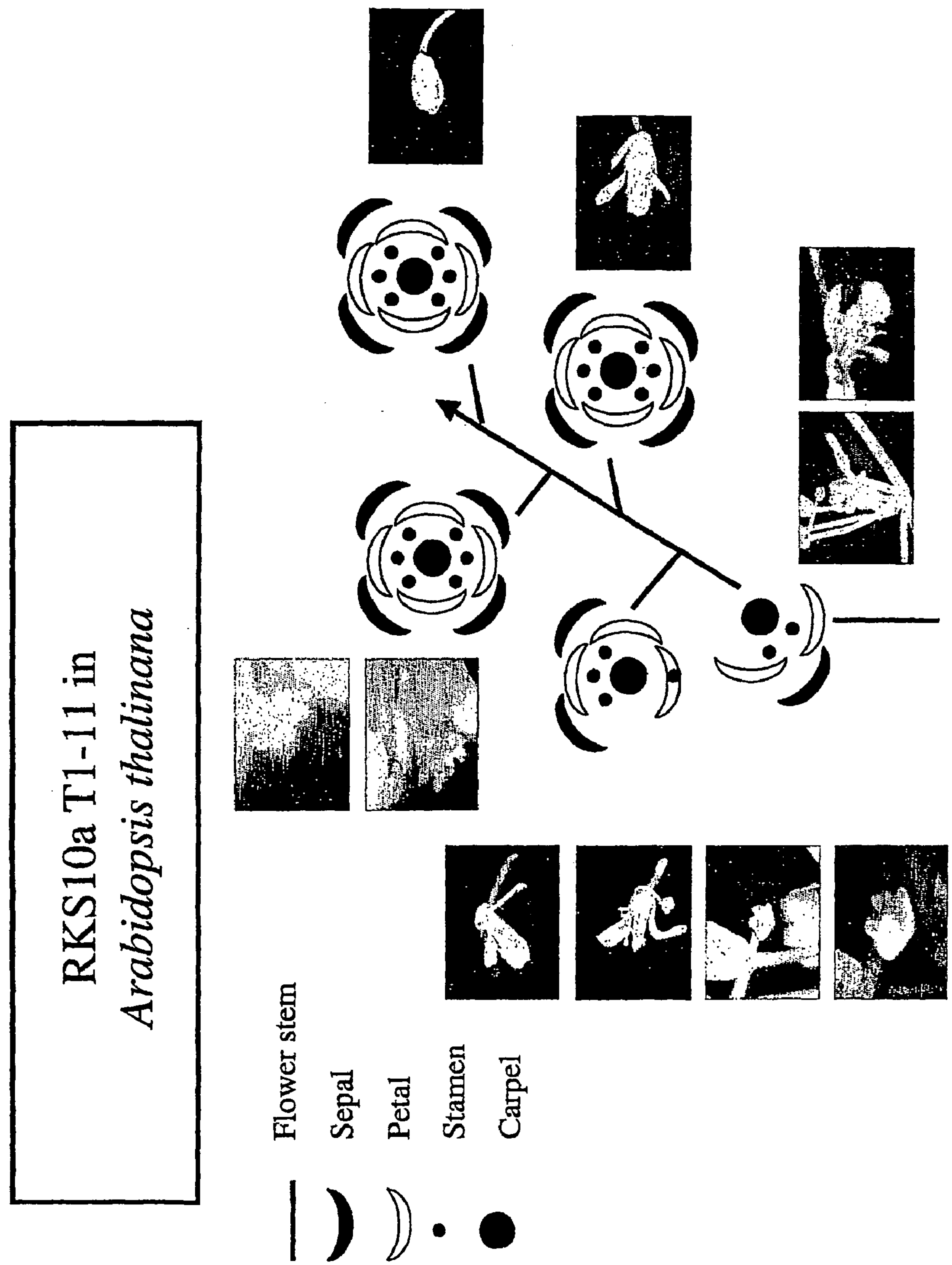
Figure 32:
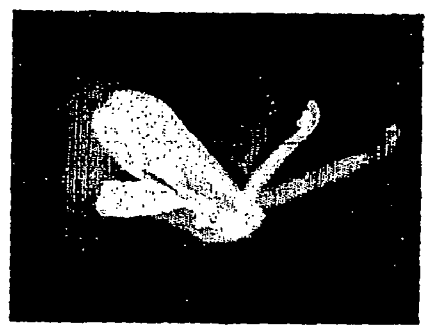
Figure 32:
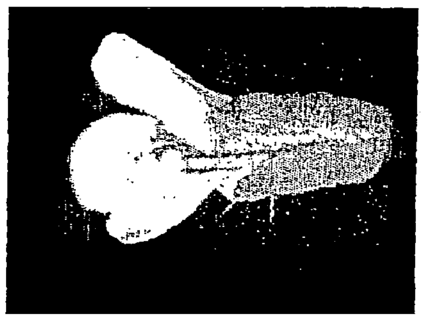
Figure 33:
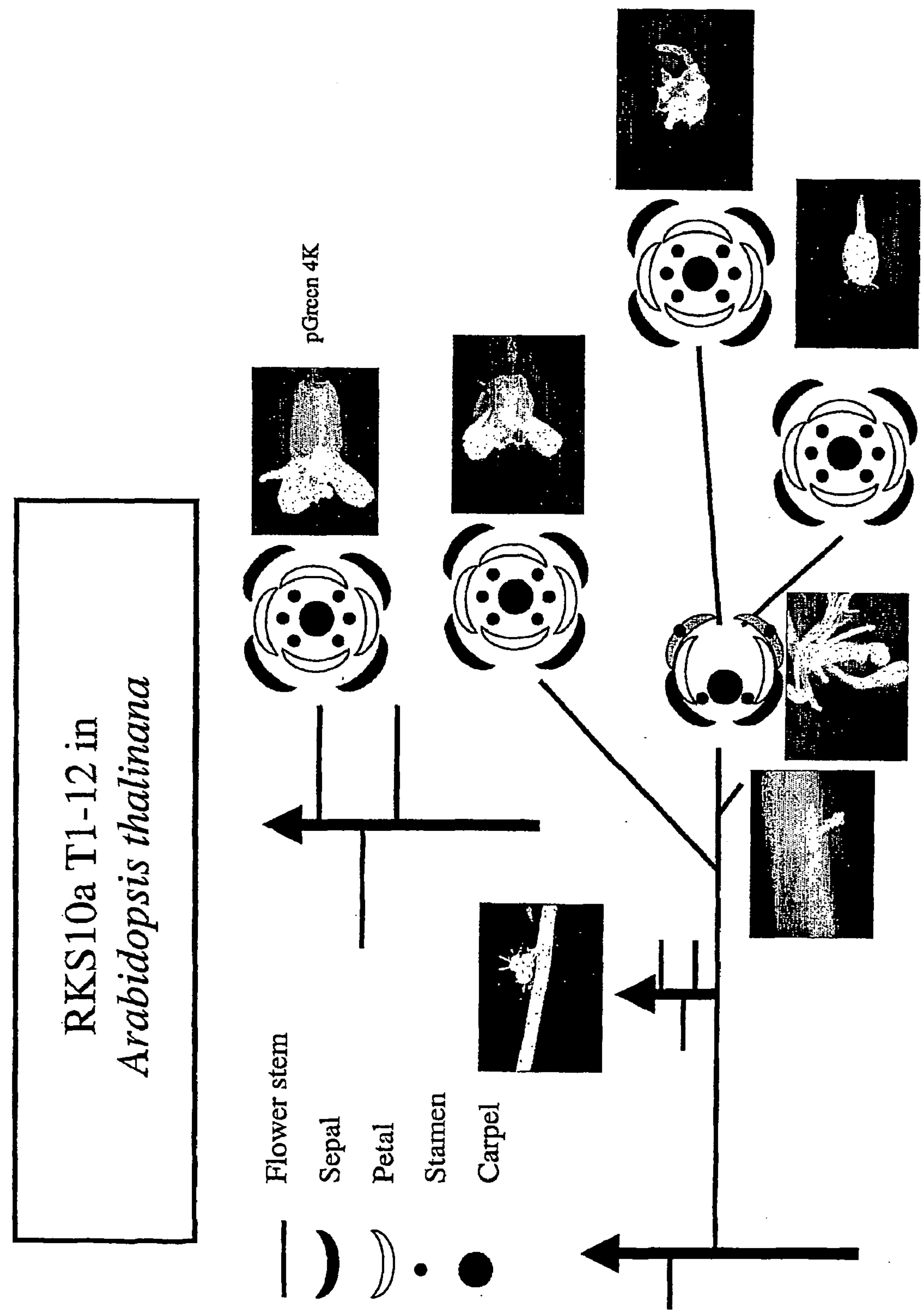
Figure 34:
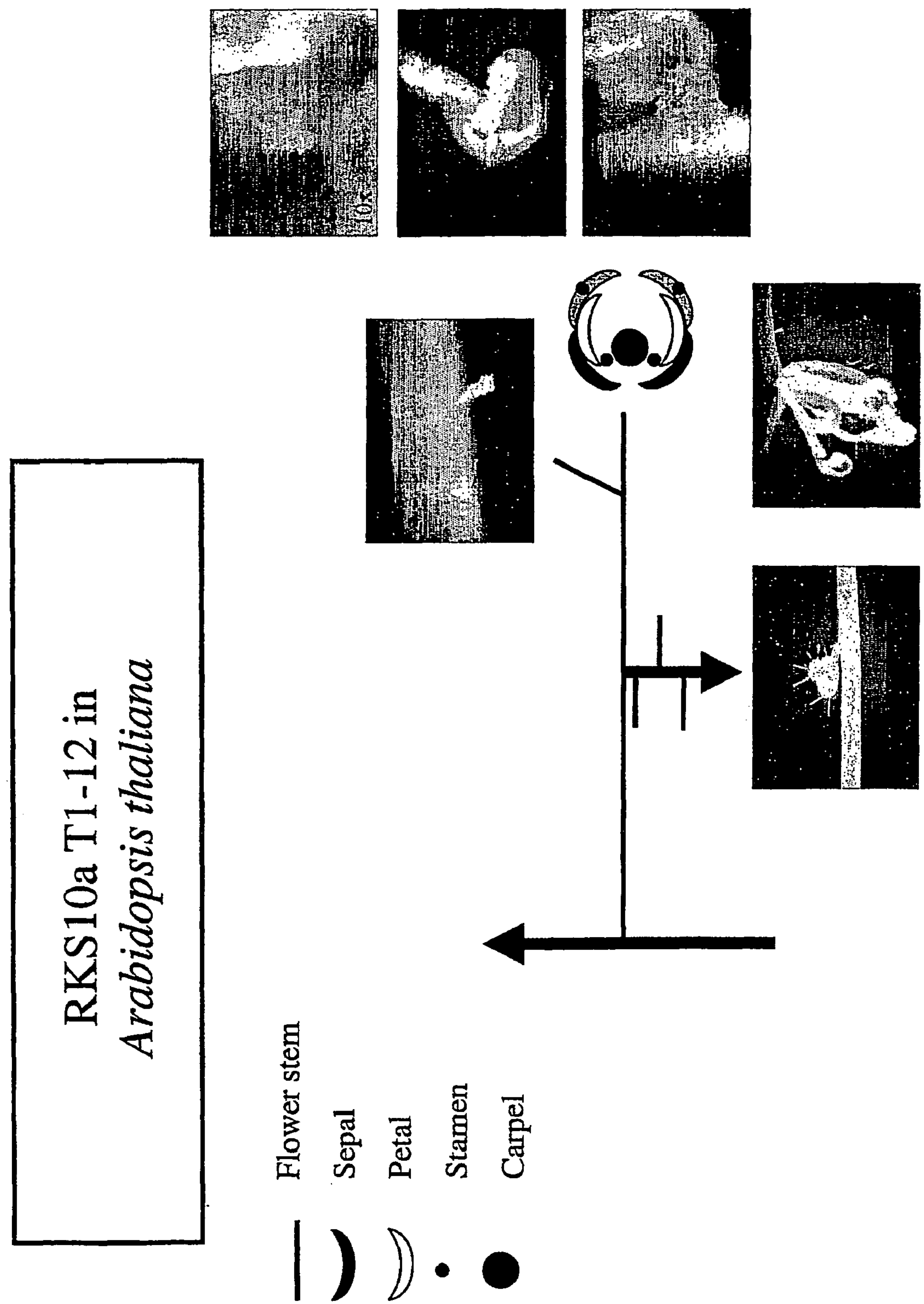
Figure 35:
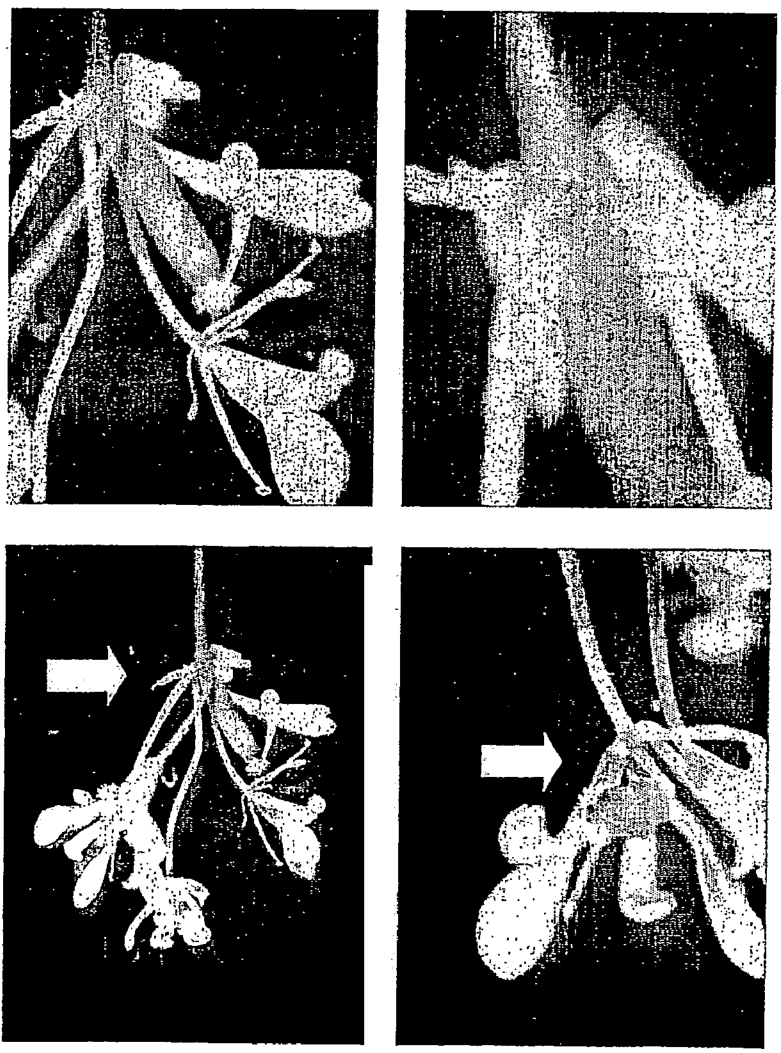

Compared with the control empty vector transgenic pGreen4K plants, large number of meristems are initiated at places were normally no meristems initiate and/or develop. A clear example is shown by co-suppressing the RKS8 gene (FIG. 29), where many new inflorescence meristems are initiated from the central generative meristem compared with control pGreen4K plants of the same age. This phenotype is even more extreme in RKS10 overexpressing plants where the resulting plants are extremely bushy with very large numbers of generative meristems formed. Inactivation of the endogenous RKS10 gene in *Arabidopsis* results in modification of meristematic identity as can be shown in FIG. 30. A determined flower meristem develops into two new normal terminal flower meristems and a number of terminal flower organ primordia. Another example is shown in FIG. 31 where meristem determination is switched from a terminal flower meristem, that normally result only in the normal numbers of terminal organ primordia, towards a number of organ primordia, a new undetermined generative meristem that develop into normal flowers or in a new terminal flower meristem with developmental abnormalities. Only half of the terminal flower primordia develop normally while an extra structure arises resembling a new flower stem with a petal/stamen like organ. The few pollen detectable on this structure (FIG. 32) were able to pollinate a MS1 (male sterile) *Arabidopsis* flower. FIG. 33 shows the meristematic developmental switch from a terminal flower meristem into a new undetermined generative meristem, that gives rise to a new formation of another undetermined meristem, and several normal and abnormal terminal flowers. The abnormal flowers again show the fusion of different structures, in this case from sepals, petals and stamen together (FIG. 34). Surprisingly, directly on the generative stem another structure, resembling a single stamen was detectable. All these data indicate that a decrease in RKS1 expression levels results in switches in the meristematic identity. Meristems can switch forward and backward between developmental stages, indicating that RKS10 is normally involved in regulating the meristematic identity and the developmental order of meristematic development. RKS13 seems to be involved in similar processes, as can be concluded from the switches in flower meristematic outgrowths observed in FIG. 35. Modification of the expression levels of RKS1 also results in modified meristem identity. Suppression of endogenous RKS1 levels results in a developmental switching of generative meristems towards vegetative meristems, together with other phenotypes (results not shown).

LITERATURE

To be, or not to be a flower-control of floral meristem identity. H. Ma 1998. Trends in Genetics 14: 26-32

A genetic framework for floral patterning. F. Parcy et al. 1998 Nature 395: 561-566

Evolution of flowers and inflorescences. E. S. Coen and J. M. Nugent 1994. Development supplement 107-116

Control of shoot cell fate: beyond homeoboxes. M. Tsiantis 2001. the Plant Cell 13: 733-738

Floral induction and determinations: where is flowering controlled? F. D. Hempel et al. 2000. Trends in plant science 5: 17-21

The *Arabidopsis* compact inflorescence genes: phase-specific growth regulation and the determination of inflorescence architecture. L. Goosey and R. Sharrock 2001. the Plant Journal 26: 549-559.

7. Male sterility

Male sterility is a highly desired trait in many plant species. For example, manipulation of pollen development is crucial for F1 hybrid seed production, to reduce labour costs and for the production of low-environmental impact genetically engineered crops. In order to produce hybrid seed from inbred plant lines, the male organs are removed from each flower, and pollen from another parent is applied manually to produce the hybrid seed. This labour-intensive method is used with a number of vegetables (e.g. hybrid tomatoes) and with many ornamental plants. Transgenic approaches, in which one or more introduced gene products interfere with normal pollen initiation and development is therefore highly desired. Especially when the number of revertants (growing normal pollen) is extremely low.

Male sterility in plants is a desired trait that has been shown already in many plant species as a result of the inactivation of expression of a number of genes essential for proper stamen development, mitotic divisions in the pollen stem cells, or male gametogenesis. A method for modulating a developmental pathway of a plant or plant cell comprising modifying a gene or modifying expression of said gene, wherein said gene is encoding a protein belonging to a signaling complex comprising RKS protein, ELS protein, NDR/NHL protein, SBP/SPL protein and RKS/ELS ligand protein, allowing modulating pollen development, in particular wherein said gene comprises an ELS2 or RKS10 gene or functional equivalent thereof.

Here we present data that show that overexpression of gene products, like transmembrane receptor kinases (RKS) and extracellular proteins (ELS) can also result in the formation of male sterility. The ability to induce male sterility by overexpressing specific genes as provided herein allows the opportunity to produce transgenic overexpressing plants in which the pollen development is inhibited. Stable single copy homozygous integration of such overexpressing traits into the plant genome will render such plants completely sterile, making them excellent material for the production of F1 hybrid seed. Furthermore, the combined integration of a male sterility inducing overexpressing gene coupled directly with another desired transgene result in transgenic plants which are unable to produce transgenic seed, making these transgenic plants excellent material for outside growth without problems affecting transgenic pollen spreading throughout the environment, thereby eliminating possible crosses with wild plant species or other non-transgenic crops. The combination of a desired transgene flanked on both sites by different male-sterility inducing overexpressing genes would decrease the frequency of pollen formation to an extremely low level.

An example is an overexpressing construct of RKS10 at the 5'end of integrated DNA fragment, the desired transgene expression cassette in the middle and at the 3'end of the integrated DNA the ELS2 overexpressing construct. This complete DNA fragment is integrated into the genome by conventional techniques, like particle bombardment, *Agrobacterium* transformation etc. Another possible application concerns the modification of pollen in ornamental plant species like lily, where the release of pollen from cut flowers can be avoided by making transgenic plants in which pollen development is initiated by release from the stamen is prevented (a desired trait that can be obtained by overexpressing for example ELS2, resulting in partial pollen development). Hereby the ornamental value of the stamen with pollen is not lost, but release of pollen is inhibited.

Results Obtained

Overexpression and antisense constructs of full length RKS cDNA clones have been made under the control of 35S promoters. Transgenic plants have been produced in *Arabidopsis thaliana*. Subsequent generations of stably transformed plants were investigated for phenotypes and analyzed in detail.

Figure 36:
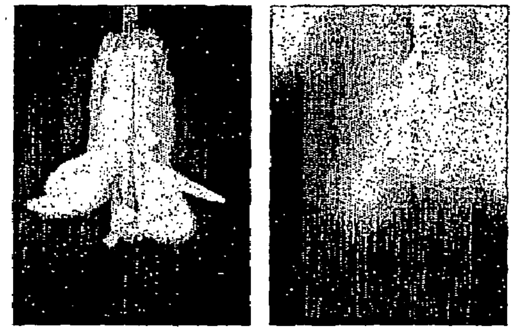
Figure 36:
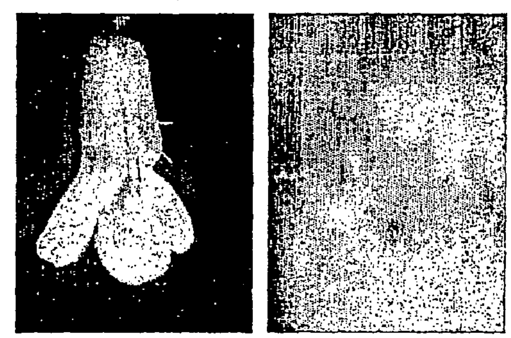
Figure 36:
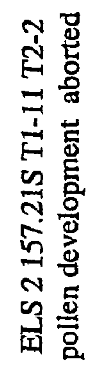

T2 transgenic seedlings of *Arabidopsis* were germinated on MS agar plates without hormones. Control transgenic plants containing a negative control vector pGreen4K (empty expression vector) were included as references for normal stamen and pollen development. RKS10 and ELS2 resulted in sterile plants when overexpressed in *Arabidopsis*. Antisense RKS10 plants resulted in a strong reduction in the number of pollen formed (FIG. 36). In order to determine whether pollen development itself was the reason for sterility (and not a combination of pollen developmental mutants coupled to either embryo lethals or female gametogenesis defects), reciprocal crosses were performed between sterile transgenic plants and wildtype *Arabidopsis thaliana* WS plants. These results confirmed that the sterile plants with overexpressing RKS10 and ELS2 constructs were male sterile but completely female fertile. No defects could be observed in embryo development from crosses between female transgenic overexpressors and male wildtype pollen (results not shown). Since both antisense and overexpressing constructs of the RKS10 gene showed defects in proper pollen development we conclude that normal levels of endogenous RKS10 gene product are essential for proper pollen formation, outgrowth and differentiation. In the ELS2 overexpressing plants the initiation of pollen grains was not inhibited. However the proper development of pollen grains in full grown viable pollen was clearly inhibited.

LITERATURE

The Arabidopsis male sterility1 (MS1) gene is a transcriptional regulator of male gametogenesis, with homology to the PHD-finger family of transcription factors. Wilson et al. 2001. the Plant Journal 28: 27-39

Transposon tagging of a male sterility gene in Arabidopsis. Aarts et al. 1993. Nature 363: 715-717

8. Resistance Mechanisms

Two-hybrid interaction experiments have already shown in vitro interaction between RKS and NDR0-NHL and members of the SBP/SPL family. Here we show that in vivo the individual components of this signalling cascade are regulating identical processes, as based on functional genomics on transgenics plants, overexpressing or co-suppressing single components or combinations of components in this transmembrane signalling complex.

Here we show a large number of new members of the NDR/NHL gene family and we postulate a function as syntaxins in the pathogen resistance:

```
At2g27080;                                      (SEQ ID NO: 66)
MAERVYPADS         PPQSGQFSGN         FSSGEFPKKP
APPPSTYVIQ         VPKDQIYRIP         PPENAHRFEQ
LSRKKTNRSN         CRCCFCSFLA         AVFILIVLAG
ISFAVLYLIY         RPEAPKYSIE         GFSVSGINLN
STSPISPSFN         VTVRSRNGNG         KIGVYYEKES
SVDVYYNDVD         ISNGVMPVFY         QPAKNVTVVK
LVLSGSKIQL         TSGMRKEMRN         EVSKKTVPFK
LKIKAPVKIK         FGSVKTWTMI         VNVDCDVTVD
KLTAPSRIVS         RKCSHDVDLW         **

At5g21130                                       (SEQ ID NO: 67)
MTVEKPQEMT         GDTNSDGFLT         NKDVHRIKHP
SLDTNDSSSS         RYSVDSQKSR         IGPPPGTYVI
KLPKDQIYRV         PPPENAHRYE         YLSRRKTNKS
CCRRCLCYSL         SALLIIIVLA         AIAFGFFYLV
YQPHKPQFSV         SGVSVTGINL         TSSSPFSPVI
RIKLRSQNVK         GKLGLIYEKG         NEADVFFNGT
KLGNGEFTAF         KQPAGNVTVI         VTVLKGSSVK
LKSSSRKELT         ESQKKGKVPF         GLRIKAPVKF
KVGSVTTWTM         TITVDCKITV         DKLTASATVK
TENCETGLSL         L*

At1g65690                                       (SEQ ID NO: 68)
MSQHQKIYPV         QDPEAATARP         TAPLVPRGSS
RSEHGDPSKV         PLNQRPQRFV         PLAPPKKRRS
CCCRCFCYTF         CFLLLLVVAV         GASIGILYLV
FKPKLPDYSI         DRLQLTRFAL         NQDSSLTTAF
NVTITAKNPN         EKIGIYYEDG         SKITVWYMEH
QLSNGSLPKF         YQGHENTTVI         YVEMTGQTQN
ASGLRTTLEE         QQQRTGNIPL         RIRVNQPVRV
KFGKLKLFEV         RFLVRCGVFV         DSLATNNVIK
IQSSSCKFRL         RL*

At5g36970                                       (SEQ ID NO: 69)
MSDHQKIHPV         SDPEAPPHPT         APLVPRGSSR
SEHGDPTKTQ         QAAPLDPPRE         KKGSRS
CWCRCVCYTLLVLF     LLIVIVGAIV         GILYLVFRPK
FPDYNIDRLQ         LTRFQLNQDL         SLSTAFNVTI
TAKNPNEKIG         IYYEDGSKIS         VLYMQTRISN
GSLPKFYQGH         ENTTIILVEM         TGFTQNATSL
MTTLQEQQRL         TGSIPLRIRV         TQPVRIKLGK
LKLMKVRFLV         RCGVSVDSLA         ANSVIRVRSS
NCKYRFRL*

At1g54540                                       (SEQ ID NO: 70)
MGDQQKIHPV         LQMEANKTKT         TTPAPGKTVL
LPVQRPIPPP         VIPSKNRNMC         CKIFCWVLSL
LVIALIALAI         AVAVVYFVFH         PKLPSYEVNS
LRVTNLGINL         DLSLSAEFKV         EITARNPNEK
IGIYYEKGGH         IGVWYDKTKL         CEGPIPRFYQ
GHRNVTKLNV         ALTGRAQYGN         TVLAALQQQQ
QTGRVPLDLK         VNAPVAIKLG         NLKMKKIRIL
GSCKLVVDSL         STNNNINIKA         SDCSFKAKL*

At5g06320                                       (SEQ ID NO: 71)
MADLNGAYYG         PSIPPPKKVS         HSHGRRGGGC
GCLGDCLGCC         GCCILSVIFN         ILITIAVLLG
IAALIIWLIF         RPNAIKFHVT         DAKLTEFTLD
PTNNLRYNLD         LNFTIRNPNR         RIGVYYDEIE
VRGYYGDQRF         GMSNNISKFY         QGHKNTTVVG
TKLVGQQLVL         LDGGERKDLN         EDVNSQIYRI
DAKLRLKIRF         KFGLIKSWRF         KPKIKCDLKV
PLTSNSTSGF         VFQPTKCDVD         F**

At5g11890                                       (SEQ ID NO: 72)
MTDRVFPASK         PPTATNGAPP         VGSIPPPPAP
ATVTSNGTTN         GMANQKPQVY         IPANRPVYRP
QPYSRRHHHQ         SRPSCRRICC         CCCFWSILII
LILALMTAIA         ATAMYVIYHP         RPPSFSVPSI
RISRVNLTTS         SDSSVSHLSS         FFNFTLISEN
PNQHLSFSYD         PFTVTVNSAK         SGTMLGNGTV
PAFFSDNGNK         TSFHGVIATS         TAARELDPDE
AKHLRSDLTR         ARVGYEIEMR         TKVKMIMGKL
KSEGVEIKVT         CEGFEGTIPK         GKTPIVATSK
KTKCKSDLSV         KVWKWSF*
```

-continued

At1g17620 (SEQ ID NO: 73)
MTDDRVVPAS KPPAIVGGGA PTTNPTFPAN
KAQLYNANRP AYRPPAGRRR TSHTRG
CCCRCCCWTIFVII LLLLIVAAAS AVVYLIYRPQ
RPSFTVSELK ISTLNFTSAV RLTTAISLSV
IARNPNKNVG FIYDVTDITL YKASTGGDDD
VVIGKGTIAA FSHGKKNTTT LRSTIGSPPD
ELDEISAGKL KGDLKAKKAV AIKIVLNSKV
KVKMGALKTP KSGIRVTCEG IKVVAPTGKK
ATTATTSAAK CKVDPRFKIW KITF**

At3g11650 (SEQ ID NO: 74)
MGSKQPYLNG AYYGPSIPPP PKAHRSYNSP
GFGCCCFSCL GSCLRCCGCC ILSLICNILI
AVAVILGVAA LILWLIFRPN AVKPYVADAN
LNRFSFDPNN NLHYSLDLNF TIRNPNQRVG
VYYDEFSVSG YYGDQRFGSA NVSSFYQGHK
NTTVILTKIE GQNLVVLGDG ARTDLKDDEK
SGIYRINAKL RLSVRFKFWF IKSWKLKPKI
KCDDLKIPLG SSNSTGGFKF QPVQCDFDLS**

At2g22180 (SEQ ID NO: 75)
MEGPRRPPSA TAPDSDDDKP DDPPSVWHRP
TSSLPALPSL DPPSHGSHHW RNHSLNLSPL
PTTSSPPLPP PDSIPELETY VVQVPRDQVY
WTPPPEHAKY VEKRSKNPEK NKKKGCSKRL
LWFFIILVIF GFLLGAIILI LHFAFNPTLP
VFAVERLTVN PSNFEVTLRA ENPTSNMGVR
YMMRKNGVVS LTYKNKSLGS GKFPGLSQAA
SGSDKVNVKL NGSTKNAVVQ PRGSKQPVVL
MLNMELKAEY EAGPVKRNKE VVVTCDVKVK
GLLDAKKVEI VSENCESEFK N*

At5g22870 (SEQ ID NO: 76)
MCHKPKLELM PMETSPAQPL RRPSLICYIF
LVILTLIFMA AVGFLITWLE TKPKKLRYTV
ENASVQNFNL TNDNHMSATF QFTIQSHNPN
HRISVYYSSV EIFVKFKDQT LAFDTVEPFH
QPRMNVKQID ETLIAENVAV SKSNGKDLRS
QNSLGKIGFE VFVKARVRFK VGIWKSSHRT
AKIKCSHVTV SLSQPNKSQN SSCDADI*

At2g35980 (SEQ ID NO: 77)
MAAEQPLNGA FYGPSVPPPA PKGYYRRGHG
RGCGCCLLSL FVKVIISLIV ILGVAALIFW
LIVRPRAIKF HVTDASLTRF DHTSPDNILR
YNLALTVPVR NPNKRIGLYY DRIEAHAYYE
GKRFSTITLT PFYQGHKNTT VLTPTFQGQN
LVIFNAGQSR TLNAERISGV YNIEIKFRLR
VRFKLGDLKF RRIKPKVDCD DLRLPLSTSN
GTTTTSTVFP IKCDFDF**

At2g46300 (SEQ ID NO: 78)
MADYQMNPVL QKPPGYRDPN MSSPPPPPPP
IQQQPMRKAV PMPTSYRPKK KRRSCCRFCC
CCICITLVLF IFLLLVGTAV FYLWFDPKLP
TPSLASFRLD GFKLADDPDG ASLSATAVAR
VEMKNPNSKL VFYYGNTAVD LSVGSGNDET
GMGETTMNGF RQGPKNSTSV KVETTVKNQL
VERGLAKRLA AKFQSKDLVI NVVAKTKVGL
GVGGIKIGML AVNLRCGGVS LNKLDTDSPK
CILNTLKWYK IISN*

At4g05220 (SEQ ID NO: 79)
MTPDRTTIPI RTSPVPRAQP MKRHHSASYY
AHRVRESLST RISKFICAMF LLVLFFVGVI
AFILWLSLRP HRPRFHIQDF VVQGLDQPTG
VENARIAFNV TILNPNQHMG VYFDSMEGSI
YYKDQRVGLI PLLNPFFQQP TNTTIVTGTL
TGASLTVNSN RWTEFSNDRA QGTVGFRLDI
VSTIRFKLHR WISKHRRMHA NCNIVVGRDG
LILPKFNHKR CPVYFT*

At2g35460 (SEQ ID NO: 80)
MANGLNGASY GPPIKPPVKT YYSHGRRGSD
VGCGICGCFS SCLLCCGGCL VNIICNILIG
VLVCLGVVAL ILWFILRPNV VKFQVTEADL
TRFEFDPRSH NLHYNISLNF SIRNPNQRLG
IHYDQLEVRG YYGDQRFSAA NMTSFYQGHK
NTTVVGTELN GQKLVLLGAG GRRDFREDRR
SGVYRIDVKL RFKLRFKFGF LNSWAVRPKI
KCHLKVPLST SSSDERFQFH PTKCHVDL*

At2g27260 (SEQ ID NO: 81)
MQDPSRPATG YPYPYPYPNP QQQQPPTNGY
PNPAAGTAYP YQNHNPYYAP QPNPRAVIIR
RLFIVFTTFL LLLGLILFIF FLIVRPQLPD
VNLNSLSVSN FNVSNNQVSG KWDLQLQFRN
PNSKMSLHYE TALCAMYYNR VSLSETRLQP
FDQGKKDQTV VNATLSVSGT YVDGRLVDSI
GKERSVKGNV EFDLRMISYV TFRYGAFRRR
RYVTVYCDDV AVGVPVSSGE GKMVGSSKRC
KTY**

At4g01410 (SEQ ID NO: 82)
MGEGEAKAEH AAKADHKNAP SASSTPESYS
KEGGGGGGDA RRAICGAIFT ILVILGIIAL
ILWLVYRPHK PRLTVVGAAI YDLNFTAPPL
ISTSVQFSVL ARNPNRRVSI HYDKLSMYVT
YKDQIITPPL PLPPLRLGHK STVVIAPVMG
GNGIPVSPEV ANGLKNDEAY GVVLMRVVIF
GRLRWKAGAI KTGRYGFYAR CDVWLRFNPS
SNGQVPLLAP STCKVDV*

At5g22200 (SEQ ID NO: 83)
NTGRYCDQHN GYEERRMRMM MRRIAWACLG
LIVAVAFVVF LVWAILHPHG PRFVLQDVTI
NDFNVSQPNF LSSNLQVTVS SRNPNDKIGI
FYDRLDIYVT YRNQEVTLAR LLPSTYQGHL
EVTVWSPFLI GSAVPVAPYL SSALNEDLFA
GLVLLNIKID GWVRWKVGSW VSGSYRLHVN
CPAFITVTGK LTGTGPAIKY QLVQRCAVDV
*

At1g61760 (SEQ ID NO: 84)
MHNKVDSLPV RSNPSTRPIS RHHSASNIVH
RVKESLTTRV SKLICAIFLS LLLCLGIITF
ILWISLQPHR PRVHIRQFSI SGLSRPDGFE
TSHISFKITA HNPNQNVGIY YDSMEGSVYY
KEKRIGSTKL TNPFYQDPKN TSSIDGALSR
PAMAVNKDRW MEMERDRNQG KIMFRLKVRS
MIRFKVYTWH SKSHKMYASC YIEIGWDGML
LSATKDKRCP VYFT*

At3g52470 (SEQ ID NO: 85)
MSKDCGNHGG GKEVVVRKLC AAIIAFIVIV
LITIFLVWVI LRPTKPRFVL QDATVYAFNL
SQPNLLTSNF QVTIASRNPN SKIGIYYDRL
HVYATYMNQQ ITLRTAIPPT YQGHKEVNVW
SPFVYGTAVP IAPYNSVALG EEKDRGFVGL
MIRADGTVRW KVRTLITGKY HIHVRCQAFI
NLGNKAAGVL VGDNAVKYTL ANKCSVNV**

At5g53730 (SEQ ID NO: 86)
MSQISITSPK HCAKKGGINI NNRHKKLFFT
FSTFFSGLLL IIFLVWLILH PERPEFSLTE
ADIYSLNLTT SSTHLLNSSV QLTLFSKNPN
KKVGIYYDKL LVYAAYRGQQ ITSEASLPPF
YQSHEEINLL TAFLQGTELP VAQSFGYQIS
RERSTGKIII GMKMDGKLRW KIGTWVSGAY
RFNVNCLAIV AFGMNMTTPP LASLQGTRCS
TTI*

At4g01110 (SEQ ID NO: 87)
MAGETLLKPV LQKPPGYREL HSQPQTPLGS
SSSSSSMLRR PPKHAIPAAF YPTKKRQWSR
CRVFCCCVCI TVAIVILLLI LTVSVFFLYY
SPRLPVVRLS SFRVSNFNFS GGKAGDGLSQ
LTAEATARLD FRNPNGKLRY YYGNVDVAVS
VGEDDFETSL GSTKVKGFVE KPGNRTVVIV
PIKVKKQQVD DPTVKRLRAD MKSKKLVVKV
MAKTKVGLGV GRRKIVTVGV TISCGGVRLQ
TLDSKMSKCT IKMLKWYVPI QVKCI*

At2g35960 (SEQ ID NO: 88)
MTTKDCGNHG GGGGGGTASR ICGVIIGFII
IVLITIFLVW IILQPTKPRF ILQDATVYAP
NLSQPNLLTS NFQITIASRN RNSRIGIYYD
RLHVYATYRN QQITLRTAIP PTYQGHKEDN

-continued

```
VWSPFVYGNS  VPIAPFNAVA  LGDEQNRGFV
TLIIRADGRV  RWKVGTLITG  KYHLHVRCQA
FINLADKAAG  VHVGENAVKY  MLINKCSVNV
*

At3g52460                           (SEQ ID NO: 89)
MPSPPEEETQ  PKPDTGPGQN  SERDINQPPP
PPPQSQPPPP  QTQQQTYPPV  MGYPGYHQPP
PPYPNYPNAP  YQQYPYAQAP  PASYYGSSYP
AQQNPVYQRP  ASSGFVRGIF  TGLIVLVVLL
CISTTITWLV  LRPQIPLFSV  NNFSVSNFNV
TGPVFSAQWT  ANLTIENQNT  KLKGYFDRIQ
GLVYHQNAVG  EDEFLATAFF  QPVFVETKKS
VVIGETLTAG  DKEQPKVPSW  VVDEMKKERE
TGTVTFSLRM  AVWVTFKTDG  WAARESGLKV
FCGKLKVGFE  GISGNGAVLL  PKPLPCVVYV*

At4g09590                           (SEQ ID NO: 90)
MTTKECGNHG  GGGGGGGTAC  RICGAIIGFI
IIVLMTIFLV  WIILQPKNPE  FILQDTTVYA
FNLSQPNLLT  SKFQITIASR  NRNSNIGIYY
DHLHAYASYR  NQQITLASDL  PPTYQRHKED
SVWSPLLYGN  QVPIAPFNAV  ALGDEQNSGV
FTLTICVDGQ  VRWKVGTLTI  GNYHLHVRCQ
AFINQADKAA  GVHVGENTVK  YTLINKCSVN
F*

At2g35970                           (SEQ ID NO: 91)
MTTKECGNHG  GGGGGGGTAC  RICGAIIGFI
IIVLMTIFLV  SIILQPKKPE  FILQDTTVYA
FNLSQPNLLT  SKFQITIASR  NRNSNIGIYY
DHLHAYASYR  NQQITLASDL  PPTYQRHKEN
SVWSPLLYGN  QVPIAPFNAV  ALGDEQNSGV
FTLTICVDGR  VRWKVGTLTI  GNYHLHVRCQ
AFINQADKAA  GVHVGRNTVK  YTLINKCSVN
F*

At3g26350                           (SEQ ID NO: 92)
MSHHHHHETN  PHFARIPSQN  PHLKSGGAST
SQTSSNQPHI  PPIPHPKKSH  HKTTQPHPVA
PPGILIKTRG  RHRENPIQEP  KHSVIPVPLS
PEERLPPRKT  QNSSKRPLLL  SPEDNQQQRP
PPPQAPQRNG  GGYGSTLPPI  PKPSPWRTAP
TPSPHHRRGP  RLPPPSRETN  AMTWSAAFCC
AIFWVILILG  GLIILIVYLV  YRPRSPYVDI
SAANLNAAYL  DMGFLLNGDL  TILANVTNPS
KKSSVEFSYV  TFELYYYNTL  IATQYIEPFK
VPKKTSMFAN  VHLVSSQVQL  QATQSRELQR
QIETGPVLLN  LRGMFHARSH  IGPLFRYSYK
LHTHCSVSLN  GPPLGAMRAR  RCNTKR*

At3g11660                           (SEQ ID NO: 93)
MKDCENHGHS  RRKLIRRIFW  SIIFVLFIIF
LTILLIWAIL  QPSKPRFILQ  DATVYAPNVS
GNPPNLLTSN  FQITLSSRNP  NNKIGIYYDR
LDVYATYRSQ  QITFPTSIPP  TYQGHKDVDI
WSPFVYGTSV  PIAPFNGVSL  DTDKDNGVVL
LIIRADGRVR  WKVGTFITGK  YHLHVKCPAY
INFGNKANGV  IVGDNAVKYT  FTTSCSVSV**

At3g44220                           (SEQ ID NO: 94)
MTEKECEHHH  DEDEKMRKRI  GALVLGFLAA
VLFVVFLVWA  ILHPHGPRFV  LQDATIYAFN
VSQPNYLTSN  LQVTLSSRNP  NDKIGIFYDR
LDIYASYRNQ  QVTLATLLPA  TYQGHLDVTI
WSPFLYGTTV  PVAPYFSPAL  SQDLTAGMVL
LNIKIDGWVR  WKVGTWVSGR  YRLHVNCPAY
ITLAGHFSGD  GPAVKYQLVQ  RCAVDV*

At1g08160                           (SEQ ID NO: 95)
MVPPNPAHQP  ARRTQPQLQP  QSQPRAQPLP
GRPMNPVLCI  IVALVLLGLL  VGLAILITYL
TLRPKRLIYT  VEAASVQEFA  IGNNDDHINA
KFSYVIKSYN  PEKHVSVRYH  SMRISTAHHN
QSVAHKNISP  FKQRPKNETR  IETQLVSHNV
ALSKFNARDL  RAEKSKGTIE  MEVYITARVS
YKTWIFRSRR  RTLKAVCTPV  MINVTSSSLD
GFQRVLCKTR  L**
```

-continued

```
At2g01080                           (SEQ ID NO: 96)
MPPPPSSSRA  GLNGDPIAAQ  NQQPYYRSYS
SSSSASLKGC  CCCLFLLFAF  LALLVLAVVL
IVILAVKPKK  PQFDLQQVAV  VYMGISNPSA
VLDPTTASLS  LTIRMLFTAV  NPNKVGIRYG
ESSFTVMYKG  MPLGRATVPG  FYQDAHSTKN
VEATISVDRV  NLMQAHAADL  VRDASLNDRV
ELTVRGDVGA  KIRVMNFDSP  GVQVLLPSFL
PAFCSLSDLA  *

At5g06330                           (SEQ ID NO: 97)
MTSKDCGSHD  SHSSCNRKIV  IWTISIILLL
ILVVILLVWA  ILQPSKPRFV  LQDATVFNFN
VSGNPPNLLT  SNFQFTLSSR  NPNDKIGIYY
DRLDVYASYR  SQQITLPSPM  LTTYQGHKEV
NVWSPFVGGY  SVPVAPYNAF  YLDQDHSSGA
IMLMLHLDGR  VRWKVGSFIT  GKYHLHVRCH
ALINFGSSAA  GVIVGKYMLT  ETCSVSV*

At5g56050                           (SEQ ID NO: 98)
MSKFSPPPQS  QPQPPETPPW  ETPSSKWYSP
IYTPWRTTPR  STQSTPTTTP  IALTEVIVSK
SPLSNQKSPA  TPKLDSMEAH  PLHETMVLLQ
LRTSRTNPWI  WCGAALCFIF  SILLIVFGIA
TLILYLAVKP  RTPVFDISNA  KLNTILFESP
VYPNGDMLLQ  LNFTNPNKKL  NVRFENLMVE
LWFADTKIAT  QGVLPFSQRN  GKTRLEPIRL
ISNLVFLPVN  HILELRRQVT  SNRIAYEIRS
NFRVKAIFGM  IHYSYMLHGI  CQLQLSSPPA
GGLVYRNCTT  KRW*

At3g20600                           (SEQ ID NO: 99)
NDR1
MNNQNEDTEG  GRNCCTCCLS  FIFTAGLTSL
FLWLSLRADK  PKCSIQNFFI  PALGKDPNSR
DNTTLNFMVR  CDNPNKDKGI  YYDDVHLNFS
TINTTKINSS  ALVLVGNYTV  PKFYQGHKKK
AKKWGQVKPL  NNQTVLRAVL  PNGSAVFRLD
LKTQVRFKIV  FWKTKRYGVE  VGADVEVNGD
GVKAQKKGIK  MKKSDSSFPL  RSSFPISVLM
NLLVFFAIR*

At3g54200                           (SEQ ID NO: 100)
MSDFSIKPDD  KKEEEKPATA  MLPPPKPNAS
SMETQSANTG  TAKKLRRKRN  CKICICFTIL
LILLIAIVIV  ILAFTLFKPK  RPTTTIDSVT
VDRLQASVNP  LLLKVLLNLT  LNVDLSLKNP
NRIGFSYDSS  SALLNYRGQV  IGEAPLPANR
IAARKTVPLN  ITLTLMADRL  LSETQLLSDV
MAGVIPLNTF  VKVTGKVTVL  KIFKIKVQSS
SSCDLSISVS  DRNVTSQHCK  YSTKL*

At3g20590                           (SEQ ID NO: 101)
non-race specific disease resistance protein,
putative
MTKIDPEEEL  GRKCCTCFFK  FIFTTRLGAL
ILWLSLRAKK  PKCSIQNFYI  PALSKNLSSR
DNTTLNFMVR  CDNPNKDKGI  YYDDVHLTFS
TINTTTTNSS  DLVLVANYTV  PKFYQGHKKK
AKKWGQVWPL  NNQTVLRAVL  PNGSAVFRLD
LKTHVRFKIV  FWKTKWYRRI  KVGADVEVNG
DGVKAQKKGS  KTKKSDSSLP  LRSSFPIFVL
MNLLVFFAIR  *

At4g39740                           (SEQ ID NO: 102)
MSHVTATSLA  RFTKPVPKPA  SSPIVNTKLT
TSGGRTAAFM  DLSSFRLTVW  DPDTANDSSG
KFPWPRFLFF  FLTLKTGGSG  LNIKPTISAI
AQMMNPMTIT  EMNNQMHRLE  QKLLLFLPGS
LFLRLSTILH  YPGEGSNRPD  PLEHALRRSR
SLGLDQEEAA  KKVIRVGRDS  KNDYVNVVEN
QAASFLRRCG  PSKRIQSVNY  CKSTRQGHEI
PDVKPLFPTG  GGTQAPSRSR  ARYAVPAILL
GFAGFVGFLH  YNDERRAVPR  GQASSNSGCG
CGSNTTVKGP  IIGGPFTLVS  TENKIVTEND
FCGKWVLLYF  GYSFSPDVGP  EQLKMMSKAV
DKLAILLNPL  TFGCLYLYAE  FDSRILGLTG
TASAMRQMAQ  EYRVYFKKVQ  EDGEDYLVDT
SHNMYLINPK  MEIVRCFGVE  YNPDELSQEL
LKEVASVSQ*
```

-continued (SEQ ID NO: 103)

At1g32270 syntaxin, putative

```
MVRSNDVKFQ VYDAELTHFD LESNNNLQYS
LSLNLSIRNS KSSIGIHYDR FEATVYYMNQ
RLGAVPMPLF YLGSKNTMLL RALFEGQTLV
LLKGNERKKF EDDQKTGVYR IDVKLSINFR
VMVLHLVTWP MKPVVRCHLK IPLALGSSNS
TGGHKKMLLI GQLVKDTSAN LREASETDHR
RDVAQSKKIA DAKLAKDFEA ALKEFQKAQH
ITVERETSYI PFDPKGSFSS SEVDIGYDRS
QEQRVLMESR RQEIVLLDNE ISLNEARIEA
REQGIQEVKH QISEVMEMFK DLAVMVDHQG
TIDDIDEKID NLRSAAAQGK SHLVKASNTQ
GSNSSLLFSC SLLLFFFLSG DLCRCVCVGS
ENPRLNPTRR KAWCEEEDEE QRKKQQKKKT
MSEKRRREEK KVNKPNGFVF CVLGHK*
```

(SEQ ID NO: 104)

At1g13050

```
MSHHHYETNP HFVQFSLQDQ HQGGPSSSWN
SPHHHQIPQA HSVAPPRVKI KTRGRHQTEP
PETIHESPSS RPLPLRPEEP LPPRHNPNSA
RPLQLSPEEQ RPPHRGYGSE PTPWRRAPTR
PAYQQGPKRT KPMTLPATIC CAILLIVLIL
SGLILLLVYL ANRPRSPYFD ISAATLNTAN
LDMGYVLNGD LAVVVNFTNP SKKSSVDFSY
VMFELYFYNT LIATEHIEPF IVPKGMSMFT
SFHLVSSQVQ IQMIQSQDLQ LQLGTGPVLL
NLRGTFHARS NLGSLMRYSY WLHTQCSISL
NTPPAGTMRA RRCNTKR*
```

(SEQ ID NO: 105)

At5g45320

```
MPRLTSRHGT SPFIWCAAII CAIISIVVIV
GGIIVFVGYL VIHPRVPIIS VADAHLDFLK
YDIVGVLQTQ LTIVIRVEND NAKAHALFDE
TEFKLSYEGK PIAILKAPEF EVVKEKSMFL
PYLVQSYPIP LNPTMMQAVD YAVKKDVITF
ELKGGSRTRW RVGPLGSVKF ECNLSCQLRF
RPSDHSYIPS PCTSAHKH*
```

(SEQ ID NO: 106)

At3g20610

```
MDRDDAWEWF VTIVGSLMTL LYVSFLLALC
LWLSTLVHHI PRCSIHYFYI PALNKSLISS
DNTTLNFMVR LKNINAKQGI YYEDLHLSFS
TRINNSSLLV ANYTVPRFYQ GHEKKAKKWG
QALPFNNQTV IQAVLPNGSA IFRVDLKMQV
KYKVMSWKTK RYKLKASVNL EVNEDGATKV
KDKEDGIKMK ISDSSPQRLT FFQVCFSIIC
VLMNWLIFLA IR*
```

(SEQ ID NO: 107)

At4g26490

```
MVLTKPATVR FNGLDAEPRK DRVILRQPRS
SRTSLWIWCV AVFLAIRPRI PVFDIPNANL
HTIYFDTPEF FNGDLSMLVN FTNPNKKIEV
KFEKLRIELF FFNRLIAAQV VQPFLQKKHE
TRLEPIRLIS SLVGLPVNHA VELRRQLENN
KIEYEIRGTF KVKAHFGMIH YSYQLHGRCQ
LQMTGPPTGI LISRNCTTKK *
```

(SEQ ID NO: 108)

At5g42860

```
MHAKTDSEVT SLSASSPTRS PRRPAYFVQS
PSRDSHDGEK TATSFHSTPV LTSPMGSPPH
SHSSSSRFSK INGSKRKGHA GEKQFAMIEE
EGLLDDGDRE QEALPRRCYV LAFIVGFSLL
FAFFSLILYA AAKPQKPKIS VKSITFEQLK
VQAGQDAGGI GTDMITMNAT LRMLYRNTGT
FFGVHVTSSP IDLSFSQITI GSGSIKKFYQ
SRKSQRTVVV NVLGDKIPLY GSGSTLVPPP
PPAPIPKPKK KKGPIVIVEP PAPPAPVPMR
LNFTVRSRAY VLGKLVQPKF YKRIVCLINF
EHKKLSKHIP ITNNCTVTSI *
```

(SEQ ID NO: 109)

At1g45688

```
MHAKTDSEVT SLAASSPARS PRRPVYYVQS
PSRDSHDGEK TATSFHSTPV LSPMGSPPHS
HSSMGRHSRE SSSSRFSGSL KPGSRKVNPN
DGSKRKGHGG EKQWKECAVI EEEGLLDDGD
RDGGVPRRCY VLAFIVGFFI LFGFFSLILY
GAAKPMKPKI TVKSITFETL KIQAGQDAGG
VGTDMITMNA TLRMLYRNTG TFFGVHVTST
PIDLSFSQIK IGSGSVKKFY QGRKSERTVL
```

-continued

```
VHVIGEKIPL YGSGSTLLPP APPAPLPKPK
KKKGAPVPIP DPPAPPAPVP MTLSFVVRSR
AYVLGKLVQP KFYKKIECDI NFEHKNLNKH
IVITKNCTVT TV*
```

(SEQ ID NO: 110)

At4g26820

```
MDDEQNLVEE MNQQLLITVI DTEKVPELRP
ISSRSHQESE PANISHWSLL FKLFLAITIM
GACVAGVTFV ILITPTPPTV HVQSMHISFA
NHNLPVWSAT FSIKNPNEKL HVTYENPSVW
LVHRGKLVST ARADSFWQKG GEKNEVIVKR
NETKVIDEEA AWEMEDEVAV TGGVVGLDMV
FSGRVGFYPG TSALWGEQYM SAVCENVSAK
LYNVDDEIYG TNRSVLSFDG RLVCSVRLPK
YP*
```

Plants respond in a variety of ways to pathogens. After a recognition of the pathogen, normally mediated by avr and R genes, the resulting response induces a hypersensitive response, that results in inhibition of the pathogen. After the recognition, further processes appear to be non-specific. In addition to the hypersensitive response, a second line of defence, defined as the systemic acquired resistance response can be triggered, that renders unaffected parts of the plant resistant to a variety of normally virulent pathogens. Several of the RKS and ELS gene products prove to be key regulators in the regulation of the system acquired resistance response.

Overexpression of several of the RKS and/or ELS genes in plants, either by constitutive promoters, stage and/or tissue specific promoters, or inducible promoters allows the activation of a systemic acquired resistance response in plants.

Another application can be provided by the activation of a RKS/ELS specific ligand in (transgenic) plants, thereby activating the receptor complex, that finally results in triggered activation of the systemic acquired resistance response in these plants.

(ref. Generation of broad-spectrum disease resistance by overexpression of an essential regulatory gene in systemic acquired resistance. H. Cao et al. 1998. Proc. Natl. Acad. Sci. USA 95: 6531-6536). Recent literature shows the functional interaction between RKS10 and BRI-1, another class of transmembrane LRR receptor kinases (Cell Vol. 110, 213-222 2002). BAK1=RKS10 as described here, interacts with BRI-1 and modulates brassinosteroid signaling; Cell vol 110, 203-212 2002 BRI1/BAK1 a receptor kinase pair mediating brassinosteroid signaling). Brassinosteroids are known to function in a broad range of disease resistance in tobacco and rice (Plant Journal 2003, 887-898). The BRI-1 receptor is involved in the binding of systemin, an 18 amino acid polypeptide, representing the primary signal for the systemic activation of defence genes (PNAS 2002, 9585-9590).

ELS overexpression phenotypes mimic the effects of inactivation of RKS molecules gene products. Either ELS is competing for ligand binding, or ELS inhibits the interactions between RKS and BRI-1-like gene products. ELS1 overexpression results in dwarf phenotypes in Arabidopsis and tobacco plants, similar as observed for antisense RKS4 and RKS10, and for knock out plants of RKS0 and RKS4.

Deregulating expression of ELS and/or RKS genes in plant would modify the broad spectrum disease resistance in such plants. This would explain the observed data that brassinosteroids are involved in disease resistance (Plant Journal 2003, 33 887-898.)

FURTHER REFERENCES

Plant Journal 1997: 12, 2 367-377

Mol. Gen. Genet. 1996: 250, 7-16

Gene 1999, 237, 91-104
Genes and Development 1997: 11, 616-628
Proc. Natl. Acad. Sci. USA 1998: 95, 10306-10311
Plant Journal 2000: 22, 523-529
Science 1997: 278, 1963-1965
Plant Physiol. Biochem. 2000: 38, 789-796
Cell 1996: 84, 61-71
Annu. Rev. Plant Physiol. Plant Mol. Biol. 1999: 50, 505-537

The invention claimed is:

1. A method for increasing organ size or rate of cell division of a plant or plant cell, compared to a wild-type plant or plant cell of the same plant species, said method comprising:

transforming the plant or plant cell with an RKS4 gene comprising the nucleotide sequence as set forth in SEQ ID NO: 46 operably linked to a promoter, wherein expression of the RKS4 gene increases the organ size or rate of cell division of the plant or the plant cell.

2. The method of claim 1, wherein the organ comprises a vegetative organ.

3. The method of claim 1, wherein the organ comprises a reproductive organ.

4. The method of claim 1, wherein the organ is selected from the group consisting of a leaf, shoot, root, flower, pollen, and seed.

5. A method for providing pathogen resistance to a plant or plant cell comprising transforming the plant or plant cell with an RKS4 gene comprising the nucleotide sequence as set forth in SEQ ID NO: 46 operably linked to a promoter, wherein expression of the RKS4 gene provides pathogen resistance to the plant or plant cell.

6. A method for decreasing organ size or rate of cell division of a plant or plant cell, compared to a wild-type plant or plant cell of the same plant species, said method comprising:

transforming the plant or plant cell with an RKS4 gene comprising the nucleotide sequence as set forth in SEQ ID NO: 46 in antisense orientation operably linked to a promoter, wherein expression of the RKS4 gene in antisense orientation decreases the organ size or rate of cell division of the plant or the plant cell.

7. The method of claim 6, wherein the organ comprises a vegetative organ.

8. The method of claim 6, wherein the organ comprises a reproductive organ.

9. The method of claim 6, wherein the organ is selected from the group consisting of a leaf, shoot, root, flower, pollen, and seed.

* * * * *

SEQUENCE LISTING

```
<160> NUMBER OF SEQ ID NOS: 110

<210> SEQ ID NO 1
<211> LENGTH: 227
<212> TYPE: PRT
<213> ORGANISM: Arabidopsis thaliana

<400> SEQUENCE: 1

Met Ala Ala Glu Gln Pro Leu Asn Gly Ala Phe Tyr Gly Pro Ser Val
1               5                   10                  15

Pro Pro Pro Ala Pro Lys Gly Tyr Tyr Arg Arg Gly His Gly Arg Gly
            20                  25                  30

Cys Gly Cys Cys Leu Leu Ser Leu Phe Val Lys Val Ile Ile Ser Leu
        35                  40                  45

Ile Val Ile Leu Gly Val Ala Ala Leu Ile Phe Trp Leu Ile Val Arg
    50                  55                  60

Pro Arg Ala Ile Lys Phe His Val Thr Asp Ala Ser Leu Thr Arg Phe
65                  70                  75                  80

Asp His Thr Ser Pro Asp Asn Ile Leu Arg Tyr Asn Leu Ala Leu Thr
                85                  90                  95

Val Pro Val Arg Asn Pro Asn Lys Arg Ile Gly Leu Tyr Tyr Asp Arg
            100                 105                 110

Ile Glu Ala His Ala Tyr Tyr Glu Gly Lys Arg Phe Ser Thr Ile Thr
        115                 120                 125

Leu Thr Pro Phe Tyr Gln Gly His Lys Asn Thr Thr Val Leu Thr Pro
    130                 135                 140

Thr Phe Gln Gly Gln Asn Leu Val Ile Phe Asn Ala Gly Gln Ser Arg
145                 150                 155                 160

Thr Leu Asn Ala Glu Arg Ile Ser Gly Val Tyr Asn Ile Glu Ile Lys
                165                 170                 175

Phe Arg Leu Arg Val Arg Phe Lys Leu Gly Asp Leu Lys Phe Arg Arg
            180                 185                 190

Ile Lys Pro Lys Val Asp Cys Asp Asp Leu Arg Leu Pro Leu Ser Thr
        195                 200                 205

Ser Asn Gly Thr Thr Thr Thr Ser Thr Val Phe Pro Ile Lys Cys Asp
    210                 215                 220

Phe Asp Phe
225


<210> SEQ ID NO 2
<211> LENGTH: 416
<212> TYPE: PRT
<213> ORGANISM: Arabidopsis thaliana

<400> SEQUENCE: 2

Met Val Arg Ser Asn Asp Val Lys Phe Gln Val Tyr Asp Ala Glu Leu
1               5                   10                  15

Thr His Phe Asp Leu Glu Ser Asn Asn Asn Leu Gln Tyr Ser Leu Ser
            20                  25                  30

Leu Asn Leu Ser Ile Arg Asn Ser Lys Ser Ser Ile Gly Ile His Tyr
        35                  40                  45
```

-continued

```
Asp Arg Phe Glu Ala Thr Val Tyr Tyr Met Asn Gln Arg Leu Gly Ala
    50                  55                  60

Val Pro Met Pro Leu Phe Tyr Leu Gly Ser Lys Asn Thr Met Leu Leu
65                  70                  75                  80

Arg Ala Leu Phe Glu Gly Gln Thr Leu Val Leu Leu Lys Gly Asn Glu
                85                  90                  95

Arg Lys Lys Phe Glu Asp Asp Gln Lys Thr Gly Val Tyr Arg Ile Asp
            100                 105                 110

Val Lys Leu Ser Ile Asn Phe Arg Val Met Val Leu His Leu Val Thr
        115                 120                 125

Trp Pro Met Lys Pro Val Val Arg Cys His Leu Lys Ile Pro Leu Ala
    130                 135                 140

Leu Gly Ser Ser Asn Ser Thr Gly Gly His Lys Lys Met Leu Leu Ile
145                 150                 155                 160

Gly Gln Leu Val Lys Asp Thr Ser Ala Asn Leu Arg Glu Ala Ser Glu
                165                 170                 175

Thr Asp His Arg Arg Asp Val Ala Gln Ser Lys Lys Ile Ala Asp Ala
            180                 185                 190

Lys Leu Ala Lys Asp Phe Glu Ala Ala Leu Lys Glu Phe Gln Lys Ala
        195                 200                 205

Gln His Ile Thr Val Glu Arg Glu Thr Ser Tyr Ile Pro Phe Asp Pro
    210                 215                 220

Lys Gly Ser Phe Ser Ser Ser Glu Val Asp Ile Gly Tyr Asp Arg Ser
225                 230                 235                 240

Gln Glu Gln Arg Val Leu Met Glu Ser Arg Arg Gln Glu Ile Val Leu
                245                 250                 255

Leu Asp Asn Glu Ile Ser Leu Asn Glu Ala Arg Ile Glu Ala Arg Glu
            260                 265                 270

Gln Gly Ile Gln Glu Val Lys His Gln Ile Ser Glu Val Met Glu Met
        275                 280                 285

Phe Lys Asp Leu Ala Val Met Val Asp His Gln Gly Thr Ile Asp Asp
    290                 295                 300

Ile Asp Glu Lys Ile Asp Asn Leu Arg Ser Ala Ala Ala Gln Gly Lys
305                 310                 315                 320

Ser His Leu Val Lys Ala Ser Asn Thr Gln Gly Ser Asn Ser Ser Leu
                325                 330                 335

Leu Phe Ser Cys Ser Leu Leu Leu Phe Phe Phe Leu Ser Gly Asp Leu
            340                 345                 350

Cys Arg Cys Val Cys Val Gly Ser Glu Asn Pro Arg Leu Asn Pro Thr
        355                 360                 365

Arg Arg Lys Ala Trp Cys Glu Glu Glu Asp Glu Glu Gln Arg Lys Lys
    370                 375                 380

Gln Gln Lys Lys Lys Thr Met Ser Glu Lys Arg Arg Arg Glu Glu Lys
385                 390                 395                 400

Lys Val Asn Lys Pro Asn Gly Phe Val Phe Cys Val Leu Gly His Lys
                405                 410                 415
```

<210> SEQ ID NO 3
<211> LENGTH: 1634
<212> TYPE: DNA
<213> ORGANISM: Arabidopsis thaliana
<220> FEATURE:
<221> NAME/KEY: CDS
<222> LOCATION: (501)..(563)
<223> OTHER INFORMATION: signal sequence (exon 1)

```
<220> FEATURE:
<221> NAME/KEY: CDS
<222> LOCATION: (655)..(708)
<223> OTHER INFORMATION: propeptide (exon 2)
<220> FEATURE:
<221> NAME/KEY: CDS
<222> LOCATION: (797)..(856)
<223> OTHER INFORMATION: propeptide (exon 3)
<220> FEATURE:
<221> NAME/KEY: CDS
<222> LOCATION: (955)..(1131)
<223> OTHER INFORMATION: conserved cysteine motif (exon 4)

<400> SEQUENCE: 3

attaaacgcc aaacactaca tctgtgtttt cgaacaatat tgcgtctgcg tttccttcat     60

ctatctctct cagtgtcaca atgtctgaac taagagacag ctgtaaacta tcattaagac    120

ataaactacc aaagtatcaa gctaatgtaa aaattactct catttccacg taacaaattg    180

agttagctta agatattagt gaaactaggt ttgaattttc ttcttcttct tccatgcatc    240

ctccgaaaaa agggaaccaa tcaaaactgt ttgcatatca aactccaaca ctttacagca    300

aatgcaatct ataatctgtg atttatccaa taaaaacctg tgatttatgt ttggctccag    360

cgatgaaagt ctatgcatgt gatctctatc caacatgagt aattgttcag aaaataaaaa    420

gtagctgaaa tgtatctata taaagaatca tccacaagta ctattttcac acactacttc    480

aaaatcacta ctcaagaaat atg aag aag atg aat gtg gtg gct ttt gtt acg    533
                      Met Lys Lys Met Asn Val Val Ala Phe Val Thr
                      1               5                   10

ctg atc atc tct ttt ctt ctg ctt tct cag gtaaactgtt aaaaccattt        583
Leu Ile Ile Ser Phe Leu Leu Leu Ser Gln
            15                  20

tcaagactac cttttctcta tttcagacaa accaaagtaa aacaatgaaa aatctctctg    643

gtctttcata g gta ctt gca gag ttg tca tca tcc agc aac aat gaa act     693
             Val Leu Ala Glu Leu Ser Ser Ser Ser Asn Asn Glu Thr
                         25                  30

tcc tct gtt tct cag gtaagagtga tacaaaaaca tactaaacaa actttcaaga      748
Ser Ser Val Ser Gln
35

gagtaatata taaggaaatg ttggcttctt ttttttgttg ctaatcag acg aat gac     805
                                                     Thr Asn Asp
                                                     40

gag aac caa act gcg gcg ttt aag aga aca tac cac cat cgt cca aga      853
Glu Asn Gln Thr Ala Ala Phe Lys Arg Thr Tyr His His Arg Pro Arg
        45                  50                  55

atc agttagtcta ctctttcaac actctaattc ctttgttcta agtatttttt           906
Ile

ttgcccccca caacctttttt tttattaaat gagccaattt ttatagat tgt ggg cat     963
                                                     Cys Gly His
                                                     60

gca tgc gca agg aga tgc agt aag aca tcg agg aag aaa gtt tgt cac     1011
Ala Cys Ala Arg Arg Cys Ser Lys Thr Ser Arg Lys Lys Val Cys His
        65                  70                  75

aga gcc tgt gga agt tgt tgt gcc aag tgt cag tgt gtg ccg ccg gga     1059
Arg Ala Cys Gly Ser Cys Cys Ala Lys Cys Gln Cys Val Pro Pro Gly
    80                  85                  90

acc tcc ggc aac aca gca tca tgt cct tgc tac gcc agt atc cgt aca     1107
Thr Ser Gly Asn Thr Ala Ser Cys Pro Cys Tyr Ala Ser Ile Arg Thr
95                  100                 105                 110

cat ggc aat aaa ctc aaa tgt cct taaaagactt ctcatttctc aactatagtc    1161
His Gly Asn Lys Leu Lys Cys Pro
                115
```

```
tcatcttctg attatgtttc ttcttttgtt atgttgcatg tgtgatgtgt gagcttatta   1221

ttatgttgat tgttgacata attcaactat ataatttgta tcgattccga ataataagat   1281

gagtgatttt attggctatt aagttttttt ttttttttt tgggcacaat ggctattaag   1341

ttttaaacat ctgattttat tggttacaaa aaacaacaaa gtttcatttt catattaaca   1401

caaaatctcc atacatatta ccaaaccaaa aaaatacaca agggggagag agaccaacgg   1461

ttcttggttc agagtttgca tcttgtttga gccgtcaccg tttcttagac ttaacagcca   1521

caacaccttt ataaagcttc acgcgatcct tcaacgcatc tcgccgaggc cgagccacct   1581

tattgtttgg atcaaacaac aaaacttctt caaacgcatt caatgccaaa ggc          1634
```

```
<210> SEQ ID NO 4
<211> LENGTH: 118
<212> TYPE: PRT
<213> ORGANISM: Arabidopsis thaliana

<400> SEQUENCE: 4

Met Lys Lys Met Asn Val Val Ala Phe Val Thr Leu Ile Ile Ser Phe
1               5                   10                  15

Leu Leu Leu Ser Gln Val Leu Ala Glu Leu Ser Ser Ser Ser Asn Asn
            20                  25                  30

Glu Thr Ser Ser Val Ser Gln Thr Asn Asp Glu Asn Gln Thr Ala Ala
        35                  40                  45

Phe Lys Arg Thr Tyr His His Arg Pro Arg Ile Cys Gly His Ala Cys
    50                  55                  60

Ala Arg Arg Cys Ser Lys Thr Ser Arg Lys Lys Val Cys His Arg Ala
65                  70                  75                  80

Cys Gly Ser Cys Cys Ala Lys Cys Gln Cys Val Pro Pro Gly Thr Ser
                85                  90                  95

Gly Asn Thr Ala Ser Cys Pro Cys Tyr Ala Ser Ile Arg Thr His Gly
            100                 105                 110

Asn Lys Leu Lys Cys Pro
        115
```

```
<210> SEQ ID NO 5
<211> LENGTH: 1453
<212> TYPE: DNA
<213> ORGANISM: Arabidopsis thaliana
<220> FEATURE:
<221> NAME/KEY: CDS
<222> LOCATION: (501)..(533)
<223> OTHER INFORMATION: signal peptide (exon 1)
<220> FEATURE:
<221> NAME/KEY: CDS
<222> LOCATION: (664)..(691)
<223> OTHER INFORMATION: propeptide (exon 2)
<220> FEATURE:
<221> NAME/KEY: CDS
<222> LOCATION: (772)..(950)
<223> OTHER INFORMATION: conserved cysteine motif (exon 3)

<400> SEQUENCE: 5

gaaaaaaaga agaaaagata atggtccgta ttaatatagt tgaaaacttg aaactacttt     60

ttagtttgta tataatacag tagactaggg atccagttga gtttctttct ttattttgag    120

tttgtgttta tgtttgattt tacgttttta tatgtaaata agatatttta cgaattatgg    180

ttttatttgg gtagaagttg tagaatgact taaacaatca agtggcagaa tgagatatat    240

aaagtaatat aatatatgta ccgttattaa cttattgtac atgtgaatga ggaagcttac    300
```

-continued

```
acacacacac cttctataaa tagctgacaa aactggttgt tacacacaac acattcataa    360

atctctcaaa gtaagaacta agagctttac tacagtccta ctctctacac atcttctctc    420

tctctcaaga gctagtcatg gccaaactca taacttcttt tctcttactc acaattttat    480

tcactttcgt ttgtctcact atg tca aaa gaa gct gag tac cat cca gaa agt    533
                      Met Ser Lys Glu Ala Glu Tyr His Pro Glu Ser
                      1               5                   10

gtaagttttt attttttggt aaaatagaaa gtgtaagttt tataattcat tcaattgttt    593

ttgcctttcc ctttctattt attgctataa atctaatacc cgcgttaaaa tttgttttga    653

aattaaacag tat gga cca gga agt ctg aaa tca tac c gtaagtaaaa          701
           Tyr Gly Pro Gly Ser Leu Lys Ser Tyr
                       15                  20

acttcttctt cttttatgaa tcttgtttct tattatatat caaataaaaa ctcgattatc    761

atgattgcag aa  tgt gga gga caa tgc aca agg aga tgt agc aac aca       809
           Gln Cys Gly Gly Gln Cys Thr Arg Arg Cys Ser Asn Thr
                           25                  30

aag tat cat aag cca tgc atg ttc ttc tgc caa aag tgt tgt gct aaa      857
Lys Tyr His Lys Pro Cys Met Phe Phe Cys Gln Lys Cys Cys Ala Lys
    35                  40                  45

tgc ctt tgt gtc cct cca ggc acg tac ggc aac aaa caa gtg tgt cct      905
Cys Leu Cys Val Pro Pro Gly Thr Tyr Gly Asn Lys Gln Val Cys Pro
50                  55                  60                  65

tgt tac aac aac tgg aag act caa caa ggt gga cca aaa tgt cca          950
Cys Tyr Asn Asn Trp Lys Thr Gln Gln Gly Gly Pro Lys Cys Pro
                70                  75                  80

taaacaaaaa cattgagaga gaaaccccaa tctgtttcct attttattta attatttcca   1010

gtatgctttt gttgtcgtga tggttaaatt atagtgtttt tgcaggtatc atttatcatc   1070

gataaacaat atcatataaa atcttctatg tttctttcac gttttgtttc ttttgttgta   1130

gtcaatacac gaaatgtgta tggaccttct aattaggaat atataaaatt ttatttatta   1190

attagataat ctttcgtata gttaaaattc caaggattac ttttgattcg tttgggacaa   1250

tctattttat attttacttt ctaagtttgt ataactatat cttaaaagtg ttagacagag   1310

tcctaatgat tttagtataa ttgttactat ttagttacgc ttcgaaaatt tggaactttt   1370

ccaaagtggt ctatatcaat ttgattcact aatctgcgct tccttctagt tttttacaat   1430

tatggagatt tttcgacgat gat                                           1453
```

<210> SEQ ID NO 6
<211> LENGTH: 80
<212> TYPE: PRT
<213> ORGANISM: Arabidopsis thaliana

<400> SEQUENCE: 6

```
Met Ser Lys Glu Ala Glu Tyr His Pro Glu Ser Tyr Gly Pro Gly Ser
1               5                   10                  15

Leu Lys Ser Tyr Gln Cys Gly Gly Gln Cys Thr Arg Arg Cys Ser Asn
            20                  25                  30

Thr Lys Tyr His Lys Pro Cys Met Phe Phe Cys Gln Lys Cys Cys Ala
        35                  40                  45

Lys Cys Leu Cys Val Pro Pro Gly Thr Tyr Gly Asn Lys Gln Val Cys
    50                  55                  60

Pro Cys Tyr Asn Asn Trp Lys Thr Gln Gln Gly Gly Pro Lys Cys Pro
65                  70                  75                  80
```

<210> SEQ ID NO 7

-continued

```
<211> LENGTH: 1472
<212> TYPE: DNA
<213> ORGANISM: Arabidopsis thaliana
<220> FEATURE:
<221> NAME/KEY: CDS
<222> LOCATION: (501)..(566)
<223> OTHER INFORMATION: signal sequence (exon 1)
<220> FEATURE:
<221> NAME/KEY: CDS
<222> LOCATION: (669)..(708)
<223> OTHER INFORMATION: propeptide (exon 2)
<220> FEATURE:
<221> NAME/KEY: CDS
<222> LOCATION: (791)..(969)
<223> OTHER INFORMATION: conserved cysteine motif (exon 3)

<400> SEQUENCE: 7

cacaactttt atacgcacca ccaaccgacc cattttgaaa aagagaaaat aaaccacaaa     60

aacacacata aataatatgc tgataacaat gtcttaaaaa tctatttacc atttctagta    120

atcaatatct attgcaaaaa atatttataa gaatacaaat gaaaaatgat aaaatacaaa    180

tgatttctca attacctaaa aaatataaaa atgtcttact ttattttcag ccactgttgg    240

aaagtacttg caatcatatc gtattttgaa ttataaaact cagaaacaat tattttccct    300

gaaaagttaa aacttttaat aagatattta taaaataaaa agaatagtct agaccgaaaa    360

tggggtcggt tgtccatcca aaggagtgct ataaatagaa ccctccaagt tctcattagg    420

acacaacaac taaaaccaca tttatcatta cagtctgatt tgagctaagt tctctcatca    480

taaactctcc ttggagaatc atg gct att tca aaa gct ctt atc gct tct ctt    533
                      Met Ala Ile Ser Lys Ala Leu Ile Ala Ser Leu
                      1               5                   10

ctc ata tct ctt ctt gtt ctc caa ctc gtc cag gctgatgtcg tacgtctttt    586
Leu Ile Ser Leu Leu Val Leu Gln Leu Val Gln
            15                  20

tcatcacaaa ctaattatac tcaatataat acttatgttt tcaaaaacat atttctcaca    646

tgttacaaca atattcttgc ag gaa aac tca cag aag aaa aat ggt tac gca     698
                         Glu Asn Ser Gln Lys Lys Asn Gly Tyr Ala
                                 25                  30

aag aag atc g gtaattatat gatttttatt aaacctaacg ttaaatttag            748
Lys Lys Ile
        35

agtgagatta ataatctgtg tttttctttc ttgtatatat ag at  tgt ggg agt       801
                                               Asp Cys Gly Ser

gcg tgt gta gca cgg tgc agg ctt tcg agg agg ccg agg ctg tgt cac      849
Ala Cys Val Ala Arg Cys Arg Leu Ser Arg Arg Pro Arg Leu Cys His
40                  45                  50                  55

aga gcg tgc ggg act tgc tgc tac agg tgc aac tgt gtg cct ccg ggt      897
Arg Ala Cys Gly Thr Cys Cys Tyr Arg Cys Asn Cys Val Pro Pro Gly
                60                  65                  70

acg tac gga aac tac gac aag tgc cag tgc tac gct agc ctc acc acc      945
Thr Tyr Gly Asn Tyr Asp Lys Cys Gln Cys Tyr Ala Ser Leu Thr Thr
            75                  80                  85

cac ggt gga cgc cgc aag tgc cca taagaagaaa caaagctctt aattgctgcg     999
His Gly Gly Arg Arg Lys Cys Pro
        90                  95

gataatggga cgatgtcgtt ttgttagtat ttactttggc gtatatatgt ggatcgaata   1059

ataaacgaga acgtacgttg tcgttgtgag tgtgagtact gtattattaa tggttctatt   1119

tgtttttact tgcaagtttt cttgttttga atttgttttt ttcatatttg tatatcgatt   1179

cgtgcattat tgtattattt caatttgtaa taagattatg ttacctttga gtggttgttt   1239
```

-continued

```
atcatacttt ttttctatgg taagaggttt tggaaaagta tcgagaatga tatataaagt   1299

aattttgata tcgacgcaag atgataacta ctagactagc tgagtataag aatattgatg   1359

tatatatttg cggacaattt tgaatttatt ataccattat ttaatcacga ccatataaaa   1419

ataattcttg tttgcgttat aatttgtgtt aatacgatag agtagacaaa tga          1472
```

```
<210> SEQ ID NO 8
<211> LENGTH: 95
<212> TYPE: PRT
<213> ORGANISM: Arabidopsis thaliana

<400> SEQUENCE: 8

Met Ala Ile Ser Lys Ala Leu Ile Ala Ser Leu Leu Ile Ser Leu Leu
1               5                   10                  15

Val Leu Gln Leu Val Gln Glu Asn Ser Gln Lys Lys Asn Gly Tyr Ala
            20                  25                  30

Lys Lys Ile Asp Cys Gly Ser Ala Cys Val Ala Arg Cys Arg Leu Ser
        35                  40                  45

Arg Arg Pro Arg Leu Cys His Arg Ala Cys Gly Thr Cys Cys Tyr Arg
    50                  55                  60

Cys Asn Cys Val Pro Pro Gly Thr Tyr Gly Asn Tyr Asp Lys Cys Gln
65                  70                  75                  80

Cys Tyr Ala Ser Leu Thr Thr His Gly Gly Arg Arg Lys Cys Pro
                85                  90                  95
```

```
<210> SEQ ID NO 9
<211> LENGTH: 1834
<212> TYPE: DNA
<213> ORGANISM: Arabidopsis thaliana
<220> FEATURE:
<221> NAME/KEY: CDS
<222> LOCATION: (501)..(579)
<223> OTHER INFORMATION: signal sequence (exon 1)
<220> FEATURE:
<221> NAME/KEY: CDS
<222> LOCATION: (1087)..(1331)
<223> OTHER INFORMATION: propetide + conserved cysteine motif (exon 2)

<400> SEQUENCE: 9

ataactaaca atggttgagt ggagatgtgc ttttagtcaa gtggttaaat atatttgact     60

tcgttttttt cattggagtt tgactctact aagttgtgtt tcctcgcgta gtaagaattg    120

gttatggatt agaccgtatc gatctaaaga tgtcaaagaa aaaaaaatgt ggttgtgtaa    180

agtaaatatg tagattgtgg cggattaaag tatgttttga ttcacatcat tattgttatt    240

ttttcatgaa ttctaaatgt aaagttctta taatcttatg ttacttttta caaattgtaa    300

ggattactct gaaatttggt atcgaattct aagacaaata caaaataaca atgactgaac    360

aagttgataa aacataatgg aaggaataat actgcagttc tattaaatac taaagaagtt    420

ggtagattgg cctataaaag gagaataaag agaccacaag aaggtctatt attcggggac    480

taaagaaagc caaagaaaac atg aaa ata ata gtc tcc atc tta gtg tta gcc    533
                      Met Lys Ile Ile Val Ser Ile Leu Val Leu Ala
                      1               5                   10

tct ctt ctt cta atc agt tca tct ctt gct tcg gct act ata tca g        579
Ser Leu Leu Leu Ile Ser Ser Ser Leu Ala Ser Ala Thr Ile Ser
            15                  20                  25

gttggttcta atctcttcaa gaatcttctt ctctctattt ttttttcttc cataaagtta    639

gttatgttat gattggttta ggtcacaatt gtttctttat gctttcgttt ccataagaaa    699

aatattacaa atattaacta gaacaacata acatgcaaac gagtaataca aaattcatta    759
```

```
ttatgatcaa aacaatcatg aattagttgg acttatttgt taaattccga aaatctcact    819

aaaataaagt gaacttcatc tacatggctt tagacgcaaa atctttaagg gtatctacac    879

aagtttggaa tgaataattt cttgcgatgg tagtgtagaa ggatctagaa gatccacaag    939

atcattagtg tatcttctag atccttttac attgagaagt gaggagatat ttgttgtatt    999

agaaagaatt atagtgaagt aaattttttta actatgtacg atcatttata tacgatactt  1059

ttattaagga tcttgtggat cttctag at  gct ttt ggt agt ggc gcg gta gct   1112
                              Asp Ala Phe Gly Ser Gly Ala Val Ala
                                          30                  35

ccg gca ccg cag agc aaa gat gga ccg gcg tta gag aaa tgg tgt gga      1160
Pro Ala Pro Gln Ser Lys Asp Gly Pro Ala Leu Glu Lys Trp Cys Gly
                40                  45                  50

cag aaa tgt gaa ggg aga tgc aaa gaa gcg ggg atg aaa gat cgg tgt      1208
Gln Lys Cys Glu Gly Arg Cys Lys Glu Ala Gly Met Lys Asp Arg Cys
            55                  60                  65

ttg aag tat tgt ggg ata tgt tgc aaa gac tgt cag tgt gtt cct tca      1256
Leu Lys Tyr Cys Gly Ile Cys Cys Lys Asp Cys Gln Cys Val Pro Ser
        70                  75                  80

ggc act tat ggg aat aag cat gaa tgt gct tgc tat cgt gac aag ctc      1304
Gly Thr Tyr Gly Asn Lys His Glu Cys Ala Cys Tyr Arg Asp Lys Leu
    85                  90                  95

agt agc aaa ggc act cct aaa tgt cct tgattctatt tctttccaac            1351
Ser Ser Lys Gly Thr Pro Lys Cys Pro
100                 105

caaaaattta aataaatgaa taagagagat ccagtaaact aatataaaac tataaatgga   1411

tcttttgttt atgatttttt ttttttcatt tctattttta cgaatttgtc ttggtctttt   1471

tgaagtaagt ttttaaatat tgaaaagtgc taaaattatg tggaaatcga taatgttaat   1531

gaatgatata atatataagt cctcagtttt tgtaagaaac ttgaatataa ataatatttc   1591

atcaaacata ataaataaat atattgtata attagattgg ctcaaccgat ataaacaatt   1651

gaatcgaatt ttttcttcta aatatttaat catccaaatt tgtattgtac caatgaatga   1711

gatggttatg aggactagaa gatagagagg agaagaacgt gtttggtaaa ataattatga   1771

tggagttgag acaactttta agagatttta aaaagactga ctaacgtgtt aggttcatca   1831

cgt                                                                  1834


<210> SEQ ID NO 10
<211> LENGTH: 108
<212> TYPE: PRT
<213> ORGANISM: Arabidopsis thaliana

<400> SEQUENCE: 10

Met Lys Ile Ile Val Ser Ile Leu Val Leu Ala Ser Leu Leu Leu Ile
1               5                   10                  15

Ser Ser Ser Leu Ala Ser Ala Thr Ile Ser Asp Ala Phe Gly Ser Gly
            20                  25                  30

Ala Val Ala Pro Ala Pro Gln Ser Lys Asp Gly Pro Ala Leu Glu Lys
        35                  40                  45

Trp Cys Gly Gln Lys Cys Glu Gly Arg Cys Lys Glu Ala Gly Met Lys
    50                  55                  60

Asp Arg Cys Leu Lys Tyr Cys Gly Ile Cys Cys Lys Asp Cys Gln Cys
65                  70                  75                  80

Val Pro Ser Gly Thr Tyr Gly Asn Lys His Glu Cys Ala Cys Tyr Arg
                85                  90                  95
```

-continued

```
Asp Lys Leu Ser Ser Lys Gly Thr Pro Lys Cys Pro
            100                 105


<210> SEQ ID NO 11
<211> LENGTH: 1782
<212> TYPE: DNA
<213> ORGANISM: Arabidopsis thaliana
<220> FEATURE:
<221> NAME/KEY: CDS
<222> LOCATION: (501)..(578)
<223> OTHER INFORMATION: signal sequence (exon 1)
<220> FEATURE:
<221> NAME/KEY: CDS
<222> LOCATION: (678)..(701)
<223> OTHER INFORMATION: propeptide (exon 2)
<220> FEATURE:
<221> NAME/KEY: CDS
<222> LOCATION: (816)..(964)
<223> OTHER INFORMATION: conserved cysteine motif (exon 3)
<220> FEATURE:
<221> NAME/KEY: CDS
<222> LOCATION: (1251)..(1269)
<223> OTHER INFORMATION: conserved cysteine motif (exon 4)

<400> SEQUENCE: 11

gccaatgggt aactgaggaa gaaggataag accaaaaaaa aaactaaaat ggacagattg     60

aattagtaaa aagataaatt ctaaaaaccg aaacaaatct taagttggtg tatatacatc    120

tgcattgacc aacaaaagaa agtagactga aatttatttg aaaatgatct tgtaaaggca    180

tattatatat ttaatttagg aaatgaatgt taaatccttt aaattgtttt gatttcacaa    240

aaggataaag aaatattggt tacatacatc ttaatgtgtt gaccaaaaca aataaaatgt    300

gataagaaac aataaaacca ttttgaccaa agttcttata gttttaatat tctttaattg    360

tcatttgtta gtgactaata atattacatt aaacctaatg tataaataga agccccatct    420

tctacgcctt tataattagc aacaaccaaa aacattcatt tgtcattttg tctcctcttt    480

tgttttctct gatcactagt atg gct gta ttc aga gtc ttg ctt gct tct ctt    533
                      Met Ala Val Phe Arg Val Leu Leu Ala Ser Leu
                      1               5                   10

ctc ata tct ctt ctt gtc ctc gac ttc gtc cat gcc gat atg gtg          578
Leu Ile Ser Leu Leu Val Leu Asp Phe Val His Ala Asp Met Val
            15                  20                  25

gtacaatttt aacaaccaaa tatattttct tatttgattt tattttttca caacttttgt    638

ctacgttcta atggaatttt tttcaaaata ttcatgcag acg tcg aat gac gcc       692
                                          Thr Ser Asn Asp Ala
                                                      30

cct aaa atc ggtaatatct ctatcatata aacacgtacg ttgaatttct              741
Pro Lys Ile

atatacgtgt gtttaattga agttttggtt ggaaattgta tgtatttgta gattgcaaca    801

gcaggtgcca agag cgg tgc agt ctt tcg agt agg cca aat ctt tgt cac      851
                Arg Cys Ser Leu Ser Ser Arg Pro Asn Leu Cys His
                35                  40                  45

aga gcg tgc ggg act tgc tgc gct agg tgc aac tgc gtg gca ccg ggc      899
Arg Ala Cys Gly Thr Cys Cys Ala Arg Cys Asn Cys Val Ala Pro Gly
            50                  55                  60

aca tcc gga aac tac gac aaa tgt ccg tgc tat ggt agc cta acc acc      947
Thr Ser Gly Asn Tyr Asp Lys Cys Pro Cys Tyr Gly Ser Leu Thr Thr
        65                  70                  75

cac gga gga cgc aga aa  gtgtccttaa aaactctgtc gctgtttgat             994
His Gly Gly Arg Arg Lys
    80

ttgatttcgt ttataatact ttacttttat gagagtaatt gtggttattt tcttgggaat   1054
```

```
tattaaaaag caaaagaaag agaatgttat acgtcatgtg caactcttcg atctttgttt   1114

tagtgtttat ccaatttgta cttgttggtt tggttcctgg ttaacattag gtctgaaaag   1174

gtattgtttt tcattataca attcactaaa taggcatcgt acttgcatat aaaataaaga   1234

atgaagagag aagtaa a aga gtt ttc ttt ttt tac tcatggaagt taggcaatgg   1289
                    Arg Val Phe Phe Phe Tyr
                    85                  90

gtttaaatat ggtaacaaca gaattggagg ggacttaatg aactatgacg taaaactgag   1349

agcgattgaa tatgtaacgt taccaacaat accaataaaa ttatgaaaga tagtatatga   1409

aattacgttt aattaatgtt tccgggttga atgtattata tatagaagta acagtacgat   1469

ttttattaca tttttgtaca agattcctag aaaggtataa cctctataaa gttaataata   1529

gtcttgagtc ttgactcttc gaggcaaata aattcaccgc ataattaatc gttcaactat   1589

tattctatat tctatataac atgagcttca acaaaagaag catcaatcat atcttcaaca   1649

gtatactgca gtgtaatgta acatattcaa gatcaaaccg gacaaaaaag caagataccg   1709

tcgaaacaat caaaccccat gtatcataaa ctcccatctt ctctttccta aattccccgt   1769

cgcttgcaca atc                                                      1782
```

<210> SEQ ID NO 12
<211> LENGTH: 90
<212> TYPE: PRT
<213> ORGANISM: Arabidopsis thaliana

<400> SEQUENCE: 12

```
Met Ala Val Phe Arg Val Leu Leu Ala Ser Leu Leu Ile Ser Leu Leu
1               5                   10                  15

Val Leu Asp Phe Val His Ala Asp Met Val Thr Ser Asn Asp Ala Pro
            20                  25                  30

Lys Ile Arg Cys Ser Leu Ser Ser Arg Pro Asn Leu Cys His Arg Ala
        35                  40                  45

Cys Gly Thr Cys Cys Ala Arg Cys Asn Cys Val Ala Pro Gly Thr Ser
    50                  55                  60

Gly Asn Tyr Asp Lys Cys Pro Cys Tyr Gly Ser Leu Thr Thr His Gly
65                  70                  75                  80

Gly Arg Arg Lys Arg Val Phe Phe Phe Tyr
                85                  90
```

<210> SEQ ID NO 13
<211> LENGTH: 1594
<212> TYPE: DNA
<213> ORGANISM: Arabidopsis thaliana
<220> FEATURE:
<221> NAME/KEY: CDS
<222> LOCATION: (409)..(471)
<223> OTHER INFORMATION: exon 1
<220> FEATURE:
<221> NAME/KEY: CDS
<222> LOCATION: (555)..(599)
<223> OTHER INFORMATION: exon 2
<220> FEATURE:
<221> NAME/KEY: CDS
<222> LOCATION: (785)..(815)
<223> OTHER INFORMATION: exon 3
<220> FEATURE:
<221> NAME/KEY: CDS
<222> LOCATION: (913)..(1091)
<223> OTHER INFORMATION: exon 4

<400> SEQUENCE: 13

-continued

```
cttttatttg tttgtgaaaa aaaacaatag cttttatttg tcctaggaat tatttaatag     60

attaaataac agctattttt ctcttatttc ttagtgatta aaatatttaa aatacagacc    120

aaaattaatt gtttatgtta atatatttac tccttaatcc tttatattaa aattgtataa    180

tgcatgtagt taataaattg ttttccaaaa ttcattcata attttattcc taaattattt    240

tggtcaagaa aacacatctt tgaataatta aatgcttcct tgtatttgat aatttcttga    300

tattttaaaa taccttctat actatgccaa tgttattggt tataaatagg tttaacattg    360

atcctgaaat atatcataag aaaatcaaaa gtgaaataag agatcaaa atg atg aag     417
                                                     Met Met Lys
                                                     1

ctc ata gtt gtc ttt gtt ata tcc agt ttg ttg ttt gct act caa ttt      465
Leu Ile Val Val Phe Val Ile Ser Ser Leu Leu Phe Ala Thr Gln Phe
    5                   10                  15

tct aat gtaaaaatta ttattatttt cttcatatta tgatttatga attcagagaa       521
Ser Asn
20

ataaagtttt tttttttatg tgtgtatgta cag ggt gat gaa tta gag agt caa     575
                                     Gly Asp Glu Leu Glu Ser Gln
                                                 25

gct caa gca cct gca atc cat aag gtatatttaa attataaaat atcaaatact     629
Ala Gln Ala Pro Ala Ile His Lys
    30                  35

gaataataaa taataaatat attacaacaa gaatatcaat gttatttttc aaactacata    689

attttaaaat attttattga taacacaaat gtatattatt atcgtctcca ttgatttgca    749

ttctaaattt gtttttgtta tccaaccaat ttcag aat gga gga gaa ggc tca       802
                                       Asn Gly Gly Glu Gly Ser
                                                   40

ctt aaa cca gaa g gtaaattgtt taaaagatat tatttttatt tatatagtaa        855
Leu Lys Pro Glu
        45

atgattgatc aaatcacaac ttaaataatt taattgttga tttatatttt tctgaag       912

aa  tgt cca aag gca tgt gaa tat cga tgt tcg gcg aca tct cac agg      959
Glu Cys Pro Lys Ala Cys Glu Tyr Arg Cys Ser Ala Thr Ser His Arg
            50                  55                  60

aaa cca tgt ttg ttt ttt tgc aac aaa tgt tgt aac aaa tgt ttg tgt     1007
Lys Pro Cys Leu Phe Phe Cys Asn Lys Cys Cys Asn Lys Cys Leu Cys
        65                  70                  75

gta cca tcg gga aca tat gga cac aaa gaa gaa tgt cct tgc tac aat     1055
Val Pro Ser Gly Thr Tyr Gly His Lys Glu Glu Cys Pro Cys Tyr Asn
    80                  85                  90

aat tgg acg acc aaa gaa ggt gga cca aaa tgt cca tgaaaacaaa          1101
Asn Trp Thr Thr Lys Glu Gly Gly Pro Lys Cys Pro
95                  100                 105

aaattgtaaa agcaaaataa aatctatcgt tgttatctct caataaaatc tatgtttgta   1161

atccttgttt ttcaatatag aatataatat ggagttttca taatttcttc tattacaaaa   1221

ttaaagttaa tgcacaaata aattgaaggg acttggacct tttcgtgtaa gttctttctt   1281

taaatcacga acaatttaga tttatatttt cactcttaca aacacaaaac atggatgctc   1341

tttaactctc atccaaacaa aatgcatttc tctctttctt tttctaaaca tttcacaaca   1401

atatcccata ttatatctaa gatatatgat ctttttaaat tgaatttatt taggccatgt   1461

tttaaaatcg tgtttggtta gattgaccca tgaaatgttg acatatttta acattcctaa   1521

atatgactaa aaatgattaa agatatttaa taatatattt gctctattaa aaatgattaa   1581

ataaataata ata                                                      1594
```

<210> SEQ ID NO 14
<211> LENGTH: 106
<212> TYPE: PRT
<213> ORGANISM: Arabidopsis thaliana

<400> SEQUENCE: 14

```
Met Met Lys Leu Ile Val Val Phe Val Ile Ser Ser Leu Leu Phe Ala
1               5                   10                  15

Thr Gln Phe Ser Asn Gly Asp Glu Leu Glu Ser Gln Ala Gln Ala Pro
            20                  25                  30

Ala Ile His Lys Asn Gly Gly Glu Gly Ser Leu Lys Pro Glu Glu Cys
        35                  40                  45

Pro Lys Ala Cys Glu Tyr Arg Cys Ser Ala Thr Ser His Arg Lys Pro
    50                  55                  60

Cys Leu Phe Phe Cys Asn Lys Cys Cys Asn Lys Cys Leu Cys Val Pro
65                  70                  75                  80

Ser Gly Thr Tyr Gly His Lys Glu Glu Cys Pro Cys Tyr Asn Asn Trp
                85                  90                  95

Thr Thr Lys Glu Gly Gly Pro Lys Cys Pro
            100                 105
```

<210> SEQ ID NO 15
<211> LENGTH: 1376
<212> TYPE: DNA
<213> ORGANISM: Arabidopsis thaliana
<220> FEATURE:
<221> NAME/KEY: CDS
<222> LOCATION: (501)..(582)
<223> OTHER INFORMATION: exon 1
<220> FEATURE:
<221> NAME/KEY: CDS
<222> LOCATION: (695)..(873)
<223> OTHER INFORMATION: exon2

<400> SEQUENCE: 15

```
taatgctata cttttaatct ataatatata ttagatgtga cttaaggaat ttcaatagtt     60

atacataata ataaaaatga atatttgtta gtgttacaaa ctgtgtgtca taatcatcat    120

tcatcaggat ttcaaaaata tctcaaaatt gttgtaagtt catgtaattc gaaatgaatg    180

tgcactataa gaaataaatt tacaatttaa aaaatgcttc aatactggtt acaaaaaaaa    240

ctttcaatac tagtattata ctacttactt agtcaaaaaa gtttatgaat atggtttttt    300

ctgtatgtta atatttttaa ctgaaaatag taccgacata acaagtaaag atatctttat    360

ttaaagtaac aaacattaat ttcacttcaa attctcacta ttaaggattc ctctctttgt    420

agccacattt caccatcact actttgtttt cgcatatctt taaattttgt atacgtagca    480

aactctttcg agaaaacaag atg aag ctc gtg gtt gta caa ttc ttc ata atc    533
                      Met Lys Leu Val Val Val Gln Phe Phe Ile Ile
                      1               5                   10

tct ctt ctc ctc aca tct tca ttt tct gta ctt tca agt gct gat tcg t    582
Ser Leu Leu Leu Thr Ser Ser Phe Ser Val Leu Ser Ser Ala Asp Ser
            15                  20                  25

gtaagtgttt acttaatcta gttaataatt gtaggtcatg catgtatcat tttgaaacaa    642

gttttctgaa attctaagat tttacatata tatgtgataa atgaattagc ag ca  tgc    699
                                                           Ser Cys

ggt gga aag tgc aat gtg aga tgc tca aag gca gga caa cat gaa gaa      747
Gly Gly Lys Cys Asn Val Arg Cys Ser Lys Ala Gly Gln His Glu Glu
30                  35                  40                  45
```

-continued

```
tgc ctc aag tac tgc aat ata tgt tgc cag aag tgt aat tgt gtt cct      795
Cys Leu Lys Tyr Cys Asn Ile Cys Cys Gln Lys Cys Asn Cys Val Pro
                50                  55                  60

tcg gga act ttt gga cac aaa gat gaa tgt cct tgc tac cgt gat atg      843
Ser Gly Thr Phe Gly His Lys Asp Glu Cys Pro Cys Tyr Arg Asp Met
            65                  70                  75

aaa aac tcc aaa ggt gga tcc aag tgt cct tgaacgttct ttgaagatcc        893
Lys Asn Ser Lys Gly Gly Ser Lys Cys Pro
        80                  85

tcatcacata catataactt ctacgtacta tatgtgtgga aatattaatc acattctatg    953

tttgaaatat ataaaataaa atcaatgccc ccaatgttgg aaatcttcaa tgtgatatct   1013

taatatatat cacgaataaa aaagtttaaa tttctcaatc tcatttttaa tctttaatct   1073

aatttcttaa cacatcaacg aatctttaat ctttaatcat gtagataatt atcagagcac   1133

ctaaacattg cgccgttttg tgattataca aagtaacatc gtgctgtttt tgacttttga   1193

aaaccacaga tccaaaaact gtttactttc ctctaagaga aagcaaagcc gagtgagtcc   1253

aagcgagttt tgagagattc gttgactcac taccggagaa cgacgctatg tcagagaccg   1313

ccgtgtcaat cgattcggac cgatctaagt cggaggaaga agacgaagaa gagtattctc   1373

cac                                                                  1376


<210> SEQ ID NO 16
<211> LENGTH: 87
<212> TYPE: PRT
<213> ORGANISM: Arabidopsis thaliana

<400> SEQUENCE: 16

Met Lys Leu Val Val Val Gln Phe Phe Ile Ile Ser Leu Leu Leu Thr
1               5                   10                  15

Ser Ser Phe Ser Val Leu Ser Ser Ala Asp Ser Ser Cys Gly Gly Lys
            20                  25                  30

Cys Asn Val Arg Cys Ser Lys Ala Gly Gln His Glu Glu Cys Leu Lys
        35                  40                  45

Tyr Cys Asn Ile Cys Cys Gln Lys Cys Asn Cys Val Pro Ser Gly Thr
    50                  55                  60

Phe Gly His Lys Asp Glu Cys Pro Cys Tyr Arg Asp Met Lys Asn Ser
65                  70                  75                  80

Lys Gly Gly Ser Lys Cys Pro
                85


<210> SEQ ID NO 17
<211> LENGTH: 1689
<212> TYPE: DNA
<213> ORGANISM: Arabidopsis thaliana
<220> FEATURE:
<221> NAME/KEY: CDS
<222> LOCATION: (501)..(578)
<223> OTHER INFORMATION: exon 1
<220> FEATURE:
<221> NAME/KEY: CDS
<222> LOCATION: (739)..(772)
<223> OTHER INFORMATION: exon 2
<220> FEATURE:
<221> NAME/KEY: CDS
<222> LOCATION: (1008)..(1186)
<223> OTHER INFORMATION: exon 3

<400> SEQUENCE: 17

cgctttctat tacacttttt tttcttttta gtcgcacttc acaattagct taattaattt     60

cctaaactcg cttattttcc cctttctata tacagatatt atcattagtg acattttcat    120
```

```
tttccaaaca gagcgtttag acactagtca actacacaat ataattttcc aattttcact    180

gagagaaatg tttttttttt tttttccaa ggcaagattt tagtcttttg gttctctata    240

cgtgggtaat tagtgattag taatttacac tgttgagtct ttgacattgt ctaagagaca    300

aaaacgacaa gtgtggtacg taattagaaa ttaaaatgac ctacttcccc agaatcacgg    360

catgaacatt ggcaatacca aatttcttga ataccattga aggaaatcca cactaatcat    420

tttctctata aatatcttta atccgtttta ttgtttctta agaatcattc attggcaatc    480

aagatttttt aaccaaaaaa atg gcg aat tgt atc aga aga aat gct ctt ttc    533
                      Met Ala Asn Cys Ile Arg Arg Asn Ala Leu Phe
                      1               5                   10

ttc ttg act ctt ctc ttt tta ttg tca gtc tcc aac ctc gtt cag          578
Phe Leu Thr Leu Leu Phe Leu Leu Ser Val Ser Asn Leu Val Gln
            15                  20                  25

gtaaaccact caaaacagat tcagtttatt aaagtctgat attgaagttt tatatattac    638

aggctgctcg tggaggtaaa aatgaccaaa ggctatacat tccttaaaaa tttaatggct    698

attagttttc tgatattgaa gttttatata tatatgacag gct gct cgt ggt ggt      753
                                            Ala Ala Arg Gly Gly
                                                        30

ggc aaa ctc aaa ccc caa c gtacggactc aaaacttttg ttgtttcata           802
Gly Lys Leu Lys Pro Gln
            35

tgatcatatt aatttattaa tcactaatta ttgataatgt tgataaataa actttaaagt    862

aacaataatg gtgtttattt tgtgaaatgt cagttttcta gtatactgta tgctgtgaat    922

tataagcatg aacataaaga tctcaatgat ttgtttttttg tttgtttgtt gtgatatgct    982

tttttgatgg aaacttcaat tgtag ag  tgc aac tca aag tgt agc ttc cgt     1033
                            Gln Cys Asn Ser Lys Cys Ser Phe Arg
                                    40                  45

tgt tca gca aca tca cac aag aag cca tgc atg ttc ttt tgc ctc aag     1081
Cys Ser Ala Thr Ser His Lys Lys Pro Cys Met Phe Phe Cys Leu Lys
            50                  55                  60

tgt tgc aaa aaa tgt ctt tgt gtt cct cct ggc act ttc ggc aac aaa     1129
Cys Cys Lys Lys Cys Leu Cys Val Pro Pro Gly Thr Phe Gly Asn Lys
        65                  70                  75

caa act tgt cca tgt tac aac aac tgg aag act aaa gaa ggc cgt cca     1177
Gln Thr Cys Pro Cys Tyr Asn Asn Trp Lys Thr Lys Glu Gly Arg Pro
    80                  85                  90

aaa tgt cct taaaacttct ttttagatat atttgataat attcatctag             1226
Lys Cys Pro
95

ttttggatta tcaaacactt actactctgt tttaatctgt ttctacaagt tggcgatttg   1286

tctctacact ttttttgtgt cttttgctct taactgttgt gtttgttata cgtgtaagcc   1346

cgcccaatgt gtcatggccg aacttattat ggttacatat ttatgaaatg ggcttcatta   1406

tcaattgatt tgagcctaca aaaatgtagc cataaagccc attaagttgt aattgttaat   1466

atttcagtca taaatatgat tttctatatc tatgatttat ctctagtgtt gatgatgttt   1526

gtatgtggaa gtcatgttct atttgcttcc acggtttaaa aaccatcaac ttgctaaggt   1586

caaattctaa tattactgtg aaaaacatta tttacgtgcg taattatatg aatttatgaa   1646

taggttttaa ttccattttt tcctaatagt gttttatgtc aaa                      1689
```

<210> SEQ ID NO 18
<211> LENGTH: 97
<212> TYPE: PRT

<213> ORGANISM: Arabidopsis thaliana

<400> SEQUENCE: 18

```
Met Ala Asn Cys Ile Arg Arg Asn Ala Leu Phe Phe Leu Thr Leu Leu
1               5                   10                  15

Phe Leu Leu Ser Val Ser Asn Leu Val Gln Ala Ala Arg Gly Gly Gly
            20                  25                  30

Lys Leu Lys Pro Gln Gln Cys Asn Ser Lys Cys Ser Phe Arg Cys Ser
        35                  40                  45

Ala Thr Ser His Lys Lys Pro Cys Met Phe Phe Cys Leu Lys Cys Cys
    50                  55                  60

Lys Lys Cys Leu Cys Val Pro Pro Gly Thr Phe Gly Asn Lys Gln Thr
65                  70                  75                  80

Cys Pro Cys Tyr Asn Asn Trp Lys Thr Lys Glu Gly Arg Pro Lys Cys
                85                  90                  95

Pro
```

<210> SEQ ID NO 19
<211> LENGTH: 1500
<212> TYPE: DNA
<213> ORGANISM: Arabidopsis thaliana
<220> FEATURE:
<221> NAME/KEY: CDS
<222> LOCATION: (501)..(563)
<223> OTHER INFORMATION: exon 1
<220> FEATURE:
<221> NAME/KEY: CDS
<222> LOCATION: (665)..(719)
<223> OTHER INFORMATION: exon 2
<220> FEATURE:
<221> NAME/KEY: CDS
<222> LOCATION: (822)..(1000)
<223> OTHER INFORMATION: exon 3

<400> SEQUENCE: 19

```
taggctggca atttaactct gagacgtctt tcttgtatag agaataaaac atacgcgtgt      60

aaaagaaaac gcgtgaatcg aatgatgagt gttaacgttc gatcgagatg ccaccaaatc     120

ttttcattaa aatgaattgt ggaggacata ccacttttaa cgaggtcatt tccactgggt     180

gacatgtgga ctctactttg ggtggcatgt tcatatcttt ccacatcacc atgtaaacgt     240

gaaaacaccc accacactca cttacatctc aaacacatgt cttcattatc gtacgtagct     300

ccaaaaaaaa aaatgaaaac taggtttagt gattctattt cgcaatgtat aatatacaac     360

ttgtaaaaat aaaatatttg aataagcatt ataaataaac ccaaagaggt gttagattta     420

tatacttaat tgtagctact aaatagagaa tcagagagaa tagttttata tcttgcacga     480

aactgcatgc tttttgagac atg gca atc ttc cga agt aca cta gtt tta ctg     533
                      Met Ala Ile Phe Arg Ser Thr Leu Val Leu Leu
                      1               5                   10

ctg atc ctc ttc tgc ctc acc act ttt gag gttcataact tttgtcttta         583
Leu Ile Leu Phe Cys Leu Thr Thr Phe Glu
            15                  20

cttctccatg aatcatttgc ttcgtcttat ccttaattca tatgtgtttg atcaatgata     643

ataattcatc attctcttca g ctt cat gtt cat gct gct gaa gat tca caa       694
                        Leu His Val His Ala Ala Glu Asp Ser Gln
                                    25                  30

gtc ggt gaa ggc gta gtg aaa att g gtatgtaacg ctaacatata               739
Val Gly Glu Gly Val Val Lys Ile
            35

tgtaaagtgt tatatctctg tttatatatg atttttaaac ggttaaaaac tagtcatatg     799
```

```
tgtataaata tatcatgtga ag at  tgc ggt ggg aga tgc aaa ggt aga tgc      850
                        Asp Cys Gly Gly Arg Cys Lys Gly Arg Cys
                        40                  45

agc aaa tcg tcg agg cca aat ctg tgt ttg aga gca tgc aac agc tgt      898
Ser Lys Ser Ser Arg Pro Asn Leu Cys Leu Arg Ala Cys Asn Ser Cys
50                  55                  60                  65

tgt tac cgc tgc aac tgt gtg cca cca ggc acc gcc ggg aac cac cac      946
Cys Tyr Arg Cys Asn Cys Val Pro Pro Gly Thr Ala Gly Asn His His
                70                  75                  80

ctt tgt cct tgc tac gcc tcc att acc act cgt ggt ggc cgt ctc aag      994
Leu Cys Pro Cys Tyr Ala Ser Ile Thr Thr Arg Gly Gly Arg Leu Lys
            85                  90                  95

tgc cct taaacatata cacatacaga tgtgtgtata tgtcttccgc gagcacacac      1050
Cys Pro

gtacgtttat gttttaagga caatagtatg tatgagcagc tataaacaaa ccagaagtta   1110

atggttcatg ttgaactagt ataagttgta tgaactgtgc ttcttttgaa caaccacttt   1170

tgctgtaagt ttagcaaccc tatttaataa attagagatt acaaaaaaaa aaatgaaaaa   1230

tgtttaaaaa acgtggattt ttaaatttgg gattaaaaat taattttcat tttggttgat   1290

ttgtcaataa attagctaag ttttgtatac taggccgttt aagatatgct gttaaatttt   1350

tgataataga gttgccttag aagttcataa ctgtaaatat ctaacttcac ttcaatctca   1410

caaacacacg aatcaacttc agcactaaga atcgaattga ccagaactga aagaaagtaa   1470

aagaaaagct gaatacagag aatttaacga                                     1500


<210> SEQ ID NO 20
<211> LENGTH: 99
<212> TYPE: PRT
<213> ORGANISM: Arabidopsis thaliana

<400> SEQUENCE: 20

Met Ala Ile Phe Arg Ser Thr Leu Val Leu Leu Leu Ile Leu Phe Cys
1               5                   10                  15

Leu Thr Thr Phe Glu Leu His Val His Ala Ala Glu Asp Ser Gln Val
            20                  25                  30

Gly Glu Gly Val Val Lys Ile Asp Cys Gly Gly Arg Cys Lys Gly Arg
        35                  40                  45

Cys Ser Lys Ser Ser Arg Pro Asn Leu Cys Leu Arg Ala Cys Asn Ser
    50                  55                  60

Cys Cys Tyr Arg Cys Asn Cys Val Pro Pro Gly Thr Ala Gly Asn His
65                  70                  75                  80

His Leu Cys Pro Cys Tyr Ala Ser Ile Thr Thr Arg Gly Gly Arg Leu
                85                  90                  95

Lys Cys Pro


<210> SEQ ID NO 21
<211> LENGTH: 1647
<212> TYPE: DNA
<213> ORGANISM: Arabidopsis thaliana
<220> FEATURE:
<221> NAME/KEY: CDS
<222> LOCATION: (501)..(563)
<223> OTHER INFORMATION: exon 1
<220> FEATURE:
<221> NAME/KEY: CDS
<222> LOCATION: (661)..(715)
<223> OTHER INFORMATION: exon 2
<220> FEATURE:
<221> NAME/KEY: CDS
```

-continued

```
<222> LOCATION: (966)..(1144)
<223> OTHER INFORMATION: exon 3

<400> SEQUENCE: 21

ttaacagttt aacaccataa tgttaaactc ggtttagcat tttggtgtaa ttctacctct     60

ttaaccatac atactaaaga cgcagagaag ttcatatggt agttaatcgt aaatagctaa    120

acttttaatt ggggttaaca tattatttaa cacttaacat ttaactattg atctctcatt    180

tttttttat taaccaaaat aaattcattt tagaaccaaa cgtttcaaaa actcgtaatg    240

ttttctcatt aaatcttatc tatagctcac acaaagaaaa actacggaca tgcatgcacc    300

caattatata catggattat tatttttagt gttataatat gatacaaaat aaaaaacatt    360

tggatagccg ataggcgata gccactataa atataccaaa gaggttggat tatacatata    420

gccgtaatac caaagagagt atcagataga aatagttcta atattttgta caactcacag    480

aaattgcatg agtttcgaac atg gca gtc ttc cga agt aca ctg gtt ctg tta    533
                      Met Ala Val Phe Arg Ser Thr Leu Val Leu Leu
                      1               5                   10

cta atc atc gtc tgt ctc acc act tat gag gtttataata tttttggtct        583
Leu Ile Ile Val Cys Leu Thr Thr Tyr Glu
            15                  20

ttatagttcc ccaagaacac ctagcaatat tatactcaat tcatgtttat atgataatga    643

ctgatcattc tcttcag ctt cac gtc cac gct gct gat ggt gca aag gtc       693
                   Leu His Val His Ala Ala Asp Gly Ala Lys Val
                               25                  30

ggt gaa ggc gta gtg aaa atc g gtatgtaacc ctaacttata tataacacgt       745
Gly Glu Gly Val Val Lys Ile
        35

tggtatataa cttaatattt ctgatgggtg cactctcttc ccaacttata tatatctttg    805

ttatggagaa tgtctcaagc ttttaatgag atgttatatc tcggagaagg aaactatgaa    865

ctaaaagctt tggattcctt tgcaacaaat ataaactttt gatgggttta aacggattaa    925

attagttaca tgtgtttgat gaatgtatgt atgattgtag at  tgt ggt ggg aga      979
                                            Asp Cys Gly Gly Arg

tgc aaa gat aga tgc agc aaa tct tcg aga acg aag cta tgc ttg aga     1027
Cys Lys Asp Arg Cys Ser Lys Ser Ser Arg Thr Lys Leu Cys Leu Arg
45                  50                  55                  60

gcg tgc aac agc tgt tgt tcc cgc tgc aac tgt gtg cca cct ggt act     1075
Ala Cys Asn Ser Cys Cys Ser Arg Cys Asn Cys Val Pro Pro Gly Thr
                65                  70                  75

tct gga aac acc cac ctt tgt cct tgc tac gcc tcc att acc act cac     1123
Ser Gly Asn Thr His Leu Cys Pro Cys Tyr Ala Ser Ile Thr Thr His
            80                  85                  90

ggt ggc cgc ctc aag tgc cct taaaatttct tctgtgtctg tttctgtttc        1174
Gly Gly Arg Leu Lys Cys Pro
        95

tacttctatt tcgaatatat gtacatgtgt gtgtacgtgt gtatgtatac aagtactgct   1234

atgttttgga ggacaaaagt atatgtatga gaagctataa actaattaga agttgatggt   1294

tatgcgtatt atcaaaccgt gttacttctg aacaaccaat ttcggtttgt tccaagtttg   1354

gcaaccctaa aataaaaatt caaaatgatt ggagactact cgttaataga cattgaaaac   1414

gatgaaatct cgttacgttt ttatattttt tgaactgtaa tattattatg cagaagcggt   1474

tttgtaatgg gccgacaaaa aaaaagtggt tttgtaatgg atatgattcg gatctattct   1534

ggaaatggtc tcaaaaagta gagttgagat ctcaatacga aaatgaaccc tttcgtttga   1594

tttatcaaag ccttttattt tgaaaacgtt aaatcctcac taggatctct ctt           1647
```

<210> SEQ ID NO 22
<211> LENGTH: 99
<212> TYPE: PRT
<213> ORGANISM: Arabidopsis thaliana

<400> SEQUENCE: 22

```
Met Ala Val Phe Arg Ser Thr Leu Val Leu Leu Leu Ile Ile Val Cys
1               5                   10                  15

Leu Thr Thr Tyr Glu Leu His Val His Ala Ala Asp Gly Ala Lys Val
            20                  25                  30

Gly Glu Gly Val Val Lys Ile Asp Cys Gly Gly Arg Cys Lys Asp Arg
        35                  40                  45

Cys Ser Lys Ser Ser Arg Thr Lys Leu Cys Leu Arg Ala Cys Asn Ser
    50                  55                  60

Cys Cys Ser Arg Cys Asn Cys Val Pro Pro Gly Thr Ser Gly Asn Thr
65                  70                  75                  80

His Leu Cys Pro Cys Tyr Ala Ser Ile Thr Thr His Gly Gly Arg Leu
                85                  90                  95

Lys Cys Pro
```

<210> SEQ ID NO 23
<211> LENGTH: 2009
<212> TYPE: DNA
<213> ORGANISM: Arabidopsis thaliana
<220> FEATURE:
<221> NAME/KEY: CDS
<222> LOCATION: (501)..(566)
<223> OTHER INFORMATION: exon 1
<220> FEATURE:
<221> NAME/KEY: CDS
<222> LOCATION: (767)..(805)
<223> OTHER INFORMATION: exon 2
<220> FEATURE:
<221> NAME/KEY: CDS
<222> LOCATION: (924)..(957)
<223> OTHER INFORMATION: exon 3
<220> FEATURE:
<221> NAME/KEY: CDS
<222> LOCATION: (1328)..(1506)
<223> OTHER INFORMATION: exon 4

<400> SEQUENCE: 23

```
aaatattcac cctaaaatga atctaaaaat gtacaaaatc acaggaaaat aaaactaagc      60

agaaatgtcc taagaaaact aaagttttta aaaaataatc ttcaaagaga tactccaact     120

ggtgttataa gcaaaacttg atttatcaaa aacaggttca tagtatttta tatttagtac     180

tataagcttt ccttaaacca tgtgcaaaac catctaccgc agtctaatta ccaatagcaa     240

gtaataaaat gggactaaca ttggaggcat acgtggaata atataattgg aggaatacag     300

taataatgat atgtgttgcc acagggaata attgatacga gcaaatgtgt gtatatatag     360

cttatatgca acatcattgg gtcctcaacc aaaaactcct ctctcagtac acttcttttc     420

atacctcaag agactaaaac tagtttgagg agatttagag gagtgtttgg ttctttggat     480

aacaatatcc caaactgaaa atg gct aag tca tat gga gct atc ttc ctc ttg     533
                      Met Ala Lys Ser Tyr Gly Ala Ile Phe Leu Leu
                      1               5                   10

acc ctc att gtc ctc ttc atg ctt caa acc atg gtaacacctc tattattttt     586
Thr Leu Ile Val Leu Phe Met Leu Gln Thr Met
            15                  20

ttcttctttc aatgtttgaa aatattgaag ataatatatt tgattgtttt ccttattgac     646
```

-continued

```
gaacgatatg agacaaatgt gggttctatt attgtacttt tagttggaat atatttaatt    706

tagccttttt aatgaaatta attttacttg tttttcctct ctcttttttt cgtttttttag    766

gtt atg gcc tca agt gga tct aat gtg aag tgg agc cag gtcagtttta       815
Val Met Ala Ser Ser Gly Ser Asn Val Lys Trp Ser Gln
        25                  30                  35

ttattgaatc gactagtaat taccttttaa actatatttt atacctattg ttatctcgta    875

acttaacgaa aagtgattaa ttagttacct tttttggtta attttcag aaa cgt tat     932
                                                     Lys Arg Tyr

gga cca gga agc ctg aaa cgt acc c gtaagttttt tcttcacagc              977
Gly Pro Gly Ser Leu Lys Arg Thr
    40                  45

tattcttaaa caattttttt ttaatctcat aatcgacgaa aaataaacaa ttcaagaaat   1037

cttttattgt gttataataa aaaaaaataa gcatttcagt tgcagaaaat aagttgaaag   1097

tgaagtgtta agtggactgt ttggtcagat ccgtagactc aaaatatatt agatattgac   1157

gaaattgccc cttaatatgg tcatacagtc aaagcaaccc actatcttga gacccacaaa   1217

acagtaaaaa aaaaagctaa tgaatttcca ctagattctg ttgtttttat tagtaataaa   1277

aaatttttga gtgttaacat tttgatattg tttgtatttg aaacaaccag aa  tgc      1332
                                                        Gln Cys

cca tcg gaa tgt gat agg agg tgt aaa aag aca cag tac cac aag gct     1380
Pro Ser Glu Cys Asp Arg Arg Cys Lys Lys Thr Gln Tyr His Lys Ala
    50                  55                  60

tgc att acg ttc tgc aac aaa tgc tgc agg aag tgt ctc tgt gtg cct     1428
Cys Ile Thr Phe Cys Asn Lys Cys Cys Arg Lys Cys Leu Cys Val Pro
65                  70                  75                  80

ccg ggt tac tat ggg aac aaa caa gtt tgc tcc tgc tac aac aac tgg     1476
Pro Gly Tyr Tyr Gly Asn Lys Gln Val Cys Ser Cys Tyr Asn Asn Trp
                85                  90                  95

aaa act caa gag ggt gga cca aaa tgc cct tgaaaaaatc tcccttcgtt       1526
Lys Thr Gln Glu Gly Gly Pro Lys Cys Pro
            100                 105

cccttttttat aataaaaatt ttcaactata actaaatttc ctttgatcaa tgttttatct   1586

actttattcc taatgttgta atgttatgtc actccttttc ggattttgtt ctaaatccta    1646

aaaaaaatga gagtggccct atgaatgata tttttcatga atacttgtgt ttctaaagat    1706

attttcccat tcatccacca aaaaaaaaga tattttccat ttcgaaaata gtaatactat    1766

aaagggtaag gcaaaccaaa taatacaatt taaaaaattc ctgcgaaaga agtatgcata    1826

tgtagaaaag agtgacattg ggtctctcgg cccagtacta aaaagcccat tattgatttt    1886

tccaagcttt ttacaaaatc acgtgttcta acgcgattgc tttttgccgc aatcttcttt    1946

tatacaagac ttgggctttg ggcagttgga aataaataac gacaacgata ttttacaatc    2006

ggt                                                                  2009
```

```
<210> SEQ ID NO 24
<211> LENGTH: 106
<212> TYPE: PRT
<213> ORGANISM: Arabidopsis thaliana

<400> SEQUENCE: 24

Met Ala Lys Ser Tyr Gly Ala Ile Phe Leu Leu Thr Leu Ile Val Leu
1               5                   10                  15

Phe Met Leu Gln Thr Met Val Met Ala Ser Ser Gly Ser Asn Val Lys
            20                  25                  30

Trp Ser Gln Lys Arg Tyr Gly Pro Gly Ser Leu Lys Arg Thr Gln Cys
```

-continued

```
        35                  40                  45

Pro Ser Glu Cys Asp Arg Arg Cys Lys Lys Thr Gln Tyr His Lys Ala
    50                  55                  60

Cys Ile Thr Phe Cys Asn Lys Cys Cys Arg Lys Cys Leu Cys Val Pro
65                  70                  75                  80

Pro Gly Tyr Tyr Gly Asn Lys Gln Val Cys Ser Cys Tyr Asn Asn Trp
                85                  90                  95

Lys Thr Gln Glu Gly Gly Pro Lys Cys Pro
            100                 105


<210> SEQ ID NO 25
<211> LENGTH: 2164
<212> TYPE: DNA
<213> ORGANISM: Arabidopsis thaliana
<220> FEATURE:
<221> NAME/KEY: CDS
<222> LOCATION: (501)..(551)
<223> OTHER INFORMATION: exon 1
<220> FEATURE:
<221> NAME/KEY: CDS
<222> LOCATION: (680)..(718)
<223> OTHER INFORMATION: exon 2
<220> FEATURE:
<221> NAME/KEY: CDS
<222> LOCATION: (839)..(1391)
<223> OTHER INFORMATION: exon 3
<220> FEATURE:
<221> NAME/KEY: CDS
<222> LOCATION: (1480)..(1661)
<223> OTHER INFORMATION: exon 4

<400> SEQUENCE: 25

ttgctcactg gtgcaataat cgaagtgaag agcctcttta tatgaaatat ataagcgaca      60

cagccttatg ggcaaatcga atgctattta tttatttgat aagaagatta ataatttcaa     120

tttgtcatcc actagtctct tggggtactc aaaacatatc accaaaaagt ccatagagtt     180

atttgttctt atttactgat aaagtattcc aagttgatgt acgaataaag tggcaatttc     240

atgtattatc aatataatcc atttttggga atctgatatt ttgtttatcc tcgagctctg     300

agagatatat tttggtgcag tgaaggttca aagctggcat gcatgatgca tataataact     360

gctctggacc taatacttac tacgcattta aattaatatt tatggataat atggttaata     420

aataaggaac ttctatttat atcacaaaag gtcactggtc ttcttcgtgt gacttcacca     480

ctttctcatc tcccacaaaa atg gct ctc tca ctt ctt tca gtc ttt atc ttt     533
                      Met Ala Leu Ser Leu Leu Ser Val Phe Ile Phe
                      1               5                   10

ttc cat gtc ttt acc aat gtaagttatt cttacttttc ataacaaaag              581
Phe His Val Phe Thr Asn
            15

gtgttattat gttaaagact acataatagt atacaattat gtgcattacg ttttcgcgta     641

ttgtaactaa ctatgtattt tgattaatca ccgagcag gtt gtt ttt gct gct tca     697
                                          Val Val Phe Ala Ala Ser
                                                      20

aat gag gaa tcc aac gcc tta gtacgttttc taatttccag tttaattatt          748
Asn Glu Glu Ser Asn Ala Leu
    25                  30

tctatgcgtc tttaactata tactcaggca tttttattga ttattgtgta tgaagttaaa     808

ttttggtata tgtttgtatt aaatttatag gtt tct tta cca acg cca aca ctt      862
                                 Val Ser Leu Pro Thr Pro Thr Leu
                                                 35

cca tcg cca tct ccg gct acc aaa ccg ccg tcg cca gct ctc aaa ccg       910
```

-continued

```
Pro Ser Pro Ser Pro Ala Thr Lys Pro Pro Ser Pro Ala Leu Lys Pro
    40                  45                  50

ccg acg ccg tcg tac aag cca ccc acg ctg cca act act cct att aaa      958
Pro Thr Pro Ser Tyr Lys Pro Pro Thr Leu Pro Thr Thr Pro Ile Lys
55                  60                  65                  70

cca ccc acc aca aaa cct ccg gtc aaa cct cca act att ccg gtt aca     1006
Pro Pro Thr Thr Lys Pro Pro Val Lys Pro Pro Thr Ile Pro Val Thr
                75                  80                  85

cca gta aaa cct ccg gtt tca act cct ccg atc aaa cta ccg ccg gta     1054
Pro Val Lys Pro Pro Val Ser Thr Pro Pro Ile Lys Leu Pro Pro Val
            90                  95                  100

caa cca cct acg tac aaa ccc cca acg cca aca gtt aaa cca ccg tcc     1102
Gln Pro Pro Thr Tyr Lys Pro Pro Thr Pro Thr Val Lys Pro Pro Ser
        105                 110                 115

gtc caa cca cct acg tac aaa ccc cca act cca acg gtt aaa cca ccc     1150
Val Gln Pro Pro Thr Tyr Lys Pro Pro Thr Pro Thr Val Lys Pro Pro
    120                 125                 130

act aca tca ccg gtt aaa cca ccc act acg cca cca gtt caa tca ccg     1198
Thr Thr Ser Pro Val Lys Pro Pro Thr Thr Pro Pro Val Gln Ser Pro
135                 140                 145                 150

ccg gtc caa cca cct acg tac aaa ccc cca acg tca ccg gtt aaa cca     1246
Pro Val Gln Pro Pro Thr Tyr Lys Pro Pro Thr Ser Pro Val Lys Pro
                155                 160                 165

ccc acc aca act cca ccg gtt aaa ccc ccc acc acg acg cca ccg gtc     1294
Pro Thr Thr Thr Pro Pro Val Lys Pro Pro Thr Thr Thr Pro Pro Val
            170                 175                 180

caa cca cct acg tac aat ccc cca act aca ccg gtt aaa cca cct aca     1342
Gln Pro Pro Thr Tyr Asn Pro Pro Thr Thr Pro Val Lys Pro Pro Thr
        185                 190                 195

gcg ccg cct gtc aaa cct cca aca cca cct ccc gta aga act cgg ata g   1391
Ala Pro Pro Val Lys Pro Pro Thr Pro Pro Pro Val Arg Thr Arg Ile
    200                 205                 210

gtaataataa ttttctttca aaagtgtgat gattatcggt cgttgattag atcggatgta   1451

taattggact aaattttgga cggtttag at  tgc gtg cct tta tgt ggg acg      1502
                               Asp Cys Val Pro Leu Cys Gly Thr
                               215                 220

agg tgt ggg caa cac tcg agg aag aac gta tgt atg aga gcg tgc gtc     1550
Arg Cys Gly Gln His Ser Arg Lys Asn Val Cys Met Arg Ala Cys Val
        225                 230                 235

acg tgc tgc tac cgc tgc aag tgt gtt ccc cca ggc acc tac ggt aat     1598
Thr Cys Cys Tyr Arg Cys Lys Cys Val Pro Pro Gly Thr Tyr Gly Asn
    240                 245                 250

aag gag aag tgt gga tct tgt tac gcc aac atg aag aca cgt ggt gga     1646
Lys Glu Lys Cys Gly Ser Cys Tyr Ala Asn Met Lys Thr Arg Gly Gly
255                 260                 265                 270

aaa tcc aaa tgt cct tgaaccttta tatgacgatg gttgttaaac gaaataattt     1701
Lys Ser Lys Cys Pro
                275

aaatcaatgg agtttttata agtttgtaat gcgtttgttt ttgttatagt aatattgagt   1761

tggatctttg tttacgggac gtagaatact aaataatgaa aaaaaccttc tcgatgaatt   1821

aagggtttta tgaatttgtt ttgtattgaa taatataggg atggataaag ttttattatt   1881

ctaacaggtt actttattag gcatttcttc ggctcatgta actcttgtat cgctgaaact   1941

atgtaataga tagaagaacc taaaaaaaga aagaaaacaa gaaatgcaca tagcgaagct   2001

caaaagatga gtgttctgct agcggtaatg ttgttattca gttgggtcaa atgctctaat   2061

tgcaaatctt atttgggcct tatatagact cttatgtgca tatggtccag cctatttggg   2121
```

```
ccgatgtgtt tgaagatcat ttgggaaagt cttgcgcaag gag                   2164


<210> SEQ ID NO 26
<211> LENGTH: 275
<212> TYPE: PRT
<213> ORGANISM: Arabidopsis thaliana

<400> SEQUENCE: 26

Met Ala Leu Ser Leu Leu Ser Val Phe Ile Phe Phe His Val Phe Thr
1               5                   10                  15

Asn Val Val Phe Ala Ala Ser Asn Glu Glu Ser Asn Ala Leu Val Ser
            20                  25                  30

Leu Pro Thr Pro Thr Leu Pro Ser Pro Ser Pro Ala Thr Lys Pro Pro
        35                  40                  45

Ser Pro Ala Leu Lys Pro Pro Thr Pro Ser Tyr Lys Pro Pro Thr Leu
    50                  55                  60

Pro Thr Thr Pro Ile Lys Pro Pro Thr Thr Lys Pro Pro Val Lys Pro
65                  70                  75                  80

Pro Thr Ile Pro Val Thr Pro Val Lys Pro Pro Val Ser Thr Pro Pro
                85                  90                  95

Ile Lys Leu Pro Pro Val Gln Pro Pro Thr Tyr Lys Pro Pro Thr Pro
            100                 105                 110

Thr Val Lys Pro Pro Ser Val Gln Pro Pro Thr Tyr Lys Pro Pro Thr
        115                 120                 125

Pro Thr Val Lys Pro Pro Thr Thr Ser Pro Val Lys Pro Pro Thr Thr
    130                 135                 140

Pro Pro Val Gln Ser Pro Pro Val Gln Pro Pro Thr Tyr Lys Pro Pro
145                 150                 155                 160

Thr Ser Pro Val Lys Pro Pro Thr Thr Thr Pro Pro Val Lys Pro Pro
                165                 170                 175

Thr Thr Thr Pro Pro Val Gln Pro Pro Thr Tyr Asn Pro Pro Thr Thr
            180                 185                 190

Pro Val Lys Pro Pro Thr Ala Pro Pro Val Lys Pro Pro Thr Pro Pro
        195                 200                 205

Pro Val Arg Thr Arg Ile Asp Cys Val Pro Leu Cys Gly Thr Arg Cys
    210                 215                 220

Gly Gln His Ser Arg Lys Asn Val Cys Met Arg Ala Cys Val Thr Cys
225                 230                 235                 240

Cys Tyr Arg Cys Lys Cys Val Pro Pro Gly Thr Tyr Gly Asn Lys Glu
                245                 250                 255

Lys Cys Gly Ser Cys Tyr Ala Asn Met Lys Thr Arg Gly Gly Lys Ser
            260                 265                 270

Lys Cys Pro
        275


<210> SEQ ID NO 27
<211> LENGTH: 1366
<212> TYPE: DNA
<213> ORGANISM: Arabidopsis thaliana
<220> FEATURE:
<221> NAME/KEY: CDS
<222> LOCATION: (501)..(582)
<223> OTHER INFORMATION: exon 1
<220> FEATURE:
<221> NAME/KEY: CDS
<222> LOCATION: (679)..(863)
<223> OTHER INFORMATION: exon 2

<400> SEQUENCE: 27
```

```
gacttgagta tgaatccaat aacccaaaat ttatgcagat tttagaatac ttcttataaa     60

tcttaaatga ataacacaaa actttaacat acttttaaca aatcttgatt gaataacaac    120

agattctaca tgacatttta aatcactaaa actcttttga aatcataaac caataacaac    180

cccttagttt tttactattt gaattctgac gtactttttt attagttgaa tttctataaa    240

tgagaaaaca ttaattattt cttaatcttt gaacttaagc cccacaaaaa tcttataaat    300

tgggacagat ggactagata acaagcgttt cacctactcc aaaatttccc tataagtaac    360

tctttttgta acctcctttt cttcccaaac catcactcct tttgcattgt gtgaaacctt    420

cgagttttct cttcatcttc tcaaagtaac aaactttctc caaacagatt attattaaaa    480

caatctcatc aagaactacg atg aaa ttc ccg gct gta aaa gtt ctt att atc    533
                      Met Lys Phe Pro Ala Val Lys Val Leu Ile Ile
                      1               5                   10

tct ctt ctc atc aca tct tct ttg ttc ata ctc tca acc gcg gat tcg t    582
Ser Leu Leu Ile Thr Ser Ser Leu Phe Ile Leu Ser Thr Ala Asp Ser
            15                  20                  25

gtaagtatac acaatgcatt ttcttatttt agatactttt ctcattagaa atttagcttt    642

cttaataaaa ttgtattgtg atgatggatt aattag ca  cca tgc gga gga aaa      695
                                        Ser Pro Cys Gly Gly Lys
                                                    30

tgc aac gtg aga tgt tca aag gca gga aga caa gat agg tgt ctc aag      743
Cys Asn Val Arg Cys Ser Lys Ala Gly Arg Gln Asp Arg Cys Leu Lys
    35                  40                  45

tat tgt aat ata tgt tgc gag aag tgt aac tat tgt gtt cct tca ggc      791
Tyr Cys Asn Ile Cys Cys Glu Lys Cys Asn Tyr Cys Val Pro Ser Gly
50                  55                  60                  65

act tat gga aac aaa gat gaa tgc cct tgt tac cgc gat atg aag aac      839
Thr Tyr Gly Asn Lys Asp Glu Cys Pro Cys Tyr Arg Asp Met Lys Asn
                70                  75                  80

tcc aaa ggc acg tcc aaa tgt cct tgatcatgtt cttaagatta tccttataga     893
Ser Lys Gly Thr Ser Lys Cys Pro
            85

cacaatatct tgaaatgtta agattgtgct tgatgcctaa aataatgagc ttgagatact    953

tctatgaatg aatatgtgaa agattttgac aataaaatga tttgatgtat taaaatattc   1013

ttagtgaagt tatatatgta taaatgaagt atgaaatata cattgtatgt tgctttacat   1073

gagaaagata aatctacaac aatccaatgt atgaaaattt tactaagtta actgatcaga   1133

aacgttaatt atggtttaga atcttgtgga gagatgatta cttttgtaag agaaattgat   1193

tgtttgttgt caatgaggat aaagtaagaa gccatttctc aacacatgga cttgatagca   1253

aactaaacaa ggctcaagca ttgaaattga aacgtctcga tagataagat tggctcaaga   1313

aaagcaagtg tttttgttg tagaaaacag aaattgaaat tactgtctac ttt           1366


<210> SEQ ID NO 28
<211> LENGTH: 89
<212> TYPE: PRT
<213> ORGANISM: Arabidopsis thaliana

<400> SEQUENCE: 28

Met Lys Phe Pro Ala Val Lys Val Leu Ile Ile Ser Leu Leu Ile Thr
1               5                   10                  15

Ser Ser Leu Phe Ile Leu Ser Thr Ala Asp Ser Ser Pro Cys Gly Gly
            20                  25                  30

Lys Cys Asn Val Arg Cys Ser Lys Ala Gly Arg Gln Asp Arg Cys Leu
        35                  40                  45
```

```
Lys Tyr Cys Asn Ile Cys Cys Glu Lys Cys Asn Tyr Cys Val Pro Ser
    50                  55                  60

Gly Thr Tyr Gly Asn Lys Asp Glu Cys Pro Cys Tyr Arg Asp Met Lys
65                  70                  75                  80

Asn Ser Lys Gly Thr Ser Lys Cys Pro
                85


<210> SEQ ID NO 29
<211> LENGTH: 750
<212> TYPE: DNA
<213> ORGANISM: Arabidopsis thaliana
<220> FEATURE:
<221> NAME/KEY: CDS
<222> LOCATION: (14)..(85)
<223> OTHER INFORMATION: exon 1
<220> FEATURE:
<221> NAME/KEY: CDS
<222> LOCATION: (395)..(631)
<223> OTHER INFORMATION: exon 2

<400> SEQUENCE: 29

ctgttttcag aaa atg gca aca aaa ctt agc atc att gtt ttc tcc att        49
               Met Ala Thr Lys Leu Ser Ile Ile Val Phe Ser Ile
               1               5                   10

gtt gtg tta cat ctt ctt ctg tct gcc cat atg cat gtaagtgttt            95
Val Val Leu His Leu Leu Leu Ser Ala His Met His
        15                  20

caacactcta ttcctctatg ttcacattta tcaactttat cttatacgtc cctgaataaa    155

acacagccta tatacttgga atctcctgct cgacaaccac aaccaccaca gtcgcaacca    215

caactgccgc atcacaataa ctctcaagtg agtttctcgg ttcatcacta ctcaaaaaaa    275

gagtttcatc gaatctacaa aaccttttta acatcctttg catcttcttg ttgattttgg    335

cagtacggta ctactcaagg cagtcttcaa ccccaaggta aacccactga ctagcctag     394

ttt tta att aat gtt tgt gct gaa tgc gaa act aaa tcc gct att cca      442
Phe Leu Ile Asn Val Cys Ala Glu Cys Glu Thr Lys Ser Ala Ile Pro
25                  30                  35                  40

cct tta tta gag tgc ggg cca agg tgt gga gat aga tgc tcg aat aca      490
Pro Leu Leu Glu Cys Gly Pro Arg Cys Gly Asp Arg Cys Ser Asn Thr
                45                  50                  55

caa tac aag aag ccg tgt ttg ttc ttc tgc aac aaa tgt tgt aac aag      538
Gln Tyr Lys Lys Pro Cys Leu Phe Phe Cys Asn Lys Cys Cys Asn Lys
            60                  65                  70

tgc ttg tgt gtg ccc cca ggt act tat ggc aat aag caa gta tgt cct      586
Cys Leu Cys Val Pro Pro Gly Thr Tyr Gly Asn Lys Gln Val Cys Pro
        75                  80                  85

tgc tat aac aac tgg aag acc aag agc ggt gga cca aaa tgc cct          631
Cys Tyr Asn Asn Trp Lys Thr Lys Ser Gly Gly Pro Lys Cys Pro
    90                  95                  100

tagtttctcc tcttaattac tttagcataa actccatgta atttgttaat ctacctatca    691

taatttatat atgtattgga ctcttccata atcacatcag ttctctgtga ttatgacgt     750


<210> SEQ ID NO 30
<211> LENGTH: 103
<212> TYPE: PRT
<213> ORGANISM: Arabidopsis thaliana

<400> SEQUENCE: 30

Met Ala Thr Lys Leu Ser Ile Ile Val Phe Ser Ile Val Val Leu His
1               5                   10                  15
```

-continued

```
Leu Leu Leu Ser Ala His Met His Phe Leu Ile Asn Val Cys Ala Glu
            20                  25                  30

Cys Glu Thr Lys Ser Ala Ile Pro Pro Leu Leu Glu Cys Gly Pro Arg
        35                  40                  45

Cys Gly Asp Arg Cys Ser Asn Thr Gln Tyr Lys Lys Pro Cys Leu Phe
    50                  55                  60

Phe Cys Asn Lys Cys Cys Asn Lys Cys Leu Cys Val Pro Pro Gly Thr
65                  70                  75                  80

Tyr Gly Asn Lys Gln Val Cys Pro Cys Tyr Asn Asn Trp Lys Thr Lys
                85                  90                  95

Ser Gly Gly Pro Lys Cys Pro
            100


<210> SEQ ID NO 31
<211> LENGTH: 56
<212> TYPE: PRT
<213> ORGANISM: Arabidopsis thaliana
<220> FEATURE:
<221> NAME/KEY: PEPTIDE
<222> LOCATION: (1)..(56)
<223> OTHER INFORMATION: Xaa at position 25 is either R or K
      Xaa at position 25 is either P or S
      Xaa at position 25 is either N or H
      Other Xaa may be any amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(50)
<223> OTHER INFORMATION: Xaa can be any naturally occurring amino acid
<220> FEATURE:
```

```
<221> NAME/KEY: misc_feature
<222> LOCATION: (52)..(53)
<223> OTHER INFORMATION: Xaa can be any naturally occurring amino acid

<400> SEQUENCE: 31

Cys Xaa Cys Xaa Arg Cys Xaa Xaa Xaa Xaa Xaa Xaa Xaa Xaa Cys Xaa
1               5                   10                  15

Xaa Xaa Cys Xaa Xaa Cys Cys Xaa Xaa Cys Xaa Cys Val Pro Xaa Gly
            20                  25                  30

Thr Xaa Gly Xaa Xaa Xaa Xaa Cys Xaa Cys Tyr Xaa Xaa Xaa Xaa Xaa
        35                  40                  45

Xaa Xaa Gly Xaa Xaa Lys Cys Pro
    50                  55


<210> SEQ ID NO 32
<211> LENGTH: 832
<212> TYPE: DNA
<213> ORGANISM: Arabidopsis thaliana
<220> FEATURE:
<221> NAME/KEY: CDS
<222> LOCATION: (53)..(703)

<400> SEQUENCE: 32

ttactctcaa attccttttc gatttccctc tcttaaacct ccgaaagctc ac atg gcg      58
                                                          Met Ala
                                                          1

tct cga aac tat cgg tgg gag ctc ttc gca gct tcg tta acc cta acc       106
Ser Arg Asn Tyr Arg Trp Glu Leu Phe Ala Ala Ser Leu Thr Leu Thr
        5                   10                  15

tta gct ttg att cac ctg gtc gaa gca aac tcc gaa gga gat gct ctc       154
Leu Ala Leu Ile His Leu Val Glu Ala Asn Ser Glu Gly Asp Ala Leu
    20                  25                  30

tac gct ctt cgc cgg agt ttg aca gat cca gac cat gtc ctc cag agc       202
Tyr Ala Leu Arg Arg Ser Leu Thr Asp Pro Asp His Val Leu Gln Ser
35                  40                  45                  50

tgg gat cca act ctt gtt aat cct tgt acc tgg ttc cat gtc acc tgt       250
Trp Asp Pro Thr Leu Val Asn Pro Cys Thr Trp Phe His Val Thr Cys
                55                  60                  65

aac caa gac aac cgc gtc act cgt gtg gat ttg gga aat tca aac ctc       298
Asn Gln Asp Asn Arg Val Thr Arg Val Asp Leu Gly Asn Ser Asn Leu
            70                  75                  80

tct gga cat ctt gcg cct gag ctt ggg aag ctt gaa cat tta cag tat       346
Ser Gly His Leu Ala Pro Glu Leu Gly Lys Leu Glu His Leu Gln Tyr
        85                  90                  95

cta gag ctc tac aaa aac aac atc caa gga act ata cct tcc gaa ctt       394
Leu Glu Leu Tyr Lys Asn Asn Ile Gln Gly Thr Ile Pro Ser Glu Leu
    100                 105                 110

gga aat ctg aag aat ctc atc agc ttg gat ctg tac aac aac aat ctt       442
Gly Asn Leu Lys Asn Leu Ile Ser Leu Asp Leu Tyr Asn Asn Asn Leu
115                 120                 125                 130

aca ggg ata gtt ccc act tct ttg gga aaa ttg aag tct ctg gtc ttt       490
Thr Gly Ile Val Pro Thr Ser Leu Gly Lys Leu Lys Ser Leu Val Phe
                135                 140                 145

tta cgg ctt aat gac aac cga ttg acg gtc caa tcc cta gag cac tca       538
Leu Arg Leu Asn Asp Asn Arg Leu Thr Val Gln Ser Leu Glu His Ser
            150                 155                 160

cgg caa tcc caa gcc ttt aaa gtt gtg acg tct caa gca atg att tgt       586
Arg Gln Ser Gln Ala Phe Lys Val Val Thr Ser Gln Ala Met Ile Cys
        165                 170                 175

gtg gac aat ccc aca aac gga ccc ttt gct cac att cct tta cag aac       634
Val Asp Asn Pro Thr Asn Gly Pro Phe Ala His Ile Pro Leu Gln Asn
```

```
    180                 185                 190

ttt gag aac aac ccg aga ttg gag gga ccg gaa tta ctc ggt ctt gca      682
Phe Glu Asn Asn Pro Arg Leu Glu Gly Pro Glu Leu Leu Gly Leu Ala
195                 200                 205                 210

agc tac gac act aac tgc acc tgaacaactg gcaaaacctg aaaatgaaga         733
Ser Tyr Asp Thr Asn Cys Thr
                215

attggggggt gaccttgtaa gaacacttca ccactttatc aaatatcaca tctactatgt    793

aataagtata tatatgtagt ccaaaaaaaa aaaaaaaaa                           832


<210> SEQ ID NO 33
<211> LENGTH: 217
<212> TYPE: PRT
<213> ORGANISM: Arabidopsis thaliana

<400> SEQUENCE: 33

Met Ala Ser Arg Asn Tyr Arg Trp Glu Leu Phe Ala Ala Ser Leu Thr
1               5                   10                  15

Leu Thr Leu Ala Leu Ile His Leu Val Glu Ala Asn Ser Glu Gly Asp
            20                  25                  30

Ala Leu Tyr Ala Leu Arg Arg Ser Leu Thr Asp Pro Asp His Val Leu
        35                  40                  45

Gln Ser Trp Asp Pro Thr Leu Val Asn Pro Cys Thr Trp Phe His Val
    50                  55                  60

Thr Cys Asn Gln Asp Asn Arg Val Thr Arg Val Asp Leu Gly Asn Ser
65                  70                  75                  80

Asn Leu Ser Gly His Leu Ala Pro Glu Leu Gly Lys Leu Glu His Leu
                85                  90                  95

Gln Tyr Leu Glu Leu Tyr Lys Asn Asn Ile Gln Gly Thr Ile Pro Ser
            100                 105                 110

Glu Leu Gly Asn Leu Lys Asn Leu Ile Ser Leu Asp Leu Tyr Asn Asn
        115                 120                 125

Asn Leu Thr Gly Ile Val Pro Thr Ser Leu Gly Lys Leu Lys Ser Leu
    130                 135                 140

Val Phe Leu Arg Leu Asn Asp Asn Arg Leu Thr Val Gln Ser Leu Glu
145                 150                 155                 160

His Ser Arg Gln Ser Gln Ala Phe Lys Val Val Thr Ser Gln Ala Met
                165                 170                 175

Ile Cys Val Asp Asn Pro Thr Asn Gly Pro Phe Ala His Ile Pro Leu
            180                 185                 190

Gln Asn Phe Glu Asn Asn Pro Arg Leu Glu Gly Pro Glu Leu Leu Gly
        195                 200                 205

Leu Ala Ser Tyr Asp Thr Asn Cys Thr
    210                 215


<210> SEQ ID NO 34
<211> LENGTH: 988
<212> TYPE: DNA
<213> ORGANISM: Arabidopsis thaliana
<220> FEATURE:
<221> NAME/KEY: CDS
<222> LOCATION: (53)..(709)

<400> SEQUENCE: 34

aaaattactc aaattcctat tagattactc tcttcgacct ccgatagctc ac atg gcg     58
                                                          Met Ala
                                                          1
```

-continued

```
tct cga aac tat cgg tgg gag ctc ttc gca gct tcg tta atc cta acc      106
Ser Arg Asn Tyr Arg Trp Glu Leu Phe Ala Ala Ser Leu Ile Leu Thr
        5                   10                  15

tta gct ttg att cac ctg gtc gaa gca aac tcc gaa gga gat gct ctt      154
Leu Ala Leu Ile His Leu Val Glu Ala Asn Ser Glu Gly Asp Ala Leu
    20                  25                  30

tac gct ctt cgc cgg agt tta aca gat ccg gac cat gtc ctc cag agc      202
Tyr Ala Leu Arg Arg Ser Leu Thr Asp Pro Asp His Val Leu Gln Ser
35                  40                  45                  50

tgg gat cca act ctt gtt aat cct tgt acc tgg ttc cat gtc acc tgt      250
Trp Asp Pro Thr Leu Val Asn Pro Cys Thr Trp Phe His Val Thr Cys
                55                  60                  65

aac caa gac aac cgc gtc act cgt gtg gat ttg ggg aat tca aac ctc      298
Asn Gln Asp Asn Arg Val Thr Arg Val Asp Leu Gly Asn Ser Asn Leu
            70                  75                  80

tct gga cat ctt gcg cct gag ctt ggg aag ctt gaa cat tta cag tat      346
Ser Gly His Leu Ala Pro Glu Leu Gly Lys Leu Glu His Leu Gln Tyr
        85                  90                  95

cta gag ctc tac aaa aac aac atc caa gga act ata cct tcc gaa ctt      394
Leu Glu Leu Tyr Lys Asn Asn Ile Gln Gly Thr Ile Pro Ser Glu Leu
    100                 105                 110

gga aat ctg aag aat ctc atc agc ttg gat ctg tac aac aac aat ctt      442
Gly Asn Leu Lys Asn Leu Ile Ser Leu Asp Leu Tyr Asn Asn Asn Leu
115                 120                 125                 130

aca ggg ata gtt ccc act tct ttg gga aaa ttg aag tct ctg gtc ttt      490
Thr Gly Ile Val Pro Thr Ser Leu Gly Lys Leu Lys Ser Leu Val Phe
                135                 140                 145

tta cgg ctt aat gac aac cga ttg acg ggg caa tcc cta gag cac tca      538
Leu Arg Leu Asn Asp Asn Arg Leu Thr Gly Gln Ser Leu Glu His Ser
            150                 155                 160

ctg cca atc cca agc ctt aaa agt tgt gga tgt cta agc aat gat ttg      586
Leu Pro Ile Pro Ser Leu Lys Ser Cys Gly Cys Leu Ser Asn Asp Leu
        165                 170                 175

tgt gga aca atc cca aca aac gga cct ttt gct cac att cct tta cag      634
Cys Gly Thr Ile Pro Thr Asn Gly Pro Phe Ala His Ile Pro Leu Gln
    180                 185                 190

aac ttt gag aac aac ccg agg ttg gag gga ccg gaa tta ctc ggt ctt      682
Asn Phe Glu Asn Asn Pro Arg Leu Glu Gly Pro Glu Leu Leu Gly Leu
195                 200                 205                 210

gca agc tac gac act aac tgc acc tga agaaattggc aaaacctgaa            729
Ala Ser Tyr Asp Thr Asn Cys Thr
                215

aatgaagaat tggggggac cttgtaagaa cacttcacca ctttatcaaa tatcacatct     789

actatgtaat aagtatatat atgtagtcca aaaaaaaaat gaagaatcga atagtaatat    849

catctggtct caattgagaa ctttgaggtc tgtgtatgaa aattaaagat tgtactgtaa    909

tgttcggttg tgggattctg agaagtaaca tttgtattgg tatggtatca agttgttctg    969

ccttgtctgc aaaaaaaaa                                                 988


<210> SEQ ID NO 35
<211> LENGTH: 218
<212> TYPE: PRT
<213> ORGANISM: Arabidopsis thaliana

<400> SEQUENCE: 35

Met Ala Ser Arg Asn Tyr Arg Trp Glu Leu Phe Ala Ala Ser Leu Ile
1               5                   10                  15

Leu Thr Leu Ala Leu Ile His Leu Val Glu Ala Asn Ser Glu Gly Asp
            20                  25                  30
```

-continued

```
Ala Leu Tyr Ala Leu Arg Arg Ser Leu Thr Asp Pro Asp His Val Leu
        35                  40                  45

Gln Ser Trp Asp Pro Thr Leu Val Asn Pro Cys Thr Trp Phe His Val
    50                  55                  60

Thr Cys Asn Gln Asp Asn Arg Val Thr Arg Val Asp Leu Gly Asn Ser
65                  70                  75                  80

Asn Leu Ser Gly His Leu Ala Pro Glu Leu Gly Lys Leu Glu His Leu
                85                  90                  95

Gln Tyr Leu Glu Leu Tyr Lys Asn Asn Ile Gln Gly Thr Ile Pro Ser
            100                 105                 110

Glu Leu Gly Asn Leu Lys Asn Leu Ile Ser Leu Asp Leu Tyr Asn Asn
        115                 120                 125

Asn Leu Thr Gly Ile Val Pro Thr Ser Leu Gly Lys Leu Lys Ser Leu
    130                 135                 140

Val Phe Leu Arg Leu Asn Asp Asn Arg Leu Thr Gly Gln Ser Leu Glu
145                 150                 155                 160

His Ser Leu Pro Ile Pro Ser Leu Lys Ser Cys Gly Cys Leu Ser Asn
                165                 170                 175

Asp Leu Cys Gly Thr Ile Pro Thr Asn Gly Pro Phe Ala His Ile Pro
            180                 185                 190

Leu Gln Asn Phe Glu Asn Asn Pro Arg Leu Glu Gly Pro Glu Leu Leu
        195                 200                 205

Gly Leu Ala Ser Tyr Asp Thr Asn Cys Thr
    210                 215


<210> SEQ ID NO 36
<211> LENGTH: 677
<212> TYPE: DNA
<213> ORGANISM: Arabidopsis thaliana
<220> FEATURE:
<221> NAME/KEY: CDS
<222> LOCATION: (21)..(662)

<400> SEQUENCE: 36

ttctctctcc ggcgaaaacc atg gtg gcg caa aac agt cgg cgg gag ctt cta      53
                      Met Val Ala Gln Asn Ser Arg Arg Glu Leu Leu
                      1               5                   10

gca gct tcc ctg atc cta act tta gct cta att cgt cta acg gaa gca       101
Ala Ala Ser Leu Ile Leu Thr Leu Ala Leu Ile Arg Leu Thr Glu Ala
            15                  20                  25

aac tcc gaa ggg gac gct ctt cac gcg ctt cgc cgg agc tta tca gat       149
Asn Ser Glu Gly Asp Ala Leu His Ala Leu Arg Arg Ser Leu Ser Asp
        30                  35                  40

cca gac aat gtt gtt cag agt tgg gat cca act ctt gtt aat cct tgt       197
Pro Asp Asn Val Val Gln Ser Trp Asp Pro Thr Leu Val Asn Pro Cys
    45                  50                  55

act tgg ttt cat gtc act tgt aat caa cac cat caa gtc act cgt ctg       245
Thr Trp Phe His Val Thr Cys Asn Gln His His Gln Val Thr Arg Leu
60                  65                  70                  75

gat ttg ggg aat tca aac tta tct gga cat cta gta cct gaa ctt ggg       293
Asp Leu Gly Asn Ser Asn Leu Ser Gly His Leu Val Pro Glu Leu Gly
                80                  85                  90

aag ctt gaa cat tta caa tat ctt gaa ctc tac aaa aac gag att caa       341
Lys Leu Glu His Leu Gln Tyr Leu Glu Leu Tyr Lys Asn Glu Ile Gln
            95                  100                 105

gga act ata cct tct gag ctt gga aat ctg aag agt cta atc agt ttg       389
Gly Thr Ile Pro Ser Glu Leu Gly Asn Leu Lys Ser Leu Ile Ser Leu
        110                 115                 120
```

-continued

```
gat ctg tac aac aac aat ctc acc ggg aaa atc cca tct tct ttg gga      437
Asp Leu Tyr Asn Asn Asn Leu Thr Gly Lys Ile Pro Ser Ser Leu Gly
    125                 130                 135

aaa ttg aag cgg ctt aac gaa aac cga ttg acc ggt cct att cct aga      485
Lys Leu Lys Arg Leu Asn Glu Asn Arg Leu Thr Gly Pro Ile Pro Arg
140                 145                 150                 155

gaa ctc aca gtt att tca agc ctt aaa gtt gtt gat gtc tca ggg aat      533
Glu Leu Thr Val Ile Ser Ser Leu Lys Val Val Asp Val Ser Gly Asn
                160                 165                 170

gat ttg tgt gga aca att cca gta gaa gga cct ttt gaa cac att cct      581
Asp Leu Cys Gly Thr Ile Pro Val Glu Gly Pro Phe Glu His Ile Pro
            175                 180                 185

atg caa aac ttt gag aac aac ctg aga ttg gag gga cca gaa cta cta      629
Met Gln Asn Phe Glu Asn Asn Leu Arg Leu Glu Gly Pro Glu Leu Leu
        190                 195                 200

ggt ctt gcg agc tat gac acc aat tgc act taa aaagaagttg aagaa         677
Gly Leu Ala Ser Tyr Asp Thr Asn Cys Thr
    205                 210


<210> SEQ ID NO 37
<211> LENGTH: 213
<212> TYPE: PRT
<213> ORGANISM: Arabidopsis thaliana

<400> SEQUENCE: 37

Met Val Ala Gln Asn Ser Arg Arg Glu Leu Leu Ala Ala Ser Leu Ile
1               5                   10                  15

Leu Thr Leu Ala Leu Ile Arg Leu Thr Glu Ala Asn Ser Glu Gly Asp
            20                  25                  30

Ala Leu His Ala Leu Arg Arg Ser Leu Ser Asp Pro Asp Asn Val Val
        35                  40                  45

Gln Ser Trp Asp Pro Thr Leu Val Asn Pro Cys Thr Trp Phe His Val
    50                  55                  60

Thr Cys Asn Gln His His Gln Val Thr Arg Leu Asp Leu Gly Asn Ser
65                  70                  75                  80

Asn Leu Ser Gly His Leu Val Pro Glu Leu Gly Lys Leu Glu His Leu
                85                  90                  95

Gln Tyr Leu Glu Leu Tyr Lys Asn Glu Ile Gln Gly Thr Ile Pro Ser
            100                 105                 110

Glu Leu Gly Asn Leu Lys Ser Leu Ile Ser Leu Asp Leu Tyr Asn Asn
        115                 120                 125

Asn Leu Thr Gly Lys Ile Pro Ser Ser Leu Gly Lys Leu Lys Arg Leu
    130                 135                 140

Asn Glu Asn Arg Leu Thr Gly Pro Ile Pro Arg Glu Leu Thr Val Ile
145                 150                 155                 160

Ser Ser Leu Lys Val Val Asp Val Ser Gly Asn Asp Leu Cys Gly Thr
                165                 170                 175

Ile Pro Val Glu Gly Pro Phe Glu His Ile Pro Met Gln Asn Phe Glu
            180                 185                 190

Asn Asn Leu Arg Leu Glu Gly Pro Glu Leu Leu Gly Leu Ala Ser Tyr
        195                 200                 205

Asp Thr Asn Cys Thr
    210


<210> SEQ ID NO 38
<211> LENGTH: 2087
<212> TYPE: DNA
```

-continued

```
<213> ORGANISM: Arabidopsis thaliana
<220> FEATURE:
<221> NAME/KEY: CDS
<222> LOCATION: (193)..(2070)

<400> SEQUENCE: 38

atttttattt tattttttac tctttgtttg ttttaatgct aatgggtttt taaaagggtt      60

atcgaaaaaa tgagtgagtt tgtgttgagg ttgtctctgt aaagtgttaa tggtggtgat     120

tttcggaagt tagggttttc tcggatctga agagatcaaa tcaagattcg aaatttacca     180

ttgttgtttg aa atg gag tcg agt tat gtg gtg ttt atc tta ctt tca ctg     231
              Met Glu Ser Ser Tyr Val Val Phe Ile Leu Leu Ser Leu
              1               5                   10

atc tta ctt ccg aat cat tca ctg tgg ctt gct tct gct aat ttg gaa       279
Ile Leu Leu Pro Asn His Ser Leu Trp Leu Ala Ser Ala Asn Leu Glu
    15                  20                  25

ggt gat gct ttg cat act ttg agg gtt act cta gtt gat cca aac aat       327
Gly Asp Ala Leu His Thr Leu Arg Val Thr Leu Val Asp Pro Asn Asn
30                  35                  40                  45

gtc ttg cag agc tgg gat cct acg cta gtg aat cct tgc aca tgg ttc       375
Val Leu Gln Ser Trp Asp Pro Thr Leu Val Asn Pro Cys Thr Trp Phe
                50                  55                  60

cat gtc act tgc aac aac gag aac agt gtc ata aga gtt gat ttg ggg       423
His Val Thr Cys Asn Asn Glu Asn Ser Val Ile Arg Val Asp Leu Gly
            65                  70                  75

aat gca gag tta tct ggc cat tta gtt cca gag ctt ggt gtg ctc aag       471
Asn Ala Glu Leu Ser Gly His Leu Val Pro Glu Leu Gly Val Leu Lys
        80                  85                  90

aat ttg cag tat ttg gag ctt tac agt aac aac ata act ggc ccg att       519
Asn Leu Gln Tyr Leu Glu Leu Tyr Ser Asn Asn Ile Thr Gly Pro Ile
    95                  100                 105

cct agt aat ctt gga aat ctg aca aac tta gtg agt ttg gat ctt tac       567
Pro Ser Asn Leu Gly Asn Leu Thr Asn Leu Val Ser Leu Asp Leu Tyr
110                 115                 120                 125

tta aac agc ttc tcc ggt cct att ccg gaa tca ttg gga aag ctt tca       615
Leu Asn Ser Phe Ser Gly Pro Ile Pro Glu Ser Leu Gly Lys Leu Ser
                130                 135                 140

aag ctg aga ttt ctc cgg ctt aac aac aac agt ctc act ggg tca att       663
Lys Leu Arg Phe Leu Arg Leu Asn Asn Asn Ser Leu Thr Gly Ser Ile
            145                 150                 155

cct atg tca ctg acc aat att act acc ctt caa gtg tta gat cta tca       711
Pro Met Ser Leu Thr Asn Ile Thr Thr Leu Gln Val Leu Asp Leu Ser
        160                 165                 170

aat aac aga ctc tct ggt tca gtt cct gac aat ggc tcc ttc tca ctc       759
Asn Asn Arg Leu Ser Gly Ser Val Pro Asp Asn Gly Ser Phe Ser Leu
    175                 180                 185

ttc aca ccc atc agt ttt gct aat aac tta gac cta tgt gga cct gtt       807
Phe Thr Pro Ile Ser Phe Ala Asn Asn Leu Asp Leu Cys Gly Pro Val
190                 195                 200                 205

aca agt cac cca tgt cct gga tct ccc ccg ttt tct cct cca cca cct       855
Thr Ser His Pro Cys Pro Gly Ser Pro Pro Phe Ser Pro Pro Pro Pro
                210                 215                 220

ttt att caa cct ccc cca gtt tcc acc ccg agt ggg tat ggt ata act       903
Phe Ile Gln Pro Pro Pro Val Ser Thr Pro Ser Gly Tyr Gly Ile Thr
            225                 230                 235

gga gca ata gct ggt gga gtt gct gca ggt gct gct ttg ccc ttt gct       951
Gly Ala Ile Ala Gly Gly Val Ala Ala Gly Ala Ala Leu Pro Phe Ala
        240                 245                 250

gct cct gca ata gcc ttt gct tgg tgg cga cga aga agc cca cta gat       999
Ala Pro Ala Ile Ala Phe Ala Trp Trp Arg Arg Arg Ser Pro Leu Asp
```

-continued

```
    255                 260                 265

att ttc ttc gat gtc cct gcc gaa gaa gat cca gaa gtt cat ctg gga      1047
Ile Phe Phe Asp Val Pro Ala Glu Glu Asp Pro Glu Val His Leu Gly
270                 275                 280                 285

cag ctc aag agg ttt tct ttg cgg gag cta caa gtg gcg agt gat ggg      1095
Gln Leu Lys Arg Phe Ser Leu Arg Glu Leu Gln Val Ala Ser Asp Gly
                290                 295                 300

ttt agt aac aag aac att ttg ggc aga ggt ggg ttt ggg aaa gtc tac      1143
Phe Ser Asn Lys Asn Ile Leu Gly Arg Gly Gly Phe Gly Lys Val Tyr
            305                 310                 315

aag gga cgc ttg gca gac gga act ctt gtt gct gtc aag aga ctg aag      1191
Lys Gly Arg Leu Ala Asp Gly Thr Leu Val Ala Val Lys Arg Leu Lys
        320                 325                 330

gaa gag cga act cca ggt gga gag ctc cag ttt caa aca gaa gta gag      1239
Glu Glu Arg Thr Pro Gly Gly Glu Leu Gln Phe Gln Thr Glu Val Glu
    335                 340                 345

atg ata agt atg gca gtt cat cga aac ctg ttg aga tta cga ggt ttc      1287
Met Ile Ser Met Ala Val His Arg Asn Leu Leu Arg Leu Arg Gly Phe
350                 355                 360                 365

tgt atg aca ccg acc gag aga ttg ctt gtg tat cct tac atg gcc aat      1335
Cys Met Thr Pro Thr Glu Arg Leu Leu Val Tyr Pro Tyr Met Ala Asn
                370                 375                 380

gga agt gtt gct tcg tgt ctc aga gag agg cca ccg tca caa cct ccg      1383
Gly Ser Val Ala Ser Cys Leu Arg Glu Arg Pro Pro Ser Gln Pro Pro
            385                 390                 395

ctt gat tgg cca acg cgg aag aga atc gcg cta ggc tca gct cga ggt      1431
Leu Asp Trp Pro Thr Arg Lys Arg Ile Ala Leu Gly Ser Ala Arg Gly
        400                 405                 410

ttg tct tac cta cat gat cac tgc gat ccg aag atc att cac cgt gac      1479
Leu Ser Tyr Leu His Asp His Cys Asp Pro Lys Ile Ile His Arg Asp
    415                 420                 425

gta aaa gca gca aac atc ctc tta gac gaa gaa ttc gaa gcg gtt gtt      1527
Val Lys Ala Ala Asn Ile Leu Leu Asp Glu Glu Phe Glu Ala Val Val
430                 435                 440                 445

gga gat ttc ggg ttg gca aag ctt atg gac tat aaa gac act cac gtg      1575
Gly Asp Phe Gly Leu Ala Lys Leu Met Asp Tyr Lys Asp Thr His Val
                450                 455                 460

aca aca gca gtc cgt ggc acc atc ggt cac atc gct cca gaa tat ctc      1623
Thr Thr Ala Val Arg Gly Thr Ile Gly His Ile Ala Pro Glu Tyr Leu
            465                 470                 475

tca acc gga aaa tct tca gag aaa acc gac gtt ttc gga tac gga atc      1671
Ser Thr Gly Lys Ser Ser Glu Lys Thr Asp Val Phe Gly Tyr Gly Ile
        480                 485                 490

atg ctt cta gaa cta atc aca gga caa aga gct ttc gat ctc gct cgg      1719
Met Leu Leu Glu Leu Ile Thr Gly Gln Arg Ala Phe Asp Leu Ala Arg
    495                 500                 505

cta gct aac gac gac gac gtc atg tta ctt gac tgg gtg aaa gga ttg      1767
Leu Ala Asn Asp Asp Asp Val Met Leu Leu Asp Trp Val Lys Gly Leu
510                 515                 520                 525

ttg aag gag aag aag cta gag atg tta gtg gat cca gat ctt caa aca      1815
Leu Lys Glu Lys Lys Leu Glu Met Leu Val Asp Pro Asp Leu Gln Thr
                530                 535                 540

aac tac gag gag aga gaa ctg gaa caa gtg ata caa gtg gcg ttg cta      1863
Asn Tyr Glu Glu Arg Glu Leu Glu Gln Val Ile Gln Val Ala Leu Leu
            545                 550                 555

tgc acg caa gga tca cca atg gaa aga cca aag atg tct gaa gtt gta      1911
Cys Thr Gln Gly Ser Pro Met Glu Arg Pro Lys Met Ser Glu Val Val
        560                 565                 570

agg atg ctg gaa gga gat ggg ctt gcg gag aaa tgg gac gaa tgg caa      1959
```

-continued

```
Arg Met Leu Glu Gly Asp Gly Leu Ala Glu Lys Trp Asp Glu Trp Gln
    575                 580                 585

aaa gtt gag att ttg agg gaa gag att gat ttg agt cct aat cct aac     2007
Lys Val Glu Ile Leu Arg Glu Glu Ile Asp Leu Ser Pro Asn Pro Asn
590                 595                 600                 605

tct gat tgg att ctt gat tct act tac aat ttg cac gcc gtt gag tta     2055
Ser Asp Trp Ile Leu Asp Ser Thr Tyr Asn Leu His Ala Val Glu Leu
                610                 615                 620

tct ggt cca agg taa aaaaaaaaaa aaaaaaa                              2087
Ser Gly Pro Arg
            625


<210> SEQ ID NO 39
<211> LENGTH: 625
<212> TYPE: PRT
<213> ORGANISM: Arabidopsis thaliana

<400> SEQUENCE: 39

Met Glu Ser Ser Tyr Val Val Phe Ile Leu Leu Ser Leu Ile Leu Leu
1               5                   10                  15

Pro Asn His Ser Leu Trp Leu Ala Ser Ala Asn Leu Glu Gly Asp Ala
            20                  25                  30

Leu His Thr Leu Arg Val Thr Leu Val Asp Pro Asn Asn Val Leu Gln
        35                  40                  45

Ser Trp Asp Pro Thr Leu Val Asn Pro Cys Thr Trp Phe His Val Thr
    50                  55                  60

Cys Asn Asn Glu Asn Ser Val Ile Arg Val Asp Leu Gly Asn Ala Glu
65                  70                  75                  80

Leu Ser Gly His Leu Val Pro Glu Leu Gly Val Leu Lys Asn Leu Gln
                85                  90                  95

Tyr Leu Glu Leu Tyr Ser Asn Asn Ile Thr Gly Pro Ile Pro Ser Asn
            100                 105                 110

Leu Gly Asn Leu Thr Asn Leu Val Ser Leu Asp Leu Tyr Leu Asn Ser
        115                 120                 125

Phe Ser Gly Pro Ile Pro Glu Ser Leu Gly Lys Leu Ser Lys Leu Arg
    130                 135                 140

Phe Leu Arg Leu Asn Asn Asn Ser Leu Thr Gly Ser Ile Pro Met Ser
145                 150                 155                 160

Leu Thr Asn Ile Thr Thr Leu Gln Val Leu Asp Leu Ser Asn Asn Arg
                165                 170                 175

Leu Ser Gly Ser Val Pro Asp Asn Gly Ser Phe Ser Leu Phe Thr Pro
            180                 185                 190

Ile Ser Phe Ala Asn Asn Leu Asp Leu Cys Gly Pro Val Thr Ser His
        195                 200                 205

Pro Cys Pro Gly Ser Pro Pro Phe Ser Pro Pro Pro Pro Phe Ile Gln
    210                 215                 220

Pro Pro Pro Val Ser Thr Pro Ser Gly Tyr Gly Ile Thr Gly Ala Ile
225                 230                 235                 240

Ala Gly Gly Val Ala Ala Gly Ala Ala Leu Pro Phe Ala Ala Pro Ala
                245                 250                 255

Ile Ala Phe Ala Trp Trp Arg Arg Arg Ser Pro Leu Asp Ile Phe Phe
            260                 265                 270

Asp Val Pro Ala Glu Glu Asp Pro Glu Val His Leu Gly Gln Leu Lys
        275                 280                 285

Arg Phe Ser Leu Arg Glu Leu Gln Val Ala Ser Asp Gly Phe Ser Asn
    290                 295                 300
```

-continued

```
Lys Asn Ile Leu Gly Arg Gly Gly Phe Gly Lys Val Tyr Lys Gly Arg
305                 310                 315                 320

Leu Ala Asp Gly Thr Leu Val Ala Val Lys Arg Leu Lys Glu Glu Arg
                325                 330                 335

Thr Pro Gly Gly Glu Leu Gln Phe Gln Thr Glu Val Glu Met Ile Ser
            340                 345                 350

Met Ala Val His Arg Asn Leu Leu Arg Leu Arg Gly Phe Cys Met Thr
        355                 360                 365

Pro Thr Glu Arg Leu Leu Val Tyr Pro Tyr Met Ala Asn Gly Ser Val
    370                 375                 380

Ala Ser Cys Leu Arg Glu Arg Pro Pro Ser Gln Pro Pro Leu Asp Trp
385                 390                 395                 400

Pro Thr Arg Lys Arg Ile Ala Leu Gly Ser Ala Arg Gly Leu Ser Tyr
                405                 410                 415

Leu His Asp His Cys Asp Pro Lys Ile Ile His Arg Asp Val Lys Ala
            420                 425                 430

Ala Asn Ile Leu Leu Asp Glu Glu Phe Glu Ala Val Val Gly Asp Phe
        435                 440                 445

Gly Leu Ala Lys Leu Met Asp Tyr Lys Asp Thr His Val Thr Thr Ala
    450                 455                 460

Val Arg Gly Thr Ile Gly His Ile Ala Pro Glu Tyr Leu Ser Thr Gly
465                 470                 475                 480

Lys Ser Ser Glu Lys Thr Asp Val Phe Gly Tyr Gly Ile Met Leu Leu
                485                 490                 495

Glu Leu Ile Thr Gly Gln Arg Ala Phe Asp Leu Ala Arg Leu Ala Asn
            500                 505                 510

Asp Asp Asp Val Met Leu Leu Asp Trp Val Lys Gly Leu Leu Lys Glu
        515                 520                 525

Lys Lys Leu Glu Met Leu Val Asp Pro Asp Leu Gln Thr Asn Tyr Glu
    530                 535                 540

Glu Arg Glu Leu Glu Gln Val Ile Gln Val Ala Leu Leu Cys Thr Gln
545                 550                 555                 560

Gly Ser Pro Met Glu Arg Pro Lys Met Ser Glu Val Val Arg Met Leu
                565                 570                 575

Glu Gly Asp Gly Leu Ala Glu Lys Trp Asp Glu Trp Gln Lys Val Glu
            580                 585                 590

Ile Leu Arg Glu Glu Ile Asp Leu Ser Pro Asn Pro Asn Ser Asp Trp
        595                 600                 605

Ile Leu Asp Ser Thr Tyr Asn Leu His Ala Val Glu Leu Ser Gly Pro
    610                 615                 620

Arg
625


<210> SEQ ID NO 40
<211> LENGTH: 1950
<212> TYPE: DNA
<213> ORGANISM: Arabidopsis thaliana
<220> FEATURE:
<221> NAME/KEY: CDS
<222> LOCATION: (28)..(1926)

<400> SEQUENCE: 40

ccaaagttga ttgctttaag aagggat atg gaa ggt gtg aga ttt gtg gtg tgg      54
                              Met Glu Gly Val Arg Phe Val Val Trp
                              1               5
```

-continued

```
aga tta gga ttt ctg gtt ttt gta tgg ttc ttt gat atc tct tct gct      102
Arg Leu Gly Phe Leu Val Phe Val Trp Phe Phe Asp Ile Ser Ser Ala
10                  15                  20                  25

aca ctt tct cct act ggt gta aac tat gaa gtg aca gct ttg gtt gct      150
Thr Leu Ser Pro Thr Gly Val Asn Tyr Glu Val Thr Ala Leu Val Ala
                30                  35                  40

gtg aag aat gaa ttg aat gat ccg tac aaa gtt ctt gag aat tgg gat      198
Val Lys Asn Glu Leu Asn Asp Pro Tyr Lys Val Leu Glu Asn Trp Asp
            45                  50                  55

gtg aat tca gtt gat cct tgt agc tgg aga atg gtt tct tgc act gat      246
Val Asn Ser Val Asp Pro Cys Ser Trp Arg Met Val Ser Cys Thr Asp
        60                  65                  70

ggc tat gtc tct tca ctg gat ctt cct agc caa agc ttg tct ggt aca      294
Gly Tyr Val Ser Ser Leu Asp Leu Pro Ser Gln Ser Leu Ser Gly Thr
    75                  80                  85

ttg tct cct aga atc gga aac ctc acc tat tta caa tca gtg gtg ttg      342
Leu Ser Pro Arg Ile Gly Asn Leu Thr Tyr Leu Gln Ser Val Val Leu
90                  95                  100                 105

caa aac aat gca atc act ggt cca att ccg gaa acg att ggg agg ttg      390
Gln Asn Asn Ala Ile Thr Gly Pro Ile Pro Glu Thr Ile Gly Arg Leu
                110                 115                 120

gag aag ctt cag tca ctt gat ctt tcg aac aat tca ttc acc ggg gag      438
Glu Lys Leu Gln Ser Leu Asp Leu Ser Asn Asn Ser Phe Thr Gly Glu
            125                 130                 135

ata ccg gcc tca ctt gga gaa ctc aag aac ttg aat tac ttg cgg tta      486
Ile Pro Ala Ser Leu Gly Glu Leu Lys Asn Leu Asn Tyr Leu Arg Leu
        140                 145                 150

aac aat aac agt ctt ata gga act tgc cct gag tct cta tcc aag att      534
Asn Asn Asn Ser Leu Ile Gly Thr Cys Pro Glu Ser Leu Ser Lys Ile
    155                 160                 165

gag gga ctc act cta gtc gac att tcg tat aac aat ctt agt ggt tcg      582
Glu Gly Leu Thr Leu Val Asp Ile Ser Tyr Asn Asn Leu Ser Gly Ser
170                 175                 180                 185

ctg cca aaa gtt tct gcc aga act ttc aag gta att ggt aat gcg tta      630
Leu Pro Lys Val Ser Ala Arg Thr Phe Lys Val Ile Gly Asn Ala Leu
                190                 195                 200

atc tgt ggc cca aaa gct gtt tca aac tgt tct gct gtt ccc gag cct      678
Ile Cys Gly Pro Lys Ala Val Ser Asn Cys Ser Ala Val Pro Glu Pro
            205                 210                 215

ctc acg ctt cca caa gat ggt cca gat gaa tca gga act cgt acc aat      726
Leu Thr Leu Pro Gln Asp Gly Pro Asp Glu Ser Gly Thr Arg Thr Asn
        220                 225                 230

ggc cat cac gtt gct ctt gca ttt gcc gca agc ttc agt gca gca ttt      774
Gly His His Val Ala Leu Ala Phe Ala Ala Ser Phe Ser Ala Ala Phe
    235                 240                 245

ttt gtt ttc ttt aca agc gga atg ttt ctt tgg tgg aga tat cgc cgt      822
Phe Val Phe Phe Thr Ser Gly Met Phe Leu Trp Trp Arg Tyr Arg Arg
250                 255                 260                 265

aac aag caa ata ttt ttt gac gtt aat gaa caa tat gat cca gaa gtg      870
Asn Lys Gln Ile Phe Phe Asp Val Asn Glu Gln Tyr Asp Pro Glu Val
                270                 275                 280

agt tta ggg cac ttg aag agg tat aca ttc aaa gag ctt aga tct gcc      918
Ser Leu Gly His Leu Lys Arg Tyr Thr Phe Lys Glu Leu Arg Ser Ala
            285                 290                 295

acc aat cat ttc aac tcg aag aac att ctc gga aga ggc gga tac ggg      966
Thr Asn His Phe Asn Ser Lys Asn Ile Leu Gly Arg Gly Gly Tyr Gly
        300                 305                 310

att gtg tac aaa gga cac tta aac gat gga act ttg gtg gct gtc aaa     1014
Ile Val Tyr Lys Gly His Leu Asn Asp Gly Thr Leu Val Ala Val Lys
    315                 320                 325
```

-continued

```
cgt ctc aag gac tgt aac att gcg ggt gga gaa gtc cag ttt cag aca      1062
Arg Leu Lys Asp Cys Asn Ile Ala Gly Gly Glu Val Gln Phe Gln Thr
330                 335                 340                 345

gaa gta gag act ata agt ttg gct ctt cat cgc aat ctc ctc cgg ctc      1110
Glu Val Glu Thr Ile Ser Leu Ala Leu His Arg Asn Leu Leu Arg Leu
                350                 355                 360

cgc ggt ttc tgt agt agc aac cag gag aga att tta gtc tac cct tac      1158
Arg Gly Phe Cys Ser Ser Asn Gln Glu Arg Ile Leu Val Tyr Pro Tyr
            365                 370                 375

atg cca aat ggg agt gtc gca tca cgc tta aaa gat aat atc cgt gga      1206
Met Pro Asn Gly Ser Val Ala Ser Arg Leu Lys Asp Asn Ile Arg Gly
        380                 385                 390

gag cca gca tta gac tgg tcg aga agg aag aag ata gcg gtt ggg aca      1254
Glu Pro Ala Leu Asp Trp Ser Arg Arg Lys Lys Ile Ala Val Gly Thr
    395                 400                 405

gcg aga gga cta gtt tac cta cac gag caa tgt gac ccg aag att ata      1302
Ala Arg Gly Leu Val Tyr Leu His Glu Gln Cys Asp Pro Lys Ile Ile
410                 415                 420                 425

cac cgc gat gtg aaa gca gct aac att ctg tta gat gag gac ttc gaa      1350
His Arg Asp Val Lys Ala Ala Asn Ile Leu Leu Asp Glu Asp Phe Glu
                430                 435                 440

gca gtt gtt ggt gat ttt ggg tta gct aag ctt cta gac cat aga gac      1398
Ala Val Val Gly Asp Phe Gly Leu Ala Lys Leu Leu Asp His Arg Asp
            445                 450                 455

tct cat gtc aca act gca gtc cgt gga act gtt ggc cac att gca cct      1446
Ser His Val Thr Thr Ala Val Arg Gly Thr Val Gly His Ile Ala Pro
        460                 465                 470

gag tac tta tcc acg ggt cag tcc tca gag aag act gat gtc ttt ggc      1494
Glu Tyr Leu Ser Thr Gly Gln Ser Ser Glu Lys Thr Asp Val Phe Gly
    475                 480                 485

ttt ggc ata ctt ctc ctt gag ctc att act ggt cag aaa gct ctt gat      1542
Phe Gly Ile Leu Leu Leu Glu Leu Ile Thr Gly Gln Lys Ala Leu Asp
490                 495                 500                 505

ttt ggc aga tcc gca cac cag aaa ggt gta atg ctt gac tgg gtg aag      1590
Phe Gly Arg Ser Ala His Gln Lys Gly Val Met Leu Asp Trp Val Lys
                510                 515                 520

aag ctg cac caa gaa ggg aaa cta aag cag tta ata gac aaa gat cta      1638
Lys Leu His Gln Glu Gly Lys Leu Lys Gln Leu Ile Asp Lys Asp Leu
            525                 530                 535

aat gac aag ttc gat aga gta gaa ctc gaa gaa atc gtt caa gtt gcg      1686
Asn Asp Lys Phe Asp Arg Val Glu Leu Glu Glu Ile Val Gln Val Ala
        540                 545                 550

cta ctc tgc act caa ttc aat cca tct cat cga ccg aaa atg tca gaa      1734
Leu Leu Cys Thr Gln Phe Asn Pro Ser His Arg Pro Lys Met Ser Glu
    555                 560                 565

gtt atg aag atg ctt gaa ggt gac ggt ttg gct gag aga tgg gaa gcg      1782
Val Met Lys Met Leu Glu Gly Asp Gly Leu Ala Glu Arg Trp Glu Ala
570                 575                 580                 585

acg cag aac ggt act ggt gag cat cag cca ccg cca ttg cca ccg ggg      1830
Thr Gln Asn Gly Thr Gly Glu His Gln Pro Pro Pro Leu Pro Pro Gly
                590                 595                 600

atg gtg agt tct tcg ccg cgt gtg agg tat tac tcg gat tat att cag      1878
Met Val Ser Ser Ser Pro Arg Val Arg Tyr Tyr Ser Asp Tyr Ile Gln
            605                 610                 615

gaa tcg tct ctt gta gta gaa gcc att gag ctc tcg ggt cct cga tga      1926
Glu Ser Ser Leu Val Val Glu Ala Ile Glu Leu Ser Gly Pro Arg
        620                 625                 630

ttatgactca ctgtttttaa aaaa                                            1950
```

-continued

<210> SEQ ID NO 41
<211> LENGTH: 632
<212> TYPE: PRT
<213> ORGANISM: Arabidopsis thaliana

<400> SEQUENCE: 41

```
Met Glu Gly Val Arg Phe Val Val Trp Arg Leu Gly Phe Leu Val Phe
1               5                   10                  15

Val Trp Phe Phe Asp Ile Ser Ser Ala Thr Leu Ser Pro Thr Gly Val
            20                  25                  30

Asn Tyr Glu Val Thr Ala Leu Val Ala Val Lys Asn Glu Leu Asn Asp
        35                  40                  45

Pro Tyr Lys Val Leu Glu Asn Trp Asp Val Asn Ser Val Asp Pro Cys
    50                  55                  60

Ser Trp Arg Met Val Ser Cys Thr Asp Gly Tyr Val Ser Ser Leu Asp
65                  70                  75                  80

Leu Pro Ser Gln Ser Leu Ser Gly Thr Leu Ser Pro Arg Ile Gly Asn
                85                  90                  95

Leu Thr Tyr Leu Gln Ser Val Val Leu Gln Asn Asn Ala Ile Thr Gly
            100                 105                 110

Pro Ile Pro Glu Thr Ile Gly Arg Leu Glu Lys Leu Gln Ser Leu Asp
        115                 120                 125

Leu Ser Asn Asn Ser Phe Thr Gly Glu Ile Pro Ala Ser Leu Gly Glu
    130                 135                 140

Leu Lys Asn Leu Asn Tyr Leu Arg Leu Asn Asn Asn Ser Leu Ile Gly
145                 150                 155                 160

Thr Cys Pro Glu Ser Leu Ser Lys Ile Glu Gly Leu Thr Leu Val Asp
                165                 170                 175

Ile Ser Tyr Asn Asn Leu Ser Gly Ser Leu Pro Lys Val Ser Ala Arg
            180                 185                 190

Thr Phe Lys Val Ile Gly Asn Ala Leu Ile Cys Gly Pro Lys Ala Val
        195                 200                 205

Ser Asn Cys Ser Ala Val Pro Glu Pro Leu Thr Leu Pro Gln Asp Gly
    210                 215                 220

Pro Asp Glu Ser Gly Thr Arg Thr Asn Gly His His Val Ala Leu Ala
225                 230                 235                 240

Phe Ala Ala Ser Phe Ser Ala Ala Phe Phe Val Phe Phe Thr Ser Gly
                245                 250                 255

Met Phe Leu Trp Trp Arg Tyr Arg Arg Asn Lys Gln Ile Phe Phe Asp
            260                 265                 270

Val Asn Glu Gln Tyr Asp Pro Glu Val Ser Leu Gly His Leu Lys Arg
        275                 280                 285

Tyr Thr Phe Lys Glu Leu Arg Ser Ala Thr Asn His Phe Asn Ser Lys
    290                 295                 300

Asn Ile Leu Gly Arg Gly Gly Tyr Gly Ile Val Tyr Lys Gly His Leu
305                 310                 315                 320

Asn Asp Gly Thr Leu Val Ala Val Lys Arg Leu Lys Asp Cys Asn Ile
                325                 330                 335

Ala Gly Gly Glu Val Gln Phe Gln Thr Glu Val Glu Thr Ile Ser Leu
            340                 345                 350

Ala Leu His Arg Asn Leu Leu Arg Leu Arg Gly Phe Cys Ser Ser Asn
        355                 360                 365

Gln Glu Arg Ile Leu Val Tyr Pro Tyr Met Pro Asn Gly Ser Val Ala
    370                 375                 380
```

```
Ser Arg Leu Lys Asp Asn Ile Arg Gly Glu Pro Ala Leu Asp Trp Ser
385                 390                 395                 400

Arg Arg Lys Lys Ile Ala Val Gly Thr Ala Arg Gly Leu Val Tyr Leu
                405                 410                 415

His Glu Gln Cys Asp Pro Lys Ile Ile His Arg Asp Val Lys Ala Ala
            420                 425                 430

Asn Ile Leu Leu Asp Glu Asp Phe Glu Ala Val Val Gly Asp Phe Gly
        435                 440                 445

Leu Ala Lys Leu Leu Asp His Arg Asp Ser His Val Thr Thr Ala Val
    450                 455                 460

Arg Gly Thr Val Gly His Ile Ala Pro Glu Tyr Leu Ser Thr Gly Gln
465                 470                 475                 480

Ser Ser Glu Lys Thr Asp Val Phe Gly Phe Gly Ile Leu Leu Leu Glu
                485                 490                 495

Leu Ile Thr Gly Gln Lys Ala Leu Asp Phe Gly Arg Ser Ala His Gln
            500                 505                 510

Lys Gly Val Met Leu Asp Trp Val Lys Lys Leu His Gln Glu Gly Lys
        515                 520                 525

Leu Lys Gln Leu Ile Asp Lys Asp Leu Asn Asp Lys Phe Asp Arg Val
    530                 535                 540

Glu Leu Glu Glu Ile Val Gln Val Ala Leu Leu Cys Thr Gln Phe Asn
545                 550                 555                 560

Pro Ser His Arg Pro Lys Met Ser Glu Val Met Lys Met Leu Glu Gly
                565                 570                 575

Asp Gly Leu Ala Glu Arg Trp Glu Ala Thr Gln Asn Gly Thr Gly Glu
            580                 585                 590

His Gln Pro Pro Pro Leu Pro Pro Gly Met Val Ser Ser Ser Pro Arg
        595                 600                 605

Val Arg Tyr Tyr Ser Asp Tyr Ile Gln Glu Ser Ser Leu Val Val Glu
    610                 615                 620

Ala Ile Glu Leu Ser Gly Pro Arg
625                 630


<210> SEQ ID NO 42
<211> LENGTH: 1891
<212> TYPE: DNA
<213> ORGANISM: Arabidopsis thaliana
<220> FEATURE:
<221> NAME/KEY: CDS
<222> LOCATION: (25)..(1881)

<400> SEQUENCE: 42

tcaattttgg tagctcttag aaaa atg gct ctg ctt att atc act gcc tta        51
                           Met Ala Leu Leu Ile Ile Thr Ala Leu
                           1               5

gtt ttt agt agt tta tgg tca tct gtg tca cca gat gct caa ggg gat       99
Val Phe Ser Ser Leu Trp Ser Ser Val Ser Pro Asp Ala Gln Gly Asp
10                  15                  20                  25

gca tta ttt gcg ttg agg agc tcg tta cgt gca tct cct gaa cag ctt      147
Ala Leu Phe Ala Leu Arg Ser Ser Leu Arg Ala Ser Pro Glu Gln Leu
                30                  35                  40

agt gat tgg aac cag aat caa gtc gat cct tgt act tgg tct caa gtt      195
Ser Asp Trp Asn Gln Asn Gln Val Asp Pro Cys Thr Trp Ser Gln Val
            45                  50                  55

att tgt gat gac aag aaa cat gtt act tct gta acc ttg tct tac atg      243
Ile Cys Asp Asp Lys Lys His Val Thr Ser Val Thr Leu Ser Tyr Met
        60                  65                  70
```

-continued

```
aac ttc tcc tcg gga aca ctg tct tca gga ata gga atc ttg aca act      291
Asn Phe Ser Ser Gly Thr Leu Ser Ser Gly Ile Gly Ile Leu Thr Thr
    75                  80                  85

ctc aag act ctt aca ttg aag gga aat gga ata atg ggt gga ata cca      339
Leu Lys Thr Leu Thr Leu Lys Gly Asn Gly Ile Met Gly Gly Ile Pro
90                  95                  100                 105

gaa tcc att gga aat ctg tct agc ttg acc agc tta gat ttg gag gat      387
Glu Ser Ile Gly Asn Leu Ser Ser Leu Thr Ser Leu Asp Leu Glu Asp
                110                 115                 120

aat cac tta act gat cgc att cca tcc act ctc ggt aat ctc aag aat      435
Asn His Leu Thr Asp Arg Ile Pro Ser Thr Leu Gly Asn Leu Lys Asn
            125                 130                 135

cta cag ttc ttc agg acc ttg agt agg aat aac ctt aat ggt tct atc      483
Leu Gln Phe Phe Arg Thr Leu Ser Arg Asn Asn Leu Asn Gly Ser Ile
        140                 145                 150

ccg gat tca ctt aca ggt cta tca aaa ctg ata aat att ctg ctc gac      531
Pro Asp Ser Leu Thr Gly Leu Ser Lys Leu Ile Asn Ile Leu Leu Asp
    155                 160                 165

tca aat aat ctc agt ggt gag att cct cag agt tta ttc aaa atc cca      579
Ser Asn Asn Leu Ser Gly Glu Ile Pro Gln Ser Leu Phe Lys Ile Pro
170                 175                 180                 185

aaa tac aat ttc aca gca aac aac ttg agc tgt ggt ggc act ttc ccg      627
Lys Tyr Asn Phe Thr Ala Asn Asn Leu Ser Cys Gly Gly Thr Phe Pro
                190                 195                 200

caa cct tgt gta acc gag tcc agt cct tca ggt gat tca agc agt aga      675
Gln Pro Cys Val Thr Glu Ser Ser Pro Ser Gly Asp Ser Ser Ser Arg
            205                 210                 215

aaa act gga atc atc gct gga gtt gtt agc gga ata gcg gtt att cta      723
Lys Thr Gly Ile Ile Ala Gly Val Val Ser Gly Ile Ala Val Ile Leu
        220                 225                 230

cta gga ttc ttc ttc ttt ttc ttc tgc aag gat aaa cat aaa gga tat      771
Leu Gly Phe Phe Phe Phe Phe Phe Cys Lys Asp Lys His Lys Gly Tyr
    235                 240                 245

aaa cga gac gta ttt gtg gat gtt gca gga acg aac ttt aaa aaa ggt      819
Lys Arg Asp Val Phe Val Asp Val Ala Gly Thr Asn Phe Lys Lys Gly
250                 255                 260                 265

ttg att tca ggt gaa gtg gac aga agg att gct ttt gga cag ttg aga      867
Leu Ile Ser Gly Glu Val Asp Arg Arg Ile Ala Phe Gly Gln Leu Arg
                270                 275                 280

aga ttt gca tgg aga gag ctt cag ttg gct aca gat gag ttc agt gaa      915
Arg Phe Ala Trp Arg Glu Leu Gln Leu Ala Thr Asp Glu Phe Ser Glu
            285                 290                 295

aag aat gtt ctc gga caa gga ggc ttt ggg aaa gtt tac aaa gga ttg      963
Lys Asn Val Leu Gly Gln Gly Gly Phe Gly Lys Val Tyr Lys Gly Leu
        300                 305                 310

ctt tcg gat ggc acc aaa gtc gct gta aaa aga ttg act gat ttt gaa     1011
Leu Ser Asp Gly Thr Lys Val Ala Val Lys Arg Leu Thr Asp Phe Glu
    315                 320                 325

cgt cca gga gga gat gaa gct ttc cag aga gaa gtt gag atg ata agt     1059
Arg Pro Gly Gly Asp Glu Ala Phe Gln Arg Glu Val Glu Met Ile Ser
330                 335                 340                 345

gta gct gtt cat agg aat ctg ctt cgc ctt atc ggc ttt tgt aca aca     1107
Val Ala Val His Arg Asn Leu Leu Arg Leu Ile Gly Phe Cys Thr Thr
                350                 355                 360

caa act gaa cga ctt ttg gtg tat cct ttc atg cag aat cta agt gtt     1155
Gln Thr Glu Arg Leu Leu Val Tyr Pro Phe Met Gln Asn Leu Ser Val
            365                 370                 375

gca tat tgc tta aga gag att aaa ccc ggg gat cca gtt ctg gat tgg     1203
Ala Tyr Cys Leu Arg Glu Ile Lys Pro Gly Asp Pro Val Leu Asp Trp
```

-continued

```
        380                 385                 390

ttc agg agg aaa cag att gcg tta ggt gca gca cga gga ctc gaa tat      1251
Phe Arg Arg Lys Gln Ile Ala Leu Gly Ala Ala Arg Gly Leu Glu Tyr
    395                 400                 405

ctt cat gaa cat tgc aac ccg aag atc ata cac aga gat gtg aaa gct      1299
Leu His Glu His Cys Asn Pro Lys Ile Ile His Arg Asp Val Lys Ala
410                 415                 420                 425

gca aat gtg tta cta gat gaa gac ttt gaa gca gtg gtt ggt gat ttt      1347
Ala Asn Val Leu Leu Asp Glu Asp Phe Glu Ala Val Val Gly Asp Phe
                430                 435                 440

ggt tta gcc aag ttg gta gat gtt aga agg act aat gta acc act cag      1395
Gly Leu Ala Lys Leu Val Asp Val Arg Arg Thr Asn Val Thr Thr Gln
            445                 450                 455

gtc cga gga aca atg ggt cat att gca cca gaa tgt ata tcc aca ggg      1443
Val Arg Gly Thr Met Gly His Ile Ala Pro Glu Cys Ile Ser Thr Gly
        460                 465                 470

aaa tcg tca gag aaa acc gat gtt ttc ggg tac gga att atg ctt ctg      1491
Lys Ser Ser Glu Lys Thr Asp Val Phe Gly Tyr Gly Ile Met Leu Leu
    475                 480                 485

gag ctt gta act gga caa aga gca att gat ttc tcg cgg tta gag gaa      1539
Glu Leu Val Thr Gly Gln Arg Ala Ile Asp Phe Ser Arg Leu Glu Glu
490                 495                 500                 505

gaa gat gat gtc tta ttg cta gac cat gtg aag aaa ctg gaa aga gag      1587
Glu Asp Asp Val Leu Leu Leu Asp His Val Lys Lys Leu Glu Arg Glu
                510                 515                 520

aag aga tta gaa gac ata gta gat aag aag ctt gat gag gat tat ata      1635
Lys Arg Leu Glu Asp Ile Val Asp Lys Lys Leu Asp Glu Asp Tyr Ile
            525                 530                 535

aag gaa gaa gtt gaa atg atg ata caa gta gct ctg cta tgc aca caa      1683
Lys Glu Glu Val Glu Met Met Ile Gln Val Ala Leu Leu Cys Thr Gln
        540                 545                 550

gca gca ccg gaa gaa cga cca gcg atg tcg gaa gta gta aga atg cta      1731
Ala Ala Pro Glu Glu Arg Pro Ala Met Ser Glu Val Val Arg Met Leu
    555                 560                 565

gaa gga gaa ggg ctt gca gag aga tgg gaa gag tgg cag aat ctt gaa      1779
Glu Gly Glu Gly Leu Ala Glu Arg Trp Glu Glu Trp Gln Asn Leu Glu
570                 575                 580                 585

gtg acg aga caa gaa gag ttt cag agg ttg cag agg aga ttt gat tgg      1827
Val Thr Arg Gln Glu Glu Phe Gln Arg Leu Gln Arg Arg Phe Asp Trp
                590                 595                 600

ggt gaa gat tcc att aat aat caa gat gct att gaa tta tct ggt gga      1875
Gly Glu Asp Ser Ile Asn Asn Gln Asp Ala Ile Glu Leu Ser Gly Gly
            605                 610                 615

aga tag aaacaaaaaa                                                    1891
Arg


<210> SEQ ID NO 43
<211> LENGTH: 618
<212> TYPE: PRT
<213> ORGANISM: Arabidopsis thaliana

<400> SEQUENCE: 43

Met Ala Leu Leu Ile Ile Thr Ala Leu Val Phe Ser Ser Leu Trp Ser
1               5                   10                  15

Ser Val Ser Pro Asp Ala Gln Gly Asp Ala Leu Phe Ala Leu Arg Ser
            20                  25                  30

Ser Leu Arg Ala Ser Pro Glu Gln Leu Ser Asp Trp Asn Gln Asn Gln
        35                  40                  45

Val Asp Pro Cys Thr Trp Ser Gln Val Ile Cys Asp Asp Lys Lys His
```

-continued

```
    50                  55                  60

Val Thr Ser Val Thr Leu Ser Tyr Met Asn Phe Ser Ser Gly Thr Leu
65                  70                  75                  80

Ser Ser Gly Ile Gly Ile Leu Thr Thr Leu Lys Thr Leu Thr Leu Lys
                85                  90                  95

Gly Asn Gly Ile Met Gly Gly Ile Pro Glu Ser Ile Gly Asn Leu Ser
            100                 105                 110

Ser Leu Thr Ser Leu Asp Leu Glu Asp Asn His Leu Thr Asp Arg Ile
        115                 120                 125

Pro Ser Thr Leu Gly Asn Leu Lys Asn Leu Gln Phe Phe Arg Thr Leu
    130                 135                 140

Ser Arg Asn Asn Leu Asn Gly Ser Ile Pro Asp Ser Leu Thr Gly Leu
145                 150                 155                 160

Ser Lys Leu Ile Asn Ile Leu Leu Asp Ser Asn Asn Leu Ser Gly Glu
                165                 170                 175

Ile Pro Gln Ser Leu Phe Lys Ile Pro Lys Tyr Asn Phe Thr Ala Asn
            180                 185                 190

Asn Leu Ser Cys Gly Gly Thr Phe Pro Gln Pro Cys Val Thr Glu Ser
        195                 200                 205

Ser Pro Ser Gly Asp Ser Ser Ser Arg Lys Thr Gly Ile Ile Ala Gly
    210                 215                 220

Val Val Ser Gly Ile Ala Val Ile Leu Leu Gly Phe Phe Phe Phe Phe
225                 230                 235                 240

Phe Cys Lys Asp Lys His Lys Gly Tyr Lys Arg Asp Val Phe Val Asp
                245                 250                 255

Val Ala Gly Thr Asn Phe Lys Lys Gly Leu Ile Ser Gly Glu Val Asp
            260                 265                 270

Arg Arg Ile Ala Phe Gly Gln Leu Arg Arg Phe Ala Trp Arg Glu Leu
        275                 280                 285

Gln Leu Ala Thr Asp Glu Phe Ser Glu Lys Asn Val Leu Gly Gln Gly
    290                 295                 300

Gly Phe Gly Lys Val Tyr Lys Gly Leu Leu Ser Asp Gly Thr Lys Val
305                 310                 315                 320

Ala Val Lys Arg Leu Thr Asp Phe Glu Arg Pro Gly Gly Asp Glu Ala
                325                 330                 335

Phe Gln Arg Glu Val Glu Met Ile Ser Val Ala Val His Arg Asn Leu
            340                 345                 350

Leu Arg Leu Ile Gly Phe Cys Thr Thr Gln Thr Glu Arg Leu Leu Val
        355                 360                 365

Tyr Pro Phe Met Gln Asn Leu Ser Val Ala Tyr Cys Leu Arg Glu Ile
    370                 375                 380

Lys Pro Gly Asp Pro Val Leu Asp Trp Phe Arg Arg Lys Gln Ile Ala
385                 390                 395                 400

Leu Gly Ala Ala Arg Gly Leu Glu Tyr Leu His Glu His Cys Asn Pro
                405                 410                 415

Lys Ile Ile His Arg Asp Val Lys Ala Ala Asn Val Leu Leu Asp Glu
            420                 425                 430

Asp Phe Glu Ala Val Val Gly Asp Phe Gly Leu Ala Lys Leu Val Asp
        435                 440                 445

Val Arg Arg Thr Asn Val Thr Thr Gln Val Arg Gly Thr Met Gly His
    450                 455                 460

Ile Ala Pro Glu Cys Ile Ser Thr Gly Lys Ser Ser Glu Lys Thr Asp
465                 470                 475                 480
```

```
Val Phe Gly Tyr Gly Ile Met Leu Leu Glu Leu Val Thr Gly Gln Arg
                485                 490                 495

Ala Ile Asp Phe Ser Arg Leu Glu Glu Glu Asp Asp Val Leu Leu Leu
            500                 505                 510

Asp His Val Lys Lys Leu Glu Arg Glu Lys Arg Leu Glu Asp Ile Val
        515                 520                 525

Asp Lys Lys Leu Asp Glu Asp Tyr Ile Lys Glu Glu Val Glu Met Met
    530                 535                 540

Ile Gln Val Ala Leu Leu Cys Thr Gln Ala Ala Pro Glu Glu Arg Pro
545                 550                 555                 560

Ala Met Ser Glu Val Val Arg Met Leu Glu Gly Glu Gly Leu Ala Glu
                565                 570                 575

Arg Trp Glu Glu Trp Gln Asn Leu Glu Val Thr Arg Gln Glu Glu Phe
            580                 585                 590

Gln Arg Leu Gln Arg Arg Phe Asp Trp Gly Glu Asp Ser Ile Asn Asn
        595                 600                 605

Gln Asp Ala Ile Glu Leu Ser Gly Gly Arg
    610                 615


<210> SEQ ID NO 44
<211> LENGTH: 1864
<212> TYPE: DNA
<213> ORGANISM: Arabidopsis thaliana
<220> FEATURE:
<221> NAME/KEY: CDS
<222> LOCATION: (91)..(1830)

<400> SEQUENCE: 44

aacggtgaaa gtttccatga tcctcttcga ggattcattc aaagaaattg ctttagatgg      60

aacaatcaga aattgatctt acaatgtttc atg gcc tta gct ttt gtg gga atc      114
                                 Met Ala Leu Ala Phe Val Gly Ile
                                 1               5

act tcg tca aca act caa cca gat atc gaa gga gga gct ctg ttg cag      162
Thr Ser Ser Thr Thr Gln Pro Asp Ile Glu Gly Gly Ala Leu Leu Gln
    10                  15                  20

ctc aga gat tcg ctt aat gat tcg agc aat cgt cta aaa tgg aca cgc      210
Leu Arg Asp Ser Leu Asn Asp Ser Ser Asn Arg Leu Lys Trp Thr Arg
25                  30                  35                  40

gat ttt gtg agc cct tgc tat agt tgg tct tat gtt acc tgc aga ggc      258
Asp Phe Val Ser Pro Cys Tyr Ser Trp Ser Tyr Val Thr Cys Arg Gly
                45                  50                  55

cag agt gtt gtg gct cta aat ctt gcc tcg agt gga ttc aca gga aca      306
Gln Ser Val Val Ala Leu Asn Leu Ala Ser Ser Gly Phe Thr Gly Thr
            60                  65                  70

ctc tct cca gct att aca aaa ctg aag ttc ttg gtt acc tta gag tta      354
Leu Ser Pro Ala Ile Thr Lys Leu Lys Phe Leu Val Thr Leu Glu Leu
        75                  80                  85

cag aac aat agt tta tct ggt gcc tta cca gat tct ctt ggg aac atg      402
Gln Asn Asn Ser Leu Ser Gly Ala Leu Pro Asp Ser Leu Gly Asn Met
    90                  95                  100

gtt aat cta cag act tta aac cta tca gtg aat agt ttc agc gga tcg      450
Val Asn Leu Gln Thr Leu Asn Leu Ser Val Asn Ser Phe Ser Gly Ser
105                 110                 115                 120

ata cca gcg agc tgg agt cag ctc tcg aat cta aag cac ttg gat ctc      498
Ile Pro Ala Ser Trp Ser Gln Leu Ser Asn Leu Lys His Leu Asp Leu
                125                 130                 135

tca tcc aat aat tta aca gga agc atc cca aca caa ttc ttc tca atc      546
Ser Ser Asn Asn Leu Thr Gly Ser Ile Pro Thr Gln Phe Phe Ser Ile
```

-continued

```
            140                 145                 150

cca aca ttc gat ttt tca gga act cag ctt ata tgc ggt aaa agt ttg       594
Pro Thr Phe Asp Phe Ser Gly Thr Gln Leu Ile Cys Gly Lys Ser Leu
        155                 160                 165

aat cag cct tgt tct tca agt tct cgt ctt cca gtc aca tcc tcc aag       642
Asn Gln Pro Cys Ser Ser Ser Ser Arg Leu Pro Val Thr Ser Ser Lys
    170                 175                 180

aaa aag ctg aga gac att act ttg act gca agt tgt gtt gct tct ata       690
Lys Lys Leu Arg Asp Ile Thr Leu Thr Ala Ser Cys Val Ala Ser Ile
185                 190                 195                 200

atc tta ttc ctt gga gca atg gtt atg tat cat cac cat cgc gtc cgc       738
Ile Leu Phe Leu Gly Ala Met Val Met Tyr His His His Arg Val Arg
                205                 210                 215

aga acc aaa tac gac atc ttt ttt gat gta gct ggg gaa gat gac agg       786
Arg Thr Lys Tyr Asp Ile Phe Phe Asp Val Ala Gly Glu Asp Asp Arg
            220                 225                 230

aag att tcc ttt gga caa cta aaa cga ttc tct tta cgt gaa atc cag       834
Lys Ile Ser Phe Gly Gln Leu Lys Arg Phe Ser Leu Arg Glu Ile Gln
        235                 240                 245

ctc gca aca gat agt ttc aac gag agc aat ttg ata gga caa gga gga       882
Leu Ala Thr Asp Ser Phe Asn Glu Ser Asn Leu Ile Gly Gln Gly Gly
    250                 255                 260

ttt ggt aaa gta tac aga ggt ttg ctt cca gac aaa aca aaa gtt gca       930
Phe Gly Lys Val Tyr Arg Gly Leu Leu Pro Asp Lys Thr Lys Val Ala
265                 270                 275                 280

gtg aaa cgc ctt gcg gat tac ttc agt cct gga gga gaa gct gct ttc       978
Val Lys Arg Leu Ala Asp Tyr Phe Ser Pro Gly Gly Glu Ala Ala Phe
                285                 290                 295

caa aga gag att cag ctc ata agc gtt gcg gtt cat aaa aat ctc tta      1026
Gln Arg Glu Ile Gln Leu Ile Ser Val Ala Val His Lys Asn Leu Leu
            300                 305                 310

cgc ctt att ggc ttc tgc aca act tcc tct gag aga atc ctt gtt tat      1074
Arg Leu Ile Gly Phe Cys Thr Thr Ser Ser Glu Arg Ile Leu Val Tyr
        315                 320                 325

cca tac atg gaa aat ctt agt gtt gca tat cga cta aga gat ttg aaa      1122
Pro Tyr Met Glu Asn Leu Ser Val Ala Tyr Arg Leu Arg Asp Leu Lys
    330                 335                 340

gcg gga gag gaa gga tta gac tgg cca aca agg aag cgt gta gct ttt      1170
Ala Gly Glu Glu Gly Leu Asp Trp Pro Thr Arg Lys Arg Val Ala Phe
345                 350                 355                 360

ggt tca gct cac ggt tta gag tat cta cac gaa cat tgt aac ccg aag      1218
Gly Ser Ala His Gly Leu Glu Tyr Leu His Glu His Cys Asn Pro Lys
                365                 370                 375

atc ata cac cgc gat ctc aag gct gca aac ata ctt tta gac aac aat      1266
Ile Ile His Arg Asp Leu Lys Ala Ala Asn Ile Leu Leu Asp Asn Asn
            380                 385                 390

ttt gag cca gtt ctt gga gat ttc ggt tta gct aag ctt gtg gac aca      1314
Phe Glu Pro Val Leu Gly Asp Phe Gly Leu Ala Lys Leu Val Asp Thr
        395                 400                 405

tct ctg act cat gtc aca act caa gtc cga ggc aca atg ggt cac att      1362
Ser Leu Thr His Val Thr Thr Gln Val Arg Gly Thr Met Gly His Ile
    410                 415                 420

gcg cca gag tat ctc tgc aca gga aaa tca tct gaa aaa acc gat gtt      1410
Ala Pro Glu Tyr Leu Cys Thr Gly Lys Ser Ser Glu Lys Thr Asp Val
425                 430                 435                 440

ttt ggt tac ggt ata acg ctt ctt gag ctt gtt act ggt cag cgc gca      1458
Phe Gly Tyr Gly Ile Thr Leu Leu Glu Leu Val Thr Gly Gln Arg Ala
                445                 450                 455

atc gat ttt tca cgc ttg gaa gaa gag gaa aat att ctc ttg ctt gat      1506
```

-continued

```
Ile Asp Phe Ser Arg Leu Glu Glu Glu Glu Asn Ile Leu Leu Leu Asp
            460                 465                 470

cat ata aag aag ttg ctt aga gaa cag aga ctt aga gac att gtt gat     1554
His Ile Lys Lys Leu Leu Arg Glu Gln Arg Leu Arg Asp Ile Val Asp
        475                 480                 485

agc aat ttg act aca tat gac tcc aaa gaa gtt gaa aca atc gtt caa     1602
Ser Asn Leu Thr Thr Tyr Asp Ser Lys Glu Val Glu Thr Ile Val Gln
    490                 495                 500

gtg gct ctt ctc tgc aca caa ggc tca cca gaa gat aga cca gcg atg     1650
Val Ala Leu Leu Cys Thr Gln Gly Ser Pro Glu Asp Arg Pro Ala Met
505                 510                 515                 520

tct gaa gtg gtc aaa atg ctt caa ggg act ggt ggt ttg gct gag aaa     1698
Ser Glu Val Val Lys Met Leu Gln Gly Thr Gly Gly Leu Ala Glu Lys
                525                 530                 535

tgg act gaa tgg gaa caa ctt gaa gaa gtt agg aac aaa gaa gca ttg     1746
Trp Thr Glu Trp Glu Gln Leu Glu Glu Val Arg Asn Lys Glu Ala Leu
            540                 545                 550

ttg ctt ccg act tta ccg gct act tgg gat gaa gaa gaa acc acc gtt     1794
Leu Leu Pro Thr Leu Pro Ala Thr Trp Asp Glu Glu Glu Thr Thr Val
        555                 560                 565

gat caa gaa tct atc cga tta tcg aca gca aga tga agaagaaaca          1840
Asp Gln Glu Ser Ile Arg Leu Ser Thr Ala Arg
    570                 575

gagagagaaa gatatctatg aaaa                                          1864


<210> SEQ ID NO 45
<211> LENGTH: 579
<212> TYPE: PRT
<213> ORGANISM: Arabidopsis thaliana

<400> SEQUENCE: 45

Met Ala Leu Ala Phe Val Gly Ile Thr Ser Ser Thr Thr Gln Pro Asp
1               5                   10                  15

Ile Glu Gly Gly Ala Leu Leu Gln Leu Arg Asp Ser Leu Asn Asp Ser
            20                  25                  30

Ser Asn Arg Leu Lys Trp Thr Arg Asp Phe Val Ser Pro Cys Tyr Ser
        35                  40                  45

Trp Ser Tyr Val Thr Cys Arg Gly Gln Ser Val Val Ala Leu Asn Leu
    50                  55                  60

Ala Ser Ser Gly Phe Thr Gly Thr Leu Ser Pro Ala Ile Thr Lys Leu
65                  70                  75                  80

Lys Phe Leu Val Thr Leu Glu Leu Gln Asn Asn Ser Leu Ser Gly Ala
                85                  90                  95

Leu Pro Asp Ser Leu Gly Asn Met Val Asn Leu Gln Thr Leu Asn Leu
            100                 105                 110

Ser Val Asn Ser Phe Ser Gly Ser Ile Pro Ala Ser Trp Ser Gln Leu
        115                 120                 125

Ser Asn Leu Lys His Leu Asp Leu Ser Ser Asn Asn Leu Thr Gly Ser
    130                 135                 140

Ile Pro Thr Gln Phe Phe Ser Ile Pro Thr Phe Asp Phe Ser Gly Thr
145                 150                 155                 160

Gln Leu Ile Cys Gly Lys Ser Leu Asn Gln Pro Cys Ser Ser Ser Ser
                165                 170                 175

Arg Leu Pro Val Thr Ser Ser Lys Lys Lys Leu Arg Asp Ile Thr Leu
            180                 185                 190

Thr Ala Ser Cys Val Ala Ser Ile Ile Leu Phe Leu Gly Ala Met Val
        195                 200                 205
```

-continued

```
Met Tyr His His His Arg Val Arg Arg Thr Lys Tyr Asp Ile Phe Phe
    210                 215                 220

Asp Val Ala Gly Glu Asp Asp Arg Lys Ile Ser Phe Gly Gln Leu Lys
225                 230                 235                 240

Arg Phe Ser Leu Arg Glu Ile Gln Leu Ala Thr Asp Ser Phe Asn Glu
                245                 250                 255

Ser Asn Leu Ile Gly Gln Gly Gly Phe Gly Lys Val Tyr Arg Gly Leu
            260                 265                 270

Leu Pro Asp Lys Thr Lys Val Ala Val Lys Arg Leu Ala Asp Tyr Phe
        275                 280                 285

Ser Pro Gly Gly Glu Ala Ala Phe Gln Arg Glu Ile Gln Leu Ile Ser
    290                 295                 300

Val Ala Val His Lys Asn Leu Leu Arg Leu Ile Gly Phe Cys Thr Thr
305                 310                 315                 320

Ser Ser Glu Arg Ile Leu Val Tyr Pro Tyr Met Glu Asn Leu Ser Val
                325                 330                 335

Ala Tyr Arg Leu Arg Asp Leu Lys Ala Gly Glu Glu Gly Leu Asp Trp
            340                 345                 350

Pro Thr Arg Lys Arg Val Ala Phe Gly Ser Ala His Gly Leu Glu Tyr
        355                 360                 365

Leu His Glu His Cys Asn Pro Lys Ile Ile His Arg Asp Leu Lys Ala
    370                 375                 380

Ala Asn Ile Leu Leu Asp Asn Asn Phe Glu Pro Val Leu Gly Asp Phe
385                 390                 395                 400

Gly Leu Ala Lys Leu Val Asp Thr Ser Leu Thr His Val Thr Thr Gln
                405                 410                 415

Val Arg Gly Thr Met Gly His Ile Ala Pro Glu Tyr Leu Cys Thr Gly
            420                 425                 430

Lys Ser Ser Glu Lys Thr Asp Val Phe Gly Tyr Gly Ile Thr Leu Leu
        435                 440                 445

Glu Leu Val Thr Gly Gln Arg Ala Ile Asp Phe Ser Arg Leu Glu Glu
    450                 455                 460

Glu Glu Asn Ile Leu Leu Leu Asp His Ile Lys Lys Leu Leu Arg Glu
465                 470                 475                 480

Gln Arg Leu Arg Asp Ile Val Asp Ser Asn Leu Thr Thr Tyr Asp Ser
                485                 490                 495

Lys Glu Val Glu Thr Ile Val Gln Val Ala Leu Leu Cys Thr Gln Gly
            500                 505                 510

Ser Pro Glu Asp Arg Pro Ala Met Ser Glu Val Val Lys Met Leu Gln
        515                 520                 525

Gly Thr Gly Gly Leu Ala Glu Lys Trp Thr Glu Trp Glu Gln Leu Glu
    530                 535                 540

Glu Val Arg Asn Lys Glu Ala Leu Leu Leu Pro Thr Leu Pro Ala Thr
545                 550                 555                 560

Trp Asp Glu Glu Glu Thr Thr Val Asp Gln Glu Ser Ile Arg Leu Ser
                565                 570                 575

Thr Ala Arg
```

<210> SEQ ID NO 46
<211> LENGTH: 1980
<212> TYPE: DNA
<213> ORGANISM: Arabidopsis thaliana
<220> FEATURE:
<221> NAME/KEY: CDS

```
<222> LOCATION: (40)..(1923)

<400> SEQUENCE: 46

tcttccttct ccttctggta atctaatcta aagcttttc atg gtg gtg atg aag        54
                                           Met Val Val Met Lys
                                           1               5

ata ttc tct gtt ctg tta cta cta tgt ttc ttc gtt act tgt tct ctc      102
Ile Phe Ser Val Leu Leu Leu Leu Cys Phe Phe Val Thr Cys Ser Leu
                10                  15                  20

tct tct gaa ccc aga aac cct gaa gtg gag gcg ttg ata aac ata aag      150
Ser Ser Glu Pro Arg Asn Pro Glu Val Glu Ala Leu Ile Asn Ile Lys
            25                  30                  35

aac gag tta cat gat cca cat ggt gtt ttc aaa aac tgg gat gag ttt      198
Asn Glu Leu His Asp Pro His Gly Val Phe Lys Asn Trp Asp Glu Phe
        40                  45                  50

tct gtt gat cct tgt agc tgg act atg atc tct tgt tct tca gac aac      246
Ser Val Asp Pro Cys Ser Trp Thr Met Ile Ser Cys Ser Ser Asp Asn
    55                  60                  65

ctc gta att ggc tta gga gct cca agt cag tct ctt tca gga act tta      294
Leu Val Ile Gly Leu Gly Ala Pro Ser Gln Ser Leu Ser Gly Thr Leu
70                  75                  80                  85

tct ggg tct att gga aat ctc act aat ctt cga caa gtg tca tta cag      342
Ser Gly Ser Ile Gly Asn Leu Thr Asn Leu Arg Gln Val Ser Leu Gln
                90                  95                  100

aac aat aac atc tcc ggt aaa atc cca ccg gag att tgt tct ctt ccc      390
Asn Asn Asn Ile Ser Gly Lys Ile Pro Pro Glu Ile Cys Ser Leu Pro
            105                 110                 115

aaa tta cag act ctg gat tta tcc aat aac cgg ttc tcc ggt gaa atc      438
Lys Leu Gln Thr Leu Asp Leu Ser Asn Asn Arg Phe Ser Gly Glu Ile
        120                 125                 130

ccc ggt tct gtt aac cag ctg agt aat ctc caa tat ctg ttg aac aac      486
Pro Gly Ser Val Asn Gln Leu Ser Asn Leu Gln Tyr Leu Leu Asn Asn
    135                 140                 145

aac tca tta tct ggg ccc ttt cct gct tct ctg tct caa atc cct cac      534
Asn Ser Leu Ser Gly Pro Phe Pro Ala Ser Leu Ser Gln Ile Pro His
150                 155                 160                 165

ctc tct ttc tta gac ttg tct tat aac aat ctc aga ggt cct gtt cct      582
Leu Ser Phe Leu Asp Leu Ser Tyr Asn Asn Leu Arg Gly Pro Val Pro
                170                 175                 180

aaa ttt cct gca agg aca ttc aat gtt gct ggg aac cct ttg att tgt      630
Lys Phe Pro Ala Arg Thr Phe Asn Val Ala Gly Asn Pro Leu Ile Cys
            185                 190                 195

aaa aac agc cta ccg gag att tgt tca gga tca atc agt gca agc cct      678
Lys Asn Ser Leu Pro Glu Ile Cys Ser Gly Ser Ile Ser Ala Ser Pro
        200                 205                 210

ctt tct gtc tct tta cgt tct tca tca gga cgt aga acc aac ata tta      726
Leu Ser Val Ser Leu Arg Ser Ser Ser Gly Arg Arg Thr Asn Ile Leu
    215                 220                 225

gca gtt gca ctt ggt gta agc ctt ggc ttt gct gtt agt gta atc ctc      774
Ala Val Ala Leu Gly Val Ser Leu Gly Phe Ala Val Ser Val Ile Leu
230                 235                 240                 245

tct ctc ggg ttc att tgg tat cga aag aaa caa aga cgg tta acg atg      822
Ser Leu Gly Phe Ile Trp Tyr Arg Lys Lys Gln Arg Arg Leu Thr Met
                250                 255                 260

ctt cgc att aac aag caa gag gaa ggg tta ctt ggg ttg gga aat cta      870
Leu Arg Ile Asn Lys Gln Glu Glu Gly Leu Leu Gly Leu Gly Asn Leu
            265                 270                 275

aga agc ttc aca ttc agg gaa ctt cat gta gct acg gat ggt ttt agt      918
Arg Ser Phe Thr Phe Arg Glu Leu His Val Ala Thr Asp Gly Phe Ser
        280                 285                 290
```

-continued

```
tcc aag agt att ctt ggt gct ggt ggg ttt ggt aat gtc tac aga gga      966
Ser Lys Ser Ile Leu Gly Ala Gly Gly Phe Gly Asn Val Tyr Arg Gly
    295                 300                 305

aaa ttc ggg gat ggg aca gtg gtt gca gtg aaa cga ttg aaa gat gtg     1014
Lys Phe Gly Asp Gly Thr Val Val Ala Val Lys Arg Leu Lys Asp Val
310                 315                 320                 325

aat gga acc tcc ggg aac tca cag ttt cgt act gag ctt gag atg atc     1062
Asn Gly Thr Ser Gly Asn Ser Gln Phe Arg Thr Glu Leu Glu Met Ile
                330                 335                 340

agc tta gct gtt cat agg aat ttg ctt cgg tta atc ggt tat tgt gcg     1110
Ser Leu Ala Val His Arg Asn Leu Leu Arg Leu Ile Gly Tyr Cys Ala
            345                 350                 355

agt tct agc gaa aga ctt ctt gtt tac cct tac atg tcc aat ggc agc     1158
Ser Ser Ser Glu Arg Leu Leu Val Tyr Pro Tyr Met Ser Asn Gly Ser
        360                 365                 370

gtc gcc tct agg ctc aaa gct aag cca gcg ttg gac tgg aac aca agg     1206
Val Ala Ser Arg Leu Lys Ala Lys Pro Ala Leu Asp Trp Asn Thr Arg
    375                 380                 385

aag aag ata gcg att gga gct gca aga ggg ttg ttt tat cta cac gag     1254
Lys Lys Ile Ala Ile Gly Ala Ala Arg Gly Leu Phe Tyr Leu His Glu
390                 395                 400                 405

caa tgc gat ccc aag att att cac cga gat gtc aag gca gca aac att     1302
Gln Cys Asp Pro Lys Ile Ile His Arg Asp Val Lys Ala Ala Asn Ile
                410                 415                 420

ctc cta gat gag tat ttt gaa gca gtt gtt ggg gat ttt gga cta gca     1350
Leu Leu Asp Glu Tyr Phe Glu Ala Val Val Gly Asp Phe Gly Leu Ala
            425                 430                 435

aag cta ctc aac cac gag gat tca cat gtc aca acc gcg gtt aga gga     1398
Lys Leu Leu Asn His Glu Asp Ser His Val Thr Thr Ala Val Arg Gly
        440                 445                 450

act gtt ggt cac att gca cct gag tat ctc tcc acc ggt cag tca tct     1446
Thr Val Gly His Ile Ala Pro Glu Tyr Leu Ser Thr Gly Gln Ser Ser
    455                 460                 465

gag aaa acc gat gtc ttt ggg ttc ggt ata ctt ttg cta gag ctc atc     1494
Glu Lys Thr Asp Val Phe Gly Phe Gly Ile Leu Leu Leu Glu Leu Ile
470                 475                 480                 485

aca gga atg aga gct ctc gag ttt ggc aag tct gtt agc cag aaa gga     1542
Thr Gly Met Arg Ala Leu Glu Phe Gly Lys Ser Val Ser Gln Lys Gly
                490                 495                 500

gct atg cta gaa tgg gtg agg aag cta cac aag gaa atg aaa gta gag     1590
Ala Met Leu Glu Trp Val Arg Lys Leu His Lys Glu Met Lys Val Glu
            505                 510                 515

gag cta gta gac cga gaa ctg ggg aca acc tac gat aga ata gaa gtt     1638
Glu Leu Val Asp Arg Glu Leu Gly Thr Thr Tyr Asp Arg Ile Glu Val
        520                 525                 530

gga gag atg cta caa gtg gca ctg ctc tgc act cag ttt ctt cca gct     1686
Gly Glu Met Leu Gln Val Ala Leu Leu Cys Thr Gln Phe Leu Pro Ala
    535                 540                 545

cac aga ccc aaa atg tct gaa gta gtt cag atg ctt gaa gga gat gga     1734
His Arg Pro Lys Met Ser Glu Val Val Gln Met Leu Glu Gly Asp Gly
550                 555                 560                 565

tta gct gag aga tgg gct gct tca cat gac cat tca cat ttc tac cat     1782
Leu Ala Glu Arg Trp Ala Ala Ser His Asp His Ser His Phe Tyr His
                570                 575                 580

gcc aac atg tct tac agg act att acc tct act gat ggc aac aac caa     1830
Ala Asn Met Ser Tyr Arg Thr Ile Thr Ser Thr Asp Gly Asn Asn Gln
            585                 590                 595

acc aaa cat ctg ttt ggc tcc tca gga ttt gaa gat gaa gat gat aat     1878
Thr Lys His Leu Phe Gly Ser Ser Gly Phe Glu Asp Glu Asp Asp Asn
```

-continued

```
        600                 605                 610

caa gcg tta gat tca ttc gcc atg gaa cta tct ggt cca agg tag         1923
Gln Ala Leu Asp Ser Phe Ala Met Glu Leu Ser Gly Pro Arg
    615                 620                 625

taaatcttgg acacagaaag aaacagatat aatatcccca tgacttcaat ttttgtt      1980


<210> SEQ ID NO 47
<211> LENGTH: 627
<212> TYPE: PRT
<213> ORGANISM: Arabidopsis thaliana

<400> SEQUENCE: 47

Met Val Val Met Lys Ile Phe Ser Val Leu Leu Leu Leu Cys Phe Phe
1               5                   10                  15

Val Thr Cys Ser Leu Ser Ser Glu Pro Arg Asn Pro Glu Val Glu Ala
            20                  25                  30

Leu Ile Asn Ile Lys Asn Glu Leu His Asp Pro His Gly Val Phe Lys
        35                  40                  45

Asn Trp Asp Glu Phe Ser Val Asp Pro Cys Ser Trp Thr Met Ile Ser
    50                  55                  60

Cys Ser Ser Asp Asn Leu Val Ile Gly Leu Gly Ala Pro Ser Gln Ser
65                  70                  75                  80

Leu Ser Gly Thr Leu Ser Gly Ser Ile Gly Asn Leu Thr Asn Leu Arg
                85                  90                  95

Gln Val Ser Leu Gln Asn Asn Asn Ile Ser Gly Lys Ile Pro Pro Glu
            100                 105                 110

Ile Cys Ser Leu Pro Lys Leu Gln Thr Leu Asp Leu Ser Asn Asn Arg
        115                 120                 125

Phe Ser Gly Glu Ile Pro Gly Ser Val Asn Gln Leu Ser Asn Leu Gln
    130                 135                 140

Tyr Leu Leu Asn Asn Asn Ser Leu Ser Gly Pro Phe Pro Ala Ser Leu
145                 150                 155                 160

Ser Gln Ile Pro His Leu Ser Phe Leu Asp Leu Ser Tyr Asn Asn Leu
                165                 170                 175

Arg Gly Pro Val Pro Lys Phe Pro Ala Arg Thr Phe Asn Val Ala Gly
            180                 185                 190

Asn Pro Leu Ile Cys Lys Asn Ser Leu Pro Glu Ile Cys Ser Gly Ser
        195                 200                 205

Ile Ser Ala Ser Pro Leu Ser Val Ser Leu Arg Ser Ser Ser Gly Arg
    210                 215                 220

Arg Thr Asn Ile Leu Ala Val Ala Leu Gly Val Ser Leu Gly Phe Ala
225                 230                 235                 240

Val Ser Val Ile Leu Ser Leu Gly Phe Ile Trp Tyr Arg Lys Lys Gln
                245                 250                 255

Arg Arg Leu Thr Met Leu Arg Ile Asn Lys Gln Glu Glu Gly Leu Leu
            260                 265                 270

Gly Leu Gly Asn Leu Arg Ser Phe Thr Phe Arg Glu Leu His Val Ala
        275                 280                 285

Thr Asp Gly Phe Ser Ser Lys Ser Ile Leu Gly Ala Gly Gly Phe Gly
    290                 295                 300

Asn Val Tyr Arg Gly Lys Phe Gly Asp Gly Thr Val Val Ala Val Lys
305                 310                 315                 320

Arg Leu Lys Asp Val Asn Gly Thr Ser Gly Asn Ser Gln Phe Arg Thr
                325                 330                 335
```

-continued

```
Glu Leu Glu Met Ile Ser Leu Ala Val His Arg Asn Leu Leu Arg Leu
            340                 345                 350

Ile Gly Tyr Cys Ala Ser Ser Ser Glu Arg Leu Leu Val Tyr Pro Tyr
        355                 360                 365

Met Ser Asn Gly Ser Val Ala Ser Arg Leu Lys Ala Lys Pro Ala Leu
    370                 375                 380

Asp Trp Asn Thr Arg Lys Lys Ile Ala Ile Gly Ala Ala Arg Gly Leu
385                 390                 395                 400

Phe Tyr Leu His Glu Gln Cys Asp Pro Lys Ile Ile His Arg Asp Val
                405                 410                 415

Lys Ala Ala Asn Ile Leu Leu Asp Glu Tyr Phe Glu Ala Val Val Gly
            420                 425                 430

Asp Phe Gly Leu Ala Lys Leu Leu Asn His Glu Asp Ser His Val Thr
        435                 440                 445

Thr Ala Val Arg Gly Thr Val Gly His Ile Ala Pro Glu Tyr Leu Ser
    450                 455                 460

Thr Gly Gln Ser Ser Glu Lys Thr Asp Val Phe Gly Phe Gly Ile Leu
465                 470                 475                 480

Leu Leu Glu Leu Ile Thr Gly Met Arg Ala Leu Glu Phe Gly Lys Ser
                485                 490                 495

Val Ser Gln Lys Gly Ala Met Leu Glu Trp Val Arg Lys Leu His Lys
            500                 505                 510

Glu Met Lys Val Glu Glu Leu Val Asp Arg Glu Leu Gly Thr Thr Tyr
        515                 520                 525

Asp Arg Ile Glu Val Gly Glu Met Leu Gln Val Ala Leu Leu Cys Thr
    530                 535                 540

Gln Phe Leu Pro Ala His Arg Pro Lys Met Ser Glu Val Val Gln Met
545                 550                 555                 560

Leu Glu Gly Asp Gly Leu Ala Glu Arg Trp Ala Ala Ser His Asp His
                565                 570                 575

Ser His Phe Tyr His Ala Asn Met Ser Tyr Arg Thr Ile Thr Ser Thr
            580                 585                 590

Asp Gly Asn Asn Gln Thr Lys His Leu Phe Gly Ser Ser Gly Phe Glu
        595                 600                 605

Asp Glu Asp Asp Asn Gln Ala Leu Asp Ser Phe Ala Met Glu Leu Ser
    610                 615                 620

Gly Pro Arg
625
```

<210> SEQ ID NO 48
<211> LENGTH: 1893
<212> TYPE: DNA
<213> ORGANISM: Arabidopsis thaliana
<220> FEATURE:
<221> NAME/KEY: CDS
<222> LOCATION: (28)..(1839)

<400> SEQUENCE: 48

```
ctagagaatt cttatacttt ttctacg atg gag att tct ttg atg aag ttt ctg      54
                              Met Glu Ile Ser Leu Met Lys Phe Leu
                              1               5

ttt tta gga atc tgg gtt tat tat tac tct gtt ctt gac tct gtt tct       102
Phe Leu Gly Ile Trp Val Tyr Tyr Tyr Ser Val Leu Asp Ser Val Ser
10                  15                  20                  25

gcc atg gat agt ctt tta tct ccc aag gtg gct gcg tta atg tca gtg       150
Ala Met Asp Ser Leu Leu Ser Pro Lys Val Ala Ala Leu Met Ser Val
                30                  35                  40
```

-continued

```
aag aac aag atg aaa gat gag aaa gag gtt ttg tct ggt tgg gat att      198
Lys Asn Lys Met Lys Asp Glu Lys Glu Val Leu Ser Gly Trp Asp Ile
            45                  50                  55

aac tct gtt gat cct tgt act tgg aac atg gtt ggt tgt tct tct gaa      246
Asn Ser Val Asp Pro Cys Thr Trp Asn Met Val Gly Cys Ser Ser Glu
        60                  65                  70

ggt ttt gtg gtt tct cta gag atg gct agt aaa gga tta tca ggg ata      294
Gly Phe Val Val Ser Leu Glu Met Ala Ser Lys Gly Leu Ser Gly Ile
    75                  80                  85

cta tct act agt att ggg gaa tta act cat ctt cat act ttg tta ctt      342
Leu Ser Thr Ser Ile Gly Glu Leu Thr His Leu His Thr Leu Leu Leu
90                  95                  100                 105

cag aat aat cag tta act ggt ccg att cct tct gag tta ggc caa ctc      390
Gln Asn Asn Gln Leu Thr Gly Pro Ile Pro Ser Glu Leu Gly Gln Leu
                110                 115                 120

tct gag ctt gaa acg ctt gat tta tcg ggg aat cgg ttt agt ggt gaa      438
Ser Glu Leu Glu Thr Leu Asp Leu Ser Gly Asn Arg Phe Ser Gly Glu
            125                 130                 135

atc cca gct tct tta ggg ttc tta act cac tta aac tac ttg cgg ctt      486
Ile Pro Ala Ser Leu Gly Phe Leu Thr His Leu Asn Tyr Leu Arg Leu
        140                 145                 150

agc agg aat ctt tta tct ggg caa gtc cct cac ctc gtc gct ggc ctc      534
Ser Arg Asn Leu Leu Ser Gly Gln Val Pro His Leu Val Ala Gly Leu
    155                 160                 165

tca ggt ctt tct ttc ttg gat cta tct ttc aac aat cta agc gga cca      582
Ser Gly Leu Ser Phe Leu Asp Leu Ser Phe Asn Asn Leu Ser Gly Pro
170                 175                 180                 185

act ccg aat ata tca gca aaa gat tac agg aaa tgc att tct ttg tgg      630
Thr Pro Asn Ile Ser Ala Lys Asp Tyr Arg Lys Cys Ile Ser Leu Trp
                190                 195                 200

tcc agc ttc cca aga gct ttg ctc aga tgc tac acc tgt gag aaa tgc      678
Ser Ser Phe Pro Arg Ala Leu Leu Arg Cys Tyr Thr Cys Glu Lys Cys
            205                 210                 215

tgc aat cga tct gca gcg acg ggt ttg tct gaa aag gac aat agc aaa      726
Cys Asn Arg Ser Ala Ala Thr Gly Leu Ser Glu Lys Asp Asn Ser Lys
        220                 225                 230

cat cac agc tta gtg ctc tct ttt gca ttt ggc att gtt gtt gcc ttt      774
His His Ser Leu Val Leu Ser Phe Ala Phe Gly Ile Val Val Ala Phe
    235                 240                 245

atc atc tcc cta atg ttt ctc ttc ttc tgg gtg ctt tgg cat cga tca      822
Ile Ile Ser Leu Met Phe Leu Phe Phe Trp Val Leu Trp His Arg Ser
250                 255                 260                 265

cgt ctc tca aga tca cac gtg cag caa gac tac gaa ttt gaa atc ggc      870
Arg Leu Ser Arg Ser His Val Gln Gln Asp Tyr Glu Phe Glu Ile Gly
                270                 275                 280

cat ctg aaa agg ttc agt ttt cgc gaa ata caa acc gca aca agc aat      918
His Leu Lys Arg Phe Ser Phe Arg Glu Ile Gln Thr Ala Thr Ser Asn
            285                 290                 295

ttt agt cca aag aac att ttg gga caa gga ggg ttt ggg atg gtt tat      966
Phe Ser Pro Lys Asn Ile Leu Gly Gln Gly Gly Phe Gly Met Val Tyr
        300                 305                 310

aaa ggg tat ctc cca aat gga act gtg gtg gca gtt aaa aga ttg aaa     1014
Lys Gly Tyr Leu Pro Asn Gly Thr Val Val Ala Val Lys Arg Leu Lys
    315                 320                 325

gat ccg att tat aca gga gaa gtt cag ttt caa acc gaa gta gag atg     1062
Asp Pro Ile Tyr Thr Gly Glu Val Gln Phe Gln Thr Glu Val Glu Met
330                 335                 340                 345

att ggc tta gct gtt cac cgt aac ctt tta cgc ctc ttt gga ttc tgt     1110
Ile Gly Leu Ala Val His Arg Asn Leu Leu Arg Leu Phe Gly Phe Cys
```

```
                350                 355                 360

atg acc ccg gaa gag aga atg ctt gtg tat ccg tac atg cca aat gga      1158
Met Thr Pro Glu Glu Arg Met Leu Val Tyr Pro Tyr Met Pro Asn Gly
            365                 370                 375

agc gta gct gat cgt ctg aga gat tgg aat cgg agg ata agc att gca      1206
Ser Val Ala Asp Arg Leu Arg Asp Trp Asn Arg Arg Ile Ser Ile Ala
        380                 385                 390

ctc ggc gca gct cga gga ctt gtt tac ttg cac gag caa tgc aat cca      1254
Leu Gly Ala Ala Arg Gly Leu Val Tyr Leu His Glu Gln Cys Asn Pro
    395                 400                 405

aag att att cac aga gac gtc aaa gct gca aat att cta ctt gat gag      1302
Lys Ile Ile His Arg Asp Val Lys Ala Ala Asn Ile Leu Leu Asp Glu
410                 415                 420                 425

agc ttt gaa gca ata gtt ggc gat ttt ggt cta gca aag ctt tta gac      1350
Ser Phe Glu Ala Ile Val Gly Asp Phe Gly Leu Ala Lys Leu Leu Asp
                430                 435                 440

cag aga gat tca cat gtc act acc gca gtc cga gga acc att gga cac      1398
Gln Arg Asp Ser His Val Thr Thr Ala Val Arg Gly Thr Ile Gly His
            445                 450                 455

atc gct ccc gag tac ctt tcc act gga cag tcc tca gag aaa acc gat      1446
Ile Ala Pro Glu Tyr Leu Ser Thr Gly Gln Ser Ser Glu Lys Thr Asp
        460                 465                 470

gtt ttc gga ttc gga gta cta atc ctt gaa ctc ata aca ggt cat aag      1494
Val Phe Gly Phe Gly Val Leu Ile Leu Glu Leu Ile Thr Gly His Lys
    475                 480                 485

atg att gat caa ggc aat ggt caa gtt cga aaa gga atg ata ttg agc      1542
Met Ile Asp Gln Gly Asn Gly Gln Val Arg Lys Gly Met Ile Leu Ser
490                 495                 500                 505

tgg gta agg aca ttg aaa gca gag aag aga ttt gca gag atg gtg gac      1590
Trp Val Arg Thr Leu Lys Ala Glu Lys Arg Phe Ala Glu Met Val Asp
                510                 515                 520

aga gat ttg aag gga gag ttt gat gat ttg gtg ttg gag gaa gta gtg      1638
Arg Asp Leu Lys Gly Glu Phe Asp Asp Leu Val Leu Glu Glu Val Val
            525                 530                 535

gaa ttg gct ttg ctt tgt aca cag cca cat ccg aat cta aga ccg agg      1686
Glu Leu Ala Leu Leu Cys Thr Gln Pro His Pro Asn Leu Arg Pro Arg
        540                 545                 550

atg tct caa gtg ttg aag gta cta gaa ggt tta gtg gaa cag tgt gaa      1734
Met Ser Gln Val Leu Lys Val Leu Glu Gly Leu Val Glu Gln Cys Glu
    555                 560                 565

gga ggg tat gaa gct aga gct cca agt gtc tct agg aac tac agt aat      1782
Gly Gly Tyr Glu Ala Arg Ala Pro Ser Val Ser Arg Asn Tyr Ser Asn
570                 575                 580                 585

ggt cat gaa gag cag tcc ttt att att gaa gcc att gag ctc tct gga      1830
Gly His Glu Glu Gln Ser Phe Ile Ile Glu Ala Ile Glu Leu Ser Gly
                590                 595                 600

cca cga tga tagacttcat agtgtcttaa ctagtcttct tgattttgtt              1879
Pro Arg

gtcattgtca tggc                                                      1893


<210> SEQ ID NO 49
<211> LENGTH: 603
<212> TYPE: PRT
<213> ORGANISM: Arabidopsis thaliana

<400> SEQUENCE: 49

Met Glu Ile Ser Leu Met Lys Phe Leu Phe Leu Gly Ile Trp Val Tyr
1               5                   10                  15

Tyr Tyr Ser Val Leu Asp Ser Val Ser Ala Met Asp Ser Leu Leu Ser
```

-continued

```
            20                  25                  30

Pro Lys Val Ala Ala Leu Met Ser Val Lys Asn Lys Met Lys Asp Glu
        35                  40                  45

Lys Glu Val Leu Ser Gly Trp Asp Ile Asn Ser Val Asp Pro Cys Thr
    50                  55                  60

Trp Asn Met Val Gly Cys Ser Ser Glu Gly Phe Val Val Ser Leu Glu
65                  70                  75                  80

Met Ala Ser Lys Gly Leu Ser Gly Ile Leu Ser Thr Ser Ile Gly Glu
                85                  90                  95

Leu Thr His Leu His Thr Leu Leu Leu Gln Asn Asn Gln Leu Thr Gly
            100                 105                 110

Pro Ile Pro Ser Glu Leu Gly Gln Leu Ser Glu Leu Glu Thr Leu Asp
        115                 120                 125

Leu Ser Gly Asn Arg Phe Ser Gly Glu Ile Pro Ala Ser Leu Gly Phe
    130                 135                 140

Leu Thr His Leu Asn Tyr Leu Arg Leu Ser Arg Asn Leu Leu Ser Gly
145                 150                 155                 160

Gln Val Pro His Leu Val Ala Gly Leu Ser Gly Leu Ser Phe Leu Asp
                165                 170                 175

Leu Ser Phe Asn Asn Leu Ser Gly Pro Thr Pro Asn Ile Ser Ala Lys
            180                 185                 190

Asp Tyr Arg Lys Cys Ile Ser Leu Trp Ser Ser Phe Pro Arg Ala Leu
        195                 200                 205

Leu Arg Cys Tyr Thr Cys Glu Lys Cys Cys Asn Arg Ser Ala Ala Thr
    210                 215                 220

Gly Leu Ser Glu Lys Asp Asn Ser Lys His His Ser Leu Val Leu Ser
225                 230                 235                 240

Phe Ala Phe Gly Ile Val Val Ala Phe Ile Ile Ser Leu Met Phe Leu
                245                 250                 255

Phe Phe Trp Val Leu Trp His Arg Ser Arg Leu Ser Arg Ser His Val
            260                 265                 270

Gln Gln Asp Tyr Glu Phe Glu Ile Gly His Leu Lys Arg Phe Ser Phe
        275                 280                 285

Arg Glu Ile Gln Thr Ala Thr Ser Asn Phe Ser Pro Lys Asn Ile Leu
    290                 295                 300

Gly Gln Gly Gly Phe Gly Met Val Tyr Lys Gly Tyr Leu Pro Asn Gly
305                 310                 315                 320

Thr Val Val Ala Val Lys Arg Leu Lys Asp Pro Ile Tyr Thr Gly Glu
                325                 330                 335

Val Gln Phe Gln Thr Glu Val Glu Met Ile Gly Leu Ala Val His Arg
            340                 345                 350

Asn Leu Leu Arg Leu Phe Gly Phe Cys Met Thr Pro Glu Glu Arg Met
        355                 360                 365

Leu Val Tyr Pro Tyr Met Pro Asn Gly Ser Val Ala Asp Arg Leu Arg
    370                 375                 380

Asp Trp Asn Arg Arg Ile Ser Ile Ala Leu Gly Ala Ala Arg Gly Leu
385                 390                 395                 400

Val Tyr Leu His Glu Gln Cys Asn Pro Lys Ile Ile His Arg Asp Val
                405                 410                 415

Lys Ala Ala Asn Ile Leu Leu Asp Glu Ser Phe Glu Ala Ile Val Gly
            420                 425                 430

Asp Phe Gly Leu Ala Lys Leu Leu Asp Gln Arg Asp Ser His Val Thr
        435                 440                 445
```

```
Thr Ala Val Arg Gly Thr Ile Gly His Ile Ala Pro Glu Tyr Leu Ser
    450                 455                 460

Thr Gly Gln Ser Ser Glu Lys Thr Asp Val Phe Gly Phe Gly Val Leu
465                 470                 475                 480

Ile Leu Glu Leu Ile Thr Gly His Lys Met Ile Asp Gln Gly Asn Gly
                485                 490                 495

Gln Val Arg Lys Gly Met Ile Leu Ser Trp Val Arg Thr Leu Lys Ala
            500                 505                 510

Glu Lys Arg Phe Ala Glu Met Val Asp Arg Asp Leu Lys Gly Glu Phe
        515                 520                 525

Asp Asp Leu Val Leu Glu Glu Val Val Glu Leu Ala Leu Leu Cys Thr
    530                 535                 540

Gln Pro His Pro Asn Leu Arg Pro Arg Met Ser Gln Val Leu Lys Val
545                 550                 555                 560

Leu Glu Gly Leu Val Glu Gln Cys Glu Gly Gly Tyr Glu Ala Arg Ala
                565                 570                 575

Pro Ser Val Ser Arg Asn Tyr Ser Asn Gly His Glu Glu Gln Ser Phe
            580                 585                 590

Ile Ile Glu Ala Ile Glu Leu Ser Gly Pro Arg
        595                 600


<210> SEQ ID NO 50
<211> LENGTH: 1920
<212> TYPE: DNA
<213> ORGANISM: Arabidopsis thaliana
<220> FEATURE:
<221> NAME/KEY: CDS
<222> LOCATION: (61)..(1902)

<400> SEQUENCE: 50

attgtttcct tcttttggga ttttctcctt ggatggaacc agctcaatta atgagatgag      60

atg aga atg ttc agc ttg cag aag atg gct atg gct ttt act ctc ttg      108
Met Arg Met Phe Ser Leu Gln Lys Met Ala Met Ala Phe Thr Leu Leu
1               5                   10                  15

ttt ttt gcc tgt tta tgc tca ttt gtg tct cca gat gct caa ggg gat      156
Phe Phe Ala Cys Leu Cys Ser Phe Val Ser Pro Asp Ala Gln Gly Asp
            20                  25                  30

gca ctg ttt gcg ttg agg atc tcc tta cgt gca tta ccg aat cag cta      204
Ala Leu Phe Ala Leu Arg Ile Ser Leu Arg Ala Leu Pro Asn Gln Leu
        35                  40                  45

agt gac tgg aat cag aac caa gtt aat cct tgc act tgg tcc caa gtt      252
Ser Asp Trp Asn Gln Asn Gln Val Asn Pro Cys Thr Trp Ser Gln Val
    50                  55                  60

att tgt gat gac aaa aac ttt gtc act tct ctt aca ttg tca gat atg      300
Ile Cys Asp Asp Lys Asn Phe Val Thr Ser Leu Thr Leu Ser Asp Met
65                  70                  75                  80

aac ttc tcg gga acc ttg tct tca aga gta gga atc cta gaa aat ctc      348
Asn Phe Ser Gly Thr Leu Ser Ser Arg Val Gly Ile Leu Glu Asn Leu
                85                  90                  95

aag act ctt act tta aag gga aat gga att acg ggt gaa ata cca gaa      396
Lys Thr Leu Thr Leu Lys Gly Asn Gly Ile Thr Gly Glu Ile Pro Glu
            100                 105                 110

gac ttt gga aat ctg act agc ttg act agt ttg gat ttg gag gac aat      444
Asp Phe Gly Asn Leu Thr Ser Leu Thr Ser Leu Asp Leu Glu Asp Asn
        115                 120                 125

cag cta act ggt cgt ata cca tcc act atc ggt aat ctc aag aaa ctt      492
Gln Leu Thr Gly Arg Ile Pro Ser Thr Ile Gly Asn Leu Lys Lys Leu
    130                 135                 140
```

```
cag ttc ttg acc ttg agt agg aac aaa ctt aat ggg act att ccg gag      540
Gln Phe Leu Thr Leu Ser Arg Asn Lys Leu Asn Gly Thr Ile Pro Glu
145                 150                 155                 160

tca ctc act ggt ctt cca aac ctg tta aac ctg ctg ctt gat tcc aat      588
Ser Leu Thr Gly Leu Pro Asn Leu Leu Asn Leu Leu Leu Asp Ser Asn
                165                 170                 175

agt ctc agt ggt cag att cct caa agt ctg ttt gag atc cca aaa tat      636
Ser Leu Ser Gly Gln Ile Pro Gln Ser Leu Phe Glu Ile Pro Lys Tyr
            180                 185                 190

aat ttc acg tca aac aac ttg aat tgt ggc ggt cgt caa cct cac cct      684
Asn Phe Thr Ser Asn Asn Leu Asn Cys Gly Gly Arg Gln Pro His Pro
        195                 200                 205

tgt gta tcc gcg gtt gcc cat tca ggt gat tca agc aag cct aaa act      732
Cys Val Ser Ala Val Ala His Ser Gly Asp Ser Ser Lys Pro Lys Thr
    210                 215                 220

ggc att att gct gga gtt gtt gct gga gtt aca gtt gtt ctc ttt gga      780
Gly Ile Ile Ala Gly Val Val Ala Gly Val Thr Val Val Leu Phe Gly
225                 230                 235                 240

atc ttg ttg ttt ctg ttc tgc aag gat agg cat aaa gga tat aga cgt      828
Ile Leu Leu Phe Leu Phe Cys Lys Asp Arg His Lys Gly Tyr Arg Arg
                245                 250                 255

gat gtg ttt gtg gat gtt gca ggt gaa gtg gac agg aga att gca ttt      876
Asp Val Phe Val Asp Val Ala Gly Glu Val Asp Arg Arg Ile Ala Phe
            260                 265                 270

gga cag ttg aaa agg ttt gca tgg aga gag ctc cag tta gcg aca gat      924
Gly Gln Leu Lys Arg Phe Ala Trp Arg Glu Leu Gln Leu Ala Thr Asp
        275                 280                 285

aac ttc agc gaa aag aat gta ctt ggt caa gga ggc ttt ggg aaa gtt      972
Asn Phe Ser Glu Lys Asn Val Leu Gly Gln Gly Gly Phe Gly Lys Val
    290                 295                 300

tac aaa gga gtg ctt ccg gat aca ccc aaa gtt gct gtg aag aga ttg     1020
Tyr Lys Gly Val Leu Pro Asp Thr Pro Lys Val Ala Val Lys Arg Leu
305                 310                 315                 320

acg gat ttc gaa agt cct ggt gga gat gct gct ttc caa agg gaa gta     1068
Thr Asp Phe Glu Ser Pro Gly Gly Asp Ala Ala Phe Gln Arg Glu Val
                325                 330                 335

gag atg ata agt gta gct gtt cat agg aat cta ctc cgt ctt atc ggg     1116
Glu Met Ile Ser Val Ala Val His Arg Asn Leu Leu Arg Leu Ile Gly
            340                 345                 350

ttc tgc acc aca caa aca gaa cgc ctt ttg gtt tat ccc ttc atg cag     1164
Phe Cys Thr Thr Gln Thr Glu Arg Leu Leu Val Tyr Pro Phe Met Gln
        355                 360                 365

aat cta agt ctt gca cat cgt ctg aga gag atc aaa gca ggc gac ccg     1212
Asn Leu Ser Leu Ala His Arg Leu Arg Glu Ile Lys Ala Gly Asp Pro
    370                 375                 380

gtt cta gat tgg gag acg agg aaa cgg att gcc tta gga gca gcg cgt     1260
Val Leu Asp Trp Glu Thr Arg Lys Arg Ile Ala Leu Gly Ala Ala Arg
385                 390                 395                 400

ggt ttt gag tat ctt cat gaa cat tgc aat ccg aag atc ata cat cgt     1308
Gly Phe Glu Tyr Leu His Glu His Cys Asn Pro Lys Ile Ile His Arg
                405                 410                 415

gat gtg aaa gca gct aat gtg tta cta gat gaa gat ttt gaa gca gtg     1356
Asp Val Lys Ala Ala Asn Val Leu Leu Asp Glu Asp Phe Glu Ala Val
            420                 425                 430

gtt ggt gat ttt ggt tta gcc aag cta gta gat gtt aga agg act aat     1404
Val Gly Asp Phe Gly Leu Ala Lys Leu Val Asp Val Arg Arg Thr Asn
        435                 440                 445

gtg act act caa gtt cga gga aca atg ggt cac att gca cca gaa tat     1452
Val Thr Thr Gln Val Arg Gly Thr Met Gly His Ile Ala Pro Glu Tyr
```

```
    450                 455                 460

tta tca aca ggg aaa tca tca gag aga acc gat gtt ttc ggg tat gga      1500
Leu Ser Thr Gly Lys Ser Ser Glu Arg Thr Asp Val Phe Gly Tyr Gly
465                 470                 475                 480

att atg ctt ctt gag ctt gtt aca gga caa cgc gca ata gac ttt tca      1548
Ile Met Leu Leu Glu Leu Val Thr Gly Gln Arg Ala Ile Asp Phe Ser
                485                 490                 495

cgt ttg gag gaa gaa gat gat gtc ttg tta ctt gac cac gtg aag aaa      1596
Arg Leu Glu Glu Glu Asp Asp Val Leu Leu Leu Asp His Val Lys Lys
            500                 505                 510

ctg gaa aga gag aag aga tta gga gca atc gta gat aag aat ttg gat      1644
Leu Glu Arg Glu Lys Arg Leu Gly Ala Ile Val Asp Lys Asn Leu Asp
        515                 520                 525

gga gag tat ata aaa gaa gaa gta gag atg atg ata caa gtg gct ttg      1692
Gly Glu Tyr Ile Lys Glu Glu Val Glu Met Met Ile Gln Val Ala Leu
    530                 535                 540

ctt tgt aca caa ggt tca cca gaa gac cga cca gtg atg tct gaa gtt      1740
Leu Cys Thr Gln Gly Ser Pro Glu Asp Arg Pro Val Met Ser Glu Val
545                 550                 555                 560

gtg agg atg tta gaa gga gaa ggg ctt gcg gag aga tgg gaa gag tgg      1788
Val Arg Met Leu Glu Gly Glu Gly Leu Ala Glu Arg Trp Glu Glu Trp
                565                 570                 575

caa aac gtg gaa gtc acg aga cgt cat gag ttt gaa cgg ttg cag agg      1836
Gln Asn Val Glu Val Thr Arg Arg His Glu Phe Glu Arg Leu Gln Arg
            580                 585                 590

aga ttt gat tgg ggt gaa gat tct atg cat aac caa gat gcc att gaa      1884
Arg Phe Asp Trp Gly Glu Asp Ser Met His Asn Gln Asp Ala Ile Glu
        595                 600                 605

tta tct ggt gga aga tga ccaaaaacat caaacctt                          1920
Leu Ser Gly Gly Arg
    610


<210> SEQ ID NO 51
<211> LENGTH: 613
<212> TYPE: PRT
<213> ORGANISM: Arabidopsis thaliana

<400> SEQUENCE: 51

Met Arg Met Phe Ser Leu Gln Lys Met Ala Met Ala Phe Thr Leu Leu
1               5                   10                  15

Phe Phe Ala Cys Leu Cys Ser Phe Val Ser Pro Asp Ala Gln Gly Asp
            20                  25                  30

Ala Leu Phe Ala Leu Arg Ile Ser Leu Arg Ala Leu Pro Asn Gln Leu
        35                  40                  45

Ser Asp Trp Asn Gln Asn Gln Val Asn Pro Cys Thr Trp Ser Gln Val
    50                  55                  60

Ile Cys Asp Asp Lys Asn Phe Val Thr Ser Leu Thr Leu Ser Asp Met
65                  70                  75                  80

Asn Phe Ser Gly Thr Leu Ser Ser Arg Val Gly Ile Leu Glu Asn Leu
                85                  90                  95

Lys Thr Leu Thr Leu Lys Gly Asn Gly Ile Thr Gly Glu Ile Pro Glu
            100                 105                 110

Asp Phe Gly Asn Leu Thr Ser Leu Thr Ser Leu Asp Leu Glu Asp Asn
        115                 120                 125

Gln Leu Thr Gly Arg Ile Pro Ser Thr Ile Gly Asn Leu Lys Lys Leu
    130                 135                 140

Gln Phe Leu Thr Leu Ser Arg Asn Lys Leu Asn Gly Thr Ile Pro Glu
145                 150                 155                 160
```

```
Ser Leu Thr Gly Leu Pro Asn Leu Leu Asn Leu Leu Leu Asp Ser Asn
                165                 170                 175

Ser Leu Ser Gly Gln Ile Pro Gln Ser Leu Phe Glu Ile Pro Lys Tyr
            180                 185                 190

Asn Phe Thr Ser Asn Asn Leu Asn Cys Gly Gly Arg Gln Pro His Pro
        195                 200                 205

Cys Val Ser Ala Val Ala His Ser Gly Asp Ser Ser Lys Pro Lys Thr
    210                 215                 220

Gly Ile Ile Ala Gly Val Val Ala Gly Val Thr Val Val Leu Phe Gly
225                 230                 235                 240

Ile Leu Leu Phe Leu Phe Cys Lys Asp Arg His Lys Gly Tyr Arg Arg
                245                 250                 255

Asp Val Phe Val Asp Val Ala Gly Glu Val Asp Arg Arg Ile Ala Phe
            260                 265                 270

Gly Gln Leu Lys Arg Phe Ala Trp Arg Glu Leu Gln Leu Ala Thr Asp
        275                 280                 285

Asn Phe Ser Glu Lys Asn Val Leu Gly Gln Gly Gly Phe Gly Lys Val
    290                 295                 300

Tyr Lys Gly Val Leu Pro Asp Thr Pro Lys Val Ala Val Lys Arg Leu
305                 310                 315                 320

Thr Asp Phe Glu Ser Pro Gly Gly Asp Ala Ala Phe Gln Arg Glu Val
                325                 330                 335

Glu Met Ile Ser Val Ala Val His Arg Asn Leu Leu Arg Leu Ile Gly
            340                 345                 350

Phe Cys Thr Thr Gln Thr Glu Arg Leu Leu Val Tyr Pro Phe Met Gln
        355                 360                 365

Asn Leu Ser Leu Ala His Arg Leu Arg Glu Ile Lys Ala Gly Asp Pro
    370                 375                 380

Val Leu Asp Trp Glu Thr Arg Lys Arg Ile Ala Leu Gly Ala Ala Arg
385                 390                 395                 400

Gly Phe Glu Tyr Leu His Glu His Cys Asn Pro Lys Ile Ile His Arg
                405                 410                 415

Asp Val Lys Ala Ala Asn Val Leu Leu Asp Glu Asp Phe Glu Ala Val
            420                 425                 430

Val Gly Asp Phe Gly Leu Ala Lys Leu Val Asp Val Arg Arg Thr Asn
        435                 440                 445

Val Thr Thr Gln Val Arg Gly Thr Met Gly His Ile Ala Pro Glu Tyr
    450                 455                 460

Leu Ser Thr Gly Lys Ser Ser Glu Arg Thr Asp Val Phe Gly Tyr Gly
465                 470                 475                 480

Ile Met Leu Leu Glu Leu Val Thr Gly Gln Arg Ala Ile Asp Phe Ser
                485                 490                 495

Arg Leu Glu Glu Glu Asp Asp Val Leu Leu Leu Asp His Val Lys Lys
            500                 505                 510

Leu Glu Arg Glu Lys Arg Leu Gly Ala Ile Val Asp Lys Asn Leu Asp
        515                 520                 525

Gly Glu Tyr Ile Lys Glu Glu Val Glu Met Met Ile Gln Val Ala Leu
    530                 535                 540

Leu Cys Thr Gln Gly Ser Pro Glu Asp Arg Pro Val Met Ser Glu Val
545                 550                 555                 560

Val Arg Met Leu Glu Gly Glu Gly Leu Ala Glu Arg Trp Glu Glu Trp
                565                 570                 575
```

-continued

```
Gln Asn Val Glu Val Thr Arg Arg His Glu Phe Glu Arg Leu Gln Arg
            580                 585                 590

Arg Phe Asp Trp Gly Glu Asp Ser Met His Asn Gln Asp Ala Ile Glu
        595                 600                 605

Leu Ser Gly Gly Arg
    610


<210> SEQ ID NO 52
<211> LENGTH: 2217
<212> TYPE: DNA
<213> ORGANISM: Arabidopsis thaliana
<220> FEATURE:
<221> NAME/KEY: CDS
<222> LOCATION: (36)..(1952)

<400> SEQUENCE: 52

acatcttgtt ttctgctcat tcctctgttt caaca atg gag agt act att gtt        53
                                       Met Glu Ser Thr Ile Val
                                       1               5

atg atg atg atg ata aca aga tct ttc ttt tgc ttc ttg gga ttt tta      101
Met Met Met Met Ile Thr Arg Ser Phe Phe Cys Phe Leu Gly Phe Leu
            10                  15                  20

tgc ctt ctc tgc tct tct gtt cac gga ttg ctt tct cct aaa ggt gtt      149
Cys Leu Leu Cys Ser Ser Val His Gly Leu Leu Ser Pro Lys Gly Val
        25                  30                  35

aac ttt gaa gtg caa gct ttg atg gac ata aaa gct tca tta cat gat      197
Asn Phe Glu Val Gln Ala Leu Met Asp Ile Lys Ala Ser Leu His Asp
    40                  45                  50

cct cat ggt gtt ctt gat aac tgg gat aga gat gct gtt gat cct tgt      245
Pro His Gly Val Leu Asp Asn Trp Asp Arg Asp Ala Val Asp Pro Cys
55                  60                  65                  70

agt tgg aca atg gtc act tgt tct tct gaa aac ttt gtc att ggc tta      293
Ser Trp Thr Met Val Thr Cys Ser Ser Glu Asn Phe Val Ile Gly Leu
                75                  80                  85

ggc aca cca agt cag aat tta tct ggt aca cta tct cca agc att acc      341
Gly Thr Pro Ser Gln Asn Leu Ser Gly Thr Leu Ser Pro Ser Ile Thr
            90                  95                  100

aac tta aca aat ctt cgg att gtg ctg ttg cag aac aac aac ata aaa      389
Asn Leu Thr Asn Leu Arg Ile Val Leu Leu Gln Asn Asn Asn Ile Lys
        105                 110                 115

gga aaa att cct gct gag att ggt cgg ctt acg agg ctt gag act ctt      437
Gly Lys Ile Pro Ala Glu Ile Gly Arg Leu Thr Arg Leu Glu Thr Leu
    120                 125                 130

gat ctt tct gat aat ttc ttc cac ggt gaa att cct ttt tca gta ggc      485
Asp Leu Ser Asp Asn Phe Phe His Gly Glu Ile Pro Phe Ser Val Gly
135                 140                 145                 150

tat cta caa agc ctg caa tat ctg agg ctt aac aac aat tct ctc tct      533
Tyr Leu Gln Ser Leu Gln Tyr Leu Arg Leu Asn Asn Asn Ser Leu Ser
                155                 160                 165

gga gtg ttt cct ctg tca cta tct aat atg act caa ctt gcc ttt ctt      581
Gly Val Phe Pro Leu Ser Leu Ser Asn Met Thr Gln Leu Ala Phe Leu
            170                 175                 180

gat tta tca tac aac aat ctt agt ggt cct gtt cca aga ttt gct gca      629
Asp Leu Ser Tyr Asn Asn Leu Ser Gly Pro Val Pro Arg Phe Ala Ala
        185                 190                 195

aag acg ttt agc atc gtt ggg aac ccg ctg ata tgt cca acg ggt acc      677
Lys Thr Phe Ser Ile Val Gly Asn Pro Leu Ile Cys Pro Thr Gly Thr
    200                 205                 210

gaa cca gac tgc aat gga aca aca ttg ata cct atg tct atg aac ttg      725
Glu Pro Asp Cys Asn Gly Thr Thr Leu Ile Pro Met Ser Met Asn Leu
215                 220                 225                 230
```

-continued

```
aat caa act gga gtt cct tta tac gcc ggt gga tcg agg aat cac aaa       773
Asn Gln Thr Gly Val Pro Leu Tyr Ala Gly Gly Ser Arg Asn His Lys
                235                 240                 245

atg gca atc gct gtt gga tcc agc gtt ggg act gta tca tta atc ttc       821
Met Ala Ile Ala Val Gly Ser Ser Val Gly Thr Val Ser Leu Ile Phe
            250                 255                 260

att gct gtt ggt ttg ttt ctc tgg tgg aga caa aga cat aac caa aac       869
Ile Ala Val Gly Leu Phe Leu Trp Trp Arg Gln Arg His Asn Gln Asn
        265                 270                 275

aca ttc ttt gat gtt aaa gat ggg aat cat cat gag gaa gtt tca ctt       917
Thr Phe Phe Asp Val Lys Asp Gly Asn His His Glu Glu Val Ser Leu
    280                 285                 290

gga aac ctg agg aga ttt ggt ttc agg gag ctt cag att gcg acc aat       965
Gly Asn Leu Arg Arg Phe Gly Phe Arg Glu Leu Gln Ile Ala Thr Asn
295                 300                 305                 310

aac ttc agc agt aag aac tta ttg ggg aaa ggt ggc tat gga aat gta      1013
Asn Phe Ser Ser Lys Asn Leu Leu Gly Lys Gly Gly Tyr Gly Asn Val
                315                 320                 325

tac aaa gga ata ctt gga gat agt aca gtg gtt gca gtg aaa agg ctt      1061
Tyr Lys Gly Ile Leu Gly Asp Ser Thr Val Val Ala Val Lys Arg Leu
            330                 335                 340

aaa gat gga gga gca ttg gga gga gag att cag ttt cag aca gaa gtt      1109
Lys Asp Gly Gly Ala Leu Gly Gly Glu Ile Gln Phe Gln Thr Glu Val
        345                 350                 355

gaa atg atc agt tta gct gtt cat cga aat ctc tta aga ctc tac ggt      1157
Glu Met Ile Ser Leu Ala Val His Arg Asn Leu Leu Arg Leu Tyr Gly
    360                 365                 370

ttc tgc atc aca caa act gag aag ctt cta gtt tat cct tat atg tct      1205
Phe Cys Ile Thr Gln Thr Glu Lys Leu Leu Val Tyr Pro Tyr Met Ser
375                 380                 385                 390

aat gga agc gtt gca tct cga atg aaa gca aaa cct gtt ctt gac tgg      1253
Asn Gly Ser Val Ala Ser Arg Met Lys Ala Lys Pro Val Leu Asp Trp
                395                 400                 405

agc ata agg aag agg ata gcc ata gga gct gca aga ggg ctt gtg tat      1301
Ser Ile Arg Lys Arg Ile Ala Ile Gly Ala Ala Arg Gly Leu Val Tyr
            410                 415                 420

ctc cat gag caa tgt gat ccg aag att atc cac cgc gat gtc aaa gca      1349
Leu His Glu Gln Cys Asp Pro Lys Ile Ile His Arg Asp Val Lys Ala
        425                 430                 435

gcg aat ata ctt ctt gat gac tac tgt gaa gct gtg gtt ggc gat ttt      1397
Ala Asn Ile Leu Leu Asp Asp Tyr Cys Glu Ala Val Val Gly Asp Phe
    440                 445                 450

ggt tta gct aaa ctc ttg gat cat caa gat tct cat gtg aca acc gcg      1445
Gly Leu Ala Lys Leu Leu Asp His Gln Asp Ser His Val Thr Thr Ala
455                 460                 465                 470

gtt aga ggc acg gtg ggt cac att gct cca gag tat ctc tca act ggt      1493
Val Arg Gly Thr Val Gly His Ile Ala Pro Glu Tyr Leu Ser Thr Gly
                475                 480                 485

caa tcc tct gag aaa aca gat gtt ttt ggc ttc ggg att ctt ctt ctt      1541
Gln Ser Ser Glu Lys Thr Asp Val Phe Gly Phe Gly Ile Leu Leu Leu
            490                 495                 500

gag ctt gta acc gga caa aga gct ttt gag ttt ggt aaa gcg gct aac      1589
Glu Leu Val Thr Gly Gln Arg Ala Phe Glu Phe Gly Lys Ala Ala Asn
        505                 510                 515

cag aaa ggt gtg atg ctt gat tgg gtt aaa aag att cat caa gag aag      1637
Gln Lys Gly Val Met Leu Asp Trp Val Lys Lys Ile His Gln Glu Lys
    520                 525                 530

aaa ctt gag cta ctt gtg gat aaa gag ttg ttg aag aag aag agc tac      1685
Lys Leu Glu Leu Leu Val Asp Lys Glu Leu Leu Lys Lys Lys Ser Tyr
```

-continued

```
535                 540                 545                 550

gat gag att gag tta gac gaa atg gta aga gta gct ttg ttg tgc aca      1733
Asp Glu Ile Glu Leu Asp Glu Met Val Arg Val Ala Leu Leu Cys Thr
                555                 560                 565

cag tac ctg cca gga cat aga cca aaa atg tct gaa gtt gtt cga atg      1781
Gln Tyr Leu Pro Gly His Arg Pro Lys Met Ser Glu Val Val Arg Met
            570                 575                 580

ctg gaa gga gat gga ctt gca gag aaa tgg gaa gct tct caa aga tca      1829
Leu Glu Gly Asp Gly Leu Ala Glu Lys Trp Glu Ala Ser Gln Arg Ser
        585                 590                 595

gac agt gtt tca aaa tgt agc aac agg ata aat gaa ttg atg tca tct      1877
Asp Ser Val Ser Lys Cys Ser Asn Arg Ile Asn Glu Leu Met Ser Ser
    600                 605                 610

tca gac aga tac tct gat ctt acc gat gac tct agt tta ctt gtg caa      1925
Ser Asp Arg Tyr Ser Asp Leu Thr Asp Asp Ser Ser Leu Leu Val Gln
615                 620                 625                 630

gca atg gag ctc tct ggt cct aga tga aatctataca tgaatctgaa           1972
Ala Met Glu Leu Ser Gly Pro Arg
                635

gaagaagaag aacatgcatc tgtttcttga atcaagaggg attcttgttt ttttgtataa   2032

tagagaggtt ttttggaggg aaatgttgtg tctctgtaac tgtataggct tgttgtgtaa   2092

gaagttatta ctgcacttag ggttaattca aagttcttta cataaaaaat gattagttgc   2152

gttgaataga gggaacactt tgggagattt catgtatgaa atttggaaaa aaaaaaaaaa   2212

aaaaa                                                               2217


<210> SEQ ID NO 53
<211> LENGTH: 638
<212> TYPE: PRT
<213> ORGANISM: Arabidopsis thaliana

<400> SEQUENCE: 53

Met Glu Ser Thr Ile Val Met Met Met Met Ile Thr Arg Ser Phe Phe
1               5                   10                  15

Cys Phe Leu Gly Phe Leu Cys Leu Leu Cys Ser Ser Val His Gly Leu
            20                  25                  30

Leu Ser Pro Lys Gly Val Asn Phe Glu Val Gln Ala Leu Met Asp Ile
        35                  40                  45

Lys Ala Ser Leu His Asp Pro His Gly Val Leu Asp Asn Trp Asp Arg
    50                  55                  60

Asp Ala Val Asp Pro Cys Ser Trp Thr Met Val Thr Cys Ser Ser Glu
65                  70                  75                  80

Asn Phe Val Ile Gly Leu Gly Thr Pro Ser Gln Asn Leu Ser Gly Thr
                85                  90                  95

Leu Ser Pro Ser Ile Thr Asn Leu Thr Asn Leu Arg Ile Val Leu Leu
            100                 105                 110

Gln Asn Asn Asn Ile Lys Gly Lys Ile Pro Ala Glu Ile Gly Arg Leu
        115                 120                 125

Thr Arg Leu Glu Thr Leu Asp Leu Ser Asp Asn Phe Phe His Gly Glu
    130                 135                 140

Ile Pro Phe Ser Val Gly Tyr Leu Gln Ser Leu Gln Tyr Leu Arg Leu
145                 150                 155                 160

Asn Asn Asn Ser Leu Ser Gly Val Phe Pro Leu Ser Leu Ser Asn Met
                165                 170                 175

Thr Gln Leu Ala Phe Leu Asp Leu Ser Tyr Asn Asn Leu Ser Gly Pro
            180                 185                 190
```

```
Val Pro Arg Phe Ala Ala Lys Thr Phe Ser Ile Val Gly Asn Pro Leu
        195                 200                 205

Ile Cys Pro Thr Gly Thr Glu Pro Asp Cys Asn Gly Thr Thr Leu Ile
    210                 215                 220

Pro Met Ser Met Asn Leu Asn Gln Thr Gly Val Pro Leu Tyr Ala Gly
225                 230                 235                 240

Gly Ser Arg Asn His Lys Met Ala Ile Ala Val Gly Ser Ser Val Gly
                245                 250                 255

Thr Val Ser Leu Ile Phe Ile Ala Val Gly Leu Phe Leu Trp Trp Arg
            260                 265                 270

Gln Arg His Asn Gln Asn Thr Phe Phe Asp Val Lys Asp Gly Asn His
        275                 280                 285

His Glu Glu Val Ser Leu Gly Asn Leu Arg Arg Phe Gly Phe Arg Glu
    290                 295                 300

Leu Gln Ile Ala Thr Asn Asn Phe Ser Ser Lys Asn Leu Leu Gly Lys
305                 310                 315                 320

Gly Gly Tyr Gly Asn Val Tyr Lys Gly Ile Leu Gly Asp Ser Thr Val
                325                 330                 335

Val Ala Val Lys Arg Leu Lys Asp Gly Gly Ala Leu Gly Gly Glu Ile
            340                 345                 350

Gln Phe Gln Thr Glu Val Glu Met Ile Ser Leu Ala Val His Arg Asn
        355                 360                 365

Leu Leu Arg Leu Tyr Gly Phe Cys Ile Thr Gln Thr Glu Lys Leu Leu
    370                 375                 380

Val Tyr Pro Tyr Met Ser Asn Gly Ser Val Ala Ser Arg Met Lys Ala
385                 390                 395                 400

Lys Pro Val Leu Asp Trp Ser Ile Arg Lys Arg Ile Ala Ile Gly Ala
                405                 410                 415

Ala Arg Gly Leu Val Tyr Leu His Glu Gln Cys Asp Pro Lys Ile Ile
            420                 425                 430

His Arg Asp Val Lys Ala Ala Asn Ile Leu Leu Asp Asp Tyr Cys Glu
        435                 440                 445

Ala Val Val Gly Asp Phe Gly Leu Ala Lys Leu Leu Asp His Gln Asp
    450                 455                 460

Ser His Val Thr Thr Ala Val Arg Gly Thr Val Gly His Ile Ala Pro
465                 470                 475                 480

Glu Tyr Leu Ser Thr Gly Gln Ser Ser Glu Lys Thr Asp Val Phe Gly
                485                 490                 495

Phe Gly Ile Leu Leu Leu Glu Leu Val Thr Gly Gln Arg Ala Phe Glu
            500                 505                 510

Phe Gly Lys Ala Ala Asn Gln Lys Gly Val Met Leu Asp Trp Val Lys
        515                 520                 525

Lys Ile His Gln Glu Lys Lys Leu Glu Leu Leu Val Asp Lys Glu Leu
    530                 535                 540

Leu Lys Lys Lys Ser Tyr Asp Glu Ile Glu Leu Asp Glu Met Val Arg
545                 550                 555                 560

Val Ala Leu Leu Cys Thr Gln Tyr Leu Pro Gly His Arg Pro Lys Met
                565                 570                 575

Ser Glu Val Val Arg Met Leu Glu Gly Asp Gly Leu Ala Glu Lys Trp
            580                 585                 590

Glu Ala Ser Gln Arg Ser Asp Ser Val Ser Lys Cys Ser Asn Arg Ile
        595                 600                 605
```

-continued

```
Asn Glu Leu Met Ser Ser Ser Asp Arg Tyr Ser Asp Leu Thr Asp Asp
    610                 615                 620

Ser Ser Leu Leu Val Gln Ala Met Glu Leu Ser Gly Pro Arg
625                 630                 635


<210> SEQ ID NO 54
<211> LENGTH: 2021
<212> TYPE: DNA
<213> ORGANISM: Arabidopsis thaliana
<220> FEATURE:
<221> NAME/KEY: CDS
<222> LOCATION: (61)..(1947)

<400> SEQUENCE: 54

gttttttttt ttttaccctc ttggaggatc tgggaggaga aatttgcttt tttttggtaa      60

atg ggg aga aaa aag ttt gaa gct ttt ggt ttt gtc tgc tta atc tca       108
Met Gly Arg Lys Lys Phe Glu Ala Phe Gly Phe Val Cys Leu Ile Ser
1               5                   10                  15

ctg ctt ctt ctg ttt aat tcg tta tgg ctt gcc tct tct aac atg gaa       156
Leu Leu Leu Leu Phe Asn Ser Leu Trp Leu Ala Ser Ser Asn Met Glu
            20                  25                  30

ggt gat gca ctg cac agt ttg aga gct aat cta gtt gat cca aat aat       204
Gly Asp Ala Leu His Ser Leu Arg Ala Asn Leu Val Asp Pro Asn Asn
        35                  40                  45

gtc ttg caa agc tgg gat cct acg ctt gtt aat ccg tgt act tgg ttt       252
Val Leu Gln Ser Trp Asp Pro Thr Leu Val Asn Pro Cys Thr Trp Phe
    50                  55                  60

cac gta acg tgt aac aac gag aac agt gtt ata aga gtc gat ctt ggg       300
His Val Thr Cys Asn Asn Glu Asn Ser Val Ile Arg Val Asp Leu Gly
65                  70                  75                  80

aat gca gac ttg tct ggt cag ttg gtt cct cag cta ggt cag ctc aag       348
Asn Ala Asp Leu Ser Gly Gln Leu Val Pro Gln Leu Gly Gln Leu Lys
                85                  90                  95

aac ttg cag tac ttg gag ctt tat agt aat aac ata acc ggg ccg gtt       396
Asn Leu Gln Tyr Leu Glu Leu Tyr Ser Asn Asn Ile Thr Gly Pro Val
            100                 105                 110

cca agc gat ctt ggg aat ctg aca aac tta gtg agc ttg gat ctt tac       444
Pro Ser Asp Leu Gly Asn Leu Thr Asn Leu Val Ser Leu Asp Leu Tyr
        115                 120                 125

ttg aac agc ttc act ggt cca att cca gat tct cta gga aag cta ttc       492
Leu Asn Ser Phe Thr Gly Pro Ile Pro Asp Ser Leu Gly Lys Leu Phe
    130                 135                 140

aag ctt cgc ttt ctt cgg ctc aac aat aac agt ctc acc gga cca att       540
Lys Leu Arg Phe Leu Arg Leu Asn Asn Asn Ser Leu Thr Gly Pro Ile
145                 150                 155                 160

ccc atg tca ttg act aat atc atg acc ctt caa gtt ttg gat ctg tcg       588
Pro Met Ser Leu Thr Asn Ile Met Thr Leu Gln Val Leu Asp Leu Ser
                165                 170                 175

aac aac cga tta tcc gga tct gtt cct gat aat ggt tcc ttc tcg ctc       636
Asn Asn Arg Leu Ser Gly Ser Val Pro Asp Asn Gly Ser Phe Ser Leu
            180                 185                 190

ttc act ccc atc agt ttt gct aac aac ttg gat cta tgc ggc cca gtt       684
Phe Thr Pro Ile Ser Phe Ala Asn Asn Leu Asp Leu Cys Gly Pro Val
        195                 200                 205

act agc cgt cct tgt cct gga tct ccc ccg ttt tct cct cca cca cct       732
Thr Ser Arg Pro Cys Pro Gly Ser Pro Pro Phe Ser Pro Pro Pro Pro
    210                 215                 220

ttt ata cca cct ccc ata gtt cct aca cca ggt ggg tat agt gct act       780
Phe Ile Pro Pro Pro Ile Val Pro Thr Pro Gly Gly Tyr Ser Ala Thr
225                 230                 235                 240
```

-continued

```
gga gcc att gcg gga gga gtt gct gct ggt gct gct tta cta ttt gct       828
Gly Ala Ile Ala Gly Gly Val Ala Ala Gly Ala Ala Leu Leu Phe Ala
                245                 250                 255

gcc cct gct tta gct ttt gct tgg tgg cgt aga aga aaa cct caa gaa       876
Ala Pro Ala Leu Ala Phe Ala Trp Trp Arg Arg Arg Lys Pro Gln Glu
            260                 265                 270

ttc ttc ttt gat gtt cct gcc gaa gag gac cct gag gtt cac ttg ggg       924
Phe Phe Phe Asp Val Pro Ala Glu Glu Asp Pro Glu Val His Leu Gly
        275                 280                 285

cag ctt aag cgg ttc tct cta cgg gaa ctt caa gta gca act gat agc       972
Gln Leu Lys Arg Phe Ser Leu Arg Glu Leu Gln Val Ala Thr Asp Ser
    290                 295                 300

ttc agc aac aag aac att ttg ggc cga ggt ggg ttc gga aaa gtc tac      1020
Phe Ser Asn Lys Asn Ile Leu Gly Arg Gly Gly Phe Gly Lys Val Tyr
305                 310                 315                 320

aaa ggc cgt ctt gct gat gga aca ctt gtt gca gtc aaa cgg ctt aaa      1068
Lys Gly Arg Leu Ala Asp Gly Thr Leu Val Ala Val Lys Arg Leu Lys
                325                 330                 335

gaa gag cga acc cca ggt ggc gag ctc cag ttt cag aca gaa gtg gag      1116
Glu Glu Arg Thr Pro Gly Gly Glu Leu Gln Phe Gln Thr Glu Val Glu
            340                 345                 350

atg ata agc atg gcc gtt cac aga aat ctc ctc agg cta cgc ggt ttc      1164
Met Ile Ser Met Ala Val His Arg Asn Leu Leu Arg Leu Arg Gly Phe
        355                 360                 365

tgt atg acc cct acc gag aga ttg ctt gtt tat cct tac atg gct aat      1212
Cys Met Thr Pro Thr Glu Arg Leu Leu Val Tyr Pro Tyr Met Ala Asn
    370                 375                 380

gga agt gtc gct tcc tgt ttg aga gaa cgt cca cca tca cag ttg cct      1260
Gly Ser Val Ala Ser Cys Leu Arg Glu Arg Pro Pro Ser Gln Leu Pro
385                 390                 395                 400

cta gcc tgg tca ata aga cag caa atc gcg cta gga tca gcg agg ggt      1308
Leu Ala Trp Ser Ile Arg Gln Gln Ile Ala Leu Gly Ser Ala Arg Gly
                405                 410                 415

ttg tct tat ctt cat gat cat tgc gac ccc aaa att att cac cgt gat      1356
Leu Ser Tyr Leu His Asp His Cys Asp Pro Lys Ile Ile His Arg Asp
            420                 425                 430

gtg aaa gct gct aat att ctg ttg gac gag gaa ttt gag gcg gtg gta      1404
Val Lys Ala Ala Asn Ile Leu Leu Asp Glu Glu Phe Glu Ala Val Val
        435                 440                 445

ggt gat ttc ggg tta gct aga ctt atg gac tat aaa gat act cat gtc      1452
Gly Asp Phe Gly Leu Ala Arg Leu Met Asp Tyr Lys Asp Thr His Val
    450                 455                 460

aca acg gct gtg cgt ggg act att gga cac att gct cct gag tat ctc      1500
Thr Thr Ala Val Arg Gly Thr Ile Gly His Ile Ala Pro Glu Tyr Leu
465                 470                 475                 480

tca act gga aaa tct tca gag aaa act gat gtt ttt ggc tac ggg atc      1548
Ser Thr Gly Lys Ser Ser Glu Lys Thr Asp Val Phe Gly Tyr Gly Ile
                485                 490                 495

atg ctt ttg gaa ctg att aca ggt cag aga gct ttt gat ctt gca aga      1596
Met Leu Leu Glu Leu Ile Thr Gly Gln Arg Ala Phe Asp Leu Ala Arg
            500                 505                 510

ctg gcg aat gac gat gac gtt atg ctc cta gat tgg gtg aaa ggg ctt      1644
Leu Ala Asn Asp Asp Asp Val Met Leu Leu Asp Trp Val Lys Gly Leu
        515                 520                 525

ttg aag gag aag aag ctg gag atg ctt gtg gat cct gac ctg caa agc      1692
Leu Lys Glu Lys Lys Leu Glu Met Leu Val Asp Pro Asp Leu Gln Ser
    530                 535                 540

aat tac aca gaa gca gaa gta gaa cag ctc ata caa gtg gct ctt ctc      1740
Asn Tyr Thr Glu Ala Glu Val Glu Gln Leu Ile Gln Val Ala Leu Leu
545                 550                 555                 560
```

```
tgc aca cag agc tca cct atg gaa cga cct aag atg tct gag gtt gtt     1788
Cys Thr Gln Ser Ser Pro Met Glu Arg Pro Lys Met Ser Glu Val Val
                565                 570                 575

cga atg ctt gaa ggt gac ggt tta gcg gag aaa tgg gac gag tgg cag     1836
Arg Met Leu Glu Gly Asp Gly Leu Ala Glu Lys Trp Asp Glu Trp Gln
            580                 585                 590

aaa gtg gaa gtt ctc agg caa gaa gtg gag ctc tct tct cac ccc acc     1884
Lys Val Glu Val Leu Arg Gln Glu Val Glu Leu Ser Ser His Pro Thr
        595                 600                 605

tct gac tgg atc ctt gat tcg act gat aat ctt cat gct atg gag ttg     1932
Ser Asp Trp Ile Leu Asp Ser Thr Asp Asn Leu His Ala Met Glu Leu
    610                 615                 620

tct ggt cca aga taa acgacattgt aatttgccta acagaaaaga gaaagaacag     1987
Ser Gly Pro Arg
625

agaaatatta agagaatcac ttctctgtat tctt                               2021


<210> SEQ ID NO 55
<211> LENGTH: 628
<212> TYPE: PRT
<213> ORGANISM: Arabidopsis thaliana

<400> SEQUENCE: 55

Met Gly Arg Lys Lys Phe Glu Ala Phe Gly Phe Val Cys Leu Ile Ser
1               5                   10                  15

Leu Leu Leu Leu Phe Asn Ser Leu Trp Leu Ala Ser Ser Asn Met Glu
            20                  25                  30

Gly Asp Ala Leu His Ser Leu Arg Ala Asn Leu Val Asp Pro Asn Asn
        35                  40                  45

Val Leu Gln Ser Trp Asp Pro Thr Leu Val Asn Pro Cys Thr Trp Phe
    50                  55                  60

His Val Thr Cys Asn Asn Glu Asn Ser Val Ile Arg Val Asp Leu Gly
65                  70                  75                  80

Asn Ala Asp Leu Ser Gly Gln Leu Val Pro Gln Leu Gly Gln Leu Lys
                85                  90                  95

Asn Leu Gln Tyr Leu Glu Leu Tyr Ser Asn Asn Ile Thr Gly Pro Val
            100                 105                 110

Pro Ser Asp Leu Gly Asn Leu Thr Asn Leu Val Ser Leu Asp Leu Tyr
        115                 120                 125

Leu Asn Ser Phe Thr Gly Pro Ile Pro Asp Ser Leu Gly Lys Leu Phe
    130                 135                 140

Lys Leu Arg Phe Leu Arg Leu Asn Asn Asn Ser Leu Thr Gly Pro Ile
145                 150                 155                 160

Pro Met Ser Leu Thr Asn Ile Met Thr Leu Gln Val Leu Asp Leu Ser
                165                 170                 175

Asn Asn Arg Leu Ser Gly Ser Val Pro Asp Asn Gly Ser Phe Ser Leu
            180                 185                 190

Phe Thr Pro Ile Ser Phe Ala Asn Asn Leu Asp Leu Cys Gly Pro Val
        195                 200                 205

Thr Ser Arg Pro Cys Pro Gly Ser Pro Pro Phe Ser Pro Pro Pro Pro
    210                 215                 220

Phe Ile Pro Pro Pro Ile Val Pro Thr Pro Gly Gly Tyr Ser Ala Thr
225                 230                 235                 240

Gly Ala Ile Ala Gly Gly Val Ala Ala Gly Ala Ala Leu Leu Phe Ala
                245                 250                 255
```

```
Ala Pro Ala Leu Ala Phe Ala Trp Trp Arg Arg Arg Lys Pro Gln Glu
            260                 265                 270

Phe Phe Phe Asp Val Pro Ala Glu Glu Asp Pro Glu Val His Leu Gly
        275                 280                 285

Gln Leu Lys Arg Phe Ser Leu Arg Glu Leu Gln Val Ala Thr Asp Ser
    290                 295                 300

Phe Ser Asn Lys Asn Ile Leu Gly Arg Gly Gly Phe Gly Lys Val Tyr
305                 310                 315                 320

Lys Gly Arg Leu Ala Asp Gly Thr Leu Val Ala Val Lys Arg Leu Lys
                325                 330                 335

Glu Glu Arg Thr Pro Gly Gly Glu Leu Gln Phe Gln Thr Glu Val Glu
            340                 345                 350

Met Ile Ser Met Ala Val His Arg Asn Leu Leu Arg Leu Arg Gly Phe
        355                 360                 365

Cys Met Thr Pro Thr Glu Arg Leu Leu Val Tyr Pro Tyr Met Ala Asn
    370                 375                 380

Gly Ser Val Ala Ser Cys Leu Arg Glu Arg Pro Pro Ser Gln Leu Pro
385                 390                 395                 400

Leu Ala Trp Ser Ile Arg Gln Gln Ile Ala Leu Gly Ser Ala Arg Gly
                405                 410                 415

Leu Ser Tyr Leu His Asp His Cys Asp Pro Lys Ile Ile His Arg Asp
            420                 425                 430

Val Lys Ala Ala Asn Ile Leu Leu Asp Glu Glu Phe Glu Ala Val Val
        435                 440                 445

Gly Asp Phe Gly Leu Ala Arg Leu Met Asp Tyr Lys Asp Thr His Val
    450                 455                 460

Thr Thr Ala Val Arg Gly Thr Ile Gly His Ile Ala Pro Glu Tyr Leu
465                 470                 475                 480

Ser Thr Gly Lys Ser Ser Glu Lys Thr Asp Val Phe Gly Tyr Gly Ile
                485                 490                 495

Met Leu Leu Glu Leu Ile Thr Gly Gln Arg Ala Phe Asp Leu Ala Arg
            500                 505                 510

Leu Ala Asn Asp Asp Asp Val Met Leu Leu Asp Trp Val Lys Gly Leu
        515                 520                 525

Leu Lys Glu Lys Lys Leu Glu Met Leu Val Asp Pro Asp Leu Gln Ser
    530                 535                 540

Asn Tyr Thr Glu Ala Glu Val Glu Gln Leu Ile Gln Val Ala Leu Leu
545                 550                 555                 560

Cys Thr Gln Ser Ser Pro Met Glu Arg Pro Lys Met Ser Glu Val Val
                565                 570                 575

Arg Met Leu Glu Gly Asp Gly Leu Ala Glu Lys Trp Asp Glu Trp Gln
            580                 585                 590

Lys Val Glu Val Leu Arg Gln Glu Val Glu Leu Ser Ser His Pro Thr
        595                 600                 605

Ser Asp Trp Ile Leu Asp Ser Thr Asp Asn Leu His Ala Met Glu Leu
    610                 615                 620

Ser Gly Pro Arg
625
```

<210> SEQ ID NO 56
<211> LENGTH: 1992
<212> TYPE: DNA
<213> ORGANISM: Arabidopsis thaliana
<220> FEATURE:
<221> NAME/KEY: CDS

```
<222> LOCATION: (79)..(1926)

<400> SEQUENCE: 56

atcaggggtt ttaacaatga tggattttct ctgatgaggg atagttctag ggtttgtttt      60

taatctcttg aggataaa atg gaa cga aga tta atg atc cct tgc ttc ttt      111
                    Met Glu Arg Arg Leu Met Ile Pro Cys Phe Phe
                    1               5                   10

tgg ttg att ctc gtt ttg gat ttg gtt ctc aga gtc tcg ggc aac gcc      159
Trp Leu Ile Leu Val Leu Asp Leu Val Leu Arg Val Ser Gly Asn Ala
            15                  20                  25

gaa ggt gat gct cta agt gca ctg aaa aac agt tta gcc gac cct aat      207
Glu Gly Asp Ala Leu Ser Ala Leu Lys Asn Ser Leu Ala Asp Pro Asn
        30                  35                  40

aag gtg ctt caa agt tgg gat gct act ctt gtt act cca tgt aca tgg      255
Lys Val Leu Gln Ser Trp Asp Ala Thr Leu Val Thr Pro Cys Thr Trp
    45                  50                  55

ttt cat gtt act tgc aat agc gac aat agt gtt aca cgt gtt gac ctt      303
Phe His Val Thr Cys Asn Ser Asp Asn Ser Val Thr Arg Val Asp Leu
60                  65                  70                  75

ggg aat gca aat cta tct gga cag ctc gta atg caa ctt ggt cag ctt      351
Gly Asn Ala Asn Leu Ser Gly Gln Leu Val Met Gln Leu Gly Gln Leu
                80                  85                  90

cca aac ttg cag tac ttg gag ctt tat agc aat aac att act ggg aca      399
Pro Asn Leu Gln Tyr Leu Glu Leu Tyr Ser Asn Asn Ile Thr Gly Thr
            95                  100                 105

atc cca gaa cag ctt gga aat ctg acg gaa ttg gtg agc ttg gat ctt      447
Ile Pro Glu Gln Leu Gly Asn Leu Thr Glu Leu Val Ser Leu Asp Leu
        110                 115                 120

tac ttg aac aat tta agc ggg cct att cca tca act ctc ggc cga ctt      495
Tyr Leu Asn Asn Leu Ser Gly Pro Ile Pro Ser Thr Leu Gly Arg Leu
    125                 130                 135

aag aaa ctc cgt ttc ttg cgt ctt aat aac aat agc tta tct gga gaa      543
Lys Lys Leu Arg Phe Leu Arg Leu Asn Asn Asn Ser Leu Ser Gly Glu
140                 145                 150                 155

att cca agg tct ttg act gct gtc ctg acg cta caa gtt ctg gat ctc      591
Ile Pro Arg Ser Leu Thr Ala Val Leu Thr Leu Gln Val Leu Asp Leu
                160                 165                 170

tca aac aat cct ctc acc gga gat att cct gtt aat ggt tcc ttt tca      639
Ser Asn Asn Pro Leu Thr Gly Asp Ile Pro Val Asn Gly Ser Phe Ser
            175                 180                 185

ctt ttc act cca atc agt ttt gcc aac acc aag ttg act ccc ctt cct      687
Leu Phe Thr Pro Ile Ser Phe Ala Asn Thr Lys Leu Thr Pro Leu Pro
        190                 195                 200

gca tct cca ccg cct cct atc tct cct aca ccg cca tca cct gca ggg      735
Ala Ser Pro Pro Pro Pro Ile Ser Pro Thr Pro Pro Ser Pro Ala Gly
    205                 210                 215

agt aat aga att act gga gcg att gcg gga gga gtt gct gca ggt gct      783
Ser Asn Arg Ile Thr Gly Ala Ile Ala Gly Gly Val Ala Ala Gly Ala
220                 225                 230                 235

gca ctt cta ttt gct gtt ccg gcc att gca cta gct tgg tgg cga agg      831
Ala Leu Leu Phe Ala Val Pro Ala Ile Ala Leu Ala Trp Trp Arg Arg
                240                 245                 250

aaa aag ccg cag gac cac ttc ttt gat gta cca gct gaa gag gac cca      879
Lys Lys Pro Gln Asp His Phe Phe Asp Val Pro Ala Glu Glu Asp Pro
            255                 260                 265

gaa gtt cat tta gga caa ctg aag agg ttt tca ttg cgt gaa cta caa      927
Glu Val His Leu Gly Gln Leu Lys Arg Phe Ser Leu Arg Glu Leu Gln
        270                 275                 280

gtt gct tcg gat aat ttt agc aac aag aac ata ttg ggt aga ggt ggt      975
```

-continued

```
Val Ala Ser Asp Asn Phe Ser Asn Lys Asn Ile Leu Gly Arg Gly Gly
    285                 290                 295

ttt ggt aaa gtt tat aaa gga cgg tta gct gat ggt act tta gtg gcc      1023
Phe Gly Lys Val Tyr Lys Gly Arg Leu Ala Asp Gly Thr Leu Val Ala
300                 305                 310                 315

gtt aaa agg cta aaa gag gag cgc acc caa ggt ggc gaa ctg cag ttc      1071
Val Lys Arg Leu Lys Glu Glu Arg Thr Gln Gly Gly Glu Leu Gln Phe
                320                 325                 330

cag aca gag gtt gag atg att agt atg gcg gtt cac aga aac ttg ctt      1119
Gln Thr Glu Val Glu Met Ile Ser Met Ala Val His Arg Asn Leu Leu
            335                 340                 345

cgg ctt cgt gga ttt tgc atg act cca acc gaa aga ttg ctt gtt tat      1167
Arg Leu Arg Gly Phe Cys Met Thr Pro Thr Glu Arg Leu Leu Val Tyr
        350                 355                 360

ccc tac atg gct aat gga agt gtt gcc tcc tgt tta aga gaa cgt ccc      1215
Pro Tyr Met Ala Asn Gly Ser Val Ala Ser Cys Leu Arg Glu Arg Pro
    365                 370                 375

gag tcc cag cca cca ctt gat tgg cca aag aga cag cgt att gcg ttg      1263
Glu Ser Gln Pro Pro Leu Asp Trp Pro Lys Arg Gln Arg Ile Ala Leu
380                 385                 390                 395

gga tct gca aga ggg ctt gcg tat tta cat gat cat tgc gac cca aag      1311
Gly Ser Ala Arg Gly Leu Ala Tyr Leu His Asp His Cys Asp Pro Lys
                400                 405                 410

att att cat cga gat gtg aaa gct gca aat att ttg ttg gat gaa gag      1359
Ile Ile His Arg Asp Val Lys Ala Ala Asn Ile Leu Leu Asp Glu Glu
            415                 420                 425

ttt gaa gcc gtg gtt ggg gat ttt gga ctt gca aaa ctc atg gac tac      1407
Phe Glu Ala Val Val Gly Asp Phe Gly Leu Ala Lys Leu Met Asp Tyr
        430                 435                 440

aaa gac aca cat gtg aca acc gca gtg cgt ggg aca att ggt cat ata      1455
Lys Asp Thr His Val Thr Thr Ala Val Arg Gly Thr Ile Gly His Ile
    445                 450                 455

gcc cct gag tac ctt tcc act gga aaa tca tca gag aaa acc gat gtc      1503
Ala Pro Glu Tyr Leu Ser Thr Gly Lys Ser Ser Glu Lys Thr Asp Val
460                 465                 470                 475

ttt ggg tat gga gtc atg ctt ctt gag ctt atc act gga caa agg gct      1551
Phe Gly Tyr Gly Val Met Leu Leu Glu Leu Ile Thr Gly Gln Arg Ala
                480                 485                 490

ttt gat ctt gct cgc ctc gcg aat gat gat gat gtc atg tta cta gac      1599
Phe Asp Leu Ala Arg Leu Ala Asn Asp Asp Asp Val Met Leu Leu Asp
            495                 500                 505

tgg gtg aaa ggg ttg tta aaa gag aag aaa ttg gaa gca cta gta gat      1647
Trp Val Lys Gly Leu Leu Lys Glu Lys Lys Leu Glu Ala Leu Val Asp
        510                 515                 520

gtt gat ctt cag ggt aat tac aaa gac gaa gaa gtg gag cag cta atc      1695
Val Asp Leu Gln Gly Asn Tyr Lys Asp Glu Glu Val Glu Gln Leu Ile
    525                 530                 535

caa gtg gct tta ctc tgc act cag agt tca cca atg gaa aga ccc aaa      1743
Gln Val Ala Leu Leu Cys Thr Gln Ser Ser Pro Met Glu Arg Pro Lys
540                 545                 550                 555

atg tct gaa gtt gta aga atg ctt gaa gga gat ggt tta gct gag aga      1791
Met Ser Glu Val Val Arg Met Leu Glu Gly Asp Gly Leu Ala Glu Arg
                560                 565                 570

tgg gaa gag tgg caa aag gag gaa atg ttc aga caa gat ttc aac tac      1839
Trp Glu Glu Trp Gln Lys Glu Glu Met Phe Arg Gln Asp Phe Asn Tyr
            575                 580                 585

cca acc cac cat cca gcc gtg tct ggc tgg atc att ggc gat tcc act      1887
Pro Thr His His Pro Ala Val Ser Gly Trp Ile Ile Gly Asp Ser Thr
        590                 595                 600
```

-continued

```
tcc cag atc gaa aac gaa tac ccc tcg ggt cca aga taa gattcgaaac      1936
Ser Gln Ile Glu Asn Glu Tyr Pro Ser Gly Pro Arg
    605                 610                 615

acgaatgttt tttctgtatt ttgtttttct ctgtatttat tgagggtttt agcttc       1992


<210> SEQ ID NO 57
<211> LENGTH: 615
<212> TYPE: PRT
<213> ORGANISM: Arabidopsis thaliana

<400> SEQUENCE: 57

Met Glu Arg Arg Leu Met Ile Pro Cys Phe Phe Trp Leu Ile Leu Val
1               5                   10                  15

Leu Asp Leu Val Leu Arg Val Ser Gly Asn Ala Glu Gly Asp Ala Leu
            20                  25                  30

Ser Ala Leu Lys Asn Ser Leu Ala Asp Pro Asn Lys Val Leu Gln Ser
        35                  40                  45

Trp Asp Ala Thr Leu Val Thr Pro Cys Thr Trp Phe His Val Thr Cys
    50                  55                  60

Asn Ser Asp Asn Ser Val Thr Arg Val Asp Leu Gly Asn Ala Asn Leu
65                  70                  75                  80

Ser Gly Gln Leu Val Met Gln Leu Gly Gln Leu Pro Asn Leu Gln Tyr
                85                  90                  95

Leu Glu Leu Tyr Ser Asn Asn Ile Thr Gly Thr Ile Pro Glu Gln Leu
            100                 105                 110

Gly Asn Leu Thr Glu Leu Val Ser Leu Asp Leu Tyr Leu Asn Asn Leu
        115                 120                 125

Ser Gly Pro Ile Pro Ser Thr Leu Gly Arg Leu Lys Lys Leu Arg Phe
    130                 135                 140

Leu Arg Leu Asn Asn Asn Ser Leu Ser Gly Glu Ile Pro Arg Ser Leu
145                 150                 155                 160

Thr Ala Val Leu Thr Leu Gln Val Leu Asp Leu Ser Asn Asn Pro Leu
                165                 170                 175

Thr Gly Asp Ile Pro Val Asn Gly Ser Phe Ser Leu Phe Thr Pro Ile
            180                 185                 190

Ser Phe Ala Asn Thr Lys Leu Thr Pro Leu Pro Ala Ser Pro Pro Pro
        195                 200                 205

Pro Ile Ser Pro Thr Pro Pro Ser Pro Ala Gly Ser Asn Arg Ile Thr
    210                 215                 220

Gly Ala Ile Ala Gly Gly Val Ala Ala Gly Ala Ala Leu Leu Phe Ala
225                 230                 235                 240

Val Pro Ala Ile Ala Leu Ala Trp Trp Arg Arg Lys Lys Pro Gln Asp
                245                 250                 255

His Phe Phe Asp Val Pro Ala Glu Glu Asp Pro Glu Val His Leu Gly
            260                 265                 270

Gln Leu Lys Arg Phe Ser Leu Arg Glu Leu Gln Val Ala Ser Asp Asn
        275                 280                 285

Phe Ser Asn Lys Asn Ile Leu Gly Arg Gly Gly Phe Gly Lys Val Tyr
    290                 295                 300

Lys Gly Arg Leu Ala Asp Gly Thr Leu Val Ala Val Lys Arg Leu Lys
305                 310                 315                 320

Glu Glu Arg Thr Gln Gly Gly Glu Leu Gln Phe Gln Thr Glu Val Glu
                325                 330                 335

Met Ile Ser Met Ala Val His Arg Asn Leu Leu Arg Leu Arg Gly Phe
            340                 345                 350
```

```
Cys Met Thr Pro Thr Glu Arg Leu Leu Val Tyr Pro Tyr Met Ala Asn
        355                 360                 365

Gly Ser Val Ala Ser Cys Leu Arg Glu Arg Pro Glu Ser Gln Pro Pro
    370                 375                 380

Leu Asp Trp Pro Lys Arg Gln Arg Ile Ala Leu Gly Ser Ala Arg Gly
385                 390                 395                 400

Leu Ala Tyr Leu His Asp His Cys Asp Pro Lys Ile Ile His Arg Asp
                405                 410                 415

Val Lys Ala Ala Asn Ile Leu Leu Asp Glu Glu Phe Glu Ala Val Val
            420                 425                 430

Gly Asp Phe Gly Leu Ala Lys Leu Met Asp Tyr Lys Asp Thr His Val
        435                 440                 445

Thr Thr Ala Val Arg Gly Thr Ile Gly His Ile Ala Pro Glu Tyr Leu
    450                 455                 460

Ser Thr Gly Lys Ser Ser Glu Lys Thr Asp Val Phe Gly Tyr Gly Val
465                 470                 475                 480

Met Leu Leu Glu Leu Ile Thr Gly Gln Arg Ala Phe Asp Leu Ala Arg
                485                 490                 495

Leu Ala Asn Asp Asp Asp Val Met Leu Leu Asp Trp Val Lys Gly Leu
            500                 505                 510

Leu Lys Glu Lys Lys Leu Glu Ala Leu Val Asp Val Asp Leu Gln Gly
        515                 520                 525

Asn Tyr Lys Asp Glu Glu Val Glu Gln Leu Ile Gln Val Ala Leu Leu
    530                 535                 540

Cys Thr Gln Ser Ser Pro Met Glu Arg Pro Lys Met Ser Glu Val Val
545                 550                 555                 560

Arg Met Leu Glu Gly Asp Gly Leu Ala Glu Arg Trp Glu Glu Trp Gln
                565                 570                 575

Lys Glu Glu Met Phe Arg Gln Asp Phe Asn Tyr Pro Thr His His Pro
            580                 585                 590

Ala Val Ser Gly Trp Ile Ile Gly Asp Ser Thr Ser Gln Ile Glu Asn
        595                 600                 605

Glu Tyr Pro Ser Gly Pro Arg
    610                 615


<210> SEQ ID NO 58
<211> LENGTH: 2034
<212> TYPE: DNA
<213> ORGANISM: Arabidopsis thaliana
<220> FEATURE:
<221> NAME/KEY: CDS
<222> LOCATION: (30)..(1979)

<400> SEQUENCE: 58

ttgttaacct ctcgtaacta aaatcttcc atg gta gta gta aca aag aag acc       53
                                Met Val Val Val Thr Lys Lys Thr
                                1               5

atg aag att caa att cat ctc ctt tac tcg ttc ttg ttc ctc tgt ttc      101
Met Lys Ile Gln Ile His Leu Leu Tyr Ser Phe Leu Phe Leu Cys Phe
    10                  15                  20

tct act ctc act cta tct tct gag ccc aga aac cct gaa gtt gag gcg      149
Ser Thr Leu Thr Leu Ser Ser Glu Pro Arg Asn Pro Glu Val Glu Ala
25                  30                  35                  40

ttg ata agt ata agg aac aat ttg cat gat cct cat gga gct ttg aac      197
Leu Ile Ser Ile Arg Asn Asn Leu His Asp Pro His Gly Ala Leu Asn
                45                  50                  55
```

-continued

```
aat tgg gac gag ttt tca gtt gat cct tgt agc tgg gct atg atc act      245
Asn Trp Asp Glu Phe Ser Val Asp Pro Cys Ser Trp Ala Met Ile Thr
            60                  65                  70

tgc tct ccc gac aac ctc gtc att gga cta gga gcg ccg agc cag tct      293
Cys Ser Pro Asp Asn Leu Val Ile Gly Leu Gly Ala Pro Ser Gln Ser
        75                  80                  85

ctc tcg gga ggt tta tct gag tct atc gga aat ctc aca aat ctc cga      341
Leu Ser Gly Gly Leu Ser Glu Ser Ile Gly Asn Leu Thr Asn Leu Arg
    90                  95                  100

caa gtg tca ttg caa aat aac aac atc tcc ggc aaa att cca ccg gag      389
Gln Val Ser Leu Gln Asn Asn Asn Ile Ser Gly Lys Ile Pro Pro Glu
105                 110                 115                 120

ctc ggt ttt cta ccc aaa tta caa acc ttg gat ctt tcc aac aac cga      437
Leu Gly Phe Leu Pro Lys Leu Gln Thr Leu Asp Leu Ser Asn Asn Arg
                125                 130                 135

ttc tcc ggt gac atc cct gtt tcc atc gac cag cta agc agc ctt caa      485
Phe Ser Gly Asp Ile Pro Val Ser Ile Asp Gln Leu Ser Ser Leu Gln
            140                 145                 150

tat ctg aga ctc aac aac aac tct ttg tct ggg ccc ttc cct gct tct      533
Tyr Leu Arg Leu Asn Asn Asn Ser Leu Ser Gly Pro Phe Pro Ala Ser
        155                 160                 165

ttg tcc caa att cct cac ctc tcc ttc ttg gac ttg tct tac aac aat      581
Leu Ser Gln Ile Pro His Leu Ser Phe Leu Asp Leu Ser Tyr Asn Asn
    170                 175                 180

ctc agt ggc cct gtt cct aaa ttc cca gca agg act tta aac gtt gct      629
Leu Ser Gly Pro Val Pro Lys Phe Pro Ala Arg Thr Leu Asn Val Ala
185                 190                 195                 200

ggt aat cct ttg att tgt aga agc aac cca cct gag att tgt tct gga      677
Gly Asn Pro Leu Ile Cys Arg Ser Asn Pro Pro Glu Ile Cys Ser Gly
                205                 210                 215

tca atc aat gca agt cca ctt tct gtt tct ttg agc tct tca tca gga      725
Ser Ile Asn Ala Ser Pro Leu Ser Val Ser Leu Ser Ser Ser Ser Gly
            220                 225                 230

cgc agg tct aat aga ttg gca ata gct ctt agt gta agc ctt ggc tct      773
Arg Arg Ser Asn Arg Leu Ala Ile Ala Leu Ser Val Ser Leu Gly Ser
        235                 240                 245

gtt gtt ata cta gtc ctt gct ctc ggg tcc ttt tgt tgg tac cga aag      821
Val Val Ile Leu Val Leu Ala Leu Gly Ser Phe Cys Trp Tyr Arg Lys
    250                 255                 260

aaa caa aga agg cta ctg atc ctt aac tta aac gca gat aaa caa gag      869
Lys Gln Arg Arg Leu Leu Ile Leu Asn Leu Asn Ala Asp Lys Gln Glu
265                 270                 275                 280

gaa ggg ctt caa gga ctt ggg aat cta aga agc ttc aca ttc aga gaa      917
Glu Gly Leu Gln Gly Leu Gly Asn Leu Arg Ser Phe Thr Phe Arg Glu
                285                 290                 295

ctc cat gtt tat aca gat ggt ttc agt tcc aag aac att ctc ggc gct      965
Leu His Val Tyr Thr Asp Gly Phe Ser Ser Lys Asn Ile Leu Gly Ala
            300                 305                 310

ggt gga ttc ggt aat gtg tac aga ggc aag ctt gga gat ggg aca atg     1013
Gly Gly Phe Gly Asn Val Tyr Arg Gly Lys Leu Gly Asp Gly Thr Met
        315                 320                 325

gtg gca gtg aaa cgg ttg aag gat att aat gga acc tca ggg gat tca     1061
Val Ala Val Lys Arg Leu Lys Asp Ile Asn Gly Thr Ser Gly Asp Ser
    330                 335                 340

cag ttt cgt atg gag cta gag atg att agc tta gct gtt cat aag aat     1109
Gln Phe Arg Met Glu Leu Glu Met Ile Ser Leu Ala Val His Lys Asn
345                 350                 355                 360

ctg ctt cgg tta att ggt tat tgc gca act tct ggt gaa agg ctt ctt     1157
Leu Leu Arg Leu Ile Gly Tyr Cys Ala Thr Ser Gly Glu Arg Leu Leu
                365                 370                 375
```

-continued

```
gtt tac cct tac atg cct aat gga agc gtc gcc tct aag ctt aaa tct      1205
Val Tyr Pro Tyr Met Pro Asn Gly Ser Val Ala Ser Lys Leu Lys Ser
            380                 385                 390

aaa ccg gca ttg gac tgg aac atg agg aag agg ata gca att ggt gca      1253
Lys Pro Ala Leu Asp Trp Asn Met Arg Lys Arg Ile Ala Ile Gly Ala
        395                 400                 405

gcg aga ggt ttg ttg tat cta cat gag caa tgt gat ccc aag atc att      1301
Ala Arg Gly Leu Leu Tyr Leu His Glu Gln Cys Asp Pro Lys Ile Ile
    410                 415                 420

cat aga gat gta aag gca gct aat att ctc tta gac gag tgc ttt gaa      1349
His Arg Asp Val Lys Ala Ala Asn Ile Leu Leu Asp Glu Cys Phe Glu
425                 430                 435                 440

gct gtt gtt ggt gac ttt gga ctc gca aag ctc ctt aac cat gcg gat      1397
Ala Val Val Gly Asp Phe Gly Leu Ala Lys Leu Leu Asn His Ala Asp
                445                 450                 455

tct cat gtc aca act gcg gtc cgt ggt acg gtt ggc cac att gca cct      1445
Ser His Val Thr Thr Ala Val Arg Gly Thr Val Gly His Ile Ala Pro
            460                 465                 470

gaa tat ctc tcc act ggt cag tct tct gag aaa acc gat gtg ttt ggg      1493
Glu Tyr Leu Ser Thr Gly Gln Ser Ser Glu Lys Thr Asp Val Phe Gly
        475                 480                 485

ttc ggt ata cta ttg ctc gag ctc ata acc gga ctg aga gct ctt gag      1541
Phe Gly Ile Leu Leu Leu Glu Leu Ile Thr Gly Leu Arg Ala Leu Glu
    490                 495                 500

ttt ggt aaa acc gtt agc cag aaa gga gct atg ctt gaa tgg gtg agg      1589
Phe Gly Lys Thr Val Ser Gln Lys Gly Ala Met Leu Glu Trp Val Arg
505                 510                 515                 520

aaa tta cat gaa gag atg aaa gta gag gaa cta ttg gat cga gaa ctc      1637
Lys Leu His Glu Glu Met Lys Val Glu Glu Leu Leu Asp Arg Glu Leu
                525                 530                 535

gga act aac tac gat aag att gaa gtt gga gag atg ttg caa gtg gct      1685
Gly Thr Asn Tyr Asp Lys Ile Glu Val Gly Glu Met Leu Gln Val Ala
            540                 545                 550

ttg cta tgc aca caa tat ctg cca gct cat cgt cct aaa atg tct gaa      1733
Leu Leu Cys Thr Gln Tyr Leu Pro Ala His Arg Pro Lys Met Ser Glu
        555                 560                 565

gtt gtt ttg atg ctt gaa ggc gat gga tta gcc gag aga tgg gct gct      1781
Val Val Leu Met Leu Glu Gly Asp Gly Leu Ala Glu Arg Trp Ala Ala
    570                 575                 580

tcg cat aac cat tca cat ttc tac cat gcc aat atc tct ttc aag aca      1829
Ser His Asn His Ser His Phe Tyr His Ala Asn Ile Ser Phe Lys Thr
585                 590                 595                 600

atc tct tct ctg tct act act tct gtc tca agg ctt gac gca cat tgc      1877
Ile Ser Ser Leu Ser Thr Thr Ser Val Ser Arg Leu Asp Ala His Cys
                605                 610                 615

aat gat cca act tat caa atg ttt gga tct tcg gct ttc gat gat gac      1925
Asn Asp Pro Thr Tyr Gln Met Phe Gly Ser Ser Ala Phe Asp Asp Asp
            620                 625                 630

gat gat cat cag cct tta gat tcc ttt gcc atg gaa cta tcc ggt cca      1973
Asp Asp His Gln Pro Leu Asp Ser Phe Ala Met Glu Leu Ser Gly Pro
        635                 640                 645

aga taa cacaatgaaa gaaagatatc atttttacga tggatcaaac aatccaatga      2029
Arg

aaaaa                                                                2034
```

<210> SEQ ID NO 59
<211> LENGTH: 649
<212> TYPE: PRT
<213> ORGANISM: Arabidopsis thaliana

<400> SEQUENCE: 59

```
Met Val Val Val Thr Lys Lys Thr Met Lys Ile Gln Ile His Leu Leu
1               5                   10                  15

Tyr Ser Phe Leu Phe Leu Cys Phe Ser Thr Leu Thr Leu Ser Ser Glu
            20                  25                  30

Pro Arg Asn Pro Glu Val Glu Ala Leu Ile Ser Ile Arg Asn Asn Leu
        35                  40                  45

His Asp Pro His Gly Ala Leu Asn Asn Trp Asp Glu Phe Ser Val Asp
    50                  55                  60

Pro Cys Ser Trp Ala Met Ile Thr Cys Ser Pro Asp Asn Leu Val Ile
65                  70                  75                  80

Gly Leu Gly Ala Pro Ser Gln Ser Leu Ser Gly Gly Leu Ser Glu Ser
                85                  90                  95

Ile Gly Asn Leu Thr Asn Leu Arg Gln Val Ser Leu Gln Asn Asn Asn
            100                 105                 110

Ile Ser Gly Lys Ile Pro Pro Glu Leu Gly Phe Leu Pro Lys Leu Gln
        115                 120                 125

Thr Leu Asp Leu Ser Asn Asn Arg Phe Ser Gly Asp Ile Pro Val Ser
    130                 135                 140

Ile Asp Gln Leu Ser Ser Leu Gln Tyr Leu Arg Leu Asn Asn Asn Ser
145                 150                 155                 160

Leu Ser Gly Pro Phe Pro Ala Ser Leu Ser Gln Ile Pro His Leu Ser
                165                 170                 175

Phe Leu Asp Leu Ser Tyr Asn Asn Leu Ser Gly Pro Val Pro Lys Phe
            180                 185                 190

Pro Ala Arg Thr Leu Asn Val Ala Gly Asn Pro Leu Ile Cys Arg Ser
        195                 200                 205

Asn Pro Pro Glu Ile Cys Ser Gly Ser Ile Asn Ala Ser Pro Leu Ser
    210                 215                 220

Val Ser Leu Ser Ser Ser Ser Gly Arg Arg Ser Asn Arg Leu Ala Ile
225                 230                 235                 240

Ala Leu Ser Val Ser Leu Gly Ser Val Val Ile Leu Val Leu Ala Leu
                245                 250                 255

Gly Ser Phe Cys Trp Tyr Arg Lys Lys Gln Arg Arg Leu Leu Ile Leu
            260                 265                 270

Asn Leu Asn Ala Asp Lys Gln Glu Glu Gly Leu Gln Gly Leu Gly Asn
        275                 280                 285

Leu Arg Ser Phe Thr Phe Arg Glu Leu His Val Tyr Thr Asp Gly Phe
    290                 295                 300

Ser Ser Lys Asn Ile Leu Gly Ala Gly Gly Phe Gly Asn Val Tyr Arg
305                 310                 315                 320

Gly Lys Leu Gly Asp Gly Thr Met Val Ala Val Lys Arg Leu Lys Asp
                325                 330                 335

Ile Asn Gly Thr Ser Gly Asp Ser Gln Phe Arg Met Glu Leu Glu Met
            340                 345                 350

Ile Ser Leu Ala Val His Lys Asn Leu Leu Arg Leu Ile Gly Tyr Cys
        355                 360                 365

Ala Thr Ser Gly Glu Arg Leu Leu Val Tyr Pro Tyr Met Pro Asn Gly
    370                 375                 380

Ser Val Ala Ser Lys Leu Lys Ser Lys Pro Ala Leu Asp Trp Asn Met
385                 390                 395                 400

Arg Lys Arg Ile Ala Ile Gly Ala Ala Arg Gly Leu Leu Tyr Leu His
```

-continued

```
            405                 410                 415

Glu Gln Cys Asp Pro Lys Ile Ile His Arg Asp Val Lys Ala Ala Asn
        420                 425                 430

Ile Leu Leu Asp Glu Cys Phe Glu Ala Val Val Gly Asp Phe Gly Leu
    435                 440                 445

Ala Lys Leu Leu Asn His Ala Asp Ser His Val Thr Thr Ala Val Arg
    450                 455                 460

Gly Thr Val Gly His Ile Ala Pro Glu Tyr Leu Ser Thr Gly Gln Ser
465                 470                 475                 480

Ser Glu Lys Thr Asp Val Phe Gly Phe Gly Ile Leu Leu Leu Glu Leu
                485                 490                 495

Ile Thr Gly Leu Arg Ala Leu Glu Phe Gly Lys Thr Val Ser Gln Lys
            500                 505                 510

Gly Ala Met Leu Glu Trp Val Arg Lys Leu His Glu Glu Met Lys Val
        515                 520                 525

Glu Glu Leu Leu Asp Arg Glu Leu Gly Thr Asn Tyr Asp Lys Ile Glu
    530                 535                 540

Val Gly Glu Met Leu Gln Val Ala Leu Leu Cys Thr Gln Tyr Leu Pro
545                 550                 555                 560

Ala His Arg Pro Lys Met Ser Glu Val Val Leu Met Leu Glu Gly Asp
                565                 570                 575

Gly Leu Ala Glu Arg Trp Ala Ala Ser His Asn His Ser His Phe Tyr
            580                 585                 590

His Ala Asn Ile Ser Phe Lys Thr Ile Ser Ser Leu Ser Thr Thr Ser
        595                 600                 605

Val Ser Arg Leu Asp Ala His Cys Asn Asp Pro Thr Tyr Gln Met Phe
    610                 615                 620

Gly Ser Ser Ala Phe Asp Asp Asp Asp Asp His Gln Pro Leu Asp Ser
625                 630                 635                 640

Phe Ala Met Glu Leu Ser Gly Pro Arg
                645


<210> SEQ ID NO 60
<211> LENGTH: 1976
<212> TYPE: DNA
<213> ORGANISM: Arabidopsis thaliana
<220> FEATURE:
<221> NAME/KEY: CDS
<222> LOCATION: (61)..(1866)

<400> SEQUENCE: 60

tttaaaaacc ttgctagttc tcaattctca tgactttgct tttagtctta gaagtggaaa      60

atg gaa cat gga tca tcc cgt ggc ttt att tgg ctg att cta ttt ctc      108
Met Glu His Gly Ser Ser Arg Gly Phe Ile Trp Leu Ile Leu Phe Leu
1               5                   10                  15

gat ttt gtt tcc aga gtc acc gga aaa aca caa gtt gat gct ctc att      156
Asp Phe Val Ser Arg Val Thr Gly Lys Thr Gln Val Asp Ala Leu Ile
            20                  25                  30

gct cta aga agc agt tta tca tca ggt gac cat aca aac aat ata ctc      204
Ala Leu Arg Ser Ser Leu Ser Ser Gly Asp His Thr Asn Asn Ile Leu
        35                  40                  45

caa agc tgg aat gcc act cac gtt act cca tgt tca tgg ttt cat gtt      252
Gln Ser Trp Asn Ala Thr His Val Thr Pro Cys Ser Trp Phe His Val
    50                  55                  60

act tgc aat act gaa aac agt gtt act cgt ctt gac ctg ggg agt gct      300
Thr Cys Asn Thr Glu Asn Ser Val Thr Arg Leu Asp Leu Gly Ser Ala
65                  70                  75                  80
```

-continued

```
aat cta tct gga gaa ctg gtg cca cag ctt gct cag ctt cca aat ttg      348
Asn Leu Ser Gly Glu Leu Val Pro Gln Leu Ala Gln Leu Pro Asn Leu
                85                  90                  95

cag tac ttg gaa ctt ttt aac aat aat att act ggg gag ata cct gag      396
Gln Tyr Leu Glu Leu Phe Asn Asn Asn Ile Thr Gly Glu Ile Pro Glu
            100                 105                 110

gag ctt ggc gac ttg atg gaa cta gta agc ttg gac ctt ttt gca aac      444
Glu Leu Gly Asp Leu Met Glu Leu Val Ser Leu Asp Leu Phe Ala Asn
        115                 120                 125

aac ata agc ggt ccc atc cct tcc tct ctt ggc aaa cta gga aaa ctc      492
Asn Ile Ser Gly Pro Ile Pro Ser Ser Leu Gly Lys Leu Gly Lys Leu
    130                 135                 140

cgc ttc ttg cgt ctt tat aac aac agc tta tct gga gaa att cca agg      540
Arg Phe Leu Arg Leu Tyr Asn Asn Ser Leu Ser Gly Glu Ile Pro Arg
145                 150                 155                 160

tct ttg act gct ctg ccg ctg gat gtt ctt gat atc tca aac aat cgg      588
Ser Leu Thr Ala Leu Pro Leu Asp Val Leu Asp Ile Ser Asn Asn Arg
                165                 170                 175

ctc agt gga gat att cct gtt aat ggt tcc ttt tcg cag ttc act tct      636
Leu Ser Gly Asp Ile Pro Val Asn Gly Ser Phe Ser Gln Phe Thr Ser
            180                 185                 190

atg agt ttt gcc aat aat aaa tta agg ccg cga cct gca tct cct tca      684
Met Ser Phe Ala Asn Asn Lys Leu Arg Pro Arg Pro Ala Ser Pro Ser
        195                 200                 205

cca tca cct tca gga acg tct gca gca ata gta gtg gga gtt gct gcg      732
Pro Ser Pro Ser Gly Thr Ser Ala Ala Ile Val Val Gly Val Ala Ala
    210                 215                 220

ggt gca gca ctt cta ttt gcg ctt gct tgg tgg ctg aga aga aaa ctg      780
Gly Ala Ala Leu Leu Phe Ala Leu Ala Trp Trp Leu Arg Arg Lys Leu
225                 230                 235                 240

cag ggt cac ttt ctt gat gta cct gct gaa gaa gac cca gag gtt tat      828
Gln Gly His Phe Leu Asp Val Pro Ala Glu Glu Asp Pro Glu Val Tyr
                245                 250                 255

tta gga caa ttt aaa agg ttc tcc ttg cgt gaa ctg cta gtt gct aca      876
Leu Gly Gln Phe Lys Arg Phe Ser Leu Arg Glu Leu Leu Val Ala Thr
            260                 265                 270

gag aaa ttt agc aaa aga aat gta ttg ggc aaa gga cgt ttt ggt ata      924
Glu Lys Phe Ser Lys Arg Asn Val Leu Gly Lys Gly Arg Phe Gly Ile
        275                 280                 285

ttg tat aaa gga cgt tta gct gat gac act cta gtg gct gtg aaa cgg      972
Leu Tyr Lys Gly Arg Leu Ala Asp Asp Thr Leu Val Ala Val Lys Arg
    290                 295                 300

cta aat gaa gaa cgt acc aag ggt ggg gaa ctg cag ttt caa acc gaa     1020
Leu Asn Glu Glu Arg Thr Lys Gly Gly Glu Leu Gln Phe Gln Thr Glu
305                 310                 315                 320

gtt gag atg atc agt atg gcc gtt cat agg aac ttg ctt cgg ctt cgt     1068
Val Glu Met Ile Ser Met Ala Val His Arg Asn Leu Leu Arg Leu Arg
                325                 330                 335

ggc ttt tgc atg act cca act gaa aga tta ctt gtt tat ccc tac atg     1116
Gly Phe Cys Met Thr Pro Thr Glu Arg Leu Leu Val Tyr Pro Tyr Met
            340                 345                 350

gct aat gga agt gtt gct tct tgt tta aga gag cgt cct gaa ggc aat     1164
Ala Asn Gly Ser Val Ala Ser Cys Leu Arg Glu Arg Pro Glu Gly Asn
        355                 360                 365

cca gcc ctt gac tgg cca aaa aga aag cat att gct ctg gga tca gca     1212
Pro Ala Leu Asp Trp Pro Lys Arg Lys His Ile Ala Leu Gly Ser Ala
    370                 375                 380

agg ggg ctc gca tat tta cac gat cat tgc gac caa aag atc att cac     1260
Arg Gly Leu Ala Tyr Leu His Asp His Cys Asp Gln Lys Ile Ile His
```

-continued

```
385                 390                 395                 400

ctg gat gtg aaa gct gca aat ata ctg tta gat gaa gag ttt gaa gct      1308
Leu Asp Val Lys Ala Ala Asn Ile Leu Leu Asp Glu Glu Phe Glu Ala
                405                 410                 415

gtt gtt gga gat ttt ggg cta gca aaa tta atg aat tat aac gac tcc      1356
Val Val Gly Asp Phe Gly Leu Ala Lys Leu Met Asn Tyr Asn Asp Ser
            420                 425                 430

cat gtg aca act gct gta cgg ggt acg att ggc cat ata gcg ccc gag      1404
His Val Thr Thr Ala Val Arg Gly Thr Ile Gly His Ile Ala Pro Glu
        435                 440                 445

tac ctc tcg aca gga aaa tct tct gag aag act gat gtt ttt ggg tac      1452
Tyr Leu Ser Thr Gly Lys Ser Ser Glu Lys Thr Asp Val Phe Gly Tyr
    450                 455                 460

ggg gtc atg ctt ctc gag ctc atc act gga caa aag gct ttc gat ctt      1500
Gly Val Met Leu Leu Glu Leu Ile Thr Gly Gln Lys Ala Phe Asp Leu
465                 470                 475                 480

gct cgg ctt gca aat gat gat gat atc atg tta ctc gac tgg gtg aaa      1548
Ala Arg Leu Ala Asn Asp Asp Asp Ile Met Leu Leu Asp Trp Val Lys
                485                 490                 495

gag gtt ttg aaa gag aag aag ttg gaa agc ctt gtg gat gca gaa ctc      1596
Glu Val Leu Lys Glu Lys Lys Leu Glu Ser Leu Val Asp Ala Glu Leu
            500                 505                 510

gaa gga aag tac gtg gaa aca gaa gtg gag cag ctg ata caa atg gct      1644
Glu Gly Lys Tyr Val Glu Thr Glu Val Glu Gln Leu Ile Gln Met Ala
        515                 520                 525

ctg ctc tgc act caa agt tct gca atg gaa cgt cca aag atg tca gaa      1692
Leu Leu Cys Thr Gln Ser Ser Ala Met Glu Arg Pro Lys Met Ser Glu
    530                 535                 540

gta gtg aga atg ctg gaa gga gat ggt tta gct gag aga tgg gaa gaa      1740
Val Val Arg Met Leu Glu Gly Asp Gly Leu Ala Glu Arg Trp Glu Glu
545                 550                 555                 560

tgg caa aag gag gag atg cca ata cat gat ttt aac tat caa gcc tat      1788
Trp Gln Lys Glu Glu Met Pro Ile His Asp Phe Asn Tyr Gln Ala Tyr
                565                 570                 575

cct cat gct ggc act gac tgg ctc atc ccc tat tcc aat tcc ctt atc      1836
Pro His Ala Gly Thr Asp Trp Leu Ile Pro Tyr Ser Asn Ser Leu Ile
            580                 585                 590

gaa aac gat tac ccc tcg ggg cca aga taa cctttagaa agggtcattt      1886
Glu Asn Asp Tyr Pro Ser Gly Pro Arg
        595                 600

cttgtgggtt cttcaacaag tatatatata ggtagtgaag ttgtaagaag caaaacccca   1946

cattcacctt tgaatatcac tactctataa                                    1976


<210> SEQ ID NO 61
<211> LENGTH: 601
<212> TYPE: PRT
<213> ORGANISM: Arabidopsis thaliana

<400> SEQUENCE: 61

Met Glu His Gly Ser Ser Arg Gly Phe Ile Trp Leu Ile Leu Phe Leu
1               5                   10                  15

Asp Phe Val Ser Arg Val Thr Gly Lys Thr Gln Val Asp Ala Leu Ile
            20                  25                  30

Ala Leu Arg Ser Ser Leu Ser Ser Gly Asp His Thr Asn Asn Ile Leu
        35                  40                  45

Gln Ser Trp Asn Ala Thr His Val Thr Pro Cys Ser Trp Phe His Val
    50                  55                  60

Thr Cys Asn Thr Glu Asn Ser Val Thr Arg Leu Asp Leu Gly Ser Ala
```

```
65                  70                  75                  80

Asn Leu Ser Gly Glu Leu Val Pro Gln Leu Ala Gln Leu Pro Asn Leu
                85                  90                  95

Gln Tyr Leu Glu Leu Phe Asn Asn Asn Ile Thr Gly Glu Ile Pro Glu
            100                 105                 110

Glu Leu Gly Asp Leu Met Glu Leu Val Ser Leu Asp Leu Phe Ala Asn
        115                 120                 125

Asn Ile Ser Gly Pro Ile Pro Ser Ser Leu Gly Lys Leu Gly Lys Leu
    130                 135                 140

Arg Phe Leu Arg Leu Tyr Asn Asn Ser Leu Ser Gly Glu Ile Pro Arg
145                 150                 155                 160

Ser Leu Thr Ala Leu Pro Leu Asp Val Leu Asp Ile Ser Asn Asn Arg
                165                 170                 175

Leu Ser Gly Asp Ile Pro Val Asn Gly Ser Phe Ser Gln Phe Thr Ser
            180                 185                 190

Met Ser Phe Ala Asn Asn Lys Leu Arg Pro Arg Pro Ala Ser Pro Ser
        195                 200                 205

Pro Ser Pro Ser Gly Thr Ser Ala Ala Ile Val Val Gly Val Ala Ala
    210                 215                 220

Gly Ala Ala Leu Leu Phe Ala Leu Ala Trp Trp Leu Arg Arg Lys Leu
225                 230                 235                 240

Gln Gly His Phe Leu Asp Val Pro Ala Glu Glu Asp Pro Glu Val Tyr
                245                 250                 255

Leu Gly Gln Phe Lys Arg Phe Ser Leu Arg Glu Leu Leu Val Ala Thr
            260                 265                 270

Glu Lys Phe Ser Lys Arg Asn Val Leu Gly Lys Gly Arg Phe Gly Ile
        275                 280                 285

Leu Tyr Lys Gly Arg Leu Ala Asp Asp Thr Leu Val Ala Val Lys Arg
    290                 295                 300

Leu Asn Glu Glu Arg Thr Lys Gly Gly Glu Leu Gln Phe Gln Thr Glu
305                 310                 315                 320

Val Glu Met Ile Ser Met Ala Val His Arg Asn Leu Leu Arg Leu Arg
                325                 330                 335

Gly Phe Cys Met Thr Pro Thr Glu Arg Leu Leu Val Tyr Pro Tyr Met
            340                 345                 350

Ala Asn Gly Ser Val Ala Ser Cys Leu Arg Glu Arg Pro Glu Gly Asn
        355                 360                 365

Pro Ala Leu Asp Trp Pro Lys Arg Lys His Ile Ala Leu Gly Ser Ala
    370                 375                 380

Arg Gly Leu Ala Tyr Leu His Asp His Cys Asp Gln Lys Ile Ile His
385                 390                 395                 400

Leu Asp Val Lys Ala Ala Asn Ile Leu Leu Asp Glu Glu Phe Glu Ala
                405                 410                 415

Val Val Gly Asp Phe Gly Leu Ala Lys Leu Met Asn Tyr Asn Asp Ser
            420                 425                 430

His Val Thr Thr Ala Val Arg Gly Thr Ile Gly His Ile Ala Pro Glu
        435                 440                 445

Tyr Leu Ser Thr Gly Lys Ser Ser Glu Lys Thr Asp Val Phe Gly Tyr
    450                 455                 460

Gly Val Met Leu Leu Glu Leu Ile Thr Gly Gln Lys Ala Phe Asp Leu
465                 470                 475                 480

Ala Arg Leu Ala Asn Asp Asp Asp Ile Met Leu Leu Asp Trp Val Lys
                485                 490                 495
```

```
Glu Val Leu Lys Glu Lys Lys Leu Glu Ser Leu Val Asp Ala Glu Leu
            500                 505                 510

Glu Gly Lys Tyr Val Glu Thr Glu Val Glu Gln Leu Ile Gln Met Ala
        515                 520                 525

Leu Leu Cys Thr Gln Ser Ser Ala Met Glu Arg Pro Lys Met Ser Glu
    530                 535                 540

Val Val Arg Met Leu Glu Gly Asp Gly Leu Ala Glu Arg Trp Glu Glu
545                 550                 555                 560

Trp Gln Lys Glu Glu Met Pro Ile His Asp Phe Asn Tyr Gln Ala Tyr
                565                 570                 575

Pro His Ala Gly Thr Asp Trp Leu Ile Pro Tyr Ser Asn Ser Leu Ile
            580                 585                 590

Glu Asn Asp Tyr Pro Ser Gly Pro Arg
        595                 600


<210> SEQ ID NO 62
<211> LENGTH: 1982
<212> TYPE: DNA
<213> ORGANISM: Arabidopsis thaliana
<220> FEATURE:
<221> NAME/KEY: CDS
<222> LOCATION: (55)..(1902)

<400> SEQUENCE: 62

taataaacct ctaataataa tggctttgct tttactctga tgacaagttc aaaa atg       57
                                                            Met
                                                            1

gaa caa aga tca ctc ctt tgc ttc ctt tat ctg ctc cta cta ttc aat      105
Glu Gln Arg Ser Leu Leu Cys Phe Leu Tyr Leu Leu Leu Leu Phe Asn
            5                   10                  15

ttc act ctc aga gtc gct gga aac gct gaa ggt gat gct ttg act cag      153
Phe Thr Leu Arg Val Ala Gly Asn Ala Glu Gly Asp Ala Leu Thr Gln
        20                  25                  30

ctg aaa aac agt ttg tca tca ggt gac cct gca aac aat gta ctc caa      201
Leu Lys Asn Ser Leu Ser Ser Gly Asp Pro Ala Asn Asn Val Leu Gln
    35                  40                  45

agc tgg gat gct act ctt gtt act cca tgt act tgg ttt cat gtt act      249
Ser Trp Asp Ala Thr Leu Val Thr Pro Cys Thr Trp Phe His Val Thr
50                  55                  60                  65

tgc aat cct gag aat aaa gtt act cgt gtt gac ctt ggg aat gca aaa      297
Cys Asn Pro Glu Asn Lys Val Thr Arg Val Asp Leu Gly Asn Ala Lys
                70                  75                  80

cta tct gga aag ttg gtt cca gaa ctt ggt cag ctt tta aac ttg cag      345
Leu Ser Gly Lys Leu Val Pro Glu Leu Gly Gln Leu Leu Asn Leu Gln
            85                  90                  95

tac ttg gag ctt tat agc aat aac att aca ggg gag ata cct gag gag      393
Tyr Leu Glu Leu Tyr Ser Asn Asn Ile Thr Gly Glu Ile Pro Glu Glu
        100                 105                 110

ctt ggc gac ttg gtg gaa cta gta agc ttg gat ctt tac gca aac agc      441
Leu Gly Asp Leu Val Glu Leu Val Ser Leu Asp Leu Tyr Ala Asn Ser
    115                 120                 125

ata agc ggt ccc atc cct tcg tct ctt ggc aaa cta gga aaa ctc cgg      489
Ile Ser Gly Pro Ile Pro Ser Ser Leu Gly Lys Leu Gly Lys Leu Arg
130                 135                 140                 145

ttc ttg cgt ctt aac aac aat agc tta tca ggg gaa att cca atg act      537
Phe Leu Arg Leu Asn Asn Asn Ser Leu Ser Gly Glu Ile Pro Met Thr
                150                 155                 160

ttg act tct gtg cag ctg caa gtt ctg gat atc tca aac aat cgg ctc      585
Leu Thr Ser Val Gln Leu Gln Val Leu Asp Ile Ser Asn Asn Arg Leu
```

-continued

```
            165                 170                 175

agt gga gat att cct gtt aat ggt tct ttt tcg ctc ttc act cct atc      633
Ser Gly Asp Ile Pro Val Asn Gly Ser Phe Ser Leu Phe Thr Pro Ile
        180                 185                 190

agt ttt gcg aat aat agc tta acg gat ctt ccc gaa cct ccg cct act      681
Ser Phe Ala Asn Asn Ser Leu Thr Asp Leu Pro Glu Pro Pro Pro Thr
    195                 200                 205

tct acc tct cct acg cca cca cca cct tca ggg ggg caa atg act gca      729
Ser Thr Ser Pro Thr Pro Pro Pro Pro Ser Gly Gly Gln Met Thr Ala
210                 215                 220                 225

gca ata gca ggg gga gtt gct gca ggt gca gca ctt cta ttt gct gtt      777
Ala Ile Ala Gly Gly Val Ala Ala Gly Ala Ala Leu Leu Phe Ala Val
                230                 235                 240

cca gcc att gcg ttt gct tgg tgg ctc aga aga aaa cca cag gac cac      825
Pro Ala Ile Ala Phe Ala Trp Trp Leu Arg Arg Lys Pro Gln Asp His
            245                 250                 255

ttt ttt gat gta cct gct gaa gaa gac cca gag gtt cat tta gga caa      873
Phe Phe Asp Val Pro Ala Glu Glu Asp Pro Glu Val His Leu Gly Gln
        260                 265                 270

ctc aaa agg ttt acc ttg cgt gaa ctg tta gtt gct act gat aac ttt      921
Leu Lys Arg Phe Thr Leu Arg Glu Leu Leu Val Ala Thr Asp Asn Phe
    275                 280                 285

agc aat aaa aat gta ttg ggt aga ggt ggt ttt ggt aaa gtg tat aaa      969
Ser Asn Lys Asn Val Leu Gly Arg Gly Gly Phe Gly Lys Val Tyr Lys
290                 295                 300                 305

gga cgt tta gcc gat ggc aat cta gtg gct gtc aaa agg cta aaa gaa     1017
Gly Arg Leu Ala Asp Gly Asn Leu Val Ala Val Lys Arg Leu Lys Glu
                310                 315                 320

gaa cgt acc aag ggt ggg gaa ctg cag ttt caa acc gaa gtt gag atg     1065
Glu Arg Thr Lys Gly Gly Glu Leu Gln Phe Gln Thr Glu Val Glu Met
            325                 330                 335

atc agt atg gcc gtt cat agg aac ttg ctt cgg ctt cgt ggc ttt tgc     1113
Ile Ser Met Ala Val His Arg Asn Leu Leu Arg Leu Arg Gly Phe Cys
        340                 345                 350

atg act cca act gaa aga tta ctt gtt tat ccc tac atg gct aat gga     1161
Met Thr Pro Thr Glu Arg Leu Leu Val Tyr Pro Tyr Met Ala Asn Gly
    355                 360                 365

agt gtt gct tct tgt tta aga gag cgt cct gaa ggc aat cca gca ctt     1209
Ser Val Ala Ser Cys Leu Arg Glu Arg Pro Glu Gly Asn Pro Ala Leu
370                 375                 380                 385

gat tgg cca aaa aga aag cat att gct ctg gga tca gca agg ggg ctt     1257
Asp Trp Pro Lys Arg Lys His Ile Ala Leu Gly Ser Ala Arg Gly Leu
                390                 395                 400

gcg tat tta cat gat cat tgc gac caa aaa atc att cac cgg gat gtt     1305
Ala Tyr Leu His Asp His Cys Asp Gln Lys Ile Ile His Arg Asp Val
            405                 410                 415

aaa gct gct aat ata ttg tta gat gaa gag ttt gaa gct gtt gtt gga     1353
Lys Ala Ala Asn Ile Leu Leu Asp Glu Glu Phe Glu Ala Val Val Gly
        420                 425                 430

gat ttt ggg ctc gca aaa tta atg aat tat aat gac tcc cat gtg aca     1401
Asp Phe Gly Leu Ala Lys Leu Met Asn Tyr Asn Asp Ser His Val Thr
    435                 440                 445

act gct gta cgc ggt aca att ggc cat ata gcg ccc gag tac ctc tcg     1449
Thr Ala Val Arg Gly Thr Ile Gly His Ile Ala Pro Glu Tyr Leu Ser
450                 455                 460                 465

aca gga aaa tct tct gag aag act gat gtt ttt ggg tac ggg gtc atg     1497
Thr Gly Lys Ser Ser Glu Lys Thr Asp Val Phe Gly Tyr Gly Val Met
                470                 475                 480

ctt ctc gag ctc atc act gga caa aag gct ttc gat ctt gct cgg ctt     1545
```

-continued

```
Leu Leu Glu Leu Ile Thr Gly Gln Lys Ala Phe Asp Leu Ala Arg Leu
            485                 490                 495

gca aat gat gat gat atc atg tta ctc gac tgg gtg aaa gag gtt ttg     1593
Ala Asn Asp Asp Asp Ile Met Leu Leu Asp Trp Val Lys Glu Val Leu
        500                 505                 510

aaa gag aag aag ttg gaa agc ctt gtg gat gca gaa ctc gaa gga aag     1641
Lys Glu Lys Lys Leu Glu Ser Leu Val Asp Ala Glu Leu Glu Gly Lys
    515                 520                 525

tac gtg gaa aca gaa gtg gag cag ctg ata caa atg gct ctg ctc tgc     1689
Tyr Val Glu Thr Glu Val Glu Gln Leu Ile Gln Met Ala Leu Leu Cys
530                 535                 540                 545

act caa agt tct gca atg gaa cgt cca aag atg tca gaa gta gtg aga     1737
Thr Gln Ser Ser Ala Met Glu Arg Pro Lys Met Ser Glu Val Val Arg
                550                 555                 560

atg ctg gaa gga gat ggt tta gct gag aga tgg gaa gaa tgg caa aag     1785
Met Leu Glu Gly Asp Gly Leu Ala Glu Arg Trp Glu Glu Trp Gln Lys
            565                 570                 575

gag gag atg cca ata cat gat ttt aac tat caa gcc tat cct cat gct     1833
Glu Glu Met Pro Ile His Asp Phe Asn Tyr Gln Ala Tyr Pro His Ala
        580                 585                 590

ggc act gac tgg ctc atc ccc tat tcc aat tcc ctt atc gaa aac gat     1881
Gly Thr Asp Trp Leu Ile Pro Tyr Ser Asn Ser Leu Ile Glu Asn Asp
    595                 600                 605

tac ccc tcg ggt cca aga taa ccttttagaa agggtctttt cttgtgggtt       1932
Tyr Pro Ser Gly Pro Arg
610                 615

cttcaacaag tatatatata gattggtgaa gttttaagat gcaaaaaaaa              1982


<210> SEQ ID NO 63
<211> LENGTH: 615
<212> TYPE: PRT
<213> ORGANISM: Arabidopsis thaliana

<400> SEQUENCE: 63

Met Glu Gln Arg Ser Leu Leu Cys Phe Leu Tyr Leu Leu Leu Leu Phe
1               5                   10                  15

Asn Phe Thr Leu Arg Val Ala Gly Asn Ala Glu Gly Asp Ala Leu Thr
            20                  25                  30

Gln Leu Lys Asn Ser Leu Ser Ser Gly Asp Pro Ala Asn Asn Val Leu
        35                  40                  45

Gln Ser Trp Asp Ala Thr Leu Val Thr Pro Cys Thr Trp Phe His Val
    50                  55                  60

Thr Cys Asn Pro Glu Asn Lys Val Thr Arg Val Asp Leu Gly Asn Ala
65                  70                  75                  80

Lys Leu Ser Gly Lys Leu Val Pro Glu Leu Gly Gln Leu Leu Asn Leu
                85                  90                  95

Gln Tyr Leu Glu Leu Tyr Ser Asn Asn Ile Thr Gly Glu Ile Pro Glu
            100                 105                 110

Glu Leu Gly Asp Leu Val Glu Leu Val Ser Leu Asp Leu Tyr Ala Asn
        115                 120                 125

Ser Ile Ser Gly Pro Ile Pro Ser Ser Leu Gly Lys Leu Gly Lys Leu
    130                 135                 140

Arg Phe Leu Arg Leu Asn Asn Asn Ser Leu Ser Gly Glu Ile Pro Met
145                 150                 155                 160

Thr Leu Thr Ser Val Gln Leu Gln Val Leu Asp Ile Ser Asn Asn Arg
                165                 170                 175

Leu Ser Gly Asp Ile Pro Val Asn Gly Ser Phe Ser Leu Phe Thr Pro
```

-continued

```
            180                 185                 190

Ile Ser Phe Ala Asn Asn Ser Leu Thr Asp Leu Pro Glu Pro Pro Pro
        195                 200                 205

Thr Ser Thr Ser Pro Thr Pro Pro Pro Pro Ser Gly Gly Gln Met Thr
    210                 215                 220

Ala Ala Ile Ala Gly Gly Val Ala Ala Gly Ala Ala Leu Leu Phe Ala
225                 230                 235                 240

Val Pro Ala Ile Ala Phe Ala Trp Trp Leu Arg Arg Lys Pro Gln Asp
                245                 250                 255

His Phe Phe Asp Val Pro Ala Glu Glu Asp Pro Glu Val His Leu Gly
            260                 265                 270

Gln Leu Lys Arg Phe Thr Leu Arg Glu Leu Leu Val Ala Thr Asp Asn
        275                 280                 285

Phe Ser Asn Lys Asn Val Leu Gly Arg Gly Gly Phe Gly Lys Val Tyr
    290                 295                 300

Lys Gly Arg Leu Ala Asp Gly Asn Leu Val Ala Val Lys Arg Leu Lys
305                 310                 315                 320

Glu Glu Arg Thr Lys Gly Gly Glu Leu Gln Phe Gln Thr Glu Val Glu
                325                 330                 335

Met Ile Ser Met Ala Val His Arg Asn Leu Leu Arg Leu Arg Gly Phe
            340                 345                 350

Cys Met Thr Pro Thr Glu Arg Leu Leu Val Tyr Pro Tyr Met Ala Asn
        355                 360                 365

Gly Ser Val Ala Ser Cys Leu Arg Glu Arg Pro Glu Gly Asn Pro Ala
    370                 375                 380

Leu Asp Trp Pro Lys Arg Lys His Ile Ala Leu Gly Ser Ala Arg Gly
385                 390                 395                 400

Leu Ala Tyr Leu His Asp His Cys Asp Gln Lys Ile Ile His Arg Asp
                405                 410                 415

Val Lys Ala Ala Asn Ile Leu Leu Asp Glu Glu Phe Glu Ala Val Val
            420                 425                 430

Gly Asp Phe Gly Leu Ala Lys Leu Met Asn Tyr Asn Asp Ser His Val
        435                 440                 445

Thr Thr Ala Val Arg Gly Thr Ile Gly His Ile Ala Pro Glu Tyr Leu
    450                 455                 460

Ser Thr Gly Lys Ser Ser Glu Lys Thr Asp Val Phe Gly Tyr Gly Val
465                 470                 475                 480

Met Leu Leu Glu Leu Ile Thr Gly Gln Lys Ala Phe Asp Leu Ala Arg
                485                 490                 495

Leu Ala Asn Asp Asp Asp Ile Met Leu Leu Asp Trp Val Lys Glu Val
            500                 505                 510

Leu Lys Glu Lys Lys Leu Glu Ser Leu Val Asp Ala Glu Leu Glu Gly
        515                 520                 525

Lys Tyr Val Glu Thr Glu Val Glu Gln Leu Ile Gln Met Ala Leu Leu
    530                 535                 540

Cys Thr Gln Ser Ser Ala Met Glu Arg Pro Lys Met Ser Glu Val Val
545                 550                 555                 560

Arg Met Leu Glu Gly Asp Gly Leu Ala Glu Arg Trp Glu Glu Trp Gln
                565                 570                 575

Lys Glu Glu Met Pro Ile His Asp Phe Asn Tyr Gln Ala Tyr Pro His
            580                 585                 590

Ala Gly Thr Asp Trp Leu Ile Pro Tyr Ser Asn Ser Leu Ile Glu Asn
        595                 600                 605
```

```
Asp Tyr Pro Ser Gly Pro Arg
    610                 615


<210> SEQ ID NO 64
<211> LENGTH: 1971
<212> TYPE: DNA
<213> ORGANISM: Arabidopsis thaliana
<220> FEATURE:
<221> NAME/KEY: CDS
<222> LOCATION: (55)..(1932)

<400> SEQUENCE: 64

ctgcacctta gagattaata ctctcaagaa aaacaagttt tgattcggac aaag atg       57
                                                            Met
                                                            1

ttg caa gga aga aga gaa gca aaa aag agt tat gct ttg ttc tct tca      105
Leu Gln Gly Arg Arg Glu Ala Lys Lys Ser Tyr Ala Leu Phe Ser Ser
            5                   10                  15

act ttc ttc ttc ttc ttt atc tgt ttt ctt tct tct tct tct gca gaa      153
Thr Phe Phe Phe Phe Phe Ile Cys Phe Leu Ser Ser Ser Ser Ala Glu
        20                  25                  30

ctc aca gac aaa gtt gtt gcc tta ata gga atc aaa agc tca ctg act      201
Leu Thr Asp Lys Val Val Ala Leu Ile Gly Ile Lys Ser Ser Leu Thr
    35                  40                  45

gat cct cat gga gtt cta atg aat tgg gat gac aca gca gtt gat cca      249
Asp Pro His Gly Val Leu Met Asn Trp Asp Asp Thr Ala Val Asp Pro
50                  55                  60                  65

tgt agc tgg aac atg atc act tgt tct gat ggt ttt gtc ata agg cta      297
Cys Ser Trp Asn Met Ile Thr Cys Ser Asp Gly Phe Val Ile Arg Leu
                70                  75                  80

gaa gct cca agc caa aac tta tca gga act ctt tca tca agt att gga      345
Glu Ala Pro Ser Gln Asn Leu Ser Gly Thr Leu Ser Ser Ser Ile Gly
            85                  90                  95

aat tta aca aat ctt caa act gta tac agg tta ttg cag aac aat tac      393
Asn Leu Thr Asn Leu Gln Thr Val Tyr Arg Leu Leu Gln Asn Asn Tyr
        100                 105                 110

ata aca gga aac atc cct cat gag att ggg aaa ttg atg aaa ctc aaa      441
Ile Thr Gly Asn Ile Pro His Glu Ile Gly Lys Leu Met Lys Leu Lys
    115                 120                 125

aca ctt gat ctc tct acc aat aac ttc act ggt caa atc cca ttc act      489
Thr Leu Asp Leu Ser Thr Asn Asn Phe Thr Gly Gln Ile Pro Phe Thr
130                 135                 140                 145

ctt tct tac tcc aaa aat ctt cac agg agg gtt aat aat aac agc ctg      537
Leu Ser Tyr Ser Lys Asn Leu His Arg Arg Val Asn Asn Asn Ser Leu
                150                 155                 160

aca gga aca att cct agc tca ttg gca aac atg acc caa ctc act ttt      585
Thr Gly Thr Ile Pro Ser Ser Leu Ala Asn Met Thr Gln Leu Thr Phe
            165                 170                 175

ttg gat ttg tcg tat aat aac ttg agt gga cca gtt cca aga tca ctt      633
Leu Asp Leu Ser Tyr Asn Asn Leu Ser Gly Pro Val Pro Arg Ser Leu
        180                 185                 190

gcc aaa aca ttc aat gtt atg ggc aat tct cag att tgt cca aca gga      681
Ala Lys Thr Phe Asn Val Met Gly Asn Ser Gln Ile Cys Pro Thr Gly
    195                 200                 205

act gag aaa gac tgt aat ggg act cag cct aag cca atg tca atc acc      729
Thr Glu Lys Asp Cys Asn Gly Thr Gln Pro Lys Pro Met Ser Ile Thr
210                 215                 220                 225

ttg aac agt tct caa aga act aaa aac cgg aaa atc gcg gta gtc ttc      777
Leu Asn Ser Ser Gln Arg Thr Lys Asn Arg Lys Ile Ala Val Val Phe
                230                 235                 240
```

-continued

```
ggt gta agc ttg aca tgt gtt tgc ttg ttg atc att ggc ttt ggt ttt      825
Gly Val Ser Leu Thr Cys Val Cys Leu Leu Ile Ile Gly Phe Gly Phe
            245                 250                 255

ctt ctt tgg tgg aga aga aga cat aac aaa caa gta tta ttc ttt gac      873
Leu Leu Trp Trp Arg Arg Arg His Asn Lys Gln Val Leu Phe Phe Asp
        260                 265                 270

att aat gag caa aac aag gaa gaa atg tgt cta ggg aat cta agg agg      921
Ile Asn Glu Gln Asn Lys Glu Glu Met Cys Leu Gly Asn Leu Arg Arg
    275                 280                 285

ttt aat ttc aaa gaa ctt caa tcc gca act agt aac ttc agc agc aag      969
Phe Asn Phe Lys Glu Leu Gln Ser Ala Thr Ser Asn Phe Ser Ser Lys
290                 295                 300                 305

aat ctg gtc gga aaa gga ggg ttt gga aat gtg tat aaa ggt tgt ctt     1017
Asn Leu Val Gly Lys Gly Gly Phe Gly Asn Val Tyr Lys Gly Cys Leu
                310                 315                 320

cat gat gga agt atc atc gcg gtg aag aga tta aag gat ata aac aat     1065
His Asp Gly Ser Ile Ile Ala Val Lys Arg Leu Lys Asp Ile Asn Asn
            325                 330                 335

ggt ggt gga gag gtt cag ttt cag aca gag ctt gaa atg ata agc ctt     1113
Gly Gly Gly Glu Val Gln Phe Gln Thr Glu Leu Glu Met Ile Ser Leu
        340                 345                 350

gcc gtc cac cgg aat ctc ctc cgc tta tac ggt ttc tgt act act tcc     1161
Ala Val His Arg Asn Leu Leu Arg Leu Tyr Gly Phe Cys Thr Thr Ser
    355                 360                 365

tct gaa cgg ctt ctc gtt tat cct tac atg tcc aat ggc agt gtc gct     1209
Ser Glu Arg Leu Leu Val Tyr Pro Tyr Met Ser Asn Gly Ser Val Ala
370                 375                 380                 385

tct cgt ctc aaa gct aaa ccg gta ttg gat tgg ggc aca aga aag cga     1257
Ser Arg Leu Lys Ala Lys Pro Val Leu Asp Trp Gly Thr Arg Lys Arg
                390                 395                 400

ata gca tta gga gca gga aga ggg ttg ctg tat ttg cat gag caa tgt     1305
Ile Ala Leu Gly Ala Gly Arg Gly Leu Leu Tyr Leu His Glu Gln Cys
            405                 410                 415

gat cca aag atc att cac cgt gat gtc aaa gct gcg aac ata ctt ctt     1353
Asp Pro Lys Ile Ile His Arg Asp Val Lys Ala Ala Asn Ile Leu Leu
        420                 425                 430

gac gat tac ttt gaa gct gtt gtc gga gat ttc ggg ttg gct aag ctt     1401
Asp Asp Tyr Phe Glu Ala Val Val Gly Asp Phe Gly Leu Ala Lys Leu
    435                 440                 445

ttg gat cat gag gag tcg cat gtg aca acc gcc gtg aga gga aca gtg     1449
Leu Asp His Glu Glu Ser His Val Thr Thr Ala Val Arg Gly Thr Val
450                 455                 460                 465

ggt cac att gca cct gag tat ctc tca aca gga caa tct tct gag aag     1497
Gly His Ile Ala Pro Glu Tyr Leu Ser Thr Gly Gln Ser Ser Glu Lys
                470                 475                 480

aca gat gtg ttc ggt ttc ggg att ctt ctt ctc gaa ttg att act gga     1545
Thr Asp Val Phe Gly Phe Gly Ile Leu Leu Leu Glu Leu Ile Thr Gly
            485                 490                 495

ttg aga gct ctt gaa ttc gga aaa gca gca aac caa aga gga gcg ata     1593
Leu Arg Ala Leu Glu Phe Gly Lys Ala Ala Asn Gln Arg Gly Ala Ile
        500                 505                 510

ctt gat tgg gta aag aaa cta caa caa gag aag aag cta gaa cag ata     1641
Leu Asp Trp Val Lys Lys Leu Gln Gln Glu Lys Lys Leu Glu Gln Ile
    515                 520                 525

gta gac aag gat ttg aag agc aac tac gat aga ata gaa gtg gaa gaa     1689
Val Asp Lys Asp Leu Lys Ser Asn Tyr Asp Arg Ile Glu Val Glu Glu
530                 535                 540                 545

atg gtt caa gtg gct ttg ctt tgt aca cag tat ctt ccc att cac cgt     1737
Met Val Gln Val Ala Leu Leu Cys Thr Gln Tyr Leu Pro Ile His Arg
                550                 555                 560
```

```
cct aag atg tct gaa gtt gtg aga atg ctt gaa ggc gat ggt ctt gtt     1785
Pro Lys Met Ser Glu Val Val Arg Met Leu Glu Gly Asp Gly Leu Val
            565                 570                 575

gag aaa tgg gaa gct tct tct cag aga gca gaa acc aat aga agt tac     1833
Glu Lys Trp Glu Ala Ser Ser Gln Arg Ala Glu Thr Asn Arg Ser Tyr
        580                 585                 590

agt aaa cct aac gag ttt tct tcc tct gaa cgt tat tcg gat ctt aca     1881
Ser Lys Pro Asn Glu Phe Ser Ser Ser Glu Arg Tyr Ser Asp Leu Thr
    595                 600                 605

gat gat tcc tcg gtg ctg gtt caa gcc atg gag tta tca ggt cca aga     1929
Asp Asp Ser Ser Val Leu Val Gln Ala Met Glu Leu Ser Gly Pro Arg
610                 615                 620                 625

tga caagagaaac tatatgaatg gctttgggtt tgtaaaaaa                      1971


<210> SEQ ID NO 65
<211> LENGTH: 625
<212> TYPE: PRT
<213> ORGANISM: Arabidopsis thaliana

<400> SEQUENCE: 65

Met Leu Gln Gly Arg Arg Glu Ala Lys Lys Ser Tyr Ala Leu Phe Ser
1               5                   10                  15

Ser Thr Phe Phe Phe Phe Phe Ile Cys Phe Leu Ser Ser Ser Ser Ala
            20                  25                  30

Glu Leu Thr Asp Lys Val Val Ala Leu Ile Gly Ile Lys Ser Ser Leu
        35                  40                  45

Thr Asp Pro His Gly Val Leu Met Asn Trp Asp Asp Thr Ala Val Asp
    50                  55                  60

Pro Cys Ser Trp Asn Met Ile Thr Cys Ser Asp Gly Phe Val Ile Arg
65                  70                  75                  80

Leu Glu Ala Pro Ser Gln Asn Leu Ser Gly Thr Leu Ser Ser Ser Ile
                85                  90                  95

Gly Asn Leu Thr Asn Leu Gln Thr Val Tyr Arg Leu Leu Gln Asn Asn
            100                 105                 110

Tyr Ile Thr Gly Asn Ile Pro His Glu Ile Gly Lys Leu Met Lys Leu
        115                 120                 125

Lys Thr Leu Asp Leu Ser Thr Asn Asn Phe Thr Gly Gln Ile Pro Phe
    130                 135                 140

Thr Leu Ser Tyr Ser Lys Asn Leu His Arg Arg Val Asn Asn Asn Ser
145                 150                 155                 160

Leu Thr Gly Thr Ile Pro Ser Ser Leu Ala Asn Met Thr Gln Leu Thr
                165                 170                 175

Phe Leu Asp Leu Ser Tyr Asn Asn Leu Ser Gly Pro Val Pro Arg Ser
            180                 185                 190

Leu Ala Lys Thr Phe Asn Val Met Gly Asn Ser Gln Ile Cys Pro Thr
        195                 200                 205

Gly Thr Glu Lys Asp Cys Asn Gly Thr Gln Pro Lys Pro Met Ser Ile
    210                 215                 220

Thr Leu Asn Ser Ser Gln Arg Thr Lys Asn Arg Lys Ile Ala Val Val
225                 230                 235                 240

Phe Gly Val Ser Leu Thr Cys Val Cys Leu Leu Ile Ile Gly Phe Gly
                245                 250                 255

Phe Leu Leu Trp Trp Arg Arg Arg His Asn Lys Gln Val Leu Phe Phe
            260                 265                 270

Asp Ile Asn Glu Gln Asn Lys Glu Glu Met Cys Leu Gly Asn Leu Arg
```

```
        275                 280                 285

Arg Phe Asn Phe Lys Glu Leu Gln Ser Ala Thr Ser Asn Phe Ser Ser
    290                 295                 300

Lys Asn Leu Val Gly Lys Gly Gly Phe Gly Asn Val Tyr Lys Gly Cys
305                 310                 315                 320

Leu His Asp Gly Ser Ile Ile Ala Val Lys Arg Leu Lys Asp Ile Asn
                325                 330                 335

Asn Gly Gly Gly Glu Val Gln Phe Gln Thr Glu Leu Glu Met Ile Ser
            340                 345                 350

Leu Ala Val His Arg Asn Leu Leu Arg Leu Tyr Gly Phe Cys Thr Thr
        355                 360                 365

Ser Ser Glu Arg Leu Leu Val Tyr Pro Tyr Met Ser Asn Gly Ser Val
    370                 375                 380

Ala Ser Arg Leu Lys Ala Lys Pro Val Leu Asp Trp Gly Thr Arg Lys
385                 390                 395                 400

Arg Ile Ala Leu Gly Ala Gly Arg Gly Leu Leu Tyr Leu His Glu Gln
                405                 410                 415

Cys Asp Pro Lys Ile Ile His Arg Asp Val Lys Ala Ala Asn Ile Leu
            420                 425                 430

Leu Asp Asp Tyr Phe Glu Ala Val Val Gly Asp Phe Gly Leu Ala Lys
        435                 440                 445

Leu Leu Asp His Glu Glu Ser His Val Thr Thr Ala Val Arg Gly Thr
    450                 455                 460

Val Gly His Ile Ala Pro Glu Tyr Leu Ser Thr Gly Gln Ser Ser Glu
465                 470                 475                 480

Lys Thr Asp Val Phe Gly Phe Gly Ile Leu Leu Leu Glu Leu Ile Thr
                485                 490                 495

Gly Leu Arg Ala Leu Glu Phe Gly Lys Ala Ala Asn Gln Arg Gly Ala
            500                 505                 510

Ile Leu Asp Trp Val Lys Lys Leu Gln Gln Glu Lys Lys Leu Glu Gln
        515                 520                 525

Ile Val Asp Lys Asp Leu Lys Ser Asn Tyr Asp Arg Ile Glu Val Glu
    530                 535                 540

Glu Met Val Gln Val Ala Leu Leu Cys Thr Gln Tyr Leu Pro Ile His
545                 550                 555                 560

Arg Pro Lys Met Ser Glu Val Val Arg Met Leu Glu Gly Asp Gly Leu
                565                 570                 575

Val Glu Lys Trp Glu Ala Ser Ser Gln Arg Ala Glu Thr Asn Arg Ser
            580                 585                 590

Tyr Ser Lys Pro Asn Glu Phe Ser Ser Ser Glu Arg Tyr Ser Asp Leu
        595                 600                 605

Thr Asp Asp Ser Ser Val Leu Val Gln Ala Met Glu Leu Ser Gly Pro
    610                 615                 620

Arg
625
```

<210> SEQ ID NO 66
<211> LENGTH: 260
<212> TYPE: PRT
<213> ORGANISM: Arabidopsis thaliana

<400> SEQUENCE: 66

```
Met Ala Glu Arg Val Tyr Pro Ala Asp Ser Pro Pro Gln Ser Gly Gln
1               5                   10                  15
```

-continued

```
Phe Ser Gly Asn Phe Ser Ser Gly Glu Phe Pro Lys Lys Pro Ala Pro
            20                  25                  30

Pro Pro Ser Thr Tyr Val Ile Gln Val Pro Lys Asp Gln Ile Tyr Arg
        35                  40                  45

Ile Pro Pro Pro Glu Asn Ala His Arg Phe Glu Gln Leu Ser Arg Lys
    50                  55                  60

Lys Thr Asn Arg Ser Asn Cys Arg Cys Cys Phe Cys Ser Phe Leu Ala
65                  70                  75                  80

Ala Val Phe Ile Leu Ile Val Leu Ala Gly Ile Ser Phe Ala Val Leu
                85                  90                  95

Tyr Leu Ile Tyr Arg Pro Glu Ala Pro Lys Tyr Ser Ile Glu Gly Phe
            100                 105                 110

Ser Val Ser Gly Ile Asn Leu Asn Ser Thr Ser Pro Ile Ser Pro Ser
        115                 120                 125

Phe Asn Val Thr Val Arg Ser Arg Asn Gly Asn Gly Lys Ile Gly Val
    130                 135                 140

Tyr Tyr Glu Lys Glu Ser Ser Val Asp Val Tyr Tyr Asn Asp Val Asp
145                 150                 155                 160

Ile Ser Asn Gly Val Met Pro Val Phe Tyr Gln Pro Ala Lys Asn Val
                165                 170                 175

Thr Val Val Lys Leu Val Leu Ser Gly Ser Lys Ile Gln Leu Thr Ser
            180                 185                 190

Gly Met Arg Lys Glu Met Arg Asn Glu Val Ser Lys Lys Thr Val Pro
        195                 200                 205

Phe Lys Leu Lys Ile Lys Ala Pro Val Lys Ile Lys Phe Gly Ser Val
    210                 215                 220

Lys Thr Trp Thr Met Ile Val Asn Val Asp Cys Asp Val Thr Val Asp
225                 230                 235                 240

Lys Leu Thr Ala Pro Ser Arg Ile Val Ser Arg Lys Cys Ser His Asp
                245                 250                 255

Val Asp Leu Trp
            260


<210> SEQ ID NO 67
<211> LENGTH: 281
<212> TYPE: PRT
<213> ORGANISM: Arabidopsis thaliana

<400> SEQUENCE: 67

Met Thr Val Glu Lys Pro Gln Glu Met Thr Gly Asp Thr Asn Ser Asp
1               5                   10                  15

Gly Phe Leu Thr Asn Lys Asp Val His Arg Ile Lys His Pro Ser Leu
            20                  25                  30

Asp Thr Asn Asp Ser Ser Ser Ser Arg Tyr Ser Val Asp Ser Gln Lys
        35                  40                  45

Ser Arg Ile Gly Pro Pro Pro Gly Thr Tyr Val Ile Lys Leu Pro Lys
    50                  55                  60

Asp Gln Ile Tyr Arg Val Pro Pro Pro Glu Asn Ala His Arg Tyr Glu
65                  70                  75                  80

Tyr Leu Ser Arg Arg Lys Thr Asn Lys Ser Cys Cys Arg Arg Cys Leu
                85                  90                  95

Cys Tyr Ser Leu Ser Ala Leu Leu Ile Ile Ile Val Leu Ala Ala Ile
            100                 105                 110

Ala Phe Gly Phe Phe Tyr Leu Val Tyr Gln Pro His Lys Pro Gln Phe
        115                 120                 125
```

```
Ser Val Ser Gly Val Ser Val Thr Gly Ile Asn Leu Thr Ser Ser Ser
    130                 135                 140

Pro Phe Ser Pro Val Ile Arg Ile Lys Leu Arg Ser Gln Asn Val Lys
145                 150                 155                 160

Gly Lys Leu Gly Leu Ile Tyr Glu Lys Gly Asn Glu Ala Asp Val Phe
                165                 170                 175

Phe Asn Gly Thr Lys Leu Gly Asn Gly Glu Phe Thr Ala Phe Lys Gln
            180                 185                 190

Pro Ala Gly Asn Val Thr Val Ile Val Thr Val Leu Lys Gly Ser Ser
        195                 200                 205

Val Lys Leu Lys Ser Ser Ser Arg Lys Glu Leu Thr Glu Ser Gln Lys
    210                 215                 220

Lys Gly Lys Val Pro Phe Gly Leu Arg Ile Lys Ala Pro Val Lys Phe
225                 230                 235                 240

Lys Val Gly Ser Val Thr Thr Trp Thr Met Thr Ile Thr Val Asp Cys
                245                 250                 255

Lys Ile Thr Val Asp Lys Leu Thr Ala Ser Ala Thr Val Lys Thr Glu
            260                 265                 270

Asn Cys Glu Thr Gly Leu Ser Leu Leu
        275                 280


<210> SEQ ID NO 68
<211> LENGTH: 252
<212> TYPE: PRT
<213> ORGANISM: Arabidopsis thaliana

<400> SEQUENCE: 68

Met Ser Gln His Gln Lys Ile Tyr Pro Val Gln Asp Pro Glu Ala Ala
1               5                   10                  15

Thr Ala Arg Pro Thr Ala Pro Leu Val Pro Arg Gly Ser Ser Arg Ser
            20                  25                  30

Glu His Gly Asp Pro Ser Lys Val Pro Leu Asn Gln Arg Pro Gln Arg
        35                  40                  45

Phe Val Pro Leu Ala Pro Pro Lys Lys Arg Arg Ser Cys Cys Cys Arg
    50                  55                  60

Cys Phe Cys Tyr Thr Phe Cys Phe Leu Leu Leu Leu Val Val Ala Val
65                  70                  75                  80

Gly Ala Ser Ile Gly Ile Leu Tyr Leu Val Phe Lys Pro Lys Leu Pro
                85                  90                  95

Asp Tyr Ser Ile Asp Arg Leu Gln Leu Thr Arg Phe Ala Leu Asn Gln
            100                 105                 110

Asp Ser Ser Leu Thr Thr Ala Phe Asn Val Thr Ile Thr Ala Lys Asn
        115                 120                 125

Pro Asn Glu Lys Ile Gly Ile Tyr Tyr Glu Asp Gly Ser Lys Ile Thr
    130                 135                 140

Val Trp Tyr Met Glu His Gln Leu Ser Asn Gly Ser Leu Pro Lys Phe
145                 150                 155                 160

Tyr Gln Gly His Glu Asn Thr Thr Val Ile Tyr Val Glu Met Thr Gly
                165                 170                 175

Gln Thr Gln Asn Ala Ser Gly Leu Arg Thr Thr Leu Glu Glu Gln Gln
            180                 185                 190

Gln Arg Thr Gly Asn Ile Pro Leu Arg Ile Arg Val Asn Gln Pro Val
        195                 200                 205

Arg Val Lys Phe Gly Lys Leu Lys Leu Phe Glu Val Arg Phe Leu Val
```

-continued

```
    210                 215                 220

Arg Cys Gly Val Phe Val Asp Ser Leu Ala Thr Asn Asn Val Ile Lys
225                 230                 235                 240

Ile Gln Ser Ser Ser Cys Lys Phe Arg Leu Arg Leu
                245                 250


<210> SEQ ID NO 69
<211> LENGTH: 248
<212> TYPE: PRT
<213> ORGANISM: Arabidopsis thaliana

<400> SEQUENCE: 69

Met Ser Asp His Gln Lys Ile His Pro Val Ser Asp Pro Glu Ala Pro
1               5                   10                  15

Pro His Pro Thr Ala Pro Leu Val Pro Arg Gly Ser Ser Arg Ser Glu
            20                  25                  30

His Gly Asp Pro Thr Lys Thr Gln Gln Ala Ala Pro Leu Asp Pro Pro
        35                  40                  45

Arg Glu Lys Lys Gly Ser Arg Ser Cys Trp Cys Arg Cys Val Cys Tyr
    50                  55                  60

Thr Leu Leu Val Leu Phe Leu Leu Ile Val Ile Val Gly Ala Ile Val
65                  70                  75                  80

Gly Ile Leu Tyr Leu Val Phe Arg Pro Lys Phe Pro Asp Tyr Asn Ile
                85                  90                  95

Asp Arg Leu Gln Leu Thr Arg Phe Gln Leu Asn Gln Asp Leu Ser Leu
            100                 105                 110

Ser Thr Ala Phe Asn Val Thr Ile Thr Ala Lys Asn Pro Asn Glu Lys
        115                 120                 125

Ile Gly Ile Tyr Tyr Glu Asp Gly Ser Lys Ile Ser Val Leu Tyr Met
    130                 135                 140

Gln Thr Arg Ile Ser Asn Gly Ser Leu Pro Lys Phe Tyr Gln Gly His
145                 150                 155                 160

Glu Asn Thr Thr Ile Ile Leu Val Glu Met Thr Gly Phe Thr Gln Asn
                165                 170                 175

Ala Thr Ser Leu Met Thr Thr Leu Gln Glu Gln Gln Arg Leu Thr Gly
            180                 185                 190

Ser Ile Pro Leu Arg Ile Arg Val Thr Gln Pro Val Arg Ile Lys Leu
        195                 200                 205

Gly Lys Leu Lys Leu Met Lys Val Arg Phe Leu Val Arg Cys Gly Val
    210                 215                 220

Ser Val Asp Ser Leu Ala Ala Asn Ser Val Ile Arg Val Arg Ser Ser
225                 230                 235                 240

Asn Cys Lys Tyr Arg Phe Arg Leu
                245


<210> SEQ ID NO 70
<211> LENGTH: 239
<212> TYPE: PRT
<213> ORGANISM: Arabidopsis thaliana

<400> SEQUENCE: 70

Met Gly Asp Gln Gln Lys Ile His Pro Val Leu Gln Met Glu Ala Asn
1               5                   10                  15

Lys Thr Lys Thr Thr Thr Pro Ala Pro Gly Lys Thr Val Leu Leu Pro
            20                  25                  30

Val Gln Arg Pro Ile Pro Pro Pro Val Ile Pro Ser Lys Asn Arg Asn
```

```
        35                  40                  45

Met Cys Cys Lys Ile Phe Cys Trp Val Leu Ser Leu Leu Val Ile Ala
    50                  55                  60

Leu Ile Ala Leu Ala Ile Ala Val Ala Val Val Tyr Phe Val Phe His
65                  70                  75                  80

Pro Lys Leu Pro Ser Tyr Glu Val Asn Ser Leu Arg Val Thr Asn Leu
                85                  90                  95

Gly Ile Asn Leu Asp Leu Ser Leu Ser Ala Glu Phe Lys Val Glu Ile
            100                 105                 110

Thr Ala Arg Asn Pro Asn Glu Lys Ile Gly Ile Tyr Tyr Glu Lys Gly
        115                 120                 125

Gly His Ile Gly Val Trp Tyr Asp Lys Thr Lys Leu Cys Glu Gly Pro
    130                 135                 140

Ile Pro Arg Phe Tyr Gln Gly His Arg Asn Val Thr Lys Leu Asn Val
145                 150                 155                 160

Ala Leu Thr Gly Arg Ala Gln Tyr Gly Asn Thr Val Leu Ala Ala Leu
                165                 170                 175

Gln Gln Gln Gln Gln Thr Gly Arg Val Pro Leu Asp Leu Lys Val Asn
            180                 185                 190

Ala Pro Val Ala Ile Lys Leu Gly Asn Leu Lys Met Lys Lys Ile Arg
        195                 200                 205

Ile Leu Gly Ser Cys Lys Leu Val Val Asp Ser Leu Ser Thr Asn Asn
    210                 215                 220

Asn Ile Asn Ile Lys Ala Ser Asp Cys Ser Phe Lys Ala Lys Leu
225                 230                 235


<210> SEQ ID NO 71
<211> LENGTH: 231
<212> TYPE: PRT
<213> ORGANISM: Arabidopsis thaliana

<400> SEQUENCE: 71

Met Ala Asp Leu Asn Gly Ala Tyr Tyr Gly Pro Ser Ile Pro Pro Pro
1               5                   10                  15

Lys Lys Val Ser His Ser His Gly Arg Arg Gly Gly Gly Cys Gly Cys
            20                  25                  30

Leu Gly Asp Cys Leu Gly Cys Cys Gly Cys Cys Ile Leu Ser Val Ile
        35                  40                  45

Phe Asn Ile Leu Ile Thr Ile Ala Val Leu Leu Gly Ile Ala Ala Leu
    50                  55                  60

Ile Ile Trp Leu Ile Phe Arg Pro Asn Ala Ile Lys Phe His Val Thr
65                  70                  75                  80

Asp Ala Lys Leu Thr Glu Phe Thr Leu Asp Pro Thr Asn Asn Leu Arg
                85                  90                  95

Tyr Asn Leu Asp Leu Asn Phe Thr Ile Arg Asn Pro Asn Arg Arg Ile
            100                 105                 110

Gly Val Tyr Tyr Asp Glu Ile Glu Val Arg Gly Tyr Tyr Gly Asp Gln
        115                 120                 125

Arg Phe Gly Met Ser Asn Asn Ile Ser Lys Phe Tyr Gln Gly His Lys
    130                 135                 140

Asn Thr Thr Val Val Gly Thr Lys Leu Val Gly Gln Gln Leu Val Leu
145                 150                 155                 160

Leu Asp Gly Gly Glu Arg Lys Asp Leu Asn Glu Asp Val Asn Ser Gln
                165                 170                 175
```

```
Ile Tyr Arg Ile Asp Ala Lys Leu Arg Leu Lys Ile Arg Phe Lys Phe
            180                 185                 190

Gly Leu Ile Lys Ser Trp Arg Phe Lys Pro Lys Ile Lys Cys Asp Leu
        195                 200                 205

Lys Val Pro Leu Thr Ser Asn Ser Thr Ser Gly Phe Val Phe Gln Pro
    210                 215                 220

Thr Lys Cys Asp Val Asp Phe
225                 230


<210> SEQ ID NO 72
<211> LENGTH: 287
<212> TYPE: PRT
<213> ORGANISM: Arabidopsis thaliana

<400> SEQUENCE: 72

Met Thr Asp Arg Val Phe Pro Ala Ser Lys Pro Pro Thr Ala Thr Asn
1               5                   10                  15

Gly Ala Pro Pro Val Gly Ser Ile Pro Pro Pro Pro Ala Pro Ala Thr
            20                  25                  30

Val Thr Ser Asn Gly Thr Thr Asn Gly Met Ala Asn Gln Lys Pro Gln
        35                  40                  45

Val Tyr Ile Pro Ala Asn Arg Pro Val Tyr Arg Pro Gln Pro Tyr Ser
    50                  55                  60

Arg Arg His His His Gln Ser Arg Pro Ser Cys Arg Arg Ile Cys Cys
65                  70                  75                  80

Cys Cys Cys Phe Trp Ser Ile Leu Ile Ile Leu Ile Leu Ala Leu Met
                85                  90                  95

Thr Ala Ile Ala Ala Thr Ala Met Tyr Val Ile Tyr His Pro Arg Pro
            100                 105                 110

Pro Ser Phe Ser Val Pro Ser Ile Arg Ile Ser Arg Val Asn Leu Thr
        115                 120                 125

Thr Ser Ser Asp Ser Ser Val Ser His Leu Ser Ser Phe Phe Asn Phe
    130                 135                 140

Thr Leu Ile Ser Glu Asn Pro Asn Gln His Leu Ser Phe Ser Tyr Asp
145                 150                 155                 160

Pro Phe Thr Val Thr Val Asn Ser Ala Lys Ser Gly Thr Met Leu Gly
                165                 170                 175

Asn Gly Thr Val Pro Ala Phe Phe Ser Asp Asn Gly Asn Lys Thr Ser
            180                 185                 190

Phe His Gly Val Ile Ala Thr Ser Thr Ala Ala Arg Glu Leu Asp Pro
        195                 200                 205

Asp Glu Ala Lys His Leu Arg Ser Asp Leu Thr Arg Ala Arg Val Gly
    210                 215                 220

Tyr Glu Ile Glu Met Arg Thr Lys Val Lys Met Ile Met Gly Lys Leu
225                 230                 235                 240

Lys Ser Glu Gly Val Glu Ile Lys Val Thr Cys Glu Gly Phe Glu Gly
                245                 250                 255

Thr Ile Pro Lys Gly Lys Thr Pro Ile Val Ala Thr Ser Lys Lys Thr
            260                 265                 270

Lys Cys Lys Ser Asp Leu Ser Val Lys Val Trp Lys Trp Ser Phe
        275                 280                 285


<210> SEQ ID NO 73
<211> LENGTH: 264
<212> TYPE: PRT
<213> ORGANISM: Arabidopsis thaliana
```

<400> SEQUENCE: 73

```
Met Thr Asp Asp Arg Val Tyr Pro Ala Ser Lys Pro Pro Ala Ile Val
1               5                   10                  15

Gly Gly Gly Ala Pro Thr Thr Asn Pro Thr Phe Pro Ala Asn Lys Ala
            20                  25                  30

Gln Leu Tyr Asn Ala Asn Arg Pro Ala Tyr Arg Pro Pro Ala Gly Arg
        35                  40                  45

Arg Arg Thr Ser His Thr Arg Gly Cys Cys Cys Arg Cys Cys Cys Trp
    50                  55                  60

Thr Ile Phe Val Ile Ile Leu Leu Leu Leu Ile Val Ala Ala Ala Ser
65                  70                  75                  80

Ala Val Val Tyr Leu Ile Tyr Arg Pro Gln Arg Pro Ser Phe Thr Val
                85                  90                  95

Ser Glu Leu Lys Ile Ser Thr Leu Asn Phe Thr Ser Ala Val Arg Leu
            100                 105                 110

Thr Thr Ala Ile Ser Leu Ser Val Ile Ala Arg Asn Pro Asn Lys Asn
        115                 120                 125

Val Gly Phe Ile Tyr Asp Val Thr Asp Ile Thr Leu Tyr Lys Ala Ser
    130                 135                 140

Thr Gly Gly Asp Asp Asp Val Val Ile Gly Lys Gly Thr Ile Ala Ala
145                 150                 155                 160

Phe Ser His Gly Lys Lys Asn Thr Thr Thr Leu Arg Ser Thr Ile Gly
                165                 170                 175

Ser Pro Pro Asp Glu Leu Asp Glu Ile Ser Ala Gly Lys Leu Lys Gly
            180                 185                 190

Asp Leu Lys Ala Lys Lys Ala Val Ala Ile Lys Ile Val Leu Asn Ser
        195                 200                 205

Lys Val Lys Val Lys Met Gly Ala Leu Lys Thr Pro Lys Ser Gly Ile
    210                 215                 220

Arg Val Thr Cys Glu Gly Ile Lys Val Val Ala Pro Thr Gly Lys Lys
225                 230                 235                 240

Ala Thr Thr Ala Thr Thr Ser Ala Ala Lys Cys Lys Val Asp Pro Arg
                245                 250                 255

Phe Lys Ile Trp Lys Ile Thr Phe
            260
```

<210> SEQ ID NO 74
<211> LENGTH: 240
<212> TYPE: PRT
<213> ORGANISM: Arabidopsis thaliana

<400> SEQUENCE: 74

```
Met Gly Ser Lys Gln Pro Tyr Leu Asn Gly Ala Tyr Tyr Gly Pro Ser
1               5                   10                  15

Ile Pro Pro Pro Pro Lys Ala His Arg Ser Tyr Asn Ser Pro Gly Phe
            20                  25                  30

Gly Cys Cys Cys Phe Ser Cys Leu Gly Ser Cys Leu Arg Cys Cys Gly
        35                  40                  45

Cys Cys Ile Leu Ser Leu Ile Cys Asn Ile Leu Ile Ala Val Ala Val
    50                  55                  60

Ile Leu Gly Val Ala Ala Leu Ile Leu Trp Leu Ile Phe Arg Pro Asn
65                  70                  75                  80

Ala Val Lys Phe Tyr Val Ala Asp Ala Asn Leu Asn Arg Phe Ser Phe
                85                  90                  95
```

-continued

```
Asp Pro Asn Asn Asn Leu His Tyr Ser Leu Asp Leu Asn Phe Thr Ile
            100                 105                 110

Arg Asn Pro Asn Gln Arg Val Gly Val Tyr Tyr Asp Glu Phe Ser Val
        115                 120                 125

Ser Gly Tyr Tyr Gly Asp Gln Arg Phe Gly Ser Ala Asn Val Ser Ser
    130                 135                 140

Phe Tyr Gln Gly His Lys Asn Thr Thr Val Ile Leu Thr Lys Ile Glu
145                 150                 155                 160

Gly Gln Asn Leu Val Val Leu Gly Asp Gly Ala Arg Thr Asp Leu Lys
                165                 170                 175

Asp Asp Glu Lys Ser Gly Ile Tyr Arg Ile Asn Ala Lys Leu Arg Leu
            180                 185                 190

Ser Val Arg Phe Lys Phe Trp Phe Ile Lys Ser Trp Lys Leu Lys Pro
        195                 200                 205

Lys Ile Lys Cys Asp Asp Leu Lys Ile Pro Leu Gly Ser Ser Asn Ser
    210                 215                 220

Thr Gly Gly Phe Lys Phe Gln Pro Val Gln Cys Asp Phe Asp Leu Ser
225                 230                 235                 240


<210> SEQ ID NO 75
<211> LENGTH: 291
<212> TYPE: PRT
<213> ORGANISM: Arabidopsis thaliana

<400> SEQUENCE: 75

Met Glu Gly Pro Arg Arg Pro Pro Ser Ala Thr Ala Pro Asp Ser Asp
1               5                   10                  15

Asp Asp Lys Pro Asp Asp Pro Pro Ser Val Trp His Arg Pro Thr Ser
            20                  25                  30

Ser Leu Pro Ala Leu Pro Ser Leu Asp Pro Pro Ser His Gly Ser His
        35                  40                  45

His Trp Arg Asn His Ser Leu Asn Leu Ser Pro Leu Pro Thr Thr Ser
    50                  55                  60

Ser Pro Pro Leu Pro Pro Pro Asp Ser Ile Pro Glu Leu Glu Thr Tyr
65                  70                  75                  80

Val Val Gln Val Pro Arg Asp Gln Val Tyr Trp Thr Pro Pro Pro Glu
                85                  90                  95

His Ala Lys Tyr Val Glu Lys Arg Ser Lys Asn Pro Glu Lys Asn Lys
            100                 105                 110

Lys Lys Gly Cys Ser Lys Arg Leu Leu Trp Phe Phe Ile Ile Leu Val
        115                 120                 125

Ile Phe Gly Phe Leu Leu Gly Ala Ile Ile Leu Ile Leu His Phe Ala
    130                 135                 140

Phe Asn Pro Thr Leu Pro Val Phe Ala Val Glu Arg Leu Thr Val Asn
145                 150                 155                 160

Pro Ser Asn Phe Glu Val Thr Leu Arg Ala Glu Asn Pro Thr Ser Asn
                165                 170                 175

Met Gly Val Arg Tyr Met Met Glu Lys Asn Gly Val Val Ser Leu Thr
            180                 185                 190

Tyr Lys Asn Lys Ser Leu Gly Ser Gly Lys Phe Pro Gly Leu Ser Gln
        195                 200                 205

Ala Ala Ser Gly Ser Asp Lys Val Asn Val Lys Leu Asn Gly Ser Thr
    210                 215                 220

Lys Asn Ala Val Val Gln Pro Arg Gly Ser Lys Gln Pro Val Val Leu
```

```
225                 230                 235                 240

Met Leu Asn Met Glu Leu Lys Ala Glu Tyr Glu Ala Gly Pro Val Lys
                245                 250                 255

Arg Asn Lys Glu Val Val Val Thr Cys Asp Val Lys Val Lys Gly Leu
            260                 265                 270

Leu Asp Ala Lys Lys Val Glu Ile Val Ser Glu Asn Cys Glu Ser Glu
        275                 280                 285

Phe Lys Asn
    290


<210> SEQ ID NO 76
<211> LENGTH: 207
<212> TYPE: PRT
<213> ORGANISM: Arabidopsis thaliana

<400> SEQUENCE: 76

Met Cys His Lys Pro Lys Leu Glu Leu Met Pro Met Glu Thr Ser Pro
1               5                   10                  15

Ala Gln Pro Leu Arg Arg Pro Ser Leu Ile Cys Tyr Ile Phe Leu Val
            20                  25                  30

Ile Leu Thr Leu Ile Phe Met Ala Ala Val Gly Phe Leu Ile Thr Trp
        35                  40                  45

Leu Glu Thr Lys Pro Lys Lys Leu Arg Tyr Thr Val Glu Asn Ala Ser
    50                  55                  60

Val Gln Asn Phe Asn Leu Thr Asn Asp Asn His Met Ser Ala Thr Phe
65                  70                  75                  80

Gln Phe Thr Ile Gln Ser His Asn Pro Asn His Arg Ile Ser Val Tyr
                85                  90                  95

Tyr Ser Ser Val Glu Ile Phe Val Lys Phe Lys Asp Gln Thr Leu Ala
            100                 105                 110

Phe Asp Thr Val Glu Pro Phe His Gln Pro Arg Met Asn Val Lys Gln
        115                 120                 125

Ile Asp Glu Thr Leu Ile Ala Glu Asn Val Ala Val Ser Lys Ser Asn
    130                 135                 140

Gly Lys Asp Leu Arg Ser Gln Asn Ser Leu Gly Lys Ile Gly Phe Glu
145                 150                 155                 160

Val Phe Val Lys Ala Arg Val Arg Phe Lys Val Gly Ile Trp Lys Ser
                165                 170                 175

Ser His Arg Thr Ala Lys Ile Lys Cys Ser His Val Thr Val Ser Leu
            180                 185                 190

Ser Gln Pro Asn Lys Ser Gln Asn Ser Ser Cys Asp Ala Asp Ile
        195                 200                 205


<210> SEQ ID NO 77
<211> LENGTH: 227
<212> TYPE: PRT
<213> ORGANISM: Arabidopsis thaliana

<400> SEQUENCE: 77

Met Ala Ala Glu Gln Pro Leu Asn Gly Ala Phe Tyr Gly Pro Ser Val
1               5                   10                  15

Pro Pro Pro Ala Pro Lys Gly Tyr Tyr Arg Arg Gly His Gly Arg Gly
            20                  25                  30

Cys Gly Cys Cys Leu Leu Ser Leu Phe Val Lys Val Ile Ile Ser Leu
        35                  40                  45

Ile Val Ile Leu Gly Val Ala Ala Leu Ile Phe Trp Leu Ile Val Arg
```

```
    50                  55                  60

Pro Arg Ala Ile Lys Phe His Val Thr Asp Ala Ser Leu Thr Arg Phe
65                  70                  75                  80

Asp His Thr Ser Pro Asp Asn Ile Leu Arg Tyr Asn Leu Ala Leu Thr
                85                  90                  95

Val Pro Val Arg Asn Pro Asn Lys Arg Ile Gly Leu Tyr Tyr Asp Arg
            100                 105                 110

Ile Glu Ala His Ala Tyr Tyr Glu Gly Lys Arg Phe Ser Thr Ile Thr
        115                 120                 125

Leu Thr Pro Phe Tyr Gln Gly His Lys Asn Thr Thr Val Leu Thr Pro
    130                 135                 140

Thr Phe Gln Gly Gln Asn Leu Val Ile Phe Asn Ala Gly Gln Ser Arg
145                 150                 155                 160

Thr Leu Asn Ala Glu Arg Ile Ser Gly Val Tyr Asn Ile Glu Ile Lys
                165                 170                 175

Phe Arg Leu Arg Val Arg Phe Lys Leu Gly Asp Leu Lys Phe Arg Arg
            180                 185                 190

Ile Lys Pro Lys Val Asp Cys Asp Asp Leu Arg Leu Pro Leu Ser Thr
        195                 200                 205

Ser Asn Gly Thr Thr Thr Thr Ser Thr Val Phe Pro Ile Lys Cys Asp
    210                 215                 220

Phe Asp Phe
225


<210> SEQ ID NO 78
<211> LENGTH: 254
<212> TYPE: PRT
<213> ORGANISM: Arabidopsis thaliana

<400> SEQUENCE: 78

Met Ala Asp Tyr Gln Met Asn Pro Val Leu Gln Lys Pro Pro Gly Tyr
1               5                   10                  15

Arg Asp Pro Asn Met Ser Ser Pro Pro Pro Pro Pro Pro Pro Ile Gln
            20                  25                  30

Gln Gln Pro Met Arg Lys Ala Val Pro Met Pro Thr Ser Tyr Arg Pro
        35                  40                  45

Lys Lys Lys Arg Arg Ser Cys Cys Arg Phe Cys Cys Cys Cys Ile Cys
    50                  55                  60

Ile Thr Leu Val Leu Phe Ile Phe Leu Leu Leu Val Gly Thr Ala Val
65                  70                  75                  80

Phe Tyr Leu Trp Phe Asp Pro Lys Leu Pro Thr Phe Ser Leu Ala Ser
                85                  90                  95

Phe Arg Leu Asp Gly Phe Lys Leu Ala Asp Asp Pro Asp Gly Ala Ser
            100                 105                 110

Leu Ser Ala Thr Ala Val Ala Arg Val Glu Met Lys Asn Pro Asn Ser
        115                 120                 125

Lys Leu Val Phe Tyr Tyr Gly Asn Thr Ala Val Asp Leu Ser Val Gly
    130                 135                 140

Ser Gly Asn Asp Glu Thr Gly Met Gly Glu Thr Thr Met Asn Gly Phe
145                 150                 155                 160

Arg Gln Gly Pro Lys Asn Ser Thr Ser Val Lys Val Glu Thr Thr Val
                165                 170                 175

Lys Asn Gln Leu Val Glu Arg Gly Leu Ala Lys Arg Leu Ala Ala Lys
            180                 185                 190
```

-continued

```
Phe Gln Ser Lys Asp Leu Val Ile Asn Val Val Ala Lys Thr Lys Val
        195                 200                 205

Gly Leu Gly Val Gly Gly Ile Lys Ile Gly Met Leu Ala Val Asn Leu
    210                 215                 220

Arg Cys Gly Gly Val Ser Leu Asn Lys Leu Asp Thr Asp Ser Pro Lys
225                 230                 235                 240

Cys Ile Leu Asn Thr Leu Lys Trp Tyr Lys Ile Ile Ser Asn
                245                 250


<210> SEQ ID NO 79
<211> LENGTH: 226
<212> TYPE: PRT
<213> ORGANISM: Arabidopsis thaliana

<400> SEQUENCE: 79

Met Thr Pro Asp Arg Thr Thr Ile Pro Ile Arg Thr Ser Pro Val Pro
1               5                   10                  15

Arg Ala Gln Pro Met Lys Arg His His Ser Ala Ser Tyr Tyr Ala His
            20                  25                  30

Arg Val Arg Glu Ser Leu Ser Thr Arg Ile Ser Lys Phe Ile Cys Ala
        35                  40                  45

Met Phe Leu Leu Val Leu Phe Phe Val Gly Val Ile Ala Phe Ile Leu
    50                  55                  60

Trp Leu Ser Leu Arg Pro His Arg Pro Arg Phe His Ile Gln Asp Phe
65                  70                  75                  80

Val Val Gln Gly Leu Asp Gln Pro Thr Gly Val Glu Asn Ala Arg Ile
                85                  90                  95

Ala Phe Asn Val Thr Ile Leu Asn Pro Asn Gln His Met Gly Val Tyr
            100                 105                 110

Phe Asp Ser Met Glu Gly Ser Ile Tyr Tyr Lys Asp Gln Arg Val Gly
        115                 120                 125

Leu Ile Pro Leu Leu Asn Pro Phe Phe Gln Gln Pro Thr Asn Thr Thr
    130                 135                 140

Ile Val Thr Gly Thr Leu Thr Gly Ala Ser Leu Thr Val Asn Ser Asn
145                 150                 155                 160

Arg Trp Thr Glu Phe Ser Asn Asp Arg Ala Gln Gly Thr Val Gly Phe
                165                 170                 175

Arg Leu Asp Ile Val Ser Thr Ile Arg Phe Lys Leu His Arg Trp Ile
            180                 185                 190

Ser Lys His His Arg Met His Ala Asn Cys Asn Ile Val Val Gly Arg
        195                 200                 205

Asp Gly Leu Ile Leu Pro Lys Phe Asn His Lys Arg Cys Pro Val Tyr
    210                 215                 220

Phe Thr
225


<210> SEQ ID NO 80
<211> LENGTH: 238
<212> TYPE: PRT
<213> ORGANISM: Arabidopsis thaliana

<400> SEQUENCE: 80

Met Ala Asn Gly Leu Asn Gly Ala Ser Tyr Gly Pro Pro Ile Lys Pro
1               5                   10                  15

Pro Val Lys Thr Tyr Tyr Ser His Gly Arg Arg Gly Ser Asp Val Gly
            20                  25                  30
```

```
Cys Gly Ile Cys Gly Cys Phe Ser Ser Cys Leu Leu Cys Cys Gly Gly
        35                  40                  45

Cys Leu Val Asn Ile Ile Cys Asn Ile Leu Ile Gly Val Leu Val Cys
    50                  55                  60

Leu Gly Val Val Ala Leu Ile Leu Trp Phe Ile Leu Arg Pro Asn Val
65                  70                  75                  80

Val Lys Phe Gln Val Thr Glu Ala Asp Leu Thr Arg Phe Glu Phe Asp
                85                  90                  95

Pro Arg Ser His Asn Leu His Tyr Asn Ile Ser Leu Asn Phe Ser Ile
            100                 105                 110

Arg Asn Pro Asn Gln Arg Leu Gly Ile His Tyr Asp Gln Leu Glu Val
        115                 120                 125

Arg Gly Tyr Tyr Gly Asp Gln Arg Phe Ser Ala Ala Asn Met Thr Ser
    130                 135                 140

Phe Tyr Gln Gly His Lys Asn Thr Thr Val Val Gly Thr Glu Leu Asn
145                 150                 155                 160

Gly Gln Lys Leu Val Leu Leu Gly Ala Gly Gly Arg Arg Asp Phe Arg
                165                 170                 175

Glu Asp Arg Arg Ser Gly Val Tyr Arg Ile Asp Val Lys Leu Arg Phe
            180                 185                 190

Lys Leu Arg Phe Lys Phe Gly Phe Leu Asn Ser Trp Ala Val Arg Pro
        195                 200                 205

Lys Ile Lys Cys His Leu Lys Val Pro Leu Ser Thr Ser Ser Ser Asp
    210                 215                 220

Glu Arg Phe Gln Phe His Pro Thr Lys Cys His Val Asp Leu
225                 230                 235


<210> SEQ ID NO 81
<211> LENGTH: 243
<212> TYPE: PRT
<213> ORGANISM: Arabidopsis thaliana

<400> SEQUENCE: 81

Met Gln Asp Pro Ser Arg Pro Ala Thr Gly Tyr Pro Tyr Pro Tyr Pro
1               5                   10                  15

Tyr Pro Asn Pro Gln Gln Gln Gln Pro Pro Thr Asn Gly Tyr Pro Asn
            20                  25                  30

Pro Ala Ala Gly Thr Ala Tyr Pro Tyr Gln Asn His Asn Pro Tyr Tyr
        35                  40                  45

Ala Pro Gln Pro Asn Pro Arg Ala Val Ile Ile Arg Arg Leu Phe Ile
    50                  55                  60

Val Phe Thr Thr Phe Leu Leu Leu Leu Gly Leu Ile Leu Phe Ile Phe
65                  70                  75                  80

Phe Leu Ile Val Arg Pro Gln Leu Pro Asp Val Asn Leu Asn Ser Leu
                85                  90                  95

Ser Val Ser Asn Phe Asn Val Ser Asn Asn Gln Val Ser Gly Lys Trp
            100                 105                 110

Asp Leu Gln Leu Gln Phe Arg Asn Pro Asn Ser Lys Met Ser Leu His
        115                 120                 125

Tyr Glu Thr Ala Leu Cys Ala Met Tyr Tyr Asn Arg Val Ser Leu Ser
    130                 135                 140

Glu Thr Arg Leu Gln Pro Phe Asp Gln Gly Lys Lys Asp Gln Thr Val
145                 150                 155                 160

Val Asn Ala Thr Leu Ser Val Ser Gly Thr Tyr Val Asp Gly Arg Leu
                165                 170                 175
```

```
Val Asp Ser Ile Gly Lys Glu Arg Ser Val Lys Gly Asn Val Glu Phe
            180                 185                 190

Asp Leu Arg Met Ile Ser Tyr Val Thr Phe Arg Tyr Gly Ala Phe Arg
        195                 200                 205

Arg Arg Arg Tyr Val Thr Val Tyr Cys Asp Asp Val Ala Val Gly Val
    210                 215                 220

Pro Val Ser Ser Gly Glu Gly Lys Met Val Gly Ser Ser Lys Arg Cys
225                 230                 235                 240

Lys Thr Tyr


<210> SEQ ID NO 82
<211> LENGTH: 227
<212> TYPE: PRT
<213> ORGANISM: Arabidopsis thaliana

<400> SEQUENCE: 82

Met Gly Glu Gly Glu Ala Lys Ala Glu His Ala Ala Lys Ala Asp His
1               5                   10                  15

Lys Asn Ala Pro Ser Ala Ser Ser Thr Pro Glu Ser Tyr Ser Lys Glu
            20                  25                  30

Gly Gly Gly Gly Gly Gly Asp Ala Arg Arg Ala Ile Cys Gly Ala Ile
        35                  40                  45

Phe Thr Ile Leu Val Ile Leu Gly Ile Ile Ala Leu Ile Leu Trp Leu
    50                  55                  60

Val Tyr Arg Pro His Lys Pro Arg Leu Thr Val Val Gly Ala Ala Ile
65                  70                  75                  80

Tyr Asp Leu Asn Phe Thr Ala Pro Pro Leu Ile Ser Thr Ser Val Gln
                85                  90                  95

Phe Ser Val Leu Ala Arg Asn Pro Asn Arg Arg Val Ser Ile His Tyr
            100                 105                 110

Asp Lys Leu Ser Met Tyr Val Thr Tyr Lys Asp Gln Ile Ile Thr Pro
        115                 120                 125

Pro Leu Pro Leu Pro Pro Leu Arg Leu Gly His Lys Ser Thr Val Val
    130                 135                 140

Ile Ala Pro Val Met Gly Gly Asn Gly Ile Pro Val Ser Pro Glu Val
145                 150                 155                 160

Ala Asn Gly Leu Lys Asn Asp Glu Ala Tyr Gly Val Val Leu Met Arg
                165                 170                 175

Val Val Ile Phe Gly Arg Leu Arg Trp Lys Ala Gly Ala Ile Lys Thr
            180                 185                 190

Gly Arg Tyr Gly Phe Tyr Ala Arg Cys Asp Val Trp Leu Arg Phe Asn
        195                 200                 205

Pro Ser Ser Asn Gly Gln Val Pro Leu Leu Ala Pro Ser Thr Cys Lys
    210                 215                 220

Val Asp Val
225


<210> SEQ ID NO 83
<211> LENGTH: 210
<212> TYPE: PRT
<213> ORGANISM: Arabidopsis thaliana

<400> SEQUENCE: 83

Met Thr Gly Arg Tyr Cys Asp Gln His Asn Gly Tyr Glu Glu Arg Arg
1               5                   10                  15
```

-continued

```
Met Arg Met Met Met Arg Arg Ile Ala Trp Ala Cys Leu Gly Leu Ile
            20                  25                  30

Val Ala Val Ala Phe Val Val Phe Leu Val Trp Ala Ile Leu His Pro
        35                  40                  45

His Gly Pro Arg Phe Val Leu Gln Asp Val Thr Ile Asn Asp Phe Asn
    50                  55                  60

Val Ser Gln Pro Asn Phe Leu Ser Ser Asn Leu Gln Val Thr Val Ser
65                  70                  75                  80

Ser Arg Asn Pro Asn Asp Lys Ile Gly Ile Phe Tyr Asp Arg Leu Asp
                85                  90                  95

Ile Tyr Val Thr Tyr Arg Asn Gln Glu Val Thr Leu Ala Arg Leu Leu
            100                 105                 110

Pro Ser Thr Tyr Gln Gly His Leu Glu Val Thr Val Trp Ser Pro Phe
        115                 120                 125

Leu Ile Gly Ser Ala Val Pro Val Ala Pro Tyr Leu Ser Ser Ala Leu
    130                 135                 140

Asn Glu Asp Leu Phe Ala Gly Leu Val Leu Leu Asn Ile Lys Ile Asp
145                 150                 155                 160

Gly Trp Val Arg Trp Lys Val Gly Ser Trp Val Ser Gly Ser Tyr Arg
                165                 170                 175

Leu His Val Asn Cys Pro Ala Phe Ile Thr Val Thr Gly Lys Leu Thr
            180                 185                 190

Gly Thr Gly Pro Ala Ile Lys Tyr Gln Leu Val Gln Arg Cys Ala Val
        195                 200                 205

Asp Val
    210


<210> SEQ ID NO 84
<211> LENGTH: 224
<212> TYPE: PRT
<213> ORGANISM: Arabidopsis thaliana

<400> SEQUENCE: 84

Met His Asn Lys Val Asp Ser Leu Pro Val Arg Ser Asn Pro Ser Thr
1               5                   10                  15

Arg Pro Ile Ser Arg His His Ser Ala Ser Asn Ile Val His Arg Val
            20                  25                  30

Lys Glu Ser Leu Thr Thr Arg Val Ser Lys Leu Ile Cys Ala Ile Phe
        35                  40                  45

Leu Ser Leu Leu Leu Cys Leu Gly Ile Ile Thr Phe Ile Leu Trp Ile
    50                  55                  60

Ser Leu Gln Pro His Arg Pro Arg Val His Ile Arg Gly Phe Ser Ile
65                  70                  75                  80

Ser Gly Leu Ser Arg Pro Asp Gly Phe Glu Thr Ser His Ile Ser Phe
                85                  90                  95

Lys Ile Thr Ala His Asn Pro Asn Gln Asn Val Gly Ile Tyr Tyr Asp
            100                 105                 110

Ser Met Glu Gly Ser Val Tyr Tyr Lys Glu Lys Arg Ile Gly Ser Thr
        115                 120                 125

Lys Leu Thr Asn Pro Phe Tyr Gln Asp Pro Lys Asn Thr Ser Ser Ile
    130                 135                 140

Asp Gly Ala Leu Ser Arg Pro Ala Met Ala Val Asn Lys Asp Arg Trp
145                 150                 155                 160

Met Glu Met Glu Arg Asp Arg Asn Gln Gly Lys Ile Met Phe Arg Leu
                165                 170                 175
```

-continued

```
Lys Val Arg Ser Met Ile Arg Phe Lys Val Tyr Thr Trp His Ser Lys
            180                 185                 190

Ser His Lys Met Tyr Ala Ser Cys Tyr Ile Glu Ile Gly Trp Asp Gly
        195                 200                 205

Met Leu Leu Ser Ala Thr Lys Asp Lys Arg Cys Pro Val Tyr Phe Thr
    210                 215                 220


<210> SEQ ID NO 85
<211> LENGTH: 208
<212> TYPE: PRT
<213> ORGANISM: Arabidopsis thaliana

<400> SEQUENCE: 85

Met Ser Lys Asp Cys Gly Asn His Gly Gly Gly Lys Glu Val Val Val
1               5                   10                  15

Arg Lys Leu Cys Ala Ala Ile Ile Ala Phe Ile Val Ile Val Leu Ile
            20                  25                  30

Thr Ile Phe Leu Val Trp Val Ile Leu Arg Pro Thr Lys Pro Arg Phe
        35                  40                  45

Val Leu Gln Asp Ala Thr Val Tyr Ala Phe Asn Leu Ser Gln Pro Asn
    50                  55                  60

Leu Leu Thr Ser Asn Phe Gln Val Thr Ile Ala Ser Arg Asn Pro Asn
65                  70                  75                  80

Ser Lys Ile Gly Ile Tyr Tyr Asp Arg Leu His Val Tyr Ala Thr Tyr
                85                  90                  95

Met Asn Gln Gln Ile Thr Leu Arg Thr Ala Ile Pro Pro Thr Tyr Gln
            100                 105                 110

Gly His Lys Glu Val Asn Val Trp Ser Pro Phe Val Tyr Gly Thr Ala
        115                 120                 125

Val Pro Ile Ala Pro Tyr Asn Ser Val Ala Leu Gly Glu Glu Lys Asp
    130                 135                 140

Arg Gly Phe Val Gly Leu Met Ile Arg Ala Asp Gly Thr Val Arg Trp
145                 150                 155                 160

Lys Val Arg Thr Leu Ile Thr Gly Lys Tyr His Ile His Val Arg Cys
                165                 170                 175

Gln Ala Phe Ile Asn Leu Gly Asn Lys Ala Ala Gly Val Leu Val Gly
            180                 185                 190

Asp Asn Ala Val Lys Tyr Thr Leu Ala Asn Lys Cys Ser Val Asn Val
        195                 200                 205


<210> SEQ ID NO 86
<211> LENGTH: 213
<212> TYPE: PRT
<213> ORGANISM: Arabidopsis thaliana

<400> SEQUENCE: 86

Met Ser Gln Ile Ser Ile Thr Ser Pro Lys His Cys Ala Lys Lys Gly
1               5                   10                  15

Gly Ile Asn Ile Asn Asn Arg His Lys Lys Leu Phe Phe Thr Phe Ser
            20                  25                  30

Thr Phe Phe Ser Gly Leu Leu Leu Ile Ile Phe Leu Val Trp Leu Ile
        35                  40                  45

Leu His Pro Glu Arg Pro Glu Phe Ser Leu Thr Glu Ala Asp Ile Tyr
    50                  55                  60

Ser Leu Asn Leu Thr Thr Ser Ser Thr His Leu Leu Asn Ser Ser Val
65                  70                  75                  80
```

```
Gln Leu Thr Leu Phe Ser Lys Asn Pro Asn Lys Lys Val Gly Ile Tyr
                85                  90                  95

Tyr Asp Lys Leu Leu Val Tyr Ala Ala Tyr Arg Gly Gln Gln Ile Thr
            100                 105                 110

Ser Glu Ala Ser Leu Pro Pro Phe Tyr Gln Ser His Glu Glu Ile Asn
        115                 120                 125

Leu Leu Thr Ala Phe Leu Gln Gly Thr Glu Leu Pro Val Ala Gln Ser
    130                 135                 140

Phe Gly Tyr Gln Ile Ser Arg Glu Arg Ser Thr Gly Lys Ile Ile Ile
145                 150                 155                 160

Gly Met Lys Met Asp Gly Lys Leu Arg Trp Lys Ile Gly Thr Trp Val
                165                 170                 175

Ser Gly Ala Tyr Arg Phe Asn Val Asn Cys Leu Ala Ile Val Ala Phe
            180                 185                 190

Gly Met Asn Met Thr Thr Pro Pro Leu Ala Ser Leu Gln Gly Thr Arg
        195                 200                 205

Cys Ser Thr Thr Ile
    210


<210> SEQ ID NO 87
<211> LENGTH: 265
<212> TYPE: PRT
<213> ORGANISM: Arabidopsis thaliana

<400> SEQUENCE: 87

Met Ala Gly Glu Thr Leu Leu Lys Pro Val Leu Gln Lys Pro Pro Gly
1               5                   10                  15

Tyr Arg Glu Leu His Ser Gln Pro Gln Thr Pro Leu Gly Ser Ser Ser
            20                  25                  30

Ser Ser Ser Ser Met Leu Arg Arg Pro Pro Lys His Ala Ile Pro Ala
        35                  40                  45

Ala Phe Tyr Pro Thr Lys Lys Arg Gln Trp Ser Arg Cys Arg Val Phe
    50                  55                  60

Cys Cys Cys Val Cys Ile Thr Val Ala Ile Val Ile Leu Leu Leu Ile
65                  70                  75                  80

Leu Thr Val Ser Val Phe Phe Leu Tyr Tyr Ser Pro Arg Leu Pro Val
                85                  90                  95

Val Arg Leu Ser Ser Phe Arg Val Ser Asn Phe Asn Phe Ser Gly Gly
            100                 105                 110

Lys Ala Gly Asp Gly Leu Ser Gln Leu Thr Ala Glu Ala Thr Ala Arg
        115                 120                 125

Leu Asp Phe Arg Asn Pro Asn Gly Lys Leu Arg Tyr Tyr Tyr Gly Asn
    130                 135                 140

Val Asp Val Ala Val Ser Val Gly Glu Asp Asp Phe Glu Thr Ser Leu
145                 150                 155                 160

Gly Ser Thr Lys Val Lys Gly Phe Val Glu Lys Pro Gly Asn Arg Thr
                165                 170                 175

Val Val Ile Val Pro Ile Lys Val Lys Lys Gln Gln Val Asp Asp Pro
            180                 185                 190

Thr Val Lys Arg Leu Arg Ala Asp Met Lys Ser Lys Lys Leu Val Val
        195                 200                 205

Lys Val Met Ala Lys Thr Lys Val Gly Leu Gly Val Gly Arg Arg Lys
    210                 215                 220

Ile Val Thr Val Gly Val Thr Ile Ser Cys Gly Gly Val Arg Leu Gln
```

```
225                 230                 235                 240

Thr Leu Asp Ser Lys Met Ser Lys Cys Thr Ile Lys Met Leu Lys Trp
                245                 250                 255

Tyr Val Pro Ile Gln Val Lys Cys Ile
            260                 265


<210> SEQ ID NO 88
<211> LENGTH: 210
<212> TYPE: PRT
<213> ORGANISM: Arabidopsis thaliana

<400> SEQUENCE: 88

Met Thr Thr Lys Asp Cys Gly Asn His Gly Gly Gly Gly Gly Gly Gly
1               5                   10                  15

Thr Ala Ser Arg Ile Cys Gly Val Ile Ile Gly Phe Ile Ile Ile Val
            20                  25                  30

Leu Ile Thr Ile Phe Leu Val Trp Ile Ile Leu Gln Pro Thr Lys Pro
        35                  40                  45

Arg Phe Ile Leu Gln Asp Ala Thr Val Tyr Ala Phe Asn Leu Ser Gln
    50                  55                  60

Pro Asn Leu Leu Thr Ser Asn Phe Gln Ile Thr Ile Ala Ser Arg Asn
65                  70                  75                  80

Arg Asn Ser Arg Ile Gly Ile Tyr Tyr Asp Arg Leu His Val Tyr Ala
                85                  90                  95

Thr Tyr Arg Asn Gln Gln Ile Thr Leu Arg Thr Ala Ile Pro Pro Thr
            100                 105                 110

Tyr Gln Gly His Lys Glu Asp Asn Val Trp Ser Pro Phe Val Tyr Gly
        115                 120                 125

Asn Ser Val Pro Ile Ala Pro Phe Asn Ala Val Ala Leu Gly Asp Glu
    130                 135                 140

Gln Asn Arg Gly Phe Val Thr Leu Ile Ile Arg Ala Asp Gly Arg Val
145                 150                 155                 160

Arg Trp Lys Val Gly Thr Leu Ile Thr Gly Lys Tyr His Leu His Val
                165                 170                 175

Arg Cys Gln Ala Phe Ile Asn Leu Ala Asp Lys Ala Ala Gly Val His
            180                 185                 190

Val Gly Glu Asn Ala Val Lys Tyr Met Leu Ile Asn Lys Cys Ser Val
        195                 200                 205

Asn Val
    210


<210> SEQ ID NO 89
<211> LENGTH: 300
<212> TYPE: PRT
<213> ORGANISM: Arabidopsis thaliana

<400> SEQUENCE: 89

Met Pro Ser Pro Pro Glu Glu Glu Thr Gln Pro Lys Pro Asp Thr Gly
1               5                   10                  15

Pro Gly Gln Asn Ser Glu Arg Asp Ile Asn Gln Pro Pro Pro Pro Pro
            20                  25                  30

Pro Gln Ser Gln Pro Pro Pro Pro Gln Thr Gln Gln Gln Thr Tyr Pro
        35                  40                  45

Pro Val Met Gly Tyr Pro Gly Tyr His Gln Pro Pro Pro Pro Tyr Pro
    50                  55                  60

Asn Tyr Pro Asn Ala Pro Tyr Gln Gln Tyr Pro Tyr Ala Gln Ala Pro
```

-continued

```
65                  70                  75                  80

Pro Ala Ser Tyr Tyr Gly Ser Ser Tyr Pro Ala Gln Gln Asn Pro Val
                85                  90                  95

Tyr Gln Arg Pro Ala Ser Ser Gly Phe Val Arg Gly Ile Phe Thr Gly
            100                 105                 110

Leu Ile Val Leu Val Val Leu Leu Cys Ile Ser Thr Thr Ile Thr Trp
        115                 120                 125

Leu Val Leu Arg Pro Gln Ile Pro Leu Phe Ser Val Asn Asn Phe Ser
    130                 135                 140

Val Ser Asn Phe Asn Val Thr Gly Pro Val Phe Ser Ala Gln Trp Thr
145                 150                 155                 160

Ala Asn Leu Thr Ile Glu Asn Gln Asn Thr Lys Leu Lys Gly Tyr Phe
                165                 170                 175

Asp Arg Ile Gln Gly Leu Val Tyr His Gln Asn Ala Val Gly Glu Asp
            180                 185                 190

Glu Phe Leu Ala Thr Ala Phe Phe Gln Pro Val Phe Val Glu Thr Lys
        195                 200                 205

Lys Ser Val Val Ile Gly Glu Thr Leu Thr Ala Gly Asp Lys Glu Gln
    210                 215                 220

Pro Lys Val Pro Ser Trp Val Val Asp Glu Met Lys Lys Glu Arg Glu
225                 230                 235                 240

Thr Gly Thr Val Thr Phe Ser Leu Arg Met Ala Val Trp Val Thr Phe
                245                 250                 255

Lys Thr Asp Gly Trp Ala Ala Arg Glu Ser Gly Leu Lys Val Phe Cys
            260                 265                 270

Gly Lys Leu Lys Val Gly Phe Glu Gly Ile Ser Gly Asn Gly Ala Val
        275                 280                 285

Leu Leu Pro Lys Pro Leu Pro Cys Val Val Tyr Val
    290                 295                 300


<210> SEQ ID NO 90
<211> LENGTH: 211
<212> TYPE: PRT
<213> ORGANISM: Arabidopsis thaliana

<400> SEQUENCE: 90

Met Thr Thr Lys Glu Cys Gly Asn His Gly Gly Gly Gly Gly Gly Gly
1               5                   10                  15

Gly Thr Ala Cys Arg Ile Cys Gly Ala Ile Ile Gly Phe Ile Ile Ile
            20                  25                  30

Val Leu Met Thr Ile Phe Leu Val Trp Ile Ile Leu Gln Pro Lys Asn
        35                  40                  45

Pro Glu Phe Ile Leu Gln Asp Thr Thr Val Tyr Ala Phe Asn Leu Ser
    50                  55                  60

Gln Pro Asn Leu Leu Thr Ser Lys Phe Gln Ile Thr Ile Ala Ser Arg
65                  70                  75                  80

Asn Arg Asn Ser Asn Ile Gly Ile Tyr Tyr Asp His Leu His Ala Tyr
                85                  90                  95

Ala Ser Tyr Arg Asn Gln Gln Ile Thr Leu Ala Ser Asp Leu Pro Pro
            100                 105                 110

Thr Tyr Gln Arg His Lys Glu Asp Ser Val Trp Ser Pro Leu Leu Tyr
        115                 120                 125

Gly Asn Gln Val Pro Ile Ala Pro Phe Asn Ala Val Ala Leu Gly Asp
    130                 135                 140
```

-continued

```
Glu Gln Asn Ser Gly Val Phe Thr Leu Thr Ile Cys Val Asp Gly Gln
145                 150                 155                 160

Val Arg Trp Lys Val Gly Thr Leu Thr Ile Gly Asn Tyr His Leu His
                165                 170                 175

Val Arg Cys Gln Ala Phe Ile Asn Gln Ala Asp Lys Ala Ala Gly Val
            180                 185                 190

His Val Gly Glu Asn Thr Val Lys Tyr Thr Leu Ile Asn Lys Cys Ser
        195                 200                 205

Val Asn Phe
    210


<210> SEQ ID NO 91
<211> LENGTH: 211
<212> TYPE: PRT
<213> ORGANISM: Arabidopsis thaliana

<400> SEQUENCE: 91

Met Thr Thr Lys Glu Cys Gly Asn His Gly Gly Gly Gly Gly Gly Gly
1               5                   10                  15

Gly Thr Ala Cys Arg Ile Cys Gly Ala Ile Ile Gly Phe Ile Ile Ile
            20                  25                  30

Val Leu Met Thr Ile Phe Leu Val Ser Ile Ile Leu Gln Pro Lys Lys
        35                  40                  45

Pro Glu Phe Ile Leu Gln Asp Thr Thr Val Tyr Ala Phe Asn Leu Ser
    50                  55                  60

Gln Pro Asn Leu Leu Thr Ser Lys Phe Gln Ile Thr Ile Ala Ser Arg
65                  70                  75                  80

Asn Arg Asn Ser Asn Ile Gly Ile Tyr Tyr Asp His Leu His Ala Tyr
                85                  90                  95

Ala Ser Tyr Arg Asn Gln Gln Ile Thr Leu Ala Ser Asp Leu Pro Pro
            100                 105                 110

Thr Tyr Gln Arg His Lys Glu Asn Ser Val Trp Ser Pro Leu Leu Tyr
        115                 120                 125

Gly Asn Gln Val Pro Ile Ala Pro Phe Asn Ala Val Ala Leu Gly Asp
    130                 135                 140

Glu Gln Asn Ser Gly Val Phe Thr Leu Thr Ile Cys Val Asp Gly Arg
145                 150                 155                 160

Val Arg Trp Lys Val Gly Thr Leu Thr Ile Gly Asn Tyr His Leu His
                165                 170                 175

Val Arg Cys Gln Ala Phe Ile Asn Gln Ala Asp Lys Ala Ala Gly Val
            180                 185                 190

His Val Gly Glu Asn Thr Val Lys Tyr Thr Leu Ile Asn Lys Cys Ser
        195                 200                 205

Val Asn Phe
    210


<210> SEQ ID NO 92
<211> LENGTH: 356
<212> TYPE: PRT
<213> ORGANISM: Arabidopsis thaliana

<400> SEQUENCE: 92

Met Ser His His His His His Glu Thr Asn Pro His Phe Ala Arg Ile
1               5                   10                  15

Pro Ser Gln Asn Pro His Leu Lys Ser Gly Gly Ala Ser Thr Ser Gln
            20                  25                  30
```

-continued

```
Thr Ser Ser Asn Gln Pro His Ile Pro Pro Ile Pro His Pro Lys Lys
        35                  40                  45

Ser His His Lys Thr Thr Gln Pro His Pro Val Ala Pro Pro Gly Ile
    50                  55                  60

Leu Ile Lys Thr Arg Gly Arg His Arg Glu Asn Pro Ile Gln Glu Pro
65                  70                  75                  80

Lys His Ser Val Ile Pro Val Pro Leu Ser Pro Glu Glu Arg Leu Pro
                85                  90                  95

Pro Arg Lys Thr Gln Asn Ser Ser Lys Arg Pro Leu Leu Leu Ser Pro
            100                 105                 110

Glu Asp Asn Gln Gln Gln Arg Pro Pro Pro Pro Gln Ala Pro Gln Arg
        115                 120                 125

Asn Gly Gly Gly Tyr Gly Ser Thr Leu Pro Pro Ile Pro Lys Pro Ser
    130                 135                 140

Pro Trp Arg Thr Ala Pro Thr Pro Ser Pro His His Arg Arg Gly Pro
145                 150                 155                 160

Arg Leu Pro Pro Pro Ser Arg Glu Thr Asn Ala Met Thr Trp Ser Ala
                165                 170                 175

Ala Phe Cys Cys Ala Ile Phe Trp Val Ile Leu Ile Leu Gly Gly Leu
            180                 185                 190

Ile Ile Leu Ile Val Tyr Leu Val Tyr Arg Pro Arg Ser Pro Tyr Val
        195                 200                 205

Asp Ile Ser Ala Ala Asn Leu Asn Ala Ala Tyr Leu Asp Met Gly Phe
    210                 215                 220

Leu Leu Asn Gly Asp Leu Thr Ile Leu Ala Asn Val Thr Asn Pro Ser
225                 230                 235                 240

Lys Lys Ser Ser Val Glu Phe Ser Tyr Val Thr Phe Glu Leu Tyr Tyr
                245                 250                 255

Tyr Asn Thr Leu Ile Ala Thr Gln Tyr Ile Glu Pro Phe Lys Val Pro
            260                 265                 270

Lys Lys Thr Ser Met Phe Ala Asn Val His Leu Val Ser Ser Gln Val
        275                 280                 285

Gln Leu Gln Ala Thr Gln Ser Arg Glu Leu Gln Arg Gln Ile Glu Thr
    290                 295                 300

Gly Pro Val Leu Leu Asn Leu Arg Gly Met Phe His Ala Arg Ser His
305                 310                 315                 320

Ile Gly Pro Leu Phe Arg Tyr Ser Tyr Lys Leu His Thr His Cys Ser
                325                 330                 335

Val Ser Leu Asn Gly Pro Pro Leu Gly Ala Met Arg Ala Arg Arg Cys
            340                 345                 350

Asn Thr Lys Arg
        355


<210> SEQ ID NO 93
<211> LENGTH: 209
<212> TYPE: PRT
<213> ORGANISM: Arabidopsis thaliana

<400> SEQUENCE: 93

Met Lys Asp Cys Glu Asn His Gly His Ser Arg Arg Lys Leu Ile Arg
1               5                   10                  15

Arg Ile Phe Trp Ser Ile Ile Phe Val Leu Phe Ile Ile Phe Leu Thr
            20                  25                  30

Ile Leu Leu Ile Trp Ala Ile Leu Gln Pro Ser Lys Pro Arg Phe Ile
        35                  40                  45
```

```
Leu Gln Asp Ala Thr Val Tyr Ala Phe Asn Val Ser Gly Asn Pro Pro
    50                  55                  60

Asn Leu Leu Thr Ser Asn Phe Gln Ile Thr Leu Ser Ser Arg Asn Pro
65                  70                  75                  80

Asn Asn Lys Ile Gly Ile Tyr Tyr Asp Arg Leu Asp Val Tyr Ala Thr
                85                  90                  95

Tyr Arg Ser Gln Gln Ile Thr Phe Pro Thr Ser Ile Pro Pro Thr Tyr
            100                 105                 110

Gln Gly His Lys Asp Val Asp Ile Trp Ser Pro Phe Val Tyr Gly Thr
        115                 120                 125

Ser Val Pro Ile Ala Pro Phe Asn Gly Val Ser Leu Asp Thr Asp Lys
    130                 135                 140

Asp Asn Gly Val Val Leu Leu Ile Ile Arg Ala Asp Gly Arg Val Arg
145                 150                 155                 160

Trp Lys Val Gly Thr Phe Ile Thr Gly Lys Tyr His Leu His Val Lys
                165                 170                 175

Cys Pro Ala Tyr Ile Asn Phe Gly Asn Lys Ala Asn Gly Val Ile Val
            180                 185                 190

Gly Asp Asn Ala Val Lys Tyr Thr Phe Thr Thr Ser Cys Ser Val Ser
        195                 200                 205

Val


<210> SEQ ID NO 94
<211> LENGTH: 206
<212> TYPE: PRT
<213> ORGANISM: Arabidopsis thaliana

<400> SEQUENCE: 94

Met Thr Glu Lys Glu Cys Glu His His His Asp Glu Asp Glu Lys Met
1               5                   10                  15

Arg Lys Arg Ile Gly Ala Leu Val Leu Gly Phe Leu Ala Ala Val Leu
            20                  25                  30

Phe Val Val Phe Leu Val Trp Ala Ile Leu His Pro His Gly Pro Arg
        35                  40                  45

Phe Val Leu Gln Asp Ala Thr Ile Tyr Ala Phe Asn Val Ser Gln Pro
    50                  55                  60

Asn Tyr Leu Thr Ser Asn Leu Gln Val Thr Leu Ser Ser Arg Asn Pro
65                  70                  75                  80

Asn Asp Lys Ile Gly Ile Phe Tyr Asp Arg Leu Asp Ile Tyr Ala Ser
                85                  90                  95

Tyr Arg Asn Gln Gln Val Thr Leu Ala Thr Leu Leu Pro Ala Thr Tyr
            100                 105                 110

Gln Gly His Leu Asp Val Thr Ile Trp Ser Pro Phe Leu Tyr Gly Thr
        115                 120                 125

Thr Val Pro Val Ala Pro Tyr Phe Ser Pro Ala Leu Ser Gln Asp Leu
    130                 135                 140

Thr Ala Gly Met Val Leu Leu Asn Ile Lys Ile Asp Gly Trp Val Arg
145                 150                 155                 160

Trp Lys Val Gly Thr Trp Val Ser Gly Arg Tyr Arg Leu His Val Asn
                165                 170                 175

Cys Pro Ala Tyr Ile Thr Leu Ala Gly His Phe Ser Gly Asp Gly Pro
            180                 185                 190

Ala Val Lys Tyr Gln Leu Val Gln Arg Cys Ala Val Asp Val
        195                 200                 205
```

<210> SEQ ID NO 95
<211> LENGTH: 221
<212> TYPE: PRT
<213> ORGANISM: Arabidopsis thaliana

<400> SEQUENCE: 95

```
Met Val Pro Pro Asn Pro Ala His Gln Pro Ala Arg Arg Thr Gln Pro
1               5                   10                  15

Gln Leu Gln Pro Gln Ser Gln Pro Arg Ala Gln Pro Leu Pro Gly Arg
            20                  25                  30

Arg Met Asn Pro Val Leu Cys Ile Ile Val Ala Leu Val Leu Leu Gly
        35                  40                  45

Leu Leu Val Gly Leu Ala Ile Leu Ile Thr Tyr Leu Thr Leu Arg Pro
    50                  55                  60

Lys Arg Leu Ile Tyr Thr Val Glu Ala Ala Ser Val Gln Glu Phe Ala
65                  70                  75                  80

Ile Gly Asn Asn Asp Asp His Ile Asn Ala Lys Phe Ser Tyr Val Ile
                85                  90                  95

Lys Ser Tyr Asn Pro Glu Lys His Val Ser Val Arg Tyr His Ser Met
            100                 105                 110

Arg Ile Ser Thr Ala His His Asn Gln Ser Val Ala His Lys Asn Ile
        115                 120                 125

Ser Pro Phe Lys Gln Arg Pro Lys Asn Glu Thr Arg Ile Glu Thr Gln
    130                 135                 140

Leu Val Ser His Asn Val Ala Leu Ser Lys Phe Asn Ala Arg Asp Leu
145                 150                 155                 160

Arg Ala Glu Lys Ser Lys Gly Thr Ile Glu Met Glu Val Tyr Ile Thr
                165                 170                 175

Ala Arg Val Ser Tyr Lys Thr Trp Ile Phe Arg Ser Arg Arg Arg Thr
            180                 185                 190

Leu Lys Ala Val Cys Thr Pro Val Met Ile Asn Val Thr Ser Ser Ser
        195                 200                 205

Leu Asp Gly Phe Gln Arg Val Leu Cys Lys Thr Arg Leu
    210                 215                 220
```

<210> SEQ ID NO 96
<211> LENGTH: 220
<212> TYPE: PRT
<213> ORGANISM: Arabidopsis thaliana

<400> SEQUENCE: 96

```
Met Pro Pro Pro Pro Ser Ser Ser Arg Ala Gly Leu Asn Gly Asp Pro
1               5                   10                  15

Ile Ala Ala Gln Asn Gln Gln Pro Tyr Tyr Arg Ser Tyr Ser Ser Ser
            20                  25                  30

Ser Ser Ala Ser Leu Lys Gly Cys Cys Cys Cys Leu Phe Leu Leu Phe
        35                  40                  45

Ala Phe Leu Ala Leu Leu Val Leu Ala Val Val Leu Ile Val Ile Leu
    50                  55                  60

Ala Val Lys Pro Lys Lys Pro Gln Phe Asp Leu Gln Gln Val Ala Val
65                  70                  75                  80

Val Tyr Met Gly Ile Ser Asn Pro Ser Ala Val Leu Asp Pro Thr Thr
                85                  90                  95

Ala Ser Leu Ser Leu Thr Ile Arg Met Leu Phe Thr Ala Val Asn Pro
            100                 105                 110
```

```
Asn Lys Val Gly Ile Arg Tyr Gly Glu Ser Ser Phe Thr Val Met Tyr
        115                 120                 125

Lys Gly Met Pro Leu Gly Arg Ala Thr Val Pro Gly Phe Tyr Gln Asp
    130                 135                 140

Ala His Ser Thr Lys Asn Val Glu Ala Thr Ile Ser Val Asp Arg Val
145                 150                 155                 160

Asn Leu Met Gln Ala His Ala Ala Asp Leu Val Arg Asp Ala Ser Leu
                165                 170                 175

Asn Asp Arg Val Glu Leu Thr Val Arg Gly Asp Val Gly Ala Lys Ile
            180                 185                 190

Arg Val Met Asn Phe Asp Ser Pro Gly Val Gln Val Leu Leu Pro Ser
        195                 200                 205

Phe Leu Pro Ala Phe Cys Ser Leu Ser Asp Leu Ala
    210                 215                 220


<210> SEQ ID NO 97
<211> LENGTH: 207
<212> TYPE: PRT
<213> ORGANISM: Arabidopsis thaliana

<400> SEQUENCE: 97

Met Thr Ser Lys Asp Cys Gly Ser His Asp Ser His Ser Ser Cys Asn
1               5                   10                  15

Arg Lys Ile Val Ile Trp Thr Ile Ser Ile Ile Leu Leu Leu Ile Leu
            20                  25                  30

Val Val Ile Leu Leu Val Trp Ala Ile Leu Gln Pro Ser Lys Pro Arg
        35                  40                  45

Phe Val Leu Gln Asp Ala Thr Val Phe Asn Phe Asn Val Ser Gly Asn
    50                  55                  60

Pro Pro Asn Leu Leu Thr Ser Asn Phe Gln Phe Thr Leu Ser Ser Arg
65                  70                  75                  80

Asn Pro Asn Asp Lys Ile Gly Ile Tyr Tyr Asp Arg Leu Asp Val Tyr
                85                  90                  95

Ala Ser Tyr Arg Ser Gln Gln Ile Thr Leu Pro Ser Pro Met Leu Thr
            100                 105                 110

Thr Tyr Gln Gly His Lys Glu Val Asn Val Trp Ser Pro Phe Val Gly
        115                 120                 125

Gly Tyr Ser Val Pro Val Ala Pro Tyr Asn Ala Phe Tyr Leu Asp Gln
    130                 135                 140

Asp His Ser Ser Gly Ala Ile Met Leu Met Leu His Leu Asp Gly Arg
145                 150                 155                 160

Val Arg Trp Lys Val Gly Ser Phe Ile Thr Gly Lys Tyr His Leu His
                165                 170                 175

Val Arg Cys His Ala Leu Ile Asn Phe Gly Ser Ser Ala Ala Gly Val
            180                 185                 190

Ile Val Gly Lys Tyr Met Leu Thr Glu Thr Cys Ser Val Ser Val
        195                 200                 205


<210> SEQ ID NO 98
<211> LENGTH: 283
<212> TYPE: PRT
<213> ORGANISM: Arabidopsis thaliana

<400> SEQUENCE: 98

Met Ser Lys Phe Ser Pro Pro Pro Gln Ser Gln Pro Gln Pro Pro Glu
1               5                   10                  15
```

```
Thr Pro Pro Trp Glu Thr Pro Ser Ser Lys Trp Tyr Ser Pro Ile Tyr
            20                  25                  30

Thr Pro Trp Arg Thr Thr Pro Arg Ser Thr Gln Ser Thr Pro Thr Thr
        35                  40                  45

Thr Pro Ile Ala Leu Thr Glu Val Ile Val Ser Lys Ser Pro Leu Ser
    50                  55                  60

Asn Gln Lys Ser Pro Ala Thr Pro Lys Leu Asp Ser Met Glu Ala His
65                  70                  75                  80

Pro Leu His Glu Thr Met Val Leu Leu Gln Leu Arg Thr Ser Arg Thr
                85                  90                  95

Asn Pro Trp Ile Trp Cys Gly Ala Ala Leu Cys Phe Ile Phe Ser Ile
            100                 105                 110

Leu Leu Ile Val Phe Gly Ile Ala Thr Leu Ile Leu Tyr Leu Ala Val
        115                 120                 125

Lys Pro Arg Thr Pro Val Phe Asp Ile Ser Asn Ala Lys Leu Asn Thr
    130                 135                 140

Ile Leu Phe Glu Ser Pro Val Tyr Phe Asn Gly Asp Met Leu Leu Gln
145                 150                 155                 160

Leu Asn Phe Thr Asn Pro Asn Lys Lys Leu Asn Val Arg Phe Glu Asn
                165                 170                 175

Leu Met Val Glu Leu Trp Phe Ala Asp Thr Lys Ile Ala Thr Gln Gly
            180                 185                 190

Val Leu Pro Phe Ser Gln Arg Asn Gly Lys Thr Arg Leu Glu Pro Ile
        195                 200                 205

Arg Leu Ile Ser Asn Leu Val Phe Leu Pro Val Asn His Ile Leu Glu
    210                 215                 220

Leu Arg Arg Gln Val Thr Ser Asn Arg Ile Ala Tyr Glu Ile Arg Ser
225                 230                 235                 240

Asn Phe Arg Val Lys Ala Ile Phe Gly Met Ile His Tyr Ser Tyr Met
                245                 250                 255

Leu His Gly Ile Cys Gln Leu Gln Leu Ser Ser Pro Pro Ala Gly Gly
            260                 265                 270

Leu Val Tyr Arg Asn Cys Thr Thr Lys Arg Trp
        275                 280
```

<210> SEQ ID NO 99
<211> LENGTH: 219
<212> TYPE: PRT
<213> ORGANISM: Arabidopsis thaliana

<400> SEQUENCE: 99

```
Met Asn Asn Gln Asn Glu Asp Thr Glu Gly Gly Arg Asn Cys Cys Thr
1               5                   10                  15

Cys Cys Leu Ser Phe Ile Phe Thr Ala Gly Leu Thr Ser Leu Phe Leu
            20                  25                  30

Trp Leu Ser Leu Arg Ala Asp Lys Pro Lys Cys Ser Ile Gln Asn Phe
        35                  40                  45

Phe Ile Pro Ala Leu Gly Lys Asp Pro Asn Ser Arg Asp Asn Thr Thr
    50                  55                  60

Leu Asn Phe Met Val Arg Cys Asp Asn Pro Asn Lys Asp Lys Gly Ile
65                  70                  75                  80

Tyr Tyr Asp Asp Val His Leu Asn Phe Ser Thr Ile Asn Thr Thr Lys
                85                  90                  95

Ile Asn Ser Ser Ala Leu Val Leu Val Gly Asn Tyr Thr Val Pro Lys
```

-continued

```
            100                 105                 110

Phe Tyr Gln Gly His Lys Lys Lys Ala Lys Lys Trp Gly Gln Val Lys
        115                 120                 125

Pro Leu Asn Asn Gln Thr Val Leu Arg Ala Val Leu Pro Asn Gly Ser
    130                 135                 140

Ala Val Phe Arg Leu Asp Leu Lys Thr Gln Val Arg Phe Lys Ile Val
145                 150                 155                 160

Phe Trp Lys Thr Lys Arg Tyr Gly Val Glu Val Gly Ala Asp Val Glu
                165                 170                 175

Val Asn Gly Asp Gly Val Lys Ala Gln Lys Lys Gly Ile Lys Met Lys
            180                 185                 190

Lys Ser Asp Ser Ser Phe Pro Leu Arg Ser Ser Phe Pro Ile Ser Val
        195                 200                 205

Leu Met Asn Leu Leu Val Phe Phe Ala Ile Arg
    210                 215


<210> SEQ ID NO 100
<211> LENGTH: 235
<212> TYPE: PRT
<213> ORGANISM: Arabidopsis thaliana

<400> SEQUENCE: 100

Met Ser Asp Phe Ser Ile Lys Pro Asp Asp Lys Lys Glu Glu Glu Lys
1               5                   10                  15

Pro Ala Thr Ala Met Leu Pro Pro Pro Lys Pro Asn Ala Ser Ser Met
            20                  25                  30

Glu Thr Gln Ser Ala Asn Thr Gly Thr Ala Lys Lys Leu Arg Arg Lys
        35                  40                  45

Arg Asn Cys Lys Ile Cys Ile Cys Phe Thr Ile Leu Leu Ile Leu Leu
    50                  55                  60

Ile Ala Ile Val Ile Val Ile Leu Ala Phe Thr Leu Phe Lys Pro Lys
65                  70                  75                  80

Arg Pro Thr Thr Thr Ile Asp Ser Val Thr Val Asp Arg Leu Gln Ala
                85                  90                  95

Ser Val Asn Pro Leu Leu Leu Lys Val Leu Leu Asn Leu Thr Leu Asn
            100                 105                 110

Val Asp Leu Ser Leu Lys Asn Pro Asn Arg Ile Gly Phe Ser Tyr Asp
        115                 120                 125

Ser Ser Ser Ala Leu Leu Asn Tyr Arg Gly Gln Val Ile Gly Glu Ala
    130                 135                 140

Pro Leu Pro Ala Asn Arg Ile Ala Ala Arg Lys Thr Val Pro Leu Asn
145                 150                 155                 160

Ile Thr Leu Thr Leu Met Ala Asp Arg Leu Leu Ser Glu Thr Gln Leu
                165                 170                 175

Leu Ser Asp Val Met Ala Gly Val Ile Pro Leu Asn Thr Phe Val Lys
            180                 185                 190

Val Thr Gly Lys Val Thr Val Leu Lys Ile Phe Lys Ile Lys Val Gln
        195                 200                 205

Ser Ser Ser Ser Cys Asp Leu Ser Ile Ser Val Ser Asp Arg Asn Val
    210                 215                 220

Thr Ser Gln His Cys Lys Tyr Ser Thr Lys Leu
225                 230                 235


<210> SEQ ID NO 101
<211> LENGTH: 220
```

<212> TYPE: PRT
<213> ORGANISM: Arabidopsis thaliana

<400> SEQUENCE: 101

Met Thr Lys Ile Asp Pro Glu Glu Glu Leu Gly Arg Lys Cys Cys Thr
1 5 10 15

Cys Phe Phe Lys Phe Ile Phe Thr Thr Arg Leu Gly Ala Leu Ile Leu
20 25 30

Trp Leu Ser Leu Arg Ala Lys Lys Pro Lys Cys Ser Ile Gln Asn Phe
35 40 45

Tyr Ile Pro Ala Leu Ser Lys Asn Leu Ser Ser Arg Asp Asn Thr Thr
50 55 60

Leu Asn Phe Met Val Arg Cys Asp Asn Pro Asn Lys Asp Lys Gly Ile
65 70 75 80

Tyr Tyr Asp Asp Val His Leu Thr Phe Ser Thr Ile Asn Thr Thr Thr
85 90 95

Thr Asn Ser Ser Asp Leu Val Leu Val Ala Asn Tyr Thr Val Pro Lys
100 105 110

Phe Tyr Gln Gly His Lys Lys Lys Ala Lys Lys Trp Gly Gln Val Trp
115 120 125

Pro Leu Asn Asn Gln Thr Val Leu Arg Ala Val Leu Pro Asn Gly Ser
130 135 140

Ala Val Phe Arg Leu Asp Leu Lys Thr His Val Arg Phe Lys Ile Val
145 150 155 160

Phe Trp Lys Thr Lys Trp Tyr Arg Arg Ile Lys Val Gly Ala Asp Val
165 170 175

Glu Val Asn Gly Asp Gly Val Lys Ala Gln Lys Lys Gly Ser Lys Thr
180 185 190

Lys Lys Ser Asp Ser Ser Leu Pro Leu Arg Ser Ser Phe Pro Ile Phe
195 200 205

Val Leu Met Asn Leu Leu Val Phe Phe Ala Ile Arg
210 215 220

<210> SEQ ID NO 102
<211> LENGTH: 429
<212> TYPE: PRT
<213> ORGANISM: Arabidopsis thaliana

<400> SEQUENCE: 102

Met Ser His Val Thr Ala Thr Ser Leu Ala Arg Phe Thr Lys Pro Val
1 5 10 15

Pro Lys Pro Ala Ser Ser Pro Ile Val Asn Thr Lys Leu Thr Thr Ser
20 25 30

Gly Gly Arg Thr Ala Ala Phe Met Asp Leu Ser Ser Phe Arg Leu Thr
35 40 45

Val Trp Asp Pro Asp Thr Ala Asn Asp Ser Ser Gly Lys Phe Pro Trp
50 55 60

Pro Arg Phe Leu Phe Phe Phe Leu Thr Leu Lys Thr Gly Gly Ser Gly
65 70 75 80

Leu Asn Ile Lys Pro Thr Ile Ser Ala Ile Ala Gln Met Met Asn Pro
85 90 95

Met Thr Ile Thr Glu Met Asn Asn Gln Met His Arg Leu Glu Gln Lys
100 105 110

Leu Leu Leu Phe Leu Pro Gly Ser Leu Phe Leu Arg Leu Ser Thr Ile
115 120 125

-continued

```
Leu His Tyr Pro Gly Glu Gly Ser Asn Arg Pro Asp Pro Leu Glu His
    130                 135                 140

Ala Leu Arg Arg Ser Arg Ser Leu Gly Leu Asp Gln Glu Glu Ala Ala
145                 150                 155                 160

Lys Lys Val Ile Arg Val Gly Arg Asp Ser Lys Asn Asp Tyr Val Asn
                165                 170                 175

Val Val Glu Asn Gln Ala Ala Ser Phe Leu Arg Arg Cys Gly Pro Ser
            180                 185                 190

Lys Arg Ile Gln Ser Val Asn Tyr Cys Lys Ser Thr Arg Gln Gly His
        195                 200                 205

Glu Ile Pro Asp Val Lys Pro Leu Phe Pro Thr Gly Gly Gly Thr Gln
    210                 215                 220

Ala Pro Ser Arg Ser Arg Ala Arg Tyr Ala Val Pro Ala Ile Leu Leu
225                 230                 235                 240

Gly Phe Ala Gly Phe Val Gly Phe Leu His Tyr Asn Asp Glu Arg Arg
                245                 250                 255

Ala Val Pro Arg Gly Gln Ala Ser Ser Asn Ser Gly Cys Gly Cys Gly
            260                 265                 270

Ser Asn Thr Thr Val Lys Gly Pro Ile Ile Gly Gly Pro Phe Thr Leu
        275                 280                 285

Val Ser Thr Glu Asn Lys Ile Val Thr Glu Asn Asp Phe Cys Gly Lys
    290                 295                 300

Trp Val Leu Leu Tyr Phe Gly Tyr Ser Phe Ser Pro Asp Val Gly Pro
305                 310                 315                 320

Glu Gln Leu Lys Met Met Ser Lys Ala Val Asp Lys Leu Ala Ile Leu
                325                 330                 335

Leu Asn Pro Leu Thr Phe Gly Cys Leu Tyr Leu Tyr Ala Glu Phe Asp
            340                 345                 350

Ser Arg Ile Leu Gly Leu Thr Gly Thr Ala Ser Ala Met Arg Gln Met
        355                 360                 365

Ala Gln Glu Tyr Arg Val Tyr Phe Lys Lys Val Gln Glu Asp Gly Glu
    370                 375                 380

Asp Tyr Leu Val Asp Thr Ser His Asn Met Tyr Leu Ile Asn Pro Lys
385                 390                 395                 400

Met Glu Ile Val Arg Cys Phe Gly Val Glu Tyr Asn Pro Asp Glu Leu
                405                 410                 415

Ser Gln Glu Leu Leu Lys Glu Val Ala Ser Val Ser Gln
            420                 425


<210> SEQ ID NO 103
<211> LENGTH: 416
<212> TYPE: PRT
<213> ORGANISM: Arabidopsis thaliana

<400> SEQUENCE: 103

Met Val Arg Ser Asn Asp Val Lys Phe Gln Val Tyr Asp Ala Glu Leu
1               5                   10                  15

Thr His Phe Asp Leu Glu Ser Asn Asn Asn Leu Gln Tyr Ser Leu Ser
            20                  25                  30

Leu Asn Leu Ser Ile Arg Asn Ser Lys Ser Ser Ile Gly Ile His Tyr
        35                  40                  45

Asp Arg Phe Glu Ala Thr Val Tyr Tyr Met Asn Gln Arg Leu Gly Ala
    50                  55                  60

Val Pro Met Pro Leu Phe Tyr Leu Gly Ser Lys Asn Thr Met Leu Leu
65                  70                  75                  80
```

-continued

```
Arg Ala Leu Phe Glu Gly Gln Thr Leu Val Leu Leu Lys Gly Asn Glu
                85                  90                  95

Arg Lys Lys Phe Glu Asp Asp Gln Lys Thr Gly Val Tyr Arg Ile Asp
            100                 105                 110

Val Lys Leu Ser Ile Asn Phe Arg Val Met Val Leu His Leu Val Thr
        115                 120                 125

Trp Pro Met Lys Pro Val Val Arg Cys His Leu Lys Ile Pro Leu Ala
    130                 135                 140

Leu Gly Ser Ser Asn Ser Thr Gly Gly His Lys Lys Met Leu Leu Ile
145                 150                 155                 160

Gly Gln Leu Val Lys Asp Thr Ser Ala Asn Leu Arg Glu Ala Ser Glu
                165                 170                 175

Thr Asp His Arg Arg Asp Val Ala Gln Ser Lys Lys Ile Ala Asp Ala
            180                 185                 190

Lys Leu Ala Lys Asp Phe Glu Ala Ala Leu Lys Glu Phe Gln Lys Ala
        195                 200                 205

Gln His Ile Thr Val Glu Arg Glu Thr Ser Tyr Ile Pro Phe Asp Pro
    210                 215                 220

Lys Gly Ser Phe Ser Ser Ser Glu Val Asp Ile Gly Tyr Asp Arg Ser
225                 230                 235                 240

Gln Glu Gln Arg Val Leu Met Glu Ser Arg Arg Gln Glu Ile Val Leu
                245                 250                 255

Leu Asp Asn Glu Ile Ser Leu Asn Glu Ala Arg Ile Glu Ala Arg Glu
            260                 265                 270

Gln Gly Ile Gln Glu Val Lys His Gln Ile Ser Glu Val Met Glu Met
        275                 280                 285

Phe Lys Asp Leu Ala Val Met Val Asp His Gln Gly Thr Ile Asp Asp
    290                 295                 300

Ile Asp Glu Lys Ile Asp Asn Leu Arg Ser Ala Ala Ala Gln Gly Lys
305                 310                 315                 320

Ser His Leu Val Lys Ala Ser Asn Thr Gln Gly Ser Asn Ser Ser Leu
                325                 330                 335

Leu Phe Ser Cys Ser Leu Leu Leu Phe Phe Phe Leu Ser Gly Asp Leu
            340                 345                 350

Cys Arg Cys Val Cys Val Gly Ser Glu Asn Pro Arg Leu Asn Pro Thr
        355                 360                 365

Arg Arg Lys Ala Trp Cys Glu Glu Glu Asp Glu Glu Gln Arg Lys Lys
    370                 375                 380

Gln Gln Lys Lys Lys Thr Met Ser Glu Lys Arg Arg Arg Glu Glu Lys
385                 390                 395                 400

Lys Val Asn Lys Pro Asn Gly Phe Val Phe Cys Val Leu Gly His Lys
                405                 410                 415


<210> SEQ ID NO 104
<211> LENGTH: 317
<212> TYPE: PRT
<213> ORGANISM: Arabidopsis thaliana

<400> SEQUENCE: 104

Met Ser His His His Tyr Glu Thr Asn Pro His Phe Val Gln Phe Ser
1               5                   10                  15

Leu Gln Asp Gln His Gln Gly Gly Pro Ser Ser Ser Trp Asn Ser Pro
            20                  25                  30

His His His Gln Ile Pro Gln Ala His Ser Val Ala Pro Pro Arg Val
```

-continued

```
        35                  40                  45

Lys Ile Lys Thr Arg Gly Arg His Gln Thr Glu Pro Pro Glu Thr Ile
    50                  55                  60

His Glu Ser Pro Ser Ser Arg Pro Leu Pro Leu Arg Pro Glu Glu Pro
65                  70                  75                  80

Leu Pro Pro Arg His Asn Pro Asn Ser Ala Arg Pro Leu Gln Leu Ser
                85                  90                  95

Pro Glu Glu Gln Arg Pro Pro His Arg Gly Tyr Gly Ser Glu Pro Thr
            100                 105                 110

Pro Trp Arg Arg Ala Pro Thr Arg Pro Ala Tyr Gln Gln Gly Pro Lys
        115                 120                 125

Arg Thr Lys Pro Met Thr Leu Pro Ala Thr Ile Cys Cys Ala Ile Leu
    130                 135                 140

Leu Ile Val Leu Ile Leu Ser Gly Leu Ile Leu Leu Leu Val Tyr Leu
145                 150                 155                 160

Ala Asn Arg Pro Arg Ser Pro Tyr Phe Asp Ile Ser Ala Ala Thr Leu
                165                 170                 175

Asn Thr Ala Asn Leu Asp Met Gly Tyr Val Leu Asn Gly Asp Leu Ala
            180                 185                 190

Val Val Val Asn Phe Thr Asn Pro Ser Lys Lys Ser Ser Val Asp Phe
        195                 200                 205

Ser Tyr Val Met Phe Glu Leu Tyr Phe Tyr Asn Thr Leu Ile Ala Thr
    210                 215                 220

Glu His Ile Glu Pro Phe Ile Val Pro Lys Gly Met Ser Met Phe Thr
225                 230                 235                 240

Ser Phe His Leu Val Ser Ser Gln Val Gln Ile Gln Met Ile Gln Ser
                245                 250                 255

Gln Asp Leu Gln Leu Gln Leu Gly Thr Gly Pro Val Leu Leu Asn Leu
            260                 265                 270

Arg Gly Thr Phe His Ala Arg Ser Asn Leu Gly Ser Leu Met Arg Tyr
        275                 280                 285

Ser Tyr Trp Leu His Thr Gln Cys Ser Ile Ser Leu Asn Thr Pro Pro
    290                 295                 300

Ala Gly Thr Met Arg Ala Arg Arg Cys Asn Thr Lys Arg
305                 310                 315


<210> SEQ ID NO 105
<211> LENGTH: 198
<212> TYPE: PRT
<213> ORGANISM: Arabidopsis thaliana

<400> SEQUENCE: 105

Met Pro Arg Leu Thr Ser Arg His Gly Thr Ser Pro Phe Ile Trp Cys
1               5                   10                  15

Ala Ala Ile Ile Cys Ala Ile Ile Ser Ile Val Val Ile Val Gly Gly
            20                  25                  30

Ile Ile Val Phe Val Gly Tyr Leu Val Ile His Pro Arg Val Pro Ile
        35                  40                  45

Ile Ser Val Ala Asp Ala His Leu Asp Phe Leu Lys Tyr Asp Ile Val
    50                  55                  60

Gly Val Leu Gln Thr Gln Leu Thr Ile Val Ile Arg Val Glu Asn Asp
65                  70                  75                  80

Asn Ala Lys Ala His Ala Leu Phe Asp Glu Thr Glu Phe Lys Leu Ser
                85                  90                  95
```

-continued

```
Tyr Glu Gly Lys Pro Ile Ala Ile Leu Lys Ala Pro Glu Phe Glu Val
            100                 105                 110

Val Lys Glu Lys Ser Met Phe Leu Pro Tyr Leu Val Gln Ser Tyr Pro
        115                 120                 125

Ile Pro Leu Asn Pro Thr Met Met Gln Ala Val Asp Tyr Ala Val Lys
    130                 135                 140

Lys Asp Val Ile Thr Phe Glu Leu Lys Gly Gly Ser Arg Thr Arg Trp
145                 150                 155                 160

Arg Val Gly Pro Leu Gly Ser Val Lys Phe Glu Cys Asn Leu Ser Cys
                165                 170                 175

Gln Leu Arg Phe Arg Pro Ser Asp His Ser Tyr Ile Pro Ser Pro Cys
            180                 185                 190

Thr Ser Ala His Lys His
        195


<210> SEQ ID NO 106
<211> LENGTH: 222
<212> TYPE: PRT
<213> ORGANISM: Arabidopsis thaliana

<400> SEQUENCE: 106

Met Asp Arg Asp Asp Ala Trp Glu Trp Phe Val Thr Ile Val Gly Ser
1               5                   10                  15

Leu Met Thr Leu Leu Tyr Val Ser Phe Leu Leu Ala Leu Cys Leu Trp
            20                  25                  30

Leu Ser Thr Leu Val His His Ile Pro Arg Cys Ser Ile His Tyr Phe
        35                  40                  45

Tyr Ile Pro Ala Leu Asn Lys Ser Leu Ile Ser Ser Asp Asn Thr Thr
    50                  55                  60

Leu Asn Phe Met Val Arg Leu Lys Asn Ile Asn Ala Lys Gln Gly Ile
65                  70                  75                  80

Tyr Tyr Glu Asp Leu His Leu Ser Phe Ser Thr Arg Ile Asn Asn Ser
                85                  90                  95

Ser Leu Leu Val Ala Asn Tyr Thr Val Pro Arg Phe Tyr Gln Gly His
            100                 105                 110

Glu Lys Lys Ala Lys Lys Trp Gly Gln Ala Leu Pro Phe Asn Asn Gln
        115                 120                 125

Thr Val Ile Gln Ala Val Leu Pro Asn Gly Ser Ala Ile Phe Arg Val
    130                 135                 140

Asp Leu Lys Met Gln Val Lys Tyr Lys Val Met Ser Trp Lys Thr Lys
145                 150                 155                 160

Arg Tyr Lys Leu Lys Ala Ser Val Asn Leu Glu Val Asn Glu Asp Gly
                165                 170                 175

Ala Thr Lys Val Lys Asp Lys Glu Asp Gly Ile Lys Met Lys Ile Ser
            180                 185                 190

Asp Ser Ser Pro Gln Arg Leu Thr Phe Phe Gln Val Cys Phe Ser Ile
        195                 200                 205

Ile Cys Val Leu Met Asn Trp Leu Ile Phe Leu Ala Ile Arg
    210                 215                 220


<210> SEQ ID NO 107
<211> LENGTH: 200
<212> TYPE: PRT
<213> ORGANISM: Arabidopsis thaliana

<400> SEQUENCE: 107
```

-continued

```
Met Val Leu Thr Lys Pro Ala Thr Val Arg Phe Asn Gly Leu Asp Ala
1               5                   10                  15

Glu Pro Arg Lys Asp Arg Val Ile Leu Arg Gln Pro Arg Ser Ser Arg
            20                  25                  30

Thr Ser Leu Trp Ile Trp Cys Val Ala Val Phe Leu Ala Ile Arg Pro
        35                  40                  45

Arg Ile Pro Val Phe Asp Ile Pro Asn Ala Asn Leu His Thr Ile Tyr
    50                  55                  60

Phe Asp Thr Pro Glu Phe Phe Asn Gly Asp Leu Ser Met Leu Val Asn
65                  70                  75                  80

Phe Thr Asn Pro Asn Lys Lys Ile Glu Val Lys Phe Glu Lys Leu Arg
                85                  90                  95

Ile Glu Leu Phe Phe Phe Asn Arg Leu Ile Ala Ala Gln Val Val Gln
            100                 105                 110

Pro Phe Leu Gln Lys Lys His Glu Thr Arg Leu Glu Pro Ile Arg Leu
        115                 120                 125

Ile Ser Ser Leu Val Gly Leu Pro Val Asn His Ala Val Glu Leu Arg
    130                 135                 140

Arg Gln Leu Glu Asn Asn Lys Ile Glu Tyr Glu Ile Arg Gly Thr Phe
145                 150                 155                 160

Lys Val Lys Ala His Phe Gly Met Ile His Tyr Ser Tyr Gln Leu His
                165                 170                 175

Gly Arg Cys Gln Leu Gln Met Thr Gly Pro Pro Thr Gly Ile Leu Ile
            180                 185                 190

Ser Arg Asn Cys Thr Thr Lys Lys
        195                 200
```

<210> SEQ ID NO 108
<211> LENGTH: 320
<212> TYPE: PRT
<213> ORGANISM: Arabidopsis thaliana

<400> SEQUENCE: 108

```
Met His Ala Lys Thr Asp Ser Glu Val Thr Ser Leu Ser Ala Ser Ser
1               5                   10                  15

Pro Thr Arg Ser Pro Arg Arg Pro Ala Tyr Phe Val Gln Ser Pro Ser
            20                  25                  30

Arg Asp Ser His Asp Gly Glu Lys Thr Ala Thr Ser Phe His Ser Thr
        35                  40                  45

Pro Val Leu Thr Ser Pro Met Gly Ser Pro Pro His Ser His Ser Ser
    50                  55                  60

Ser Ser Arg Phe Ser Lys Ile Asn Gly Ser Lys Arg Lys Gly His Ala
65                  70                  75                  80

Gly Glu Lys Gln Phe Ala Met Ile Glu Glu Glu Gly Leu Leu Asp Asp
                85                  90                  95

Gly Asp Arg Glu Gln Glu Ala Leu Pro Arg Arg Cys Tyr Val Leu Ala
            100                 105                 110

Phe Ile Val Gly Phe Ser Leu Leu Phe Ala Phe Phe Ser Leu Ile Leu
        115                 120                 125

Tyr Ala Ala Ala Lys Pro Gln Lys Pro Lys Ile Ser Val Lys Ser Ile
    130                 135                 140

Thr Phe Glu Gln Leu Lys Val Gln Ala Gly Gln Asp Ala Gly Gly Ile
145                 150                 155                 160

Gly Thr Asp Met Ile Thr Met Asn Ala Thr Leu Arg Met Leu Tyr Arg
                165                 170                 175
```

```
Asn Thr Gly Thr Phe Phe Gly Val His Val Thr Ser Ser Pro Ile Asp
            180                 185                 190

Leu Ser Phe Ser Gln Ile Thr Ile Gly Ser Gly Ser Ile Lys Lys Phe
        195                 200                 205

Tyr Gln Ser Arg Lys Ser Gln Arg Thr Val Val Val Asn Val Leu Gly
    210                 215                 220

Asp Lys Ile Pro Leu Tyr Gly Ser Gly Ser Thr Leu Val Pro Pro Pro
225                 230                 235                 240

Pro Pro Ala Pro Ile Pro Lys Pro Lys Lys Lys Lys Gly Pro Ile Val
                245                 250                 255

Ile Val Glu Pro Pro Ala Pro Pro Ala Pro Val Pro Met Arg Leu Asn
            260                 265                 270

Phe Thr Val Arg Ser Arg Ala Tyr Val Leu Gly Lys Leu Val Gln Pro
        275                 280                 285

Lys Phe Tyr Lys Arg Ile Val Cys Leu Ile Asn Phe Glu His Lys Lys
    290                 295                 300

Leu Ser Lys His Ile Pro Ile Thr Asn Asn Cys Thr Val Thr Ser Ile
305                 310                 315                 320


<210> SEQ ID NO 109
<211> LENGTH: 342
<212> TYPE: PRT
<213> ORGANISM: Arabidopsis thaliana

<400> SEQUENCE: 109

Met His Ala Lys Thr Asp Ser Glu Val Thr Ser Leu Ala Ala Ser Ser
1               5                   10                  15

Pro Ala Arg Ser Pro Arg Arg Pro Val Tyr Tyr Val Gln Ser Pro Ser
            20                  25                  30

Arg Asp Ser His Asp Gly Glu Lys Thr Ala Thr Ser Phe His Ser Thr
        35                  40                  45

Pro Val Leu Ser Pro Met Gly Ser Pro Pro His Ser His Ser Ser Met
    50                  55                  60

Gly Arg His Ser Arg Glu Ser Ser Ser Ser Arg Phe Ser Gly Ser Leu
65                  70                  75                  80

Lys Pro Gly Ser Arg Lys Val Asn Pro Asn Asp Gly Ser Lys Arg Lys
                85                  90                  95

Gly His Gly Gly Glu Lys Gln Trp Lys Glu Cys Ala Val Ile Glu Glu
            100                 105                 110

Glu Gly Leu Leu Asp Asp Gly Asp Arg Asp Gly Gly Val Pro Arg Arg
        115                 120                 125

Cys Tyr Val Leu Ala Phe Ile Val Gly Phe Phe Ile Leu Phe Gly Phe
    130                 135                 140

Phe Ser Leu Ile Leu Tyr Gly Ala Ala Lys Pro Met Lys Pro Lys Ile
145                 150                 155                 160

Thr Val Lys Ser Ile Thr Phe Glu Thr Leu Lys Ile Gln Ala Gly Gln
                165                 170                 175

Asp Ala Gly Gly Val Gly Thr Asp Met Ile Thr Met Asn Ala Thr Leu
            180                 185                 190

Arg Met Leu Tyr Arg Asn Thr Gly Thr Phe Phe Gly Val His Val Thr
        195                 200                 205

Ser Thr Pro Ile Asp Leu Ser Phe Ser Gln Ile Lys Ile Gly Ser Gly
    210                 215                 220

Ser Val Lys Lys Phe Tyr Gln Gly Arg Lys Ser Glu Arg Thr Val Leu
```

```
225                 230                 235                 240

Val His Val Ile Gly Glu Lys Ile Pro Leu Tyr Gly Ser Gly Ser Thr
                245                 250                 255

Leu Leu Pro Pro Ala Pro Pro Ala Pro Leu Pro Lys Pro Lys Lys Lys
            260                 265                 270

Lys Gly Ala Pro Val Pro Ile Pro Asp Pro Pro Ala Pro Pro Ala Pro
        275                 280                 285

Val Pro Met Thr Leu Ser Phe Val Val Arg Ser Arg Ala Tyr Val Leu
    290                 295                 300

Gly Lys Leu Val Gln Pro Lys Phe Tyr Lys Lys Ile Glu Cys Asp Ile
305                 310                 315                 320

Asn Phe Glu His Lys Asn Leu Asn Lys His Ile Val Ile Thr Lys Asn
                325                 330                 335

Cys Thr Val Thr Thr Val
            340


<210> SEQ ID NO 110
<211> LENGTH: 242
<212> TYPE: PRT
<213> ORGANISM: Arabidopsis thaliana

<400> SEQUENCE: 110

Met Asp Asp Glu Gln Asn Leu Val Glu Glu Met Asn Gln Gln Leu Leu
1               5                   10                  15

Ile Thr Val Ile Asp Thr Glu Lys Val Pro Glu Leu Arg Pro Ile Ser
            20                  25                  30

Ser Arg Ser His Gln Glu Ser Glu Pro Ala Asn Ile Ser His Trp Ser
        35                  40                  45

Leu Leu Phe Lys Leu Phe Leu Ala Ile Thr Ile Met Gly Ala Cys Val
    50                  55                  60

Ala Gly Val Thr Phe Val Ile Leu Ile Thr Pro Thr Pro Pro Thr Val
65                  70                  75                  80

His Val Gln Ser Met His Ile Ser Phe Ala Asn His Asn Leu Pro Val
                85                  90                  95

Trp Ser Ala Thr Phe Ser Ile Lys Asn Pro Asn Glu Lys Leu His Val
            100                 105                 110

Thr Tyr Glu Asn Pro Ser Val Trp Leu Val His Arg Gly Lys Leu Val
        115                 120                 125

Ser Thr Ala Arg Ala Asp Ser Phe Trp Gln Lys Gly Gly Glu Lys Asn
    130                 135                 140

Glu Val Ile Val Lys Arg Asn Glu Thr Lys Val Ile Asp Glu Glu Ala
145                 150                 155                 160

Ala Trp Glu Met Glu Asp Glu Val Ala Val Thr Gly Gly Val Val Gly
                165                 170                 175

Leu Asp Met Val Phe Ser Gly Arg Val Gly Phe Tyr Pro Gly Thr Ser
            180                 185                 190

Ala Leu Trp Gly Glu Gln Tyr Met Ser Ala Val Cys Glu Asn Val Ser
        195                 200                 205

Ala Lys Leu Tyr Asn Val Asp Asp Glu Ile Tyr Gly Thr Asn Arg Ser
    210                 215                 220

Val Leu Ser Phe Asp Gly Arg Leu Val Cys Ser Val Arg Leu Pro Lys
225                 230                 235                 240

Tyr Pro
```